(12) United States Patent
Messing et al.

(10) Patent No.: US 9,044,019 B2
(45) Date of Patent: Jun. 2, 2015

(54) COMPOSITIONS AND METHODS FOR THE REGULATION OF CARBOHYDRATE METABOLISM AND FLOWERING IN PLANTS

(75) Inventors: Joachim Messing, Somerset, NJ (US); Martin Calviño, Highland Park, NJ (US); Rémy Bruggmann, Zurich (CH)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 365 days.

(21) Appl. No.: 13/114,675

(22) Filed: May 24, 2011

(65) Prior Publication Data

US 2011/0314574 A1    Dec. 22, 2011

Related U.S. Application Data

(60) Provisional application No. 61/347,741, filed on May 24, 2010.

(51) Int. Cl.
    *A01N 25/00* (2006.01)
    *A01H 5/00* (2006.01)
    *A01N 57/16* (2006.01)
    *C12N 15/82* (2006.01)

(52) U.S. Cl.
    CPC ............ *A01N 57/16* (2013.01); *C12N 15/8218* (2013.01); *C12N 15/8245* (2013.01); *C12N 15/827* (2013.01); *C12N 15/8271* (2013.01); *C12N 15/8273* (2013.01)

(58) Field of Classification Search
    None
    See application file for complete search history.

(56) References Cited

U.S. PATENT DOCUMENTS

| 7,723,568 B2 * | 5/2010 | Lutfiyya et al. ............... 800/285 |
| 2007/0079401 A1 * | 4/2007 | Lough et al. ................... 800/287 |

OTHER PUBLICATIONS

Kawashima et al, 2008, The Plant J., 57:313-321.*
Kawashima et al, 2011, Plant J., 66:863-876.*
Allen, E., et al. "Evolution of MicroRNA genes by inverted duplication of target gene sequences in *Arabidopsis thaliana*." Nat Genet. Dec. 2004; 36(12):1282-90. Epub Nov. 21, 2004.
Axtell, M.J., et al. "Evolution of plant microRNAs and their targets." Trends Plant Sci. Jul. 2008;13(7):343-9. Epub May 22, 2008.
Brown, P.J., et al. "Efficient mapping of plant height quantitative trait loci in a sorghum association population with introgressed dwarfing genes." Genetics. Sep. 2008;180(1):629-37. Epub Aug. 30, 2008.
Dai, X., et al. "psRNATarget a plant small RNA target analysis server." Nucleic Acids Res. Jul. 2011;39(Web Server issue):W155-9. Epub May 27, 2011.
Felippes, F.F., et al., "Evolution of *Arabidopsis thaliana* microRNAs from random sequences." RNA. Dec. 2008;14(12):2455-9. Epub Oct. 24, 2008.
Franks, S.J., et al. "Rapid evolution of flowering time by an annual plant in response to a climate fluctuation." Proc Natl Acad Sci U S A. Jan. 23, 2007;104(4):1278-82. Epub Jan. 12, 2007.
Jiang, D., et al. "Duplication and expression analysis of multicopy miRNA gene family members in *Arabidopsis* and rice." Cell Res. May 2006;16(5):507-18.
Li, W.X., et al. "The *Arabidopsis* NFYA5 transcription factor is regulated transcriptionally and posttranscriptionally to promote drought resistance." Plant Cell. Aug. 2008;20(8):2238-51. Epub Aug. 5, 2008.
Ma, Z., et al. "*Arabidopsis lyrata* small RNAs: transient MIRNA and small interfering RNA loci within the *Arabidopsis* genus." Plant Cell. Apr. 2010;22(4):1090-103. Epub Apr. 20, 2010.
Meng, Y., et al. "Construction of microRNA- and microRNA*-mediated regulatory networks in plants." RNA Biol. Nov.-Dec. 2011;8(6):1124-48. Epub Nov. 1, 2011.
Meyers, B.C., et al. "Criteria for annotation of plant MicroRNAs." Plant Cell. Dec. 2008;20(12):3186-90. Epub Dec. 12, 2008.
Salas Fernandez, M.G., et al. "From dwarves to giants? Plant height manipulation for biomass yield." Trends Plant Sci. Aug. 2009;14(8):454-61. Epub Jul. 16, 2009.
Valverde, F. "Constans and the evolutionary origin of photoperiodic timing of flowering." J Exp Bot. May 2011;62(8):2453-63. Epub Jan. 14, 2011.
Xue, L.J., et al. "Characterization and expression profiles of miRNAs in rice seeds." Nucleic Acids Res. Feb. 2009;37(3):916-30. Epub Dec. 22, 2008.
Yang, J.S., et al. "Widespread regulatory activity of vertebrate microRNA* species." RNA. Feb. 2011;17(2):312-26. Epub Dec. 22, 2010.
Zhang, L., et al. "A genome-wide characterization of microRNA genes in maize." PLoS Genet. Nov. 2009;5(11): e1000716. Epub Nov. 20, 2009.

* cited by examiner

*Primary Examiner* — David H Kruse
*Assistant Examiner* — Jason Deveau Rosen
(74) *Attorney, Agent, or Firm* — Kathleen D. Rigaut; Robert C. Netter, Jr.; Dann, Dorfman, Herrell & Skillman

(57) ABSTRACT

Compositions and methods for modulating flowering, sugar metabolism and stress response in plants are provided.

6 Claims, 66 Drawing Sheets

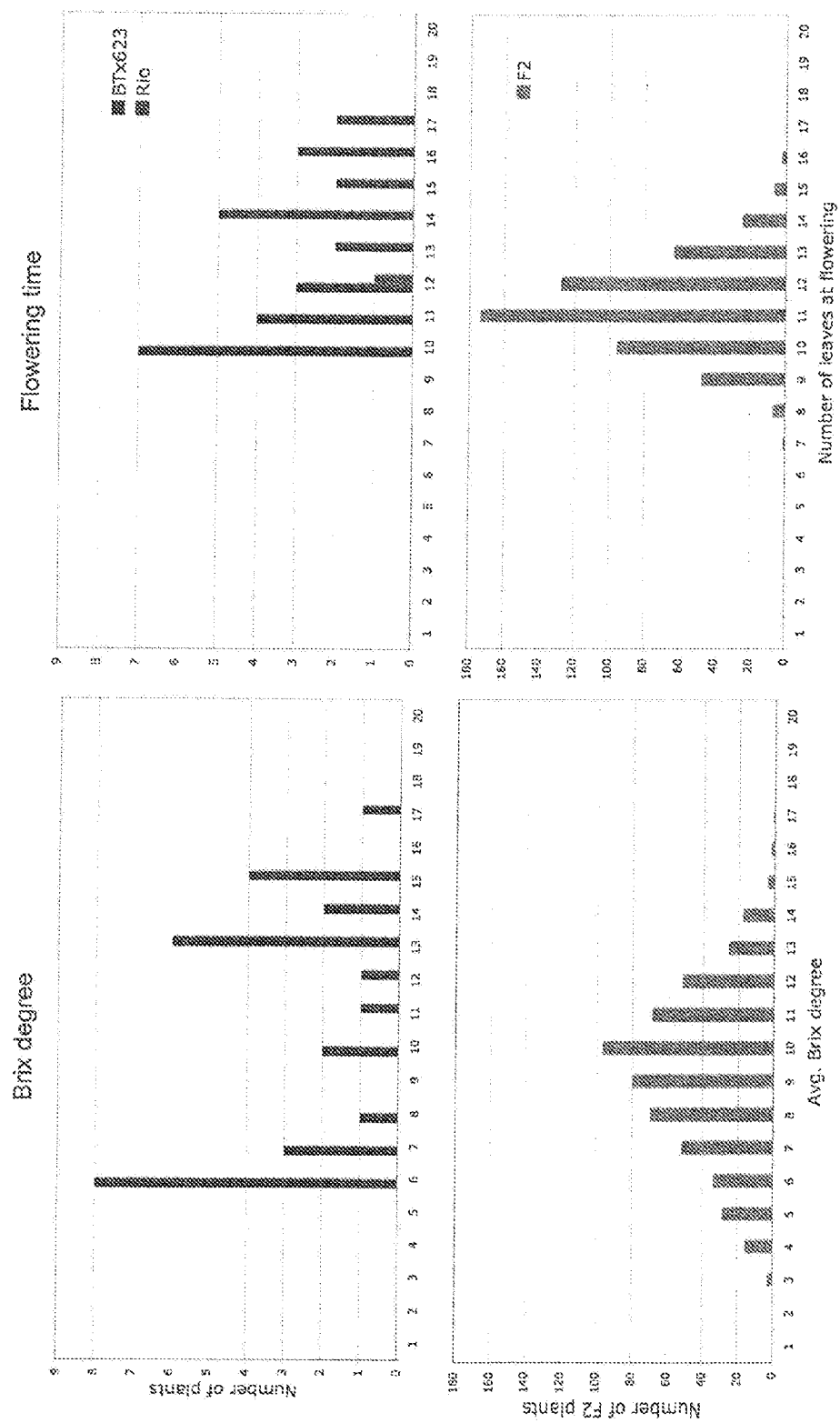

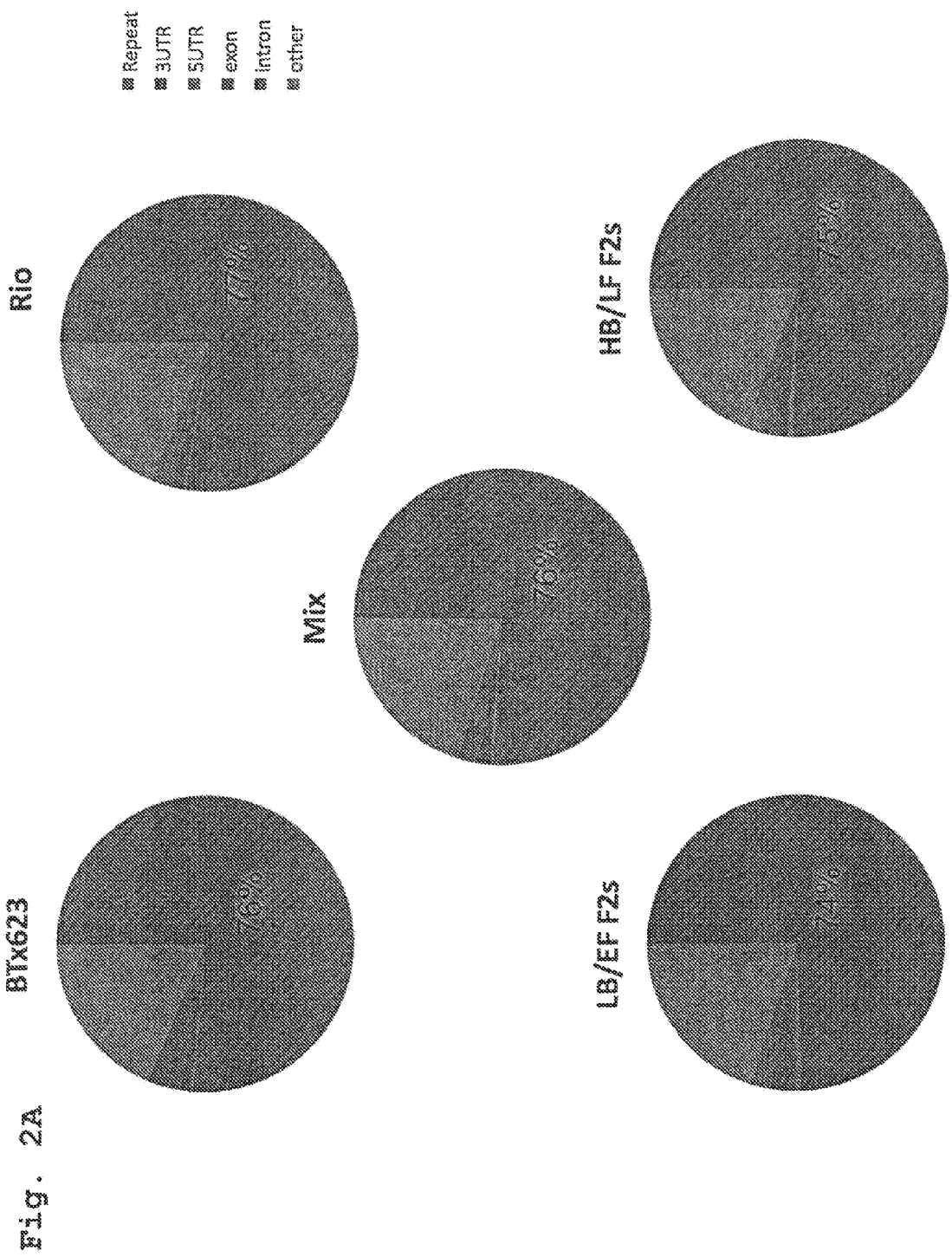

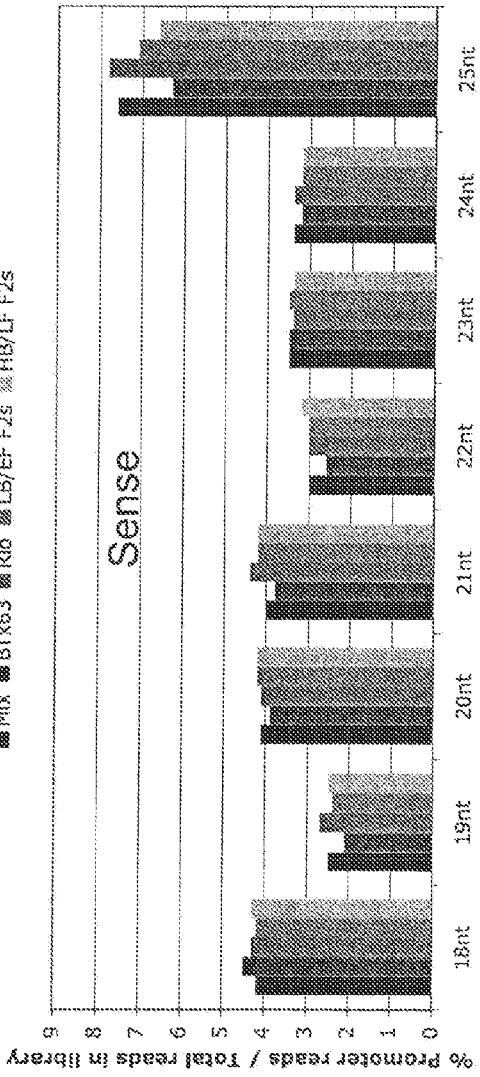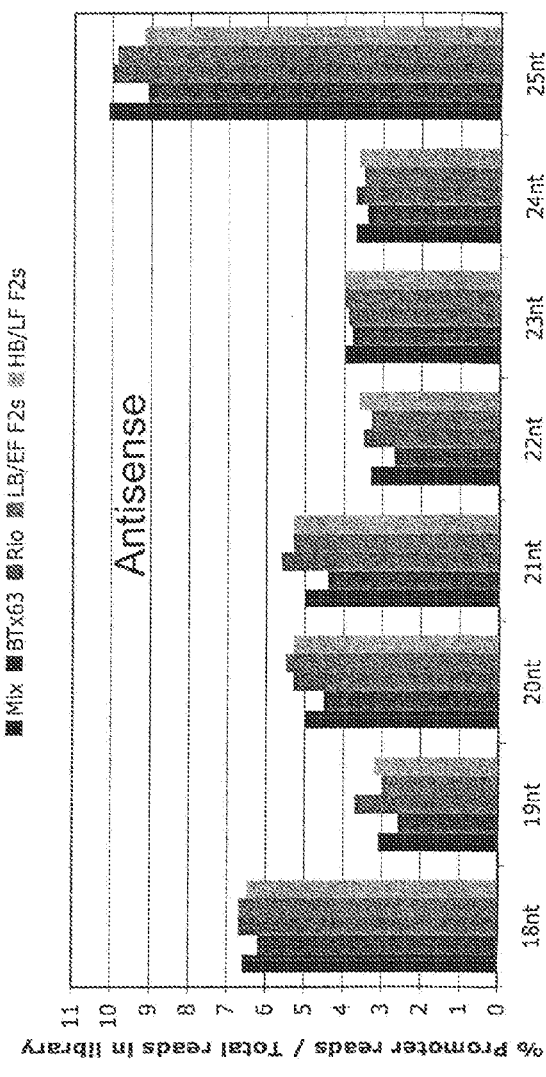
Fig. 2E

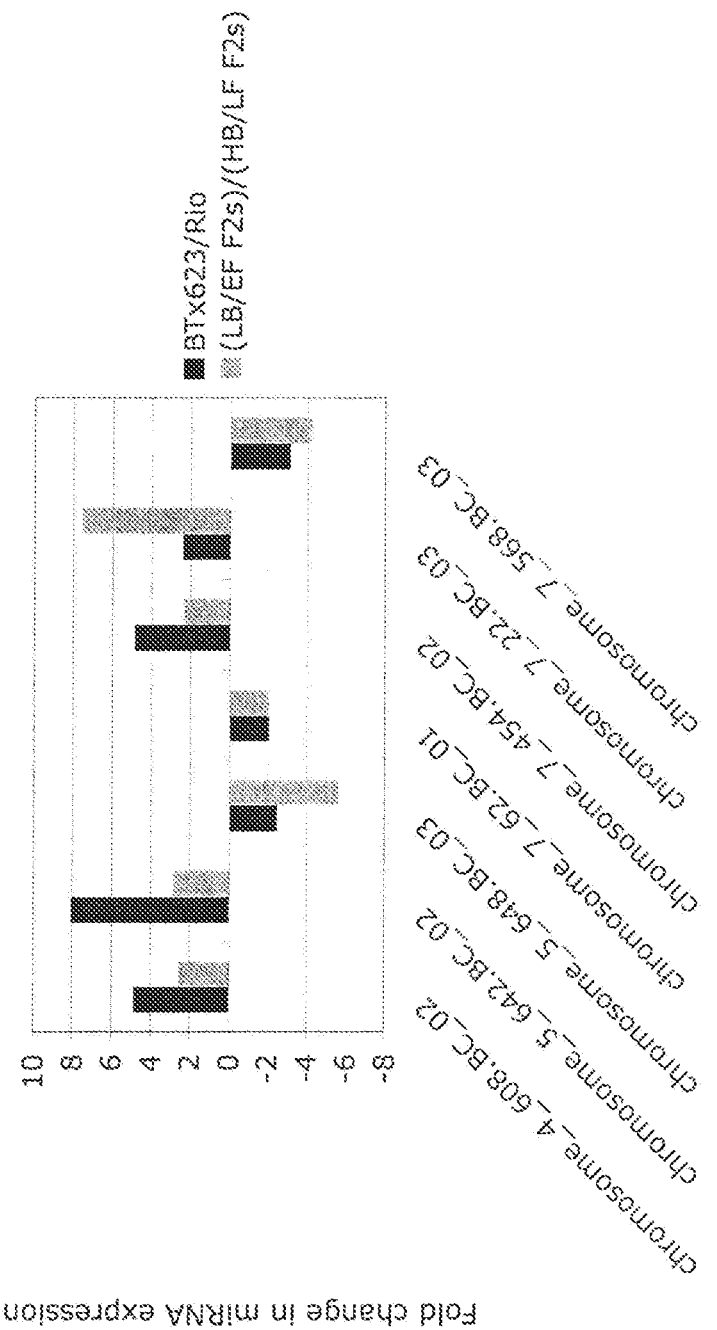

FIGURE 5B

```
                    2/10 BTx623    1/21 Rio   1/10 BTx623; 5/21 Rio
                         ↓             ↓        ↓ 1/10 BTx623; 9/21 Rio
                                                          ↓
SEQ ID NO: 20    3'-ACGUACUGUUCCUCUACU-5'                    chromosome_6_201_mature.BC_02
                    |||  || |||||||||||
SEQ ID NO: 21    5'-UGAAGGAGAGAAGGAGAUGAAUCUGCGCAAGAGCAA-3'  Sb01g049020 SOC1

3/19 BTx623
                                            ↓
                    5/19 BTx623
                         ↓
SEQ ID NO: 22    3'-A-CGUACUGUUCCUCUACU-5'                   chromosome_6_201_mature.BC_02
                    | |||||||||||||||
SEQ ID NO: 23    5'-UCACAUGACAAGGA-AUGAAGACCUUUGGAGG-3'      Sb04g003660 ZTL 1/9 BTx623
                      ↓↓
                      1/9 BTx623
                         ↓  1/9 BTx623
                               ↓
SEQ ID NO: 24    3'-ACGUACUGUUCCUCUACU-5'     chromosome_6_201_mature.BC_02
                    ||||||||||| |
SEQ ID NO: 25    5'-UCCAUGACAAGGAGAGCA-3'     Sb01g033060 Sucrose synthase 2

1/20 BTx623    3/20 BTx623
                      ↓              ↓  4/11 Rio
                                         ↓↓
SEQ ID NO: 26    3'-GGCG-ACCUGCCG--CGCGC-5'                          chromosome_4_712_mature.BC_01
                    |||- |||||||||-|||||
SEQ ID NO: 27    5'-CCUCCGGCGGACGGCGAGCGCGAGUUCAUGUUC-3'             Sb03g042460 Fructokinase-1
```

Figure 8A

```
sbi-miR169cd --> target score: 6
3'-AUCCGUUCAGUAGGAACCGAU-5'
    |||||||  |  | ||||||||
5'-UAGGCAAGGCCUACUUGGCUA-3'
Sb10g002400.1_5'UTR_chromosome --> similar to Glycine-rich protein-like sbi-miR169i --> target score: 6
3'-AUCCGUUCAGUAAGAACCGAU-5'
    ||||||||  |  | ||||||||
5'-UAGGCAAGGCCUACUUGGCUA-3'
Sb10g002400.1_5'UTR_chromosome --> similar to Glycine-rich protein-like sbi-miR395bacde --> target score: 1.0
3'-CUCAAGGGGGUUUGUGAAGUG-5'
    ||||:||||||||||||||:
5'-GAGUUUCCCCAAACACUUCAU-3'
Sb01g044100.1_5'UTR_chromosome --> similar to Putative sulfate transporter sbi-miR395f --> target score: 0.5
3'-CUCAAGGGGGUUUGUGAAGUA-5'
    ||||:|||||||||||||||
5'-GAGUUUCCCCAAACACUUCAU-3'
Sb01g044100.1_5'UTR_chromosome --> similar to Putative sulfate transporter chromosome_5_379_mature.BC_04 --> target score: 6
3'-UAGGAGCGUG-GA-GAAGGG-5'
    |||||||||-||-| ||||
5'-AUCCUCGCACGCUCCCUCCC-3'
Sb02g001110.1_5'UTR_chromosome --> similar to Casein kinase II subunit alpha chromosome_5_978_mature.BC_01 --> target score: 4.0
3'-CGUCCGAGAGCCGUUUCUU-5'
   |||  ||||||||  |:||||
5'-GCAGUCUCUCGGAAGAGAA-3'
Sb04g023680.2_5'UTR_chromosome --> similar to Cryptochrome 1a chromosome_5_978_mature.BC_01 --> target score: 4.0
3'-CGUCCGAGAGCCGUUUCUU-5'
   |||  ||||||||  |:||||
5'-GCAGUCUCUCGGAAGAGAA-3'
Sb04g023680.1_5'UTR_chromosome --> similar to Cryptochrome 1a chromosome_6_201_mature.BC_02 --> target score: 2.5
3'-ACGUACUGUUCCUCUACU-5'
    |:|||||||||| ||||
5'-AGUAUGACAAGGAAAUGA-3'
Sb06g025550.1_5'UTR_chromosome --> similar to INDETERMINATE-related protein 9 chromosome_4_557_mature.BC_02 --> target score: 2
3'-AUUCCCGUGAGUGUUACGU-5'
   ||||||||||||||||| ||
5'-UAAGGGCACUCACAAUACA-3'
Sb10g006330.3_5'UTR_chromosome --> similar to Sucrose synthase 1 chromosome_9_1189_mature.BC_05 --> target score: 5
```

Figure 8B

```
3'-GGCAGC-GCGGCGGCGGCACGC-5'
   |||||-|||||||||||- ||
5'-CCGUCGCCGCCGCCGCCG-CCG-3'
Sb01g045200.1_5'UTR_chromosome --> similar to Glycosyl transferase, group 1 family protein, expr chromosome_9_1189_mature.BC_05 --> target score: 4
3'-GGCAGC-GCGGCGGCGGCACGC-5'
   || ||-||||||||||| ||||
5'-CCGCCGCCGCCGCCGCCCUGCG-3'
Sb01g045200.1_5'UTR_chromosome --> similar to Glycosyl transferase, group 1 family protein, expr chromosome_1_827_mature.BC_01 --> target score: 4.5
3'-GGUGGGGUUGCGUACACCUAAC-5'
   ||||:|||| |||| ||||||
5'-CCACCUCAACACAUGCGGAUUG-3'
Sb03g041890.1_5'UTR_chromosome --> similar to Putative uncharacterized protein chromosome_1_827_mature.BC_01 --> target score: 3
3'-GGUGGGGUUGCGUACACCUAAC-5'
   ||| ||||| |||||||||||
5'-CCACACCAACACAUGUGGAUUG-3'
Sb06g021860.1_5'UTR_chromosome --> weakly similar to OSJNBa0014K14.20 protein chromosome_1_827_mature.BC_01 --> target score: 3.0
3'-GGUGGGGUUGCGUACACCUAAC-5'
   |||::|||| |||||||||||
5'-CCACUUCAACACAUGUGGAUUG-3'
Sb06g033900.1_5'UTR_chromosome --> similar to Os09g0111800 protein chromosome_1_827_mature.BC_01 --> target score: 2.5
3'-GGUGGGGUUGCGUACACCUAAC-5'
   |||:||||| |||||||||||
5'-CCACUCCAACACAUGUGGAUUG-3'
Sb07g021270.2_5'UTR_chromosome --> similar to Lipoate-protein ligase A-like chromosome_2_1473_mature.BC_01 --> target score: 2.5
3'-GGGGUUAGGUGAGGUUGUGUACA-5'
   :|||||||||| |||||||||||
5'-CUCCAAUCCACACCAACACAUGU-3'
Sb06g021860.1_5'UTR_chromosome --> weakly similar to OSJNBa0014K14.20 protein chromosome_2_1473_mature.BC_01 --> target score: 1.0
3'-GGGGUUAGGUGAGGUUGUGUACA-5'
   |||||||||||:|||||||||||
5'-CCCCAAUCCACUUCAACACAUGU-3'
Sb06g033900.1_5'UTR_chromosome --> similar to Os09g0111800 protein chromosome_2_1473_mature.BC_01 --> target score: 0
3'-GGGGUUAGGUGAGGUUGUGUACA-5'
   |||||||||||||||||||||||
5'-CCCCAAUCCACUCCAACACAUGU-3'
Sb07g021270.2_5'UTR_chromosome --> similar to Lipoate-protein ligase A-like chromosome_3_189_mature.BC_01 --> target score: 3
3'-GGGGUUAGGUGGA-GUUGUGUACA-5'
   |||||||||-||-|||||||||||
5'-CCCCAAUCCA-CUCCAACACAUGU-3'
```

Figure 8C

```
Sb07g021270.1_5'UTR_chromosome --> similar to Lipoate-protein ligase A-like chromosome_3_189_mature.BC_01 --> target score: 2.0
3'-GGGGUUAGGUGGAGUUGUGUACA-5'
   :||||||:||||||||||:|||
5'-CUCCAAUCUACCUCAACACGUGU-3'
Sb09g003590.2_5'UTR_chromosome --> similar to Sodium/hydrogen exchanger chromosome_3_1324_mature.BC_01 --> target score: 2.0
3'-AACCUCACCUAAUCCCACCUUAAA-5'
   ||||||  ||||:||||||||||
5'-UUGGAGUAGAUUGGGGUGGAAUUU-3'
Sb03g046332.1_5'UTR_chromosome --> Predicted protein chromosome_3_1324_mature.BC_01 --> target score: 1.0
3'-AACCUCACCUAAUCCCACCUUAAA-5'
   ||||||||||||:||||||||||
5'-UUGGAGUGGAUUGGGGUGGAAUUU-3'
Sb06g021860.1_5'UTR_chromosome --> weakly similar to OSJNBa0014K14.20 protein chromosome_3_47_mature.BC_01 --> target score: 4.0
3'-UACACACAACCACACCUAACCCUA-5'
   ||||||||||||||:||||  :|
5'-AUGUGUGUUGGUGUGGGUUGGAGU-3'
Sb09g003590.2_5'UTR_chromosome --> similar to Sodium/hydrogen exchanger
```

Figure 9A

```
sbi-miR169cd --> target score: 4.0
3'-AUC-CGUUCAGUAGGAACCGAU-5'
     ||-|||||||:||||||| ||
5'-UAGAGCAAGUCGUCCUUGGAUA-3'
Sb05g026273.1_chromosome_5_sbi --> weakly similar to GRAS family transcription factor, putative sbi-miR169b --> target score: 5
3'-GGCCGUUCAGUAGGAACCGAC-5'
   |||||| ||||| ||||||
5'-CCGGCAACUCAUCAGUGGCUG-3'
Sb06g002960.1_chromosome_6_sbi --> similar to Putative non-LTR retroelement reverse transcriptas sbi-miR169a --> target score: 4
3'-A-GCCGUUCAGUAGGAACCGAC-5'
   -|||||| |||||||||||-|
5'-UCCGGCAAAUCAUCCUUGGC-G-3'
Sb09g008100.1_chromosome_9_sbi --> similar to Putative uncharacterized protein sbi-miR169b --> target score: 3
3'--GGCCGUUCAGUAGGAACCGAC-5'
    ||||||| |||||||||||-|
5'-UCCGGCAAAUCAUCCUUGGC-G-3'
Sb09g008100.1_chromosome_9_sbi --> similar to Putative uncharacterized protein sbi-miR169cd* --> target score: 6
3'-AUCGGUUCCUACUGAACGGAU-5'
   |||||||||||-|- |||||
5'-UAGCCAAGGAUG-C-AGCCUA-3'
Sb01g020840.1_chromosome_1_sbi --> similar to HAT family dimerisation domain, putative sbi-miR169a* --> target score: 2.5
3'-GUCGG-UUCCUACUGAACGGCU-5'
   |||-:|||||||||||||||
5'-CUGCCGGAGGAUGACUUGCCGA-3'
Sb01g032770.1_chromosome_1_sbi --> weakly similar to OSMYB3 sbi-miR169b* --> target score: 4
3'-G-UC-GGUUCCUACUGAACGGCC-5'
   -||-|||||||||||||| ||||
5'-CUAGUCCAAGGAUGACUUACCGG-3'
Sb01g036110.1_chromosome_1_sbi --> similar to Insulinase containing protein, expressed sbi-miR169efgh* --> target score: 5
3'-AUC-GGUUCCUACUGAACGGAC-5'
   ||-|||||||||||||| || |
5'-UAGUCCAAGGAUGACUUACCGG-3'
Sb01g036110.1_chromosome_1_sbi --> similar to Insulinase containing protein, expressed sbi-miR169b* --> target score: 5
3'-GUCGGUUCCUACUGAACGGCC-5'
   ||-|||||| ||| ||||||
5'-CAG-CAAGGAGGACCUGCCGG-3'
Sb01g041700.1_chromosome_1_sbi --> similar to Glutamate decarboxylase sbi-miR169i* --> target score: 4
```

Figure 9B

```
3'-AUCGGUUCUUACUGAACGGAU-5'
   | |||||||||| ||||||
5'-UAACCAAGAAUGAGUUGCCUC-3'
Sb02g004450.1_chromosome_2_sbi --> similar to Putative uncharacterized protein sbi-miR169b* --> target score: 4
3'-GUCGGUUCCUACUGAACGGCC-5'
   ||||- |||||||-||||||
5'-CAGCC-UGGAUGAC-UGCCGG-3'
Sb02g026670.1_chromosome_2_sbi --> similar to Calmodulin-like protein sbi-miR169a* --> target score: 5
3'-GUCGGUUCCUACUGAACGGCU-5'
   ||||-|||||-| |||||||
5'-CAGCC-AGGAU-AGUUGCCGA-3'
Sb03g004580.1_chromosome_3_sbi --> similar to Putative RST1 sbi-miR169b* --> target score: 3.0
3'-GUCGGUUCCUACUGAACGGCC-5'
    -||||| |||||||||||:||
5'-C-GCCAAAGAUGACUUGCUGG-3'
Sb03g028620.1_chromosome_3_sbi --> similar to Cytochrome P450 sbi-miR169b* --> target score: 3.0
3'-GUCGGUUCCUACUGAACGGCC-5'
   |-|||| |||||||||||:||
5'-CA-CCAAAGAUGACUUGCUGG-3'
Sb03g028670.1_chromosome_3_sbi --> similar to Cytochrome P450 monooxygenase CYP72A26 sbi-miR169cd* --> target score: 6
3'-AUCGGUUCCUACUGAACGGAU-5'
   ||||||||||-|- |||||
5'-UAGCCAAGGAUG-C-AGCCUA-3'
Sb03g029065.1_chromosome_3_sbi --> similar to HAT family dimerisation domain, putative sbi-miR169a* --> target score: 5
3'-GUCGGU-UCCUACUGAACGGCU-5'
   |||||-|||||||| |||-|||
5'-CAGCCACAGGAUGAGUUG-CGA-3'
Sb03g038380.1_chromosome_3_sbi --> similar to Putative uncharacterized protein sbi-miR169a* --> target score: 5
3'-GUCGGUUCCUACUGAACGGCU-5'
    -|||||||-|-|||||||
5'-C-GCCAAGGA-G-CUUGCCGA-3'
Sb04g022590.1_chromosome_4_sbi --> similar to Putative uncharacterized protein sbi-miR169b* --> target score: 5
3'-GUCGGUUCCUACUGAACGGCC-5'
   |||||||||||- |||||
5'-CCGCCAAGGAUGAC-CGCCGG-3'
Sb05g002790.1_chromosome_5_sbi --> similar to Putative MFAP1 protein sbi-miR169b* --> target score: 5
3'-GUCGGUUCCUACUGAACGGCC-5'
   |||||||||||- |||||
5'-CCGCCAAGGAUGAC-CGCCGG-3'
```

Figure 9C

Sb05g002790.2_chromosome_5_sbi --> similar to Putative MFAP1 protein sbi-miR169cd* --> target score: 6
3'-AUCGGUUCCUACUGAACGGAU-5'
       ||||||:|||||-|-||-|||
5'-UAGCCAAGGAUG-C-UG-CUA-3'
Sb05g024660.1_chromosome_5_sbi --> similar to Putative uncharacterized protein sbi-miR169b* --> target score: 4
3'-GUCGGUUCCUACUGAACGGCC-5'
       ||||||||||||-||-||||
5'-AAGCCAAGGAUGA-UU-CCGG-3'
Sb10g008200.1_chromosome_10_sb --> similar to Starch synthase isoform zSTSII-1 sbi-miR172cad --> target score: 1.0
3'-ACGUCGUAGUAGUUCUAAGA-5'
      ||||||||||||:||||||
5'-UGCAGCAUCAUCAGGAUUCU-3'
Sb01g003400.1_chromosome_1_sbi --> similar to Indeterminate spikelet 1 sbi-miR172b --> target score: 3.0
3'-ACGUCGUAGUAGUUCUAAG-G-5'
      ||||||||||||:|||||-|
5'-UGCAGCAUCAUCAGGAUUCUC-3'
Sb01g003400.1_chromosome_1_sbi --> similar to Indeterminate spikelet 1 sbi-miR172b --> target score: 3.5
3'-ACGUCGUAGUAGUUCUAAGG-5'
     | |||| |||||||||||:
5'-UGGAGCACCAUCAAGAUUCU-3'
Sb01g029120.1_chromosome_1_sbi --> weakly similar to Agenet domain containing protein, expressed sbi-miR172cad --> target score: 3
3'-ACGUCGUAGUAGUUCUAAGA-5'
     | |||| |||||||||||
5'-UGGAGCACCAUCAAGAUUCU-3'
Sb01g029120.1_chromosome_1_sbi --> weakly similar to Agenet domain containing protein, expressed sbi-miR172cad --> target score: 5
3'-ACGUCGUAGUAGUUC-UAAGA-5'
    -|||||| ||||||-||||
5'-U-CAGCAUGAUCAAGCAUUCU-3'
Sb01g041110.1_chromosome_1_sbi --> similar to Expressed protein sbi-miR172b --> target score: 3
3'--ACGUCGUAGUAGUUCUAAGG-5'
      ||| |||||||-|||||||
5'-UUGCUGCAUCAU-AAGAUUCC-3'
Sb01g050166.1_chromosome_1_sbi --> similar to Putative uncharacterized protein sbi-miR172b --> target score: 1.0
3'-ACGUCGUAGUAGUUCUAAGG-5'
      ||||||||||||:||||||
5'-CGCAGCAUCAUCAGGAUUCC-3'
Sb10g025053.1_chromosome_10_sb --> similar to Glossy15 sbi-miR172cad --> target score: 2.0

Figure 9D

```
3'-ACGUCGUAGUAGUUCUAAGA-5'
   |||||||||||:|||||
5'-CGCAGCAUCAUCAGGAUUCC-3'
Sb10g025053.1_chromosome_10_sb --> similar to Glossy15 sbi-miR172cad --> target score: 4.0
3'-ACG-UCGUAGUAGUUCUAAGA-5'
   ||-|||||||||||: |||
5'-UGCAAGCAUCAUCAAGGCUCU-3'
Sb01g050570.1_chromosome_1_sbi --> similar to Phosphoglycerate mutase family protein, expressed sbi-miR172cad --> target score: 5
3'-ACGUCGUAGUAGUUCUAAG-A-5'
   |-||||||||||| ||||-|
5'-UG-AGCAUCAUCAAAAUUCAU-3'
Sb02g003020.1_chromosome_2_sbi --> similar to Putative uncharacterized protein sbi-miR172e --> target score: 4
3'-CACGU-CGUAGUAGUUCUAAGU-5'
   |||-|||||||||||||-|||
5'-GCGCAGGCAUCAUCAAGA-UCA-3'
Sb01g044240.1_chromosome_1_sbi --> similar to Expressed protein sbi-miR172e --> target score: 2.0
3'-CACGUCGUAGUAGUUCUAAGU-5'
   |||||||||||||:|||||
5'-CUGCAGCAUCAUCAGGAUUCU-3'
Sb02g007000.1_chromosome_2_sbi --> similar to Putative indeterminate spikelet 1 sbi-miR172e --> target score: 5
3'-CAC-GUCGUAGUAGUUCUAAGU-5'
   ||-||||||-||||| |||||
5'-GUGACAGCAU-AUCAACAUUCA-3'
Sb03g027080.1_chromosome_3_sbi --> similar to Os01g0601700 protein sbi-miR172e --> target score: 4
3'-CACGUCGUAGU-AGUUCUAAGU-5'
   | |||||-||-|||||||||||
5'-GUACAGCA-CACUCAAGAUUCA-3'
Sb05g020460.1_chromosome_5_sbi --> similar to Helicase-like protein sbi-miR172e --> target score: 4
3'-C-ACGUCGUAGUAGUUCUAAGU-5'
   -|||||-||||| ||||||||
5'-GCUGCAG-AUCAUGAAGAUUCA-3'
Sb06g015350.1_chromosome_6_sbi --> similar to H0321H01.9 protein sbi-miR172e --> target score: 4
3'-C-ACGUCGUAGUAGUUCUAAGU-5'
   -||||||||||||| |||||
5'-GCUGCAGCAUCAUCACGAUUCC-3'
Sb06g030670.1_chromosome_6_sbi --> similar to OSJNBa0010D21.13 protein sbi-miR172cad --> target score: 3
3'-ACGUCGUAGUAGUUCUAAGA-5'
   |||||||||||| |||||
5'-UGCAGCAUCAUCACGAUUCC-3'
```

Figure 9E

```
Sb06g030670.1_chromosome_6_sbi --> similar to OSJNBa0010D21.13 protein sbi-miR172b --> target score: 2
3'-ACGUCGUAGUAGUUCUAAGG-5'
   |||||||||||| ||||||
5'-UGCAGCAUCAUCACGAUUCC-3'
Sb06g030670.1_chromosome_6_sbi --> similar to OSJNBa0010D21.13 protein sbi-miR395bacde --> target score: 2.0
3'-CUCAAGGGGGUUUGUGAAGUG-5'
   ||||||:||||:||||||||:
5'-GAGUUCCUCCAAGCACUUCAU-3'
Sb01g008450.1_chromosome_1_sbi --> similar to ATP sulfurylase sbi-miR395f --> target score: 1.5
3'-CUCAAGGGGGUUUGUGAAGUA-5'
   ||||||:||||:|||||||||
5'-GAGUUCCUCCAAGCACUUCAU-3'
Sb01g008450.1_chromosome_1_sbi --> similar to ATP sulfurylase sbi-miR395bacde* --> target score: 5
3'-CACUUCACAAACCCCCUUGAG-5'
   |||||| |||-||||||-||
5'-GUGAAGUUUUU-GGGGAA-UC-3'
Sb03g014780.1_chromosome_3_sbi --> similar to Probable chromatin-remodeling complex ATPase chain sbi-miR395bacde* --> target score: 5
3'-CACUUCACAAACCCCCUUGAG-5'
   ||| ||||||-||||||-||
5'-GUGAUGUGUUU-GGGGAA-UC-3'
Sb03g026410.1_chromosome_3_sbi --> similar to ATP synthase beta subunit/transcription terminatio sbi-miR395f* --> target score: 5
3'-UACUUCACAAACCCCCUUGAG-5'
   ||||-||-||||||||||| ||
5'-AUGAA-UG-UUGGGGGAAAUC-3'
Sb09g023793.1_chromosome_9_sbi --> similar to NOT2/NOT3/NOT5 family protein, expressed sbi-miR395f* --> target score: 5.0
3'-UACUUCACAAACCCCCUUGAG-5'
   |||||||||| -||||:|||
5'-AUGAAGUGUUUU-GGGAGCUC-3'
Sb10g012270.1_chromosome_10_sb --> similar to Putative uncharacterized protein sbi-miR395f* --> target score: 4
3'-UACUUCACAAACCCCCUUGA-G-5'
   |||||-|-||||||||||||-|
5'-AUGAAG-G-UUGGGGGAACUAC-3'
Sb10g013750.1_chromosome_10_sb --> similar to Cryptochrome 2 chromosome_1_983_mature.BC_04 --> target score: 4.5
3'-AGUAACCUAAGUGUAAUU-5'
   ||||||||| |||| ||:
5'-UCAUUGGAUGCACAGUAG-3'
Sb0010s020250.1_super_10_sbic_ --> putative protein chromosome_1_983_mature.BC_04 --> target score: 5.0
```

Figure 9F

```
3'-AGUAACC-UAAGUGUAAUU-5'
   ||||||-||| |||||:|
5'-UCAUUGGCAUUGACAUUGA-3'
Sb04g037050.1_chromosome_4_sbi --> similar to Alcohol dehydrogenase class-3 (EC 1.1.1.1) (Alcoho chromosome_1_466_mature.BC_02 --> target score: 3
3'--UCGAGCCGUGGUGUCUAGA-5'
    ||||||||||-||||||
5'-CUGCUCGGCACCA-AGAUCU-3'
Sb10g000770.1_chromosome_10_sb --> similar to Integral membrane protein DUF6 containing protein, chromosome_1_398_mature.BC_02 --> target score: 5
3'-GUGCCGUGAUAGUCCGUGC-5'
   |||||| | |||||||||
5'-CUCGGCACCAGCAGGCACG-3'
Sb10g006910.1_chromosome_10_sb --> similar to 2-oxoglutarate-dependent oxygenase chromosome_1_345_mature.BC_03 --> target score: 3.0
3'--AGGGUGAACGUGGGAGUC-5'
    ||||||-|||||:||||
5'-CUCCCAC-UGCACCUUCAG-3'
Sb10g030730.1_chromosome_10_sb --> weakly similar to Putative uncharacterized protein chromosome_1_970_mature.BC_03 --> target score: 6
3'-GAAGCACCAAC-AGCGCCUG-5'
   ||||||| ||-||||-|||
5'-CUUCGUGGAUGUUCGC-GAC-3'
Sb10g024490.2_chromosome_10_sb --> similar to Putative cinnamoyl-CoA reductase chromosome_1_970_mature.BC_03 --> target score: 5
3'-GAAGCACCAACAGCGCCUG-5'
   |||| |||||||| |||
5'-CUUCGAGGUUGUCGAUGAC-3'
Sb09g020980.1_chromosome_9_sbi --> similar to Class III peroxidase 124 precursor chromosome_1_970_mature.BC_03 --> target score: 5
3'-GAAGCACCAACAGCGCCUG-5'
   |||| |||||||| |||
5'-CUUCGAGGUUGUCGAUGAC-3'
Sb09g021000.1_chromosome_9_sbi --> similar to Class III peroxidase 124 precursor chromosome_1_970_mature.BC_03 --> target score: 4
3'-GAAGCACCAACAGCGCCUG-5'
   |||| || |||||||||
5'-CUUCGUCGUCGUCGCGGAC-3'
Sb03g035080.1_chromosome_3_sbi --> similar to Putative Dof zinc finger protein chromosome_1_527_mature.BC_05 --> target score: 6
3'-UCACUUCAACUCGAAACA-5'
   ||||||||   |||||
5'-AGUGAAGUUGCUAUUUGU-3'
Sb10g031060.1_chromosome_10_sb --> similar to Chromosome chr1 scaffold_22, whole genome shotgun chromosome_1_527_mature.BC_05 --> target score: 6
3'-UCACUUCAACUCGAA-ACA-5'
   ||||||| ||||||- ||
5'-AGUGAAGUCGAGCUUGAGU-3'
```

Figure 9G

Sb03g042460.1_chromosome_3_sbi --> similar to Fructokinase-1 chromosome_1_52_mature.BC_04 --> target score: 4
3'-CGAGC-CGCGGUGUCUAGAA-5'
   ||||- |||||-|||||||
5'-GCUCGUUCGCCA-AGAUCUU-3'
Sb10g024900.1_chromosome_10_sb --> similar to Putative uncharacterized protein OSJNBa0019I19.51 chromosome_1_216_mature.BC_05 --> target score: 5
3'-GGGCAGCUUGGUACCCU-UC-5'
   ||| |||| |||||||-||
5'-CCCGACGAAACAUGGGACAG-3'
Sb10g030940.1_chromosome_10_sb --> similar to Calcium-binding EF hand protein-like chromosome_1_450_mature.BC_02 --> target score: 5
3'-ACGAGUGUCA-UUCCCGCCGA-5'
   | |||||||-||||||| ||
5'-UGAUCACAGUCAAGGGCGCCU-3'
Sb02g006890.1_chromosome_2_sbi --> similar to Putative uncharacterized protein OSJNBa0086N05.106 chromosome_1_754_mature.BC_04 --> target score: 4
3'-GUUAGGUGUACACAACUCC-5'
   |||||| || |||||||||
5'-AAAUCCAAAUCUGUUGAGG-3'
Sb10g022700.1_chromosome_10_sb --> similar to Os06g0574400 protein chromosome_1_1560_mature.BC_03 --> target score: 6
3'-UUGGAUAACGUCAAAG-AGGUUG-5'
   ||||||||| | |||-||||||
5'-AACCUAUUGCUGAUUCAUCCAAC-3'
Sb03g035550.1_chromosome_3_sbi --> similar to Putative uncharacterized protein chromosome_1_245_mature.BC_01 --> target score: 3
3'-CCCCUUACUUCGGACCAGGCU-5'
   ||||||||||||| |||||
5'-UGGGAAUGAAGCCUCGUCCGC-3'
Sb10g009464.1_chromosome_10_sb --> Predicted protein chromosome_1_1391_mature.BC_04 --> target score: 3.5
3'-GUGAGGUU-AGAUGGAGUU-5'
   :||||||-|||||||:||
5'-CGCUCCAACUCUACCUUAA-3'
Sb10g028850.1_chromosome_10_sb --> similar to 4-amino-4-deoxychorismate synthase chromosome_1_1391_mature.BC_04 --> target score: 3.5
3'-G-UGAGGUUAGAUGGAGUU-5'
   -|||||||-|||||||||:
5'-CUACUCCAA-CUACCUCAG-3'
Sb10g009270.1_chromosome_10_sb --> similar to Endoglucanase 17 precursor chromosome_1_882_mature.BC_04 --> target score: 4
3'-CUACGCGUGCGCCUCAGCU-CC-5'
   |||||||||||||-|||-||
5'-GAUGCGCACGCGGAG-CGACGG-3'
Sb10g003090.1_chromosome_10_sb --> similar to Pectate lyase homolog chromosome_1_686_mature.BC_02 --> target score: 5

Figure 9H

```
3'-AAAAAUGGCCAGGCUAACGU-5'
   || ||||  |||||||||||
5'-UUUAUACCACUCCGAUUGCA-3'
Sb01g035310.1_chromosome_1_sbi --> similar to Zinc finger, C3HC4 type family protein, expressed chromosome_1_862_mature.BC_02 --> target score: 3
3'-UGGUCCGAUUCCUCCUCGAGGGCG-5'
   |||||||||||||||| ||||||
5'-ACCAGGCUAAGGAGGAACUCCCGG-3'
Sb06g030515.1_chromosome_6_sbi --> similar to Putative gag-pol polyprotein chromosome_1_346_mature.BC_03 --> target score: 3
3'-GAGGGUGAACGUGGGAGUCC-GCA-5'
   ||||-||||||||||||||-|||
5'-GUCCC-CUUGCACCCUCAGGCCGU-3'
Sb03g035140.1_chromosome_3_sbi --> similar to P0460E08.3 protein chromosome_1_1241_mature.BC_03 --> target score: 5
3'-GGGGC-GGUACU-GGCCGGGUGG-5'
   ||||-||||||-|||||||  ||
5'-CCCCGUCCAUGACCCGGCCCUCC-3'
Sb03g027140.1_chromosome_3_sbi --> weakly similar to Os07g0517700 protein chromosome_1_651_mature.BC_03 --> target score: 1.5
3'-AGCGCCGGUACCGCCCGCUGAAGU-5'
   |||||:||||||||||||:|||||
5'-UCGCGGUCAUGGCGGGCGGCUUCA-3'
Sb08g022810.1_chromosome_8_sbi --> Predicted protein chromosome_2_2234_mature.BC_05 --> target score: 4.5
3'-CAUGCCGGCUCUGGCGGCAGCGGU-5'
   |||||||||||||||||||  |||:
5'-GUACGGCCGAGACCGCCGCAGCCG-3'
Sb03g024845.1_chromosome_3_sbi --> Predicted protein chromosome_2_2159_mature.BC_04 --> target score: 4
3'-GGGGC-GUGAGUGCGGGAAGCA-5'
   ||||-||-|||||| ||||||
5'-CCCCGACA-UCACGCGCUUCGU-3'
Sb09g023000.1_chromosome_9_sbi --> weakly similar to Putative uncharacterized protein chromosome_2_902_mature.BC_02 --> target score: 4.5
3'-CGUGUUGAAGAUUCUCGUU-5'
   ||||:|  |||||||||
5'-GCACAGCAACUAAGAGCAA-3'
Sb0012s004900.1_super_12_sbic_ --> putative protein chromosome_2_1490_mature.BC_04 --> target score: 4.0
3'-GGUGCAGGG-GGUGGUGCUGC-5'
   ||-|||||-||||:||||||
5'-CCA-GUCCCACCACUACGACG-3'
Sb0013s004020.1_super_13_sbic_ --> putative protein chromosome_2_1490_mature.BC_04 --> target score: 4.0
3'-GGUGCAGGGGGUGGUGCUGC-5'
   |||||:||| ||||||||
5'-CAACGUCUCCCUCCACGACG-3'
```

Figure 9I

```
Sb05g019040.1_chromosome_5_sbi --> similar to O-methyltransferase ZRP4, putative, expressed chromosome_2_3135_mature.BC_05 --> target score: 2.5
3'-UGCGGGCGACCACCCUAGACC-5'
   ||||:||||||||||| ||||
5'-ACGCCUGCUGGUGGGACCUGG-3'
Sb0013s004040.1_super_13_sbic_ --> putative protein chromosome_2_45_mature.BC_01 --> target score: 6
3'-UCCCGGACAAAUCUAACC-5'
   |||||||||| | |||
5'-AGGGCCUGUUUCCAAUGG-3'
Sb10g010410.1_chromosome_10_sb --> similar to Putative uncharacterized protein chromosome_2_3135_mature.BC_04 --> target score: 5
3'-GGAUCGAUGUCGAACAUGCC-5'
   ||||| | ||||||| |||
5'-CCUAGCCAGAGCUUGUCCGG-3'
Sb03g004450.1_chromosome_3_sbi --> similar to Putative brassinosteroid insensitive 1-associated chromosome_2_1061_mature.BC_05 --> target score: 2.0
3'--GUGUGUGCUGUUUCCGGU-5'
    |||-||||:||||||||
5'-GCAC-CACGGCAAAGGCCA-3'
Sb0010s009900.1_super_10_sbic_ --> putative protein chromosome_2_1061_mature.BC_05 --> target score: 4.5
3'-GUGUGU-GCUGUUUCCGGU-5'
   |||:|-|||-||||||||
5'-CACAUACCGA-AAAGGCCA-3'
Sb01g035890.1_chromosome_1_sbi --> similar to Sucrose synthase 3 chromosome_2_1061_mature.BC_05 --> target score: 4
3'--GUGUGUGCUGUUUCCGGU-5'
    |||||||||||| |-||
5'-UCACACACGACAAAAG-CA-3'
Sb01g048630.1_chromosome_1_sbi --> similar to Putative callose synthase 1 catalytic subunit chromosome_3_1257_mature.BC_01 --> target score: 3.5
3'-AAGCGUAACUCUUCACAC-5'
   |: ||||||| ||||||
5'-UUUACAUUGAGCAGUGUG-3'
Sb10g022220.1_chromosome_10_sb --> similar to T-complex protein 1 subunit epsilon chromosome_3_397_mature.BC_01 --> target score: 5
3'-CACCUAA-UCUCACCUUGAAC-5'
   ||||||-||| |||||-|||
5'-GUGGAUUCAGAAUGGAA-UUG-3'
Sb09g017875.1_chromosome_9_sbi --> Predicted protein chromosome_3_1435_mature.BC_05 --> target score: 3.0
3'-AUGUUAGGCUUGACUUCCACUC-5'
   ||||||| |||||:||||||
5'-UACAAUCCCAACUGGAGGUGAC-3'
Sb02g012863.1_chromosome_2_sbi --> Predicted protein chromosome_3_201_mature.BC_02 --> target score: 3
```

Figure 9J

```
3'--CGGCGGUCCCCGUAGGGCUCC-5'
     ||||||-||||||  ||||||
5'-CGCCGCC-GGGGCAGCCCGAGG-3'
Sb08g016760.1_chromosome_8_sbi --> similar to Auxin-binding protein 4 precursor chromosome_3_107_mature.BC_03 --> target score: 4
3'-GCGGUGGAGGCCGAGCUUGA-5'
   ||||||||||||||| |||
5'-CUCCACCUCCGGCUCCAACC-3'
Sb10g029400.1_chromosome_10_sb --> similar to Mitogen-activated protein kinase 12 chromosome_3_1460_mature.BC_01 --> target score: 5
3'-GGGUUAG-GUGAGGUUGUG-5'
   ||-|||-||||  ||||||
5'-CCC-AUCACACUGCAACAC-3'
Sb10g008780.1_chromosome_10_sb --> similar to Chromosome chr3 scaffold_8, whole genome shotgun s chromosome_3_1374_mature.BC_04 --> target score: 5
3'-AGGUGAGGUUAGGUGGAGUU-5'
   |||  ||||||||||  | |||
5'-UCCAAUCCAAUCCAACACAA-3'
Sb09g024050.1_chromosome_9_sbi --> weakly similar to Putative uncharacterized protein P0685G12.3 chromosome_3_235_mature.BC_02 --> target score: 5
3'-GG-UACGAACCGCCCCGUUUA-5'
    |-||||||||-||||||| |
5'-CCGAUGCUUGG-GGGGCAAUU-3'
Sb08g005330.1_chromosome_8_sbi --> similar to Os05g0239200 protein chromosome_3_133_mature.BC_04 --> target score: 5
3'-GGCUUUGCC-GAGGCUGAAG-5'
   ||||  |||-|||||||||  |
5'-CCGAACCGGACUCCGACUCC-3'
Sb0014s008210.1_super_14_sbic_ --> putative protein chromosome_3_133_mature.BC_04 --> target score: 4.0
3'-GGCUUUGCCGAGGCUGAAG-5'
   ||  |||||||:|| ||||
5'-CCGCAACGGCUUCGCCUUC-3'
Sb09g000430.1_chromosome_9_sbi --> similar to Polygalacturonase inhibiting protein 2 precursor chromosome_3_1462_mature.BC_04 --> target score: 4
3'-U-GUGACCGGGCAGGCUCG-5'
    -| |||||||||-|||||
5'-ACCUCUGGCCCGU-CGAGC-3'
Sb10g023150.1_chromosome_10_sb --> similar to Putative uncharacterized protein chromosome_3_1462_mature.BC_04 --> target score: 5.0
3'-UGUGACCGGGCAGGCUCG-5'
   ||||||  :| |||||||
5'-ACACUGGGUCCUCCGAGC-3'
Sb04g024040.1_chromosome_4_sbi --> similar to F-box protein GID2 chromosome_3_213_mature.BC_01 --> target score: 4.5
3'-AUCCCCGA-GACGACCUCAA-5'
   :||||||-|||||||  ||||
5'-UGGGGGCUGCUGCUGCAGUU-3'
```

Figure 9K

Sb08g021330.1_chromosome_8_sbi --> similar to DNAJ heat shock N-terminal domain-containing prote chromosome_3_213_mature.BC_01 --> target score: 3
3'-AUCCCC-GAGACGACCUCAA-5'
      |||||-||| ||||||||||
5'-AAGGGGUCUCCGCUGGAGUU-3'
Sb06g032760.1_chromosome_6_sbi --> similar to Endoglucanase 13 precursor chromosome_3_821_mature.BC_05 --> target score: 5
3'-AUA-CCUUCGAUCGUCGAGUCG-5'
     ||-|||||-||| |||||||||
5'-UAUGGGAAG-UAGGAGCUCAGC-3'
Sb03g006560.1_chromosome_3_sbi --> similar to Chromosome chr8 scaffold_23, whole genome shotgun chromosome_3_514_mature.BC_02 --> target score: 1.0
3'-GCCACACCCACUUCCUCGGCGACC-5'
    |||||||||||||||||||:|||||
5'-CGGUGUGGGUGAAGGAGCUGCUGG-3'
Sb02g000340.1_chromosome_2_sbi --> similar to Putative potassium transporter chromosome_3_954_mature.BC_04 --> target score: 4
3'-UCCCGGCGACUGCC-CACGAGGU-5'
    || ||||-|||||-||||||||
5'-AGGUCCGC-GACGGCGUGCUCCA-3'
Sb03g026360.1_chromosome_3_sbi --> similar to Putative uncharacterized protein chromosome_3_1128_mature.BC_01 --> target score: 5
3'-CAACCUCACCUAACCUCACCU-5'
    |||||||||||| | ||||
5'-GGUGGAGUGGAUUGUACUGGA-3'
Sb10g000900.1_chromosome_10_sb --> similar to Proteasome subunit beta type chromosome_3_216_mature.BC_05 --> target score: 5
3'-CUGCAGGGCCGG-CAACAAG-5'
    ||||-||||||-| |||||
5'-GACGU-CCGGCCGGGUGUUC-3'
Sb0610s002010.1_super_610_sbic --> putative protein chromosome_3_216_mature.BC_05 --> target score: 4
3'-CU-GCAGGGCCGGCAACAAG-5'
    |-|| |||||||||-|||||
5'-GACCGACCCGGCCG-UGUUC-3'
Sb06g000490.1_chromosome_6_sbi --> similar to Class III peroxidase 52 precursor chromosome_4_1911_mature.BC_05 --> target score: 4
3'-UCGCG-GCGGCGACG-AGACCGGCGC-5'
    || |-|||||||||-||||||||||
5'-AGCUCACGCCGCUGCAUCUGGCCGCG-3'
Sb09g025900.1_chromosome_9_sbi --> similar to Heat shock protein 101 chromosome_4_557_mature.BC_02 --> target score: 6
3'-AUUCCCGUGAGUGUUACGU-5'
    |||||| |||||| | |
5'-UAAGGGCAAUCACAAGGAA-3'
Sb10g022233.1_chromosome_10_sb --> weakly similar to Chromosome chr1 scaffold_84, whole genome s chromosome_4_2454_mature.BC_04 --> target score: 4

Figure 9L

```
3'-CACACCUCCUGUCGUC-GCGGAG-5'
    -||| |||||||||||-||||||
5'-G-GUGCAGGACAGCAGCCGCCUC-3'
Sb10g004840.1_chromosome_10_sb --> similar to RRM-containing RNA-binding protein-like chromosome_4_831_mature.BC_04 --> target score: 4
3'-UGUACACAACUUUAACUAA-5'
   ||| || |||||||||||
5'-ACAUUUGAUGAAAUUGAUG-3'
Sb10g027780.1_chromosome_10_sb --> similar to SMC5 protein chromosome_4_712_mature.BC_01 --> target score: 5
3'-GGCGACCUGCCGCCGC-GC-5'
   ||-|||| |||||||-||
5'-CCG-UGGAGGGCGGCGUCG-3'
Sb0067s002130.1_super_67_sbic_ --> putative protein chromosome_4_712_mature.BC_01 --> target score: 3
3'-GGCGACCUGCCGCCGCGC-5'
   |||||||||||||| |
5'-AAGCUGGACGGCGGCGGG-3'
Sb01g021990.1_chromosome_1_sbi --> similar to Kaurene synthase A chromosome_4_712_mature.BC_01 --> target score: 5
3'-G-GCGACCUGCCGCCG-CGC-5'
    -||||||||||||| |-|||
5'-CGCGCUGGACGGCGCCAGCG-3'
Sb03g041900.1_chromosome_3_sbi --> similar to Gibberellin 20 oxidase 2 chromosome_4_712_mature.BC_01 --> target score: 5.0
3'-GGCGACCUGCCGCCGC-GC-5'
   ||||||-|||:||||-||
5'-CCGCUGG-CGGUGGCGCCG-3'
Sb03g043030.1_chromosome_3_sbi --> similar to Gibberellin response modulator-like protein chromosome_4_712_mature.BC_01 --> target score: 4
3'-G-GCGACCUGCCGCCGCGC-5'
    -|||||||-|||||||
5'-CGCGCUGGAC-GCGGCGCU-3'
Sb03g043030.1_chromosome_3_sbi --> similar to Gibberellin response modulator-like protein chromosome_4_712_mature.BC_01 --> target score: 5
3'-GGCGACCUGCCGCCG-CGC-5'
   ||| ||-|||||||-|||
5'-CCGCAGG-CGGCGGCGGCG-3'
Sb03g047330.1_chromosome_3_sbi --> similar to SbPCL1 protein chromosome_4_712_mature.BC_01 --> target score: 5
3'-GGCG-ACCUGCCGCC-GCGC-5'
   |||-|||-||||||-||||
5'-CCGCGUGG-CGGCGGUCGCG-3'
Sb05g003660.1_chromosome_5_sbi --> similar to CCT motif family protein, expressed chromosome_4_712_mature.BC_01 --> target score: 4
3'-GGCGACCUGCCGCCG-CGC-5'
   ||||||-|||||||-|||
5'-GCGCUGG-CGGCGGCAGCG-3'
```

Figure 9M

```
Sb06g024630.1_chromosome_6_sbi --> similar to Squamosa promoter-binding-like protein 7 chromosome_4_712_mature.BC_01 --> target score: 4
3'-GGCGACCUGCCGCCG-CGC-5'
    ||| -|||||||||-|||
5'-CCGCC-GACGGCGGCGGCG-3'
Sb05g007310.1_chromosome_5_sbi --> similar to Sucrose-phosphate synthase chromosome_4_712_mature.BC_01 --> target score: 3
3'-GGCGACCUGCCGCCGCGC-5'
   |||||||||||||||| |
5'-UGGCUGGACGGCGGCGGG-3'
Sb06g031910.1_chromosome_6_sbi --> similar to Beta-fructofuranosidase, insoluble isoenzyme 6 pre chromosome_4_712_mature.BC_01 --> target score: 4
3'-GGCGACCUGCCGCCG-CGC-5'
   |||||||-||||||-|||
5'-GCGCUGGA-GGCGGCGGCG-3'
Sb07g001140.1_chromosome_7_sbi --> similar to Putative Bile acid beta-glucosidase chromosome_4_712_mature.BC_01 --> target score: 4
3'-GGCG-ACCUGCCGC-CGCGC-5'
   |||- ||||||||-|||||
5'-CCGCGCGGACGGCGAGCGCG-3'
Sb03g042460.1_chromosome_3_sbi --> similar to Fructokinase-1 chromosome_4_712_mature.BC_01 --> target score: 5
3'-GGCGAC-CUGCCGCCGCGC-5'
   ||| |-|||||||||||-|
5'-CCGCGGAGACGGCGGCG-G-3'
Sb03g010640.1_chromosome_3_sbi --> similar to Alpha-glucosidase-like chromosome_4_712_mature.BC_01 --> target score: 4
3'-GGCGACCUGCCGCCGCGC-5'
   |  |||||||||| |||
5'-CCCAUGGACGGCGGAGCGCG-3'
Sb09g019480.1_chromosome_9_sbi --> similar to Isoamylase-type starch debranching enzyme ISO2 chromosome_4_712_mature.BC_01 --> target score: 4
3'-GGCGAC-CUGCCGCCG-CGC-5'
   ||| |-|||||||||-|||
5'-CCGCCGAGACGGCGGCGCG-3'
Sb10g009270.1_chromosome_10_sb --> similar to Endoglucanase 17 precursor chromosome_4_712_mature.BC_01 --> target score: 5
3'-GGCGAC-CUGCCGCCGCGC-5'
   ||| |-|||||||||-|
5'-CCGCGGAGACGGCGGCG-G-3'
Sb10g030140.1_chromosome_10_sb --> similar to Endoglucanase 18 chromosome_4_712_mature.BC_01 --> target score: 6
3'-GGCGACCUGC-CGCCGCGC-5'
   ||||||| |-|||||-||
5'-CCGCUGGAGGUGCGGC-CG-3'
Sb04g036140.1_chromosome_4_sbi --> similar to Putative monosaccharide transporter 6 chromosome_4_712_mature.BC_01 --> target score: 4
```

Figure 9N

```
3'-G-GCGACCUGCCGCCGCGC-5'
   -||||||-|||||||||
5'-CGCGCUGG-CGGCGGCGCU-3'
Sb07g024870.1_chromosome_7_sbi --> similar to Beta-galactosidase 11 precursor chromosome_4_712_mature.BC_01 --> target score: 5
3'-GG-CGACCUGCCGCCG-CGC-5'
   |-||||||-|||||||||-|||
5'-CCUGCUGG-CGGCGGCGGCG-3'
Sb10g022620.1_chromosome_10_sb --> similar to Beta-galactosidase 9 precursor chromosome_4_712_mature.BC_01 --> target score: 3
3'-GGCGACCUGCCGCCGCGC-5'
   || |||||||||| ||||
5'-GCGAUGGACGGCGCCGCG-3'
Sb10g024490.1_chromosome_10_sb --> similar to Putative cinnamoyl-CoA reductase chromosome_4_712_mature.BC_01 --> target score: 2
3'-GGCGACCUGCCGCCGCGC-5'
   |||||||||||| ||||
5'-GCGCUGGACGGCGCCGCG-3'
Sb10g024500.1_chromosome_10_sb --> similar to Putative cinnamoyl-CoA reductase chromosome_4_712_mature.BC_01 --> target score: 4
3'-G-GCGACCUGCCGCCGCG-C-5'
   -|||-|||||||||||||-|
5'-CACGC-GGACGGCGGCGCUG-3'
Sb04g010000.1_chromosome_4_sbi --> similar to Expansin-A24 precursor chromosome_4_712_mature.BC_01 --> target score: 3
3'-GGCGACCUGCCGCCGCG-C-5'
   |||-|||||||||||||-|
5'-ACGC-GGACGGCGGCGCUG-3'
Sb04g010160.1_chromosome_4_sbi --> similar to Expansin-A23 precursor chromosome_4_712_mature.BC_01 --> target score: 4
3'-G-GCGACCUGCCGCCGCG-C-5'
   -|||-|||||||||||||-|
5'-CACGC-GGACGGCGGCGCUG-3'
Sb04g010170.1_chromosome_4_sbi --> similar to Expansin-A23 precursor chromosome_4_712_mature.BC_01 --> target score: 4.0
3'-GGCGA-CCUGCCGCCGCGC-5'
   ||||-|||-||:|||||||
5'-CCGCUCGGA-GGUGGCGCG-3'
Sb04g028090.1_chromosome_4_sbi --> similar to Expansin-A5 precursor chromosome_4_712_mature.BC_01 --> target score: 4
3'-GGCGAC-CUGCCGCCGCGC-5'
   || |-|||||||||||||
5'-CGGCAGUGACGGCGGCGCG-3'
Sb04g032830.1_chromosome_4_sbi --> similar to Expansin-B11 precursor chromosome_4_712_mature.BC_01 --> target score: 4
3'-GGCGAC-CUGCCGCCGCGC-5'
   || |-|||||||||||||
5'-CGGCAGCGACGGCGGCGCG-3'
```

Figure 9O

```
Sb06g023380.1_chromosome_6_sbi --> similar to Expansin-B17 precursor chromosome_4_712_mature.BC_01 --> target score: 4
3'-GGCGACCUGCCGCCGCGC-5'
     |||||||  ||||  ||||
5'-GCGCUGGAGGGCGUCGCG-3'
Sb02g041050.1_chromosome_2_sbi --> similar to Putative esterase chromosome_4_712_mature.BC_01 --> target score: 4.0
3'-GGCGACCUGCCGCCG-CGC-5'
     |||-||:|||||||-|||
5'-CCGC-GGGCGGCGGCGGCG-3'
Sb03g001870.1_chromosome_3_sbi --> similar to Putative esterase chromosome_4_712_mature.BC_01 --> target score: 5
3'-GGCGACCUGCCGCCGC-GC-5'
     |||  ||-|||||||||-||
5'-CCGCAGG-CGGCGGCGUCG-3'
Sb02g037310.1_chromosome_2_sbi --> similar to Putative fasciclin-like arabinogalactan-protein chromosome_4_712_mature.BC_01 --> target score: 3
3'--GGCGACCUGCCGCCGCGC-5'
      ||||-||||||||||| |
5'-GCCGC-GGACGGCGGCGAG-3'
Sb05g026710.1_chromosome_5_sbi --> similar to O-methyltransferase family protein chromosome_4_712_mature.BC_01 --> target score: 3
3'--GGCGACCUGCCGCCGCGC-5'
      ||||-||||||||||| |
5'-GCCGC-GGACGGCGGCGAG-3'
Sb05g026730.1_chromosome_5_sbi --> similar to O-methyltransferase family protein chromosome_4_712_mature.BC_01 --> target score: 6
3'-GGCGAC-CUGCCGCCGCGC-5'
     |||||- |||||||||-||
5'-CCGCUGCCACGGCGGC-CG-3'
Sb03g013070.1_chromosome_3_sbi --> similar to Putative pectinacetylesterase chromosome_4_712_mature.BC_01 --> target score: 5
3'-G-GCGACCUGCCGCCGCGC-5'
    -|||||| |||||||  ||
5'-CGCGCUGGCCGGCGGCCCG-3'
Sb02g001130.1_chromosome_2_sbi --> similar to Putative peroxidase chromosome_4_712_mature.BC_01 --> target score: 5
3'-GGCGACCUGCCGCCGC-GC-5'
     |||  |||||  |||||-||
5'-CCGCGGGACGACGGCGACG-3'
Sb10g010040.1_chromosome_10_sb --> similar to Putative Peroxidase 49 chromosome_4_712_mature.BC_01 --> target score: 5
3'-GGCGACCUGCCGCCG-CGC-5'
     |||-| |||||||||-|||
5'-CCGC-GUACGGCGGCGGCG-3'
Sb10g005820.1_chromosome_10_sb --> similar to Glutathione peroxidase chromosome_4_712_mature.BC_01 --> target score: 5
```

Figure 9P

```
3'-G-GCGACCUGCCGCCGCGC-5'
   -|||||| |||||| |||
5'-CGCGCUGGCCGGCGGGGCG-3'
Sb01g028610.1_chromosome_1_sbi --> similar to Class III peroxidase 120 precursor chromosome_4_712_mature.BC_01 --> target score: 3
3'-GGCGACCUGCCGCCGCGC-5'
   ||| ||||| |||||||
5'-CCGCCGGACGUCGGCGCG-3'
Sb02g029340.1_chromosome_2_sbi --> similar to Class III peroxidase 123 precursor chromosome_4_712_mature.BC_01 --> target score: 6
3'-GGCGACCUGCCGCCGCGC-5'
   ||||| || | |||||||
5'-CCGCUGAACUGGGGCGCG-3'
Sb04g026510.1_chromosome_4_sbi --> similar to Phenylalanine ammonia-lyase chromosome_4_712_mature.BC_01 --> target score: 2.0
3'--GGCGACCUGCCGCCGCGC-5'
    |||-||||||||:||||||
5'-UCCG-UGGACGGUGGCGCG-3'
Sb02g022220.1_chromosome_2_sbi --> similar to Polygalacturonase isoenzyme 1 beta subunit-like chromosome_4_712_mature.BC_01 --> target score: 5
3'-GGCGACCUGCCGCCGCGC-5'
   ||| || || ||||||||
5'-CCGCAGGCCGCCGGCGCG-3'
Sb03g013310.1_chromosome_3_sbi --> similar to Putative polygalacturonase PG2 chromosome_4_712_mature.BC_01 --> target score: 5
3'-GG-CGACCUGCCGC-CGCGC-5'
   |-|||||-|||||-|||||
5'-CCUGCUGG-CGGCGCGCGCG-3'
Sb07g025220.1_chromosome_7_sbi --> similar to Sorbitol dehydrogenase chromosome_4_1912_mature.BC_05 --> target score: 4
3'-UCGCG-GCGGCGACG-AGACCGGCGC-5'
   || |-|||||||||-||||||||||
5'-AGCUCACGCCGCUGCAUCUGGCCGCG-3'
Sb09g025900.1_chromosome_9_sbi --> similar to Heat shock protein 101 chromosome_4_174_mature.BC_05 --> target score: 2
3'-UGGAGCGGGACGCGGGCCCGGCG-5'
   |||||||||!||||||| |||||
5'-ACCUCGCCCUGCGCCCGCGCCGC-3'
Sb02g009005.1_chromosome_2_sbi --> weakly similar to PREDICTED: hypothetical protein chromosome_4_608_mature.BC_02 --> target score: 5
3'-CGUAACCGGCACCUCCGCC-5'
   || |||||| || |||||
5'-GCACUGGCCGCGGCGGCGG-3'
Sb10g027990.1_chromosome_10_sb --> weakly similar to Cysteine protease Mir1 chromosome_4_608_mature.BC_02 --> target score: 5
3'-CGUAACCGGCACCUCCGCC-5'
   || || || |||||||||
5'-GCACUGCCCAUGGAGGCGG-3'
```

Figure 9Q

Sb06g029476.1_chromosome_6_sbi --> similar to OSJNBa0089N06.14 protein chromosome_4_608_mature.BC_02 --> target score: 5
3'-CGUAACCGGCACCUCCGCC-5'
   ||  |||||  ||||||  ||
5'-GCAGUGGCCUUGGAGGAGG-3'
Sb09g019110.1_chromosome_9_sbi --> similar to Os05g0387700 protein chromosome_4_608_mature.BC_02 --> target score: 6
3'-CGUAACCGGCACCUCCGC-C-5'
   ||||||||  |||  ||||-|
5'-GCAUUGGCCUUGGCGGCGUG-3'
Sb09g022270.1_chromosome_9_sbi --> similar to Putative homeodomain protein chromosome_4_1677_mature.BC_05 --> target score: 5
3'-CGCCGGCGGCACCUACCU-5'
   |  ||||  |||||  ||||
5'-GCAGCCGGCGUGGCUGGA-3'
Sb0013s010110.1_super_13_sbic_ --> putative protein chromosome_4_1677_mature.BC_05 --> target score: 5
3'-CGCCGGCGGCACCUACCU-5'
   ||||  |||||||||  ||
5'-GCGGCGGCCGUGGAGGGC-3'
Sb06g023760.1_chromosome_6_sbi --> similar to Beta-fructofuranosidase 1 precursor chromosome_4_1677_mature.BC_05 --> target score: 4.0
3'-CGCCGGCGGCACCUACCU-5'
   |||  |||:||||  ||||
5'-GCGGGCGCUGUGGCUGGA-3'
Sb06g031910.1_chromosome_6_sbi --> similar to Beta-fructofuranosidase, insoluble isoenzyme 6 pre chromosome_4_1677_mature.BC_05 --> target score: 2.0
3'-CGCCGGCGGCACCUACCU-5'
   ||  |||||||||:||||
5'-GCGCCCGCCGUGGGUGGA-3'
Sb01g016730.1_chromosome_1_sbi --> similar to Monosaccharide transporter 2 chromosome_4_1677_mature.BC_05 --> target score: 5
3'-CGCCGGCG-GCACCUACCU-5'
   ||||  ||-|||||||  |||
5'-GCGGCGGCGCGUGGAAGGA-3'
Sb08g016530.1_chromosome_8_sbi --> similar to Sugar transporter family protein, expressed chromosome_4_1677_mature.BC_05 --> target score: 5.0
3'-CGCCGGCGGCACCUACCU-5'
   |||||||:|  ||||||
5'-GCGGCCGCUGGAGAUGGA-3'
Sb02g039600.1_chromosome_2_sbi --> similar to Putative alcohol dehydrogenase chromosome_4_1677_mature.BC_05 --> target score: 6
3'-CGCCGGCGGCACCUACCU-5'
   |||||||  |  ||  ||||
5'-GCGGCCGCAGGGGCUGGA-3'
Sb03g029770.1_chromosome_3_sbi --> similar to Glycosyl transferase family 1 protein-like chromosome_4_1677_mature.BC_05 --> target score: 5

Figure 9R

```
3'-CG-CCGGCGGCACCUACCU-5'
    |-||||||| |||-|||
5'-GCGGGCCGCCGAGGA-GGA-3'
Sb02g001045.1_chromosome_2_sbi --> weakly similar to Putative 4-coumarate--CoA ligase 1 chromosome_4_1677_mature.BC_05 --> target score: 5
3'-CGC-CGGCGGCACCUACCU-5'
   ||-||||||| |||-|||
5'-GCGCGCCGCCGAGGA-GGA-3'
Sb02g001050.1_chromosome_2_sbi --> weakly similar to Putative 4-coumarate--CoA ligase 1 chromosome_4_1677_mature.BC_05 --> target score: 3
3'--CGCCGGCGGCACCUACCU-5'
    || |||||||||||-|||
5'-GGCUGCCGCCGUGGA-GGA-3'
Sb07g007810.1_chromosome_7_sbi --> similar to 4-coumarate--CoA ligase 1 chromosome_4_1677_mature.BC_05 --> target score: 5
3'-CGCCGGCGGCACCUACCU-5'
   ||| ||||||||| |||
5'-GGGGCGGCCGUGGAAGGA-3'
Sb01g037900.1_chromosome_1_sbi --> similar to Pectinesterase family protein, expressed chromosome_4_1677_mature.BC_05 --> target score: 6
3'-CGCCGGCGGCACCU-ACC-U-5'
   |||||||||||||- ||-|
5'-GCGGCCGCCGUGGAGCGGCA-3'
Sb02g042780.1_chromosome_2_sbi --> similar to Putative pectinesterase chromosome_4_1677_mature.BC_05 --> target score: 5
3'-CG-CCGGCGGCACCUACCU-5'
   |-||||| |-||||||||
5'-GCAGGCCGGC-UGGAUGGA-3'
Sb03g016510.1_chromosome_3_sbi --> similar to Peroxidase family protein, expressed chromosome_4_1677_mature.BC_05 --> target score: 5
3'-C-GCCGGCGGCACCUACCU-5'
    -|||||| |||||-||||
5'-GCCGCCGGCGUGG-UGGA-3'
Sb07g026520.1_chromosome_7_sbi --> similar to UDP-glucuronic acid 4-epimerase isoform 3 chromosome_4_1677_mature.BC_05 --> target score: 3.5
3'-CGCCGGCGGCACCUACCU-5'
   | |:||||||||| |||
5'-GCUGUCGCCGUGGACGGA-3'
Sb01g020070.1_chromosome_1_sbi --> similar to Xyloglucan galactosyltransferase KATAMARI 1, putat chromosome_4_571_mature.BC_03 --> target score: 2
3'-CCGUUGCGGCUUCGGGCCC-A-5'
   |||||||||||||||||||-|
5'-GGCAACGCCGAAGCCCGGGCU-3'
Sb0139s002040.1_super_139_sbic --> putative protein chromosome_5_737_mature.BC_03 --> target score: 5
3'-CGCCCGUGAGCUGUU-UCC-5'
   || |||-|||||||-|||
5'-GCGCGCA-UCGACAACAGG-3'
```

Figure 9S

Sb10g027155.1_chromosome_10_sb --> weakly similar to Putative uncharacterized protein chromosome_5_737_mature.BC_03 --> target score: 5
3'-CGCC-CGUGAGCUGUUUCC-5'
    |||-||||-|||||| ||
5'-GCGGUGCAC-CGACAACGG-3'
Sb06g026010.1_chromosome_6_sbi --> similar to Putative xyloglucan galactosyltransferase chromosome_5_456_mature.BC_02 --> target score: 4.0
3'-GAUG-GGAGCUCGCUGGCUCAGG-5'
    |||-|||||-|||||||||||:|
5'-CUACGCCUCG-GCGACCGAGUUC-3'
Sb07g027680.1_chromosome_7_sbi --> similar to DNA-binding protein family-like chromosome_5_148_mature.BC_03 --> target score: 4
3'-CACACAUUUGU-GUGUAGAG-5'
      |||-|||||-||||||||
5'-GGGUG-AAACACCACAUCUC-3'
Sb10g004810.1_chromosome_10_sb --> similar to Putative uncharacterized protein chromosome_5_70_mature.BC_01 --> target score: 5
3'-ACGACUGC-ACCGA-CUGUGCAC-5'
   |||||||-|||||-||||||-|
5'-UGCUGACGUUGGCUGGACACG-G-3'
Sb10g006310.1_chromosome_10_sb --> similar to Os11g0622800 protein chromosome_5_509_mature.BC_03 --> target score: 1
3'-CCGUGAACUUGUACCCAUUCGGCU-5'
   ||||||| ||||||||||||||||
5'-GGCACUUGCACAUGGGUAAGCCGA-3'
Sb1994s002010.1_super_1994_sbi --> putative protein chromosome_5_978_mature.BC_01 --> target score: 4
3'-CGUCCGAGAG-CCGUUUCUU-5'
    || |||||-|||||||||
5'-GAAGCCUCUCUGGCAAAGAA-3'
Sb10g025390.1_chromosome_10_sb --> similar to Transcription initiation factor TFIID subunit 1 chromosome_5_181_mature.BC_05 --> target score: 4
3'-GUUAGAUAUAC-ACAACCC-5'
    || |||||||-||||||
5'-CAAGCUAUAUGCUGUUGGC-3'
Sb10g025390.1_chromosome_10_sb --> similar to Transcription initiation factor TFIID subunit 1 chromosome_5_181_mature.BC_05 --> target score: 5
3'-GUUAGAUAU-ACACAACCC-5'
    ||-|||||-|| ||||||
5'-CAA-CUAUACUGAGUUGGG-3'
Sb06g033440.1_chromosome_6_sbi --> similar to Glutathione peroxidase-like protein GPX15Hv chromosome_5_139_mature.BC_05 --> target score: 5
3'-GCGUACGUCCACC-CCUGGAG-5'
   |||-||||| ||-|||||||
5'-CGCA-GCAGGAGGAGGACCUC-3'
Sb09g027200.1_chromosome_9_sbi --> similar to Os01g0702700 protein chromosome_5_612_mature.BC_02 --> target score: 4

Figure 9T

```
3'-GCCGAGGUAGUAUAGA-GUUCGUU-5'
   ||||||||||||||-|||-|||
5'-UGGCUCCAUCAUAUCUACAA-CAA-3'
Sb03g043320.1_chromosome_3_sbi --> similar to P0497A05.20 protein chromosome_5_379_mature.BC_04 --> target score: 3
3'-UAGGAGCGUGGAGAAGGG-5'
   || |||| |||||||||
5'-CUCGUCGCCCCUCUUCCC-3'
Sb0013s011230.1_super_13_sbic_ --> putative protein chromosome_5_379_mature.BC_04 --> target score: 6
3'-UAGGAGC-G-UGGAGAAGGG-5'
   ||||||-|-| |||||||||
5'-AUCCUCGCCAAGCUCUUCCC-3'
Sb07g021680.1_chromosome_7_sbi --> similar to Cinnamoyl CoA reductase chromosome_5_379_mature.BC_04 --> target score: 3.0
3'-UAGGAGCGUGGAGAAGGG-5'
   |||||||||||||: |
5'-GUCCUCGCACCUCUUUGC-3'
Sb02g010110.2_chromosome_2_sbi --> similar to Cellulose synthase-7 chromosome_5_379_mature.BC_04 --> target score: 4
3'--UAGGAGCGUGGAGAAGGG-5'
    ||||||-|||||||| |||
5'-GAUCCUC-CACCUCUACCC-3'
Sb03g004320.1_chromosome_3_sbi --> similar to Cellulose synthase-1 chromosome_5_379_mature.BC_04 --> target score: 6
3'-UAGGAGCGUGGAG-AAGGG-5'
   |||||||-||||-|| ||
5'-AUCCUCGC-CCUCGUUACC-3'
Sb04g008640.1_chromosome_4_sbi --> weakly similar to Cationic peroxidase 1 precursor chromosome_5_379_mature.BC_04 --> target score: 4
3'-UAGGAGCGUGGAGAAGGG-5'
   ||||| | |||||||||
5'-CUCCUCCCUCCUCUUCCC-3'
Sb01g049890.1_chromosome_1_sbi --> similar to LysM domain containing protein, expressed chromosome_6_200_mature.BC_05 --> target score: 3.0
3'-GGUGGAAUUGUGUACACCUA-5'
   ||||||:||| |||||||||
5'-UCACCUUGACAGAUGUGGAU-3'
Sb01g038920.1_chromosome_1_sbi --> similar to Putative uncharacterized protein chromosome_6_337_mature.BC_03 --> target score: 5
3'-GUCCUCGCGGCGGCCGAGGU-GGU-5'
   || |||||||||||-|||-|||
5'-CAGCAGCGCCGCCGGC-CCAGCCA-3'
Sb09g016440.1_chromosome_9_sbi --> similar to Putative uncharacterized protein chromosome_6_202_mature.BC_05 --> target score: 3.5
3'-CG-UGCCGGGUUCAGGGUCGA-5'
   |-||||:||||||  ||||||
5'-GCGACGGUCCAAGUACCAGCU-3'
```

Figure 9U

Sb09g029260.1_chromosome_9_sbi --> similar to Putative uncharacterized protein chromosome_6_1475_mature.BC_04 --> target score: 4
3'-UGGAAGUUCUGGCCGUGACCGGAGA-5'
   ||||||||||||||| |||||  |
5'-ACCUUCAAGACCGGCACCGGCCUGU-3'
Sb10g010410.1_chromosome_10_sb --> similar to Putative uncharacterized protein chromosome_6_801_mature.BC_01 --> target score: 1.5
3'-UACUCACUAUAACCAAGCCGAGU-5'
   |:|||||||||||||||||||||
5'-CCGGGUGAUAUUGGUUCGGCUCA-3'
Sb01g040270.1_chromosome_1_sbi --> similar to Putative uncharacterized protein chromosome_6_67_mature.BC_04 --> target score: 5
3'-GCUUAGAGGAGAAGGAACCGGA-5'
   | ||||||||| |||| |||||
5'-CGCAUCUCCUCCUCCUCGGCCU-3'
Sb03g032710.1_chromosome_3_sbi --> similar to Methyltransferase-like chromosome_6_313_mature.BC_03 --> target score: 4
3'-GACCCACCGGUCUCCUCGGUCG-5'
   | | |||||||||||||  |||
5'-CUCGAUGGCCAGAGGAGCGAGC-3'
Sb05g017920.1_chromosome_5_sbi --> similar to Putative uncharacterized protein chromosome_6_657_mature.BC_01 --> target score: 4.0
3'-GAGGGUAG-GUAAUCUAAGCG-5'
   ||| |||-||||:||||||||
5'-CUCCAAUCUCAUUGGAUUCGC-3'
Sb01g002140.1_chromosome_1_sbi --> similar to Putative lysyl-tRNA synthetase chromosome_6_201_mature.BC_02 --> target score: 3
3'-ACGUACUGUUC-CUCUACU-5'
   |||| |||||-|||||||
5'-AGCAUUACAAGAGAGAUGA-3'
Sb0017s004030.1_super_17_sbic_ --> putative protein chromosome_6_201_mature.BC_02 --> target score: 5
3'-ACGU-ACUGUUCCUCUA-CU-5'
   |||-|||||||||| ||-||
5'-UGCAUUGACAAGGAAAUCGA-3'
Sb01g021990.1_chromosome_1_sbi --> similar to Kaurene synthase A chromosome_6_201_mature.BC_02 --> target score: 4
3'-A-CGUACUGUUCCUCUACU-5'
   - |||||||||||-||||
5'-UCACAUGACAAGGA-AUGA-3'
Sb04g003660.1_chromosome_4_sbi --> similar to Putative adagio-like protein 2 chromosome_6_201_mature.BC_02 --> target score: 4
3'-ACGUACUGUUCCUCUACU-5'
   | | || |||||||||||
5'-UGAAGGAGAAGGAGAUGA-3'
Sb01g049020.1_chromosome_1_sbi --> similar to MADS box protein 1 chromosome_6_201_mature.BC_02 --> target score: 5

Figure 9V

```
3'-ACGUACUGUUCCUCUACU-5'
     |||||||||||| |
5'-UCCAUGACAAGGAGAGCA-3'
Sb01g033060.1_chromosome_1_sbi --> similar to Sucrose synthase 2 chromosome_6_201_mature.BC_02 --> target score: 5
3'-ACGUAC-UGUUCCUCUACU-5'
     | |||-||||| ||||||
5'-UGGAUGUACAAGCAGAUGA-3'
Sb03g008810.1_chromosome_3_sbi --> similar to Putative ribokinase chromosome_6_201_mature.BC_02 --> target score: 4
3'-ACGU-ACUGUUCCUCUACU-5'
    | |-|||-||||||||||
5'-UGAAGUGA-AAGGAGAUGA-3'
Sb05g002900.1_chromosome_5_sbi --> similar to Pyruvate kinase chromosome_6_555_mature.BC_02 --> target score: 4
3'-UCGUGC-CGUUAAACCGGGCC-5'
   |||||-||||||||||| |
5'-AGCACGAGCAAUUUGGCCAGC-3'
Sb01g024773.1_chromosome_1_sbi --> weakly similar to Os09g0101100 protein chromosome_6_166_mature.BC_02 --> target score: 5
3'-UCGU-CACCAACCUGUGGCCCU-5'
   |||-|||||||||||  ||||
5'-AGCAUGUGGUUGGACAGGGGGA-3'
Sb04g036810.1_chromosome_4_sbi --> Predicted protein chromosome_6_166_mature.BC_01 --> target score: 5
3'-GAGGCAGUAGAAGUUGAC-UAG-5'
   |-|||||||||||||| |-|||
5'-CU-CGUCAUCUUCAACCGCAUC-3'
Sb09g025120.1_chromosome_9_sbi --> similar to Putative uncharacterized protein chromosome_6_351_mature.BC_05 --> target score: 3.5
3'-CGG-CUCACGGCCUACGAAACGG-5'
   ||-||||||||-||||||||||:
5'-GCCGGAGUGCC-GAUGCUUUGCU-3'
Sb02g036220.1_chromosome_2_sbi --> similar to Putative uncharacterized protein chromosome_6_336_mature.BC_03 --> target score: 4.5
3'-GGCACGAGAGGGAGCUG-GGCAG-5'
   ||||||:|||||||||-||| |
5'-CCGUGCUUUCCCUCGACACCGAC-3'
Sb09g027430.1_chromosome_9_sbi --> similar to Os01g0693800 protein chromosome_7_516_mature.BC_03 --> target score: 5
3'-GU-GGCCAGCCCCUCCCGG-5'
   |-|||| || |||||||||
5'-CAGCCGGCCGAGGAGGGCC-3'
Sb0019s003290.1_super_19_sbic_ --> putative protein chromosome_7_516_mature.BC_03 --> target score: 6
3'-GUGGCCA-GCCCCUC-CCGG-5'
   ||||||-| |||||-||||
5'-CACCGGUGCUGGGAGCGGCC-3'
```

Figure 9W

Sb06g017600.1_chromosome_6_sbi --> similar to Endoglucanase 11 precursor chromosome_7_516_mature.BC_03 --> target score: 5
3'-GU-GGCCAGCCCCUCCCGG-5'
   |-|||| || |||||||||
5'-CAGCCGGCCGUGGAGGGCC-3'
Sb10g031000.1_chromosome_10_sb --> similar to Hexose transporter, putative, expressed chromosome_7_627_mature.BC_05 --> target score: 5
3'-GGUGCCGCCAGCGCGAAGGGG-5'
   | |||||||| |||| |||||
5'-CCUCGGCGGUGGCGCCUCCCC-3'
Sb10g024440.1_chromosome_10_sb --> similar to Putative uncharacterized protein chromosome_7_627_mature.BC_05 --> target score: 5.0
3'-GGUGCCGCCAGCGC-GAAGGGG-5'
   ||||||||| |||-||||:||
5'-CCACGGCGGUGGCGCCUUCUCC-3'
Sb03g013170.1_chromosome_3_sbi --> similar to S-adenosylmethionine synthetase 1 chromosome_7_1887_mature.BC_05 --> target score: 4
3'-GCAGGCGUAGCCCUGGAG-5'
   | | ||| |||||||||
5'-CGCCAGCACCGGGACCUC-3'
Sb10g028600.1_chromosome_10_sb --> similar to AAA-type ATPase-like chromosome_7_1887_mature.BC_05 --> target score: 4
3'-GCAGGCGUAGC-CCUGGAG-5'
   |-|| |||||-|||||||
5'-CG-CCCCAUCGCGGACCUC-3'
Sb01g019850.1_chromosome_1_sbi --> similar to Beta-amylase chromosome_7_1887_mature.BC_05 --> target score: 6
3'-GCAGGCGUAGC-CCUGGAG-5'
   ||||||||||- ||| ||
5'-CGUCCGCAUCGCCGACGUC-3'
Sb02g033070.1_chromosome_2_sbi --> similar to Expansin-like A3 precursor chromosome_7_1887_mature.BC_05 --> target score: 4
3'-GCA-GGC-GUAGC-CCUGGAG-5'
   ||-|||-|||||-|||||||
5'-CGUCCCGUCAUCGUGGACCUC-3'
Sb02g035070.1_chromosome_2_sbi --> similar to Brittle stalk-2-like protein 5 chromosome_7_366_mature.BC_03 --> target score: 6
3'-GGUCCAUAUGGCACACGG-5'
   |||| || |||||| ||
5'-CCAGGGAUUCCGUGUUCC-3'
Sb10g028460.1_chromosome_10_sb --> similar to Class III peroxidase 93 precursor chromosome_7_366_mature.BC_03 --> target score: 5
3'-GGUCCAUAU-GGCACACGG-5'
   ||-||| |-|||||||||
5'-CCA-GUACACCCGUGUGCC-3'
Sb06g024650.1_chromosome_6_sbi --> similar to Expansin-B15 precursor chromosome_7_1053_mature.BC_04 --> target score: 3

Figure 9X

```
3'-CCGCUUAGCGCUCGCCGACGCGCG-5'
   | ||| | |||||||||||||||
5'-GGAGAACCCCGAGCGGCUGCGCGC-3'
Sb02g038550.1_chromosome_2_sbi --> similar to HDA1 chromosome_7_483_mature.BC_04 --> target score: 3
3'-CCAGGGCCGUUUCUU-UGCG-5'
   |-|||||||||||||-||||
5'-UG-CCCGGCAAAGAACACGC-3'
Sb10g027830.1_chromosome_10_sb --> weakly similar to Chromosome chr18 scaffold_59, whole genome chromosome_7_454_mature.BC_03 --> target score: 4
3'--GCGGCGGCGGCAACACGUGGGUCG-5'
    |||||||||||| ||-|||||||||
5'-GCGCCGCCGCCGCUG-GCACCCAGC-3'
Sb05g019000.1_chromosome_5_sbi --> similar to Putative uncharacterized protein chromosome_7_287_mature.BC_03 --> target score: 4
3'-C-UCGCGCGGUCGGUCGGAGGAC-5'
   -|| ||||| |||||||||||||
5'-GAAGGGCGCCUGCCAGCCUCCUG-3'
Sb09g018380.1_chromosome_9_sbi --> similar to Os07g0685900 protein chromosome_7_287_mature.BC_01 --> target score: 5
3'-AAGGGCUCGGCCACGACGG-GAA-5'
   ||||| |||||||||||||-| |
5'-UUCCCGCGCCGGUGCUGCCGCGU-3'
Sb03g035860.1_chromosome_3_sbi --> similar to Putative uncharacterized protein chromosome_7_22_mature.BC_03 --> target score: 5.0
3'-UGUACCGGACGUCGCGCGCG-5'
   ||||||||| |:|||||| |
5'-ACAUGGCCUCCGGCGCGCCC-3'
Sb10g006690.1_chromosome_10_sb --> similar to Putative growth-regulating factor 1 chromosome_7_22_mature.BC_03 --> target score: 3.0
3'-UGUACCG-GACGUCGCGCGCG-5'
   | ||||-|||||:|||||
5'-ACCUGGCGCUGCAGUGCGCGC-3'
Sb06g017230.1_chromosome_6_sbi --> similar to H0315A08.5 protein chromosome_7_22_mature.BC_03 --> target score: 5
3'-UGUACC-GGACGUCGCGCGCG-5'
   |||||-| |||||||||||-|
5'-ACAUGGUCGUGCAGCGCGC-C-3'
Sb09g027310.1_chromosome_9_sbi --> similar to Putative uncharacterized protein chromosome_7_22_mature.BC_03 --> target score: 4
3'-UGUACCGGACGUCGCGCGCG-5'
   || || ||||||||| ||
5'-ACAAGGACUGCAGCGCGAGC-3'
Sb03g028190.1_chromosome_3_sbi --> similar to Arbutin synthase-like chromosome_7_22_mature.BC_03 --> target score: 6
3'-UGUACCGGACGUCG-C-GCGCG-5'
   |||||||||| |-|-|||||
5'-ACAUGGCCUGCAACAGCCGCGC-3'
```

Figure 9Y

```
Sb03g047220.1_chromosome_3_sbi --> Predicted protein chromosome_7_22_mature.BC_03 --> target score: 6
3'-UGUACCGGACGUCG-CGCGCG-5'
   |||||||  ||  ||-||||||
5'-ACAUGGCCGGCUGCGGCGCGC-3'
Sb09g018400.1_chromosome_9_sbi --> similar to Putative esterase chromosome_7_22_mature.BC_03 --> target score: 6
3'-UGUACCGGACGUCG-CGCGCG-5'
   |||||||  ||  ||-||||||
5'-ACAUGGCCGGCUGCGGCGCGC-3'
Sb09g018440.1_chromosome_9_sbi --> similar to Putative esterase chromosome_7_243_mature.BC_01 --> target score: 4
3'-ACACAAC-CCCACCUAACCUCAC-5'
   |||  ||-|||||||||  ||||||
5'-UGUGCUGUGGGUGGAUAGGAGUG-3'
Sb10g022527.1_chromosome_10_sb --> weakly similar to Os06g0484800 protein chromosome_8_297_mature.BC_05 --> target score: 4
3'-ACA-GUAACCACCUGAAGGU-5'
   ||-||-|||||||||||||  |
5'-UGUCCA-UGGUGGACUUCAA-3'
Sb10g029360.1_chromosome_10_sb --> similar to Os06g0707000 protein chromosome_8_297_mature.BC_05 --> target score: 4
3'---ACAGUAACCACCUGAAGGU-5'
     ||||||||||||||  |-||
5'-UUGUCAUUGGUGGACCU-CA-3'
Sb03g011930.1_chromosome_3_sbi --> similar to S-adenosylmethionine synthetase 1 chromosome_8_497_mature.BC_04 --> target score: 4
3'-UGAGCCGACUAUUUGAGUUCG-5'
   |  ||||||  ||||||||||
5'-AGUAGGCUGACAAACUCAAGC-3'
Sb09g004060.1_chromosome_9_sbi --> similar to Os07g0438500 protein chromosome_8_468_mature.BC_05 --> target score: 5
3'-UGU-GAGCGAAGAGACGCGGC-5'
   ||-||||  |||-||||||||
5'-ACAGCUCGGUUC-CUGCGCCG-3'
Sb07g004840.1_chromosome_7_sbi --> similar to Ribosomal protein-like chromosome_8_401_mature.BC_01 --> target score: 4.0
3'-GCUGAUGAUGGUUCUCCG-5'
   |||  |||||  |:|||||
5'-CGACGACUACGAGGAGGC-3'
Sb1558s002010.1_super_1558_sbi --> putative protein chromosome_8_401_mature.BC_01 --> target score: 4
3'-GCUG-A-UGAUGGUUCUCCG-5'
   |||-|-|||||||||| -|||
5'-CGACUUCACUACCAAG-GGC-3'
Sb07g023020.1_chromosome_7_sbi --> similar to Alpha-amylase isozyme 3D precursor chromosome_8_618_mature.BC_05 --> target score: 6
```

Figure 9Z

```
3'-GGUGGUGGUGGUACCAGCC-5'
   ||||||  ||||  |  ||||
5'-CCACCACGACCACGUUCGG-3'
Sb0024s002110.1_super_24_sbic_ --> putative protein chromosome_8_618_mature.BC_05 --> target score: 6
3'-GGUGGUGGUGGUACCAGCC-5'
   |||||||||||||  |  |  |
5'-CCACCACCACCAUCGGCAG-3'
Sb07g024550.1_chromosome_7_sbi --> similar to INDETERMINATE-related protein 1 chromosome_8_618_mature.BC_05 --> target score: 5
3'-GGU-GGUGGUGGUACCAGCC-5'
   ||-|||||| |||||-|||
5'-CCAUCCACCAGCAUGG-CGG-3'
Sb09g025540.1_chromosome_9_sbi --> similar to O-methyltransferase ZRP4, putative, expressed chromosome_8_618_mature.BC_05 --> target score: 5
3'-GGU-GGUGGUGGUACCAGCC-5'
   ||-|||||| |||||-|||
5'-CCAUCCACCAGCAUGG-CGG-3'
Sb09g025560.1_chromosome_9_sbi --> similar to O-methyltransferase ZRP4, putative, expressed chromosome_8_618_mature.BC_05 --> target score: 6
3'-GGUGGUGGUGGUACCA-GCC-5'
   ||||||||||-| |-|||
5'-CCACCACCACCA-GCUCCGG-3'
Sb05g025950.1_chromosome_5_sbi --> similar to Extensin-like protein precursor chromosome_8_533_mature.BC_03 --> target score: 3.5
3'-AUGUGGUCGAAGCUCAGCUG-5'
     |:|||||||||||| ||||
5'-UUCGCCAGCUUCGAGACGAC-3'
Sb04g032020.1_chromosome_4_sbi --> similar to Putative uncharacterized protein chromosome_8_765_mature.BC_01 --> target score: 6
3'-UUCAAGGUGAGGUUAGGU-G-5'
   |||||||||||- ||||-|
5'-AAGUUCCACUCC-UUCCAUC-3'
Sb0012s002210.1_super_12_sbic_ --> putative protein chromosome_8_751_mature.BC_01 --> target score: 5.0
3'-CUGGGAAAUUGUGGCCAA-5'
   ||||||| :|||| |||
5'-GACCCUUUUGCACCAGUU-3'
Sb08g014065.1_chromosome_8_sbi --> weakly similar to OSJNBa0035O13.10 protein chromosome_8_751_mature.BC_01 --> target score: 4
3'-CUGGGAAAUUGU-GGCCAA-5'
   || |-||||||-||||||
5'-GACGC-UUAACAGCCGGUU-3'
Sb01g016630.1_chromosome_1_sbi --> weakly similar to Putative 4-coumarate--CoA ligase 1 chromosome_8_298_mature.BC_05 --> target score: 5
3'-UCGG-GUGGUUACUGUUGAA-5'
   |||-|| || ||||||||||
5'-AGCCACAACACUGACAACUU-3'
```

Figure 9AA

```
Sb07g028620.1_chromosome_7_sbi --> similar to Alkaline alpha galactosidase 3 chromosome_8_216_mature.BC_04 --> target score: 4.5
3'-UUGUGAACACCUAACUACG-5'
  :||||||||  |||  ||||
5'-AGCACUUGUGCAUUCAUGC-3'
Sb10g009460.1_chromosome_10_sb --> similar to Os02g0731900 protein chromosome_8_216_mature.BC_03 --> target score: 4
3'-UU-UAUCGCGAGCCGUUUAU-5'
   |-||| ||  |||||||||||
5'-AAGAUAUCGAUCGGCAAAUA-3'
Sb09g028730.1_chromosome_9_sbi --> similar to Putative uncharacterized protein OJ1781_H11.10 chromosome_9_544_mature.BC_02 --> target score: 4
3'-CGUGCUGGGUUCCCUCGUCCG-5'
   |  ||||| ||||||  ||||||
5'-GCUCGACGCAAGGGUGCAGGC-3'
Sb03g036680.1_chromosome_3_sbi --> similar to Probable indole-3-acetic acid-amido synthetase GH3 chromosome_9_1189_mature.BC_05 --> target score: 5
3'-GGC-AGCGCGGCGGCGGCACGC-5'
   ||-|||||||||||||||| | |
5'-CCGCUCGCGCCGCCGCCGCGGG-3'
Sb0011s007590.1_super_11_sbic_ --> putative protein chromosome_9_1189_mature.BC_05 --> target score: 6
3'-GGCAGCGCGGCGGCGGC-AC-GC-5'
   |||||||||||||||||| |-||-||
5'-CCGUCGCGCCGCCGCAGAUGUCG-3'
Sb07g024550.1_chromosome_7_sbi --> similar to INDETERMINATE-related protein 1 chromosome_9_1189_mature.BC_05 --> target score: 4
3'-G-GCAGCGCG-GCGGCGGCACGC-5'
    -|| |||||-|||||||||||||
5'-CACGACGCGCGCGCCGCCGUGCG-3'
Sb06g017600.1_chromosome_6_sbi --> similar to Endoglucanase 11 precursor chromosome_9_1189_mature.BC_05 --> target score: 5
3'-GGCA-GCGCGGCGGCGGCACGC-5'
   |||-|||||||-|||||  |||
5'-CCGUCCGCGCCG-CGCCGCGCG-3'
Sb10g008060.1_chromosome_10_sb --> similar to Glycosyl transferase protein A-like chromosome_9_1189_mature.BC_05 --> target score: 4
3'-GGCAGC-GCGGCGGCGGCACGC-5'
   |||||-| |||||||||-|||
5'-CCGUCGUCUCCGCCGCCG-GCG-3'
Sb10g006230.1_chromosome_10_sb --> similar to Putative pectin methylesterase chromosome_9_1189_mature.BC_05 --> target score: 4
3'-GGCAGCGCGGCGGCGGCA-CGC-5'
   || |||-||||||||||-|||
5'-CCGCCGC-CCGCCGCCGUCGCG-3'
Sb10g028480.1_chromosome_10_sb --> similar to Putative peroxidase ATP8a chromosome_9_554_mature.BC_02 --> target score: 5
```

Figure 9BB

```
3'-CACUGGACUGAUGUUUCG-GG-5'
    ||-|||||  ||||||||-||
5'-GUG-CCUGAGUACAAAGCUCC-3'
Sb02g032720.1_chromosome_2_sbi --> similar to Ribosomal protein S15-like chromosome_10_93_mature.BC_01 --> target score: 4
3'-UACACACAACCACACCUAACCC-5'
   |||||  |||||||||||| ||
5'-AAGUGUGCUGGUGUGGAUUCGG-3'
Sb08g001305.1_chromosome_8_sbi --> similar to Putative uncharacterized protein chromosome_10_77_mature.BC_03 --> target score: 4.0
3'-AGCCUCUUUCGAAAGGG-CUC-5'
   ||||||||:||||||-|||
5'-UGGGAGAAAGUUUUCCCUGAG-3'
Sb03g034510.1_chromosome_3_sbi --> similar to Hox2a protein chromosome_10_962_mature.BC_01 --> target score: 5
3'-GAGUUAGG-UGUACACAAC-5'
   ||||  ||-||-||||||||
5'-CUCAAGCCUAC-UGUGUUG-3'
Sb10g025070.2_chromosome_10_sb --> similar to Protein kinase-like chromosome_10_962_mature.BC_01 --> target score: 5
3'-GAGUUAGGUGUACAC-AAC-5'
   |||||||-|||||-|||
5'-CCCAAUCCA-AUGUGCUUG-3'
Sb10g006330.2_chromosome_10_sb --> similar to Sucrose synthase 1 chromosome_10_962_mature.BC_01 --> target score: 6
3'-GAGUUAGGU-GUACACAAC-5'
   ||||||||-||| || ||
5'-CUCAAUCCAGCAUAUGAUG-3'
Sb03g047440.1_chromosome_3_sbi --> similar to Putative pectinacetylesterase chromosome_10_792_mature.BC_03 --> target score: 4.0
3'-ACGUUGUACUAGA-CCGCU-5'
   |||  |||||||||-||:||
5'-UGCACCAUGAUCUCGGUGA-3'
Sb10g026740.1_chromosome_10_sb --> similar to Putative uncharacterized protein chromosome_10_792_mature.BC_03 --> target score: 3
3'-ACGUUGUACUAG-ACCGCU-5'
   |||  |||||||-||||||
5'-UGCACCAUGAUCAUGGCGA-3'
Sb02g000470.1_chromosome_2_sbi --> similar to Class III peroxidase 97 precursor chromosome_10_283_mature.BC_05 --> target score: 4.0
3'-GCAGCAGUAGGGGUCGCUUGC-5'
   |||||||||||:|||: ||
5'-CGUCGUCAUCCCCGGCGGCCG-3'
Sb05g022900.1_chromosome_5_sbi --> similar to Intracellular protease, PfpI family protein, expre chromosome_10_73_mature.BC_03 --> target score: 5
3'-UCCA-GAGACGUACAG-CAGGCUCGU-5'
   |||-||||||||||-||||-||||
5'-AGGUGCUCUGCAUGUCGGUCC-AGCA-3'
```

Figure 9CC

Sb01g006100.1_chromosome_1_sbi --> similar to Ferredoxin--NADP reductase, root isozyme, chloropl

Figure 10A

```
sbi-miR169a --> target score: 3.0
3'-AGCCGUUCAGUAGGAACCGAC-5'
      |||||  ||||:|||||||||
5'-UAGGCAAAUCAUUCUUGGCUG-3'
Sb08g021910.1_3'UTR --> similar to CCAAT-binding transcription factor subunit B family protein, sbi-miR169b --> target score: 2.5
3'-GGCCGUUCAGUAGGAACCGAC-5'
     :|||||  |||||||||||||
5'-CUGGCAACUCAUCCUUGGCUU-3'
Sb01g045500.1_3'UTR --> similar to RAPB protein sbi-miR169efgh --> target score: 3.0
3'-GUCCGUUCAGUAGGAACCGAU-5'
   ||||||  ||||:|||||||||
5'-CAGGCAAUUCAUUCUUGGCUU-3'
Sb01g011220.1_3'UTR --> similar to CCAAT-binding transcription factor subunit B family protein, sbi-miR169efgh --> target score: 4
3'-GUCCGUUCAGUAGGAACCG-AU-5'
     |||||  |||||||||||||-||
5'-CUGGCAACUCAUCCUUGGCUUA-3'
Sb01g045500.1_3'UTR --> similar to RAPB protein sbi-miR169cd --> target score: 4
3'-AUCCGUUCAGUAGGAACCG-AU-5'
   -|||||  |||||||||||||-||
5'-U-GGCAACUCAUCCUUGGCUUA-3'
Sb01g045500.1_3'UTR --> similar to RAPB protein sbi-miR169cd --> target score: 4.0
3'-AUCCGUUCAGUAGGAACCGA-U-5'
   ||||||  ||||:|||||||||-|
5'-UAGGCAAAUCAUUCUUGGCUGA-3'
Sb08g021910.1_3'UTR --> similar to CCAAT-binding transcription factor subunit B family protein, sbi-miR169i --> target score: 3
3'-A-UCCGUUCAGUAAGAACCGAU-5'
   -||||||  |||||||||||||
5'-UCAGGCAAUUCAUUCUUGGCUU-3'
Sb01g011220.1_3'UTR --> similar to CCAAT-binding transcription factor subunit B family protein, sbi-miR169i --> target score: 3
3'-AUCCGUUCAGUAAGAACCGAU-5'
   ||  ||||||||  |||||||||
5'-GAGUCAAGUCACUCUUGGCUA-3'
Sb02g003070.1_3'UTR --> similar to Os07g0152000 protein sbi-miR172e --> target score: 3.0
3'-C-ACGUCGUAGUAGUUCUAAGU-5'
   -|||||||||||||||:|||||
5'-GCUGCAGCAUCAUCAGGAUUCU-3'
Sb09g002080.1_3'UTR --> similar to AP2 domain transcription factor sbi-miR172e --> target score: 3.0
```

Figure 10B

```
3'-C-ACGUCGUAGUAGUUCUAAGU-5'
   -|||||-|||||||:|||||
5'-GAUGCAG-AUCAUCAGGAUUCA-3'
Sb04g038320.1_3'UTR --> similar to Type A response regulator 3 sbi-miR172b --> target score: 5
3'-ACGUCGUAGUAGUUCU-AAGG-5'
   ||| ||| |||||||-||||
5'-UGCAACAUAAUCAAGACUUCC-3'
Sb10g009462.1_3'UTR_chromosome --> similar to Putative very-long-chain fatty acid condensing sbi-miR172b --> target score: 3.0
3'-ACGUCGUAGUAGUUCUAAG-G-5'
   |||||||||||||:|||||-|
5'-UGCAGCAUCAUCAGGAUUCUC-3'
Sb09g002080.1_3'UTR_chromosome --> similar to AP2 domain transcription factor sbi-miR172cad --> target score: 1.0
3'-ACGUCGUAGUAGUUCUAAGA-5'
   |||||||||||||:||||||
5'-UGCAGCAUCAUCAGGAUUCU-3'
Sb09g002080.1_3'UTR_chromosome --> similar to AP2 domain transcription factor chromosome_1_983_mature.BC_04 --> target score: 3.5
3'-AGUAACCUAAGUGUAAUU-5'
   ||||| ||||:|||||:
5'-UCAUUGAAUUCGCAUUAG-3'
Sb10g024780.1_3'UTR_chromosome --> similar to Putative uncharacterized protein chromosome_1_466_mature.BC_02 --> target score: 2.0
3'-UCGAGCCGUGGUGUCUAGA-5'
   || |||||||||||||:|
5'-AGCCCGGCACCACAGAUUU-3'
Sb01g047670.1_3'UTR_chromosome --> similar to Expressed protein chromosome_1_970_mature.BC_03 --> target score: 4
3'-GAAGCACCAACAGCG-CCUG-5'
   ||| |-|||||||||-||||
5'-CUUCUU-GUUGUCGCUGGAC-3'
Sb01g018940.1_3'UTR_chromosome --> similar to Expressed protein chromosome_1_398_mature.BC_02 --> target score: 6
3'-GUGCCGUGAUA-GUCCGUGC-5'
   ||||||| ||-|| |||||
5'-CACGGCACCAUGCACGCACG-3'
Sb09g021890.1_3'UTR_chromosome --> similar to Putative uncharacterized protein chromosome_1_827_mature.BC_01 --> target score: 5
3'-GGUGGGGUUGCGUACACCUA-AC-5'
   ||-||||||| |||||||||-||
5'-CCA-CCCAACACAUGUGGAUGUG-3'
Sb10g001370.1_3'UTR_chromosome --> similar to High-affinity nickel-transport protein-like chromosome_1_216_mature.BC_05 --> target score: 3.0
3'-GGGCAGCUUGGUACCCUUC-5'
   |:||: |||||||||||
5'-CCUGUUCAACCAUGGGAAG-3'
```

Figure 10C

Sb10g000450.1_3'UTR_chromosome --> similar to Putative uncharacterized protein chromosome_1_754_mature.BC_04 --> target score: 1.5
3'-GUUAGGUGUACACAACUCC-5'
   |||:|||||||||||:||
5'-CAAUUCACAUGUGUUGGGG-3'
Sb09g024990.1_3'UTR_chromosome --> similar to Putative uncharacterized protein chromosome_1_1391_mature.BC_04 --> target score: 3
3'-G-UGAGGUUAGAUGGAGUU-5'
   -||||||||| |||||||
5'-CUACUCCAAUCCACCUCAA-3'
Sb09g026510.1_3'UTR_chromosome --> similar to Os05g0531400 protein chromosome_1_527_mature.BC_05 --> target score: 5
3'-UCACUUCAACUCG-AAACA-5'
   ||||| |||||-|||||
5'-AUUGAAGGUGAGCAUUUGU-3'
Sb08g004620.1_3'UTR_chromosome --> similar to Os12g0172500 protein chromosome_2_902_mature.BC_02 --> target score: 6
3'-CGUGUUGAAGAUUCUCGU-U-5'
   |||||||| |||||-||-|
5'-GCACAACUUAUAAGA-CAUA-3'
Sb09g004320.1_3'UTR_chromosome --> similar to Importin subunit alpha-1b chromosome_2_1473_mature.BC_01 --> target score: 4
3'-G-GGG-UUAGGUGAGGUUGUGUACA-5'
   -|||-||||||||-|||||||||||
5'-CACCCUAAUCCAC-CCAACACAUGU-3'
Sb10g001370.1_3'UTR_chromosome --> similar to High-affinity nickel-transport protein-like chromosome_2_573_mature.BC_04 --> target score: 2
3'-UAACUUAAACGAAACUCUUCACACG-5'
   ||| ||| |||||||||||||||
5'-AUUGUAUUCGCUUUGAGAAGUGUGC-3'
Sb05g000930.1_3'UTR_chromosome --> similar to BTB/POZ domain containing protein, expressed chromosome_2_45_mature.BC_01 --> target score: 3.0
3'-UCCCGGACAAAUCUAACC-5'
   |||||||||:|||||
5'-AAGGCCUGUUUGGAUUGU-3'
Sb10g005250.1_3'UTR_chromosome --> similar to Pyrophosphate-energized vacuolar membrane proton p chromosome_2_45_mature.BC_01 --> target score: 4.0
3'-UCCCGGACAAAUCUAACC-5'
   |||||||||:||| |
5'-AGGGCCUGUUUGGAUCGU-3'
Sb01g027960.1_3'UTR_chromosome --> similar to Xyloglucan endotransglucosylase/hydrolase protein chromosome_2_1061_mature.BC_05 --> target score: 5
3'-GU-GUGUGCUGUUUCCGGU-5'
   |-|||||||-|| |||||
5'-CACCACACGA-AAUGGCCA-3'
Sb02g034380.1_3'UTR_chromosome --> similar to Methionine aminopeptidase chromosome_3_397_mature.BC_01 --> target score: 3

Figure 10D

```
3'-CACCUAAUC-UCACCUUGAAC-5'
   ||||||-|-|||||||||
5'-GUGGAUU-GAAGUGGAACUUG-3'
Sb03g023980.1_3'UTR_chromosome --> similar to Putative uncharacterized protein chromosome_3_1222_mature.BC_01 --> target score: 4
3'-GG-UUAGAUGGGGUUGUGUACA-5'
   |-|||| |-|||||||||||||
5'-CCUAAUCCA-CCCAACACAUGU-3'
Sb10g001370.1_3'UTR --> similar to High-affinity nickel-transport protein-like chromosome_3_1257_mature.BC_01 --> target score: 5
3'-AAGCGUAACU-CUUCACAC-5'
   |||-|||||-||| ||||
5'-UUCG-AUUGAGGAAUUGUG-3'
Sb10g027000.1_3'UTR_chromosome --> similar to SEC14 cytosolic factor-like chromosome_3_1460_mature.BC_01 --> target score: 3
3'-GGG-UUAGGUGAGGUUGUG-5'
   ||-||||||||-|||||||
5'-CCCUAAUCCAC-CCAACAC-3'
Sb10g001370.1_3'UTR_chromosome --> similar to High-affinity nickel-transport protein-like chromosome_3_1374_mature.BC_04 --> target score: 0.5
3'-AGGUGAGGUUAGGUGGAGUU-5'
   |:||||||||||||||||||
5'-UCUACUCCAAUCCACCUCAA-3'
Sb09g026510.1_3'UTR_chromosome --> similar to Os05g0531400 protein chromosome_3_1324_mature.BC_01 --> target score: 6
3'-AACCUCACCUAAUCCCACCUUAAA-5'
   |||||||||||| ||| ||| ||
5'-UUGGAGUGGAUUAAGGUAGAAAUU-3'
Sb10g004900.1_3'UTR_chromosome --> similar to Putative GAMYB-binding protein chromosome_3_47_mature.BC_01 --> target score: 4.0
3'-UACACACAACCACACCUAACCCUA-5'
   | ||||||||| ||||||||||:|
5'-AUAUGUGUUGGAGUGGAUUGGGGU-3'
Sb01g022490.1_3'UTR_chromosome --> similar to Os10g0403700 protein chromosome_3_213_mature.BC_01 --> target score: 5
3'-AUCCCCGAGACGACCUCAA-5'
   || ||| |||||||||| |
5'-UAGAGGCACUGCUGGAGCU-3'
Sb08g000350.1_3'UTR_chromosome --> similar to Mitochondrial substrate carrier family protein, chromosome_3_1223_mature.BC_05 --> target score: 4.0
3'-UUGGCUCCGCCCGUAGGAUU-5'
   |||| |||||||||: |||
5'-AACCGUGGCGGGCAUUGUAA-3'
Sb06g029940.1_3'UTR_chromosome --> similar to Putative uncharacterized protein chromosome_3_1128_mature.BC_01 --> target score: 2.0
3'-CAACCUCACCUAACCUCACCU-5'
   |||| ||||:|||||||||||
5'-AUUGGUGUGGGUUGGAGUGGA-3'
```

Figure 10E

Sb09g026510.1_3'UTR --> similar to Os05g0531400 protein chromosome_4_557_mature.BC_02 --> target score: 1
3'-AUUCCCGUGAGUGUUACGU-5'
   ||||||||||||||||||
5'-UUAGGGCACUCACAAUGCA-3'
Sb09g019570.1_3'UTR_chromosome --> similar to Os05g0397700 protein chromosome_4_2454_mature.BC_04 --> target score: 4.0
3'-CACACCUCCUGUCGUCGCGGAG-5'
   || |||||:||||||||||| |
5'-GUGCGGAGGGCAGCAGCGCCAC-3'
Sb01g018940.1_3'UTR_chromosome --> similar to Expressed protein chromosome_4_831_mature.BC_04 --> target score: 4.0
3'-UGUACACAACUUUAACUAA-5'
   |||||||||:|:| ||||
5'-ACAUGUGUUGGAGUGGAUU-3'
Sb08g021620.1_3'UTR_chromosome --> similar to At1g30300 chromosome_4_712_mature.BC_01 --> target score: 6
3'-GGCGACCUGCC-GCCGCGC-5'
   ||||| | ||-|||||||
5'-CCGCUGCAAGGCCGGCGCG-3'
Sb06g030760.1_3'UTR_chromosome --> similar to OSJNBb0059K02.4 protein chromosome_4_712_mature.BC_01 --> target score: 5
3'-GGCGACCU-GCCGCCGCGC-5'
   |||| ||-|||-||||||
5'-CCGCUCGAUCGG-GGCGCG-3'
Sb03g039060.1_3'UTR_chromosome --> similar to Zinc finger CONSTANS-like protein chromosome_4_134_mature.BC_02 --> target score: 5.0
3'-UUAGACGAUCGAUAAGUUGUAACA-5'
   ||||||||||  |||:|||| |||
5'-AAUCUGCUAGCCAUUUAACAGUGU-3'
Sb09g026080.1_3'UTR_chromosome --> similar to Hexokinase chromosome_4_522_mature.BC_01 --> target score: 4.0
3'-CCUAAGUGGAGUUAGGUGUACACA-5'
   ||||||| |||||:||||  |||
5'-GGAUUCACAUCAAUCUACAUAUGU-3'
Sb10g001370.1_3'UTR_chromosome --> similar to High-affinity nickel-transport protein-like chromosome_4_608_mature.BC_02 --> target score: 5
3'-CGUAACCGGCACCUCCGCC-5'
   ||| |||||||  |||| |
5'-GCAUAGGCCGUGUAGGCAG-3'
Sb08g004570.1_3'UTR_chromosome --> similar to TRNA-nucleotidyltransferase, putative, expressed chromosome_4_1028_mature.BC_01 --> target score: 5
3'-GG-UUAGGUGAGGUUAUGUACA-5'
   |-|||||||-|||| ||||||
5'-CCUAAUCCAC-CCAACACAUGU-3'
Sb10g001370.1_3'UTR --> similar to High-affinity nickel-transport protein-like chromosome_4_1677_mature.BC_05 --> target score: 5.0

Figure 10F

```
3'-CGCCGGCGGCACCUACCU-5'
   ||||  :||||||||||
5'-GCGGCGAUCGUGGAUGGA-3'
Sb08g002310.1_3'UTR_chromosome --> similar to Putative uncharacterized protein 5 chromosome_4_1677_mature.BC_05 --> target score: 5
3'-CGCCGGCG-GCACCUACCU-5'
   |||||||-|||||-|||
5'-GCGGCCGCGCGUGG-UGGU-3'
Sb03g045360.1_3'UTR_chromosome --> similar to Hydroxyproline-rich glycoprotein-like chromosome_5_737_mature.BC_01 --> target score: 5
3'-GGGAAAUUGUGGCCAACC-5'
   | ||||||| || ||||
5'-CCAUUUAACAGCGUUUGG-3'
Sb03g011270.1_3'UTR_chromosome --> similar to Magnesium-protoporphyrin IX monomethyl ester chromosome_5_737_mature.BC_03 --> target score: 3.0
3'-CGCCCGUGAGCUGUUUC-C-5'
   |||||||||||:|||||-|
5'-UCGGGCACUCGGCAAAGAG-3'
Sb10g020140.1_3'UTR_chromosome --> weakly similar to Putative uncharacterized protein chromosome_5_148_mature.BC_03 --> target score: 1
3'-CACACAUUUGUGUGUAGAG-5'
   |||| ||||||||||||||
5'-GUGUGCAAACACACAUCUC-3'
Sb05g000930.1_3'UTR_chromosome --> similar to BTB/POZ domain containing protein, expressed chromosome_5_509_mature.BC_03 --> target score: 1
3'-CCGUGAACUUGUACCCAUUCGGCU-5'
   ||||||| ||||||||||||||||
5'-GGCACUUGCACAUGGGUAAGCCGA-3'
Sb0221s002050.1_3'UTR_super_22 --> putative protein chromosome_5_181_mature.BC_05 --> target score: 4
3'-GUUAGAUAUACACAACCC-5'
   |||||| || ||||||||
5'-CAAUCUACAUAUGUUGGG-3'
Sb10g001370.1_3'UTR_chromosome --> similar to High-affinity nickel-transport protein-like chromosome_5_181_mature.BC_05 --> target score: 5
3'-GUUAGAUAUACACAAC-CC-5'
   |||||||| |||||-||
5'-CUAUCUAUAUCUGUUGAGG-3'
Sb08g000990.1_3'UTR_chromosome --> similar to Class III peroxidase 135 precursor chromosome_5_1020_mature.BC_01 --> target score: 5
3'-UACACACAACAACACCUAACCC-5'
   | ||||||| ||||||||||||
5'-AUAUGUGUUGGAGUGGAUUGGG-3'
Sb01g022490.1_3'UTR_chromosome --> similar to Os10g0403700 protein chromosome_5_379_mature.BC_04 --> target score: 4
3'-UAGGAGCGU-GGAGAAGGG-5'
   |||-|||-|||||||||||
5'-AGCCU-GCAUCCUCUUCCC-3'
```

Figure 10G

Sb01g023950.2_3'UTR_chromosome --> similar to Major facilitator superfamily protein chromosome_6_200_mature.BC_05 --> target score: 2
3'--GGUGGAAUUGUGUACACCUA-5'
   |||||- |||||||||||||
5'-UCCACC-CAACACAUGUGGAU-3'
Sb10g001370.1_3'UTR_chromosome --> similar to High-affinity nickel-transport protein-like chromosome_6_657_mature.BC_01 --> target score: 5
3'-GA-GGGUAGGUAAUCUAAGCG-5'
   |-||||||||  |||||||
5'-CUGCCCAUCCAACAGAUUCGC-3'
Sb01g033840.1_3'UTR_chromosome --> similar to Chromosome chr18 scaffold_1, whole genome shotgun chromosome_6_201_mature.BC_02 --> target score: 5
3'-ACGUACUGUUCC-UCUACU-5'
   ||-|||||||||-||| ||
5'-UGC-UGACAAGGAAGAGGA-3'
Sb10g000830.1_3'UTR_chromosome --> similar to Putative MtN21 chromosome_6_323_mature.BC_01 --> target score: 4.0
3'-UACACACAACCACACCUAACCCUA-5'
   | |||||||| ||||||||||||:|
5'-AUAUGUGUUGGAGUGGAUUGGGGU-3'
Sb01g022490.1_3'UTR_chromosome --> similar to Os10g0403700 protein chromosome_6_351_mature.BC_05 --> target score: 4.5
3'-CGGCUCACGGCCUACGAAACGG-5'
   ||||||:|  ||||||||||
5'-GCCGAGUGUCAUAUGCUUUGCC-3'
Sb10g020140.1_3'UTR_chromosome --> weakly similar to Putative uncharacterized protein chromosome_7_516_mature.BC_03 --> target score: 3.5
3'-GUG-GCC-AGCCCCUCCCGG-5'
    :|-|||-|||||||||||
5'-CGCUCGGAUCGGGGAGGGCC-3'
Sb02g029640.1_3'UTR_chromosome --> similar to Os09g0511600 protein chromosome_7_1887_mature.BC_05 --> target score: 4
3'-GCAGGCGUAGCCCUGGAG-5'
   || ||||| |||||||
5'-CUUCAGCAUCCGGACCUC-3'
Sb01g048800.1_3'UTR_chromosome --> similar to CBS domain-containing protein, putative, expressed chromosome_7_366_mature.BC_03 --> target score: 4
3'-GGUCCAUAUGG-CACACGG-5'
   |||||||||-||||| |
5'-ACAGGUAUACCGGUGUGAC-3'
Sb08g001580.1_3'UTR_chromosome --> similar to Transporter, putative, expressed chromosome_7_62_mature.BC_01 --> target score: 3
3'-CAUAAGUGAAGUUAGGUACACACAA-5'
      |||||||||||||||||||| ||
5'-AGAUUCACUUCAAUCCAUGUGUAUU-3'
Sb09g026510.1_3'UTR_chromosome --> similar to Os05g0531400 protein chromosome_7_287_mature.BC_03 --> target score: 3

Figure 10H

```
3'-CUCGCGCGGUCGGUCGGA-GGAC-5'
   |-||||||||||||||-||||
5'-CA-CGCGCCAGCCAGCCUGCCUG-3'
Sb07g025170.1_3'UTR_chromosome --> similar to Os08g0546100 protein chromosome_7_49_mature.BC_01 --> target score: 1.5
3'-UUCAAGGUGAGGUUAGGUGGGGUU-5'
   |||||:||||||||||||||:|||
5'-AAGUUCUACUCCAAUCCACCUCAA-3'
Sb09g026510.1_3'UTR_chromosome --> similar to Os05g0531400 protein chromosome_7_294_mature.BC_01 --> target score: 3.5
3'-AACCUCACCUAACCCCACCUUAAA-5'
   ||| ||||:|||| ||||||||||
5'-UUGGUGUGGGUUGGAGUGGAAUUU-3'
Sb09g026510.1_3'UTR_chromosome --> similar to Os05g0531400 protein chromosome_7_243_mature.BC_01 --> target score: 3.0
3'-ACACAACCCCACCUAACCUCAC-5'
   || |||| ||||:|||||||||
5'-UGUAUUGGUGUGGGUUGGAGUG-3'
Sb09g026510.1_3'UTR_chromosome --> similar to Os05g0531400 protein chromosome_8_297_mature.BC_05 --> target score: 6
3'-ACAGUAACCACCUGAAGGU-5'
   |||||| |||| |||||
5'-UGUCAUUUGUGGUGUUCCA-3'
Sb03g023980.1_3'UTR_chromosome --> similar to Putative uncharacterized protein chromosome_8_497_mature.BC_04 --> target score: 2.5
3'-UGAGCCGACUAUUUGAGUUCG-5'
   :||| |||||||:||||||||
5'-AUUCGCCUGAUAAGCUCAAGC-3'
Sb09g019080.1_3'UTR --> similar to Putative uncharacterized protein chromosome_8_401_mature.BC_01 --> target score: 5
3'-GCUGAUGAUGGUU-CUCCG-5'
   |||||||||||-|| ||
5'-CUACUACUACCAAGGAAGC-3'
Sb07g023710.1_3'UTR_chromosome --> similar to Putative uncharacterized protein P0705A05.122 chromosome_8_618_mature.BC_05 --> target score: 5.0
3'-GGUGGUGGUGGUACCAG-CC-5'
   ||||||:|||-|||||-||
5'-CCACCACUACC-UGGUCUGG-3'
Sb01g037180.1_3'UTR_chromosome --> similar to Putative uncharacterized protein chromosome_8_765_mature.BC_01 --> target score: 1.0
3'-UUCAAGGUGAGGUUAGGUG-5'
   |||||:||||||||||||
5'-AAGUUCUACUCCAAUCCAC-3'
Sb09g026510.1_3'UTR_chromosome --> similar to Os05g0531400 protein chromosome_8_298_mature.BC_05 --> target score: 4
3'-UCGGGUGGUUACUGUUGAA-5'
   ||||||||| |||| ||||
5'-AGCCCACCACUGACUACUU-3'
```

Figure 10l

Sb04g021710.1_3'UTR_chromosome --> similar to Os02g0533000 protein chromosome_8_216_mature.BC_04 --> target score: 2.0
3'-UUGUGAACACCUAACUACG-5'
   |||: |||||||||||||:
5'-AACAUAUGUGGAUUGAUGU-3'
Sb09g026510.1_3'UTR_chromosome --> similar to Os05g0531400 protein chromosome_8_216_mature.BC_03 --> target score: 6
3'-UUUAUCG-CGAGCCGUUUAU-5'
   ||||||!-||| -|||||||
5'-AAAUAGCUGCUA-GCAAAUA-3'
Sb01g027760.1_3'UTR_chromosome --> similar to 50S ribosomal protein L35 chromosome_9_1189_mature.BC_05 --> target score: 4
3'-GGCAGC-GCGGCGGC-GGCACGC-5'
   || ||-|||||||||-|||||||
5'-CCGCCGCCGCCGCCGCCCGUGCG-3'
Sb09g023990.1_3'UTR --> weakly similar to Putative uncharacterized protein chromosome_9_1132_mature.BC_05 --> target score: 3.0
3'-GGCCAACCAGAGUGGUUGGCCC-5'
   |||||||||||||: |||||||
5'-CCGGUUGGUCUCAUGAACCGGG-3'
Sb03g013700.1_3'UTR_chromosome --> similar to Putative uncharacterized protein B1045F02.28 chromosome_10_880_mature.BC_05 --> target score: 4.5
3'-CACGGCACUCUGCGACUCGUCA-5'
   |||:||||||  ||||| ||||
5'-GUGCUGUGAGAGGCUGAACAGU-3'
Sb01g015870.1_3'UTR_chromosome --> similar to Putative GDSL-like lipase/acylhydrolase chromosome_10_93_mature.BC_01 --> target score: 4.0
3'-UACACACAACCACACCUAACC-C-5'
   ||||| |||||||||:||||-|
5'-AUGUGUAUUGGUGUGGUUGGAG-3'
Sb09g026510.1_3'UTR_chromosome --> similar to Os05g0531400 protein chromosome_10_293_mature.BC_01 --> target score: 4.0
3'-CAGCCUAAGCGUAGUUAGGUGUACA-5'
   |||||||| |||||||||:|||| |
5'-GUCGGAUUCACAUCAAUCUACAUAU-3'
Sb10g001370.1_3'UTR_chromosome --> similar to High-affinity nickel-transport protein-like chromosome_10_962_mature.BC_01 --> target score: 4.0
3'-G-AGUUAGGUGUACACAAC-5'
   -||||||:|||| |||||
5'-CAUCAAUCUACAUAUGUUG-3'
Sb10g001370.1_3'UTR_chromosome --> similar to High-affinity nickel-transport protein-like chromosome_10_792_mature.BC_03 --> target score: 5
3'-A-CGUUGUACUA-GACCGCU-5'
   -|||||||||-||||| |
5'-UGGCAACAUGAUGCUGGCAA-3'
Sb06g027260.1_3'UTR_chromosome --> similar to Putative uncharacterized protein

COMPOSITIONS AND METHODS FOR THE REGULATION OF CARBOHYDRATE METABOLISM AND FLOWERING IN PLANTS

This application claims priority to U.S. Provisional Application No. 61/347,741 filed May 24, 2010, the entire contents being incorporated herein by reference as though set forth in full.

FIELD OF THE INVENTION

This invention relates to the fields of plant metabolism and molecular biology. More specifically, the invention provides compositions and methods for modulating expression of target nucleic acids encoding proteins involved in a variety of important biochemical pathways, including those controlling sugar metabolism, flowering and biofuel production.

BACKGROUND OF THE INVENTION

Several publications and patent documents are cited throughout the specification in order to describe the state of the art to which this invention pertains. Each of these citations is incorporated herein by reference as though set forth in full.

Accumulation of soluble sugars is a characteristic trait in two closely related plant species, sorghum [*Sorghum bicolor* (L.) Moench] and sugarcane (*Saccharum* spp.) (1, 2). In both species, sucrose is the main type of sugar and accumulates in the parenchyma tissue of juicy stems. *Sorghum* belongs to the tribe of the *Andropogoneae* that includes potential biofuel crops like switchgrass, *Miscanthus* and successful biofuel crops like corn and sugarcane. However, from a genomics point of view *sorghum* contains a simpler genome because it lacks the additional rounds of whole genome duplication events present in other species. Therefore, it has become possible to generate a high-quality genome sequence. Furthermore, cultivars exists that rival sugarcane in levels of stem sugar so that a genetic approach can be used to investigate which genes are differentially expressed to achieve high levels of stem sugar.

Small RNAs (18-25 nt) regulate many developmental and physiological processes in plants through the regulation of gene expression at either the transcriptional or post-transcriptional level (Chuck G, et al., (2009) *Current Opinion in Plant Biology*, 12:81-86; Vaucheret H. (2006) *Genes Dev* 2006, 20:759-771; Zamore P D, Haley B. (2005) *Science*, 309: 1519-1524). They can be subdivided into short-interfering RNAs (siRNAs) and microRNAs (miRNAs) (Bartel DP. (2004) *Cel*, 116:281-297; Vazquez F. (2006) *Trends in Plant Science*, 11:460-468).

MicroRNAs are derived from capped and polyadenylated primary (pri)-miRNA transcripts that are transcribed by RNA polymerase II and can form a hairpin-loop structure by intramolecular pairing. Two sequential cleavages mediated by DICER LIKE 1 (DCL1) are required to produce a mature miRNA. In the first cleavage, DCL1 cleaves near the base of the hairpin-loop stem of the pri-miRNA to produce a miRNA precursor (pre-miRNA). The second cleavage takes place near the loop of the pre-miRNA to produce a miRNA/miRNA* duplex. The mature miRNA is then loaded into the RNA-induced silencing complex (RISC) and can guide the sequence-specific cleavage or translational inhibition of target mRNAs, as well as gene silencing through DNA methylation, whereas the non-incorporated miRNA* strand is usually degraded.

Through the use of next-generation sequencing, the small RNA component of the *Arabidopsis* and rice transcriptomes has been well characterized, more than in any other plant species (11). This is reflected in the miRBase database available on the world wide web at mirbase.org, release 16: Sep. 2010), where 213 miRNAs are described for *Arabidopsis* whereas 462 miRNAs are described for rice. Besides rice, the identification of miRNAs through deep sequencing in other grasses including maize, wheat, and *Brachypodium* have been described (Wang et al., (2009) *Plant Cell*, 21:1053-1069; Wei B. et al., (2009) *Funct Integr Genomics* 9:499-511). The identification of rice, maize and wheat miRNAs from different tissues, developmental stages and stress-treatments, provides an opportunity to understand how miRNAs regulate the expression of genes influencing traits of agronomic importance.

High sucrose content is a highly desirable trait because sugar can be fermented to produce bioethanol as a source of renewable energy (3). Although sugarcane has been extensively used as a source of biofuel, its use as a model system to understand the genetics of carbohydrate metabolism is hampered by its complex genome, with several cultivars differing greatly in their ploidy levels (4). *Sorghum* instead, provides a better system to study the genetic basis of sugar accumulation.

SUMMARY OF THE INVENTION

In accordance with the present invention, compositions comprising at least one miRNA provided in Table 2 or Table 3 or a vector encoding said at least one of said miRNA in a biologically compatible carrier for modulating expression of a plant target gene is provided. In a preferred embodiment, the target gene encodes a protein which regulates a biological parameter selected from the group consisting of flowering, and sugar metabolism.

Also provided is a method for modulating a biological parameter selected from the group consisting of flowering and sugar metabolism in a plant or plant cell comprising contacting said plant or plant cell with an effective amount of the miRNA containing compositions (e.g., miRNA expressing vectors) of the invention. The compositions and methods described herein are effective for increasing production of biofuels from plants so treated.

BRIEF DESCRIPTION OF THE DRAWINGS

FIG. 8. List of miRNAs that target genes at the 5'UTR. The mature sequences of the miRNAs are depicted together with their predicted cleavage sites at the 5' UTR region of target genes. Sequences provided are SEQ ID NOs: 46-91, from top to bottom.

FIG. 9. List of miRNAs that target genes at exons. The mature sequences of the miRNAs are depicted together with their predicted cleavage sites at the exonic region of target genes. Sequences provided are SEQ ID NOs: 92-623, from top to bottom.

FIG. 10. List of miRNAs that target genes at the 3'UTR. The mature sequences of the miRNAs are depicted together with their predicted cleavage sites at the 3' UTR region of target genes. Sequences provided are SEQ ID NOs: 624-793, from top to bottom.

DETAILED DESCRIPTION OF THE INVENTION

Figure 1A:
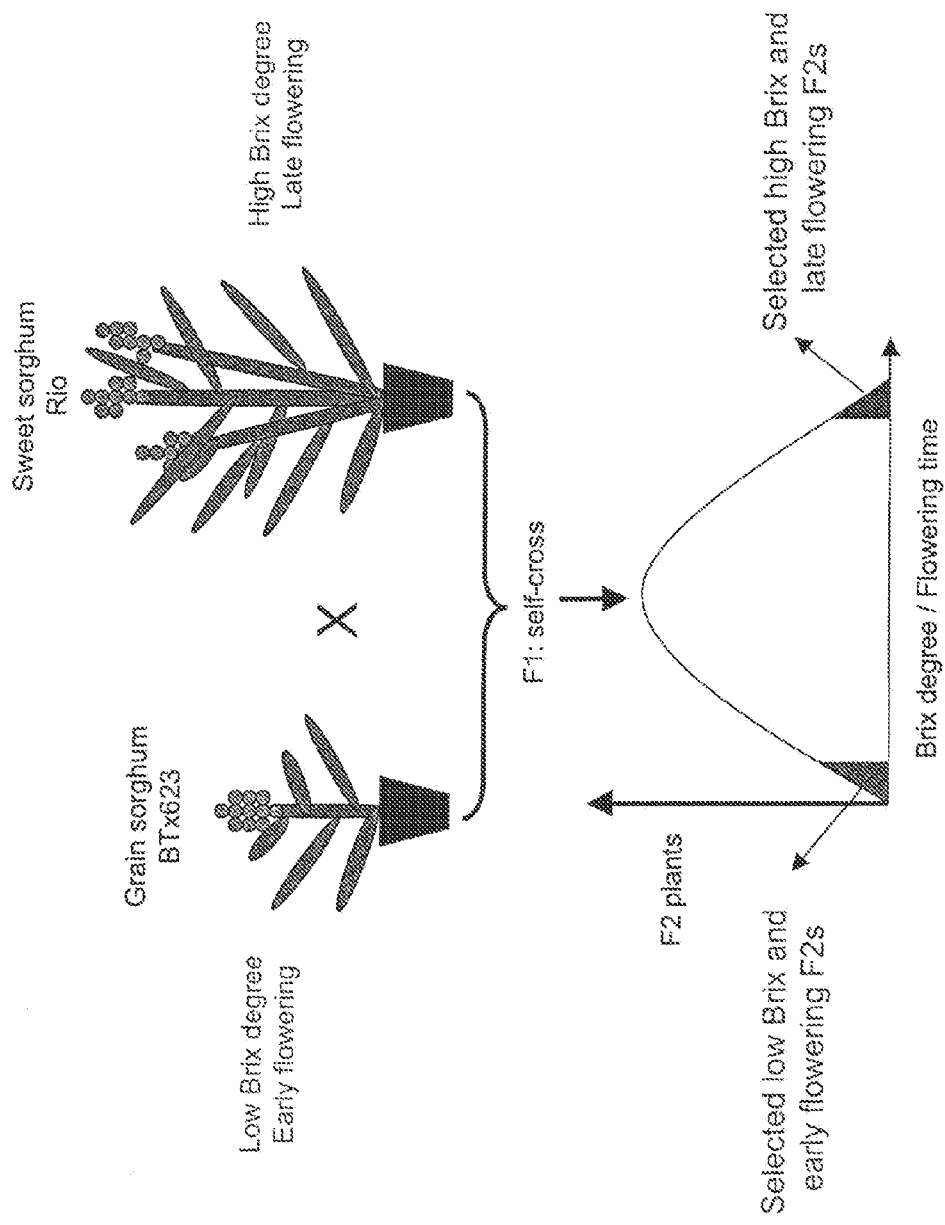
FIG. 1. Selection of *sorghum* plants and construction of small RNA libraries for deep sequencing. (A) Grain *sorghum* BTx623 with low Brix and early flowering phenotype, was crossed with sweet *sorghum* Rio with high Brix and late flowering phenotype. The resulting F1 plants were self-crossed and the obtained F2 seeds were planted on the field together with the BTx623 and Rio parents. A total of 553 F2 plants were phenotyped for flowering time (measured as the total number of leaves at flowering) and Brix degree. Using a bulked segregant analysis (BSA) approach, we selected an equal number of F2 plants with low Brix and early flowering (LB/EF) and with high Brix and late flowering (HB/LF) phenotype, respectively. (B) A flow chart describing the procedure for small RNA library construction and sequencing. (C) Histograms displaying the Brix degree and flowering time data obtained from plants grown in the field. We selected 11 LB/EF F2s displaying Brix degree≤5 and number of leaves≤9, whereas the 11 HB/LF F2s selected displayed a Brix degree≥13 and number of leaves≥14.

In *sorghum*, sugar accumulation is under quantitative inheritance (7), and the gene repertoire involved in sugar metabolism has not been well defined yet. Adding to this task is that a correlation between flowering time and sugar content has been suggested (7, 8). Indeed, we previously observed that sugar accumulation (measured as Brix degree and referred herein as Brix) in the stem of grain *sorghum* BTx623 and sweet *sorghum* Rio cultivars differed at the time of flowering. Interestingly, 80% of the differentially expressed genes in stem tissue between the two cultivars had orthologous counterparts in syntenic positions in rice (9). This suggested that the ability of *sorghum* to accumulate soluble sugars relative to rice would probably be due to gene regulation at either the transcriptional or post-transcriptional level rather than differences in gene content.

To address the latter possibility, we investigated the microRNA-mediated posttranscriptional regulation of genes involved in sugar accumulation and flowering time by characterizing the small RNA portion of transcriptomes derived from stem tissues of grain and sweet *sorghum* at flowering. Using the SOLiD next generation sequencing system, we sequenced with an unprecedented depth small RNAs libraries from BTx623 and Rio, and from a pool of selected F2 plants derived from their cross that differed in sugar content and flowering time. This allowed us to detect the expression of 110 conserved miRNAs and to discover 223 new miRNA candidates, and to correlate allelic variation of miRNA levels with sugar and flowering phenotypes. We also could find that the size distribution of small RNAs in *sorghum* stems was quite heterogeneous, with the 22 nt small RNAs highly enriched in introns. Furthermore, a new class of small RNAs with a distinct size of at least 25 nt long was found and named "piccolo RNAs" (from the Italian word small). Interestingly, the piccolo RNAs preferentially mapped to the promoter regions of *sorghum* genes.

Thus, we have characterized the small RNA component of the transcriptome from grain and sweet *sorghum* stems, and from F2 plants derived from their cross that segregated for sugar content and flowering time. In addition, completely new roles for miR169 in sugar metabolism and miR395 in flowering, respectively, were identified because their respective miRNA/miRNAs* can regulate different target genes. Finally, newly discovered microRNAs co-localized with previously described QTLs for biofuel traits.

I. Definitions

The following definitions are provided to facilitate an understanding of the present invention. Unless defined otherwise, all technical and scientific terms used herein have the same meaning as commonly understood by one of ordinary skill in the art to which this invention belongs. Generally, conventional methods of molecular biology, microbiology, recombinant DNA techniques, cell biology, and virology within the skill of the art are employed in the present invention. Such techniques are explained fully in the literature, see, e.g., Maniatis, Fritsch & Sambrook, Molecular Cloning: A Laboratory Manual (1982); DNA Cloning: A Practical Approach, Volumes I and II (D. N. Glover, ed. 1985); Oligonucleotide Synthesis (M. J. Gait, ed. 1984); Nucleic Acid Hybridization (B. D. Hames & S. J. Higgins, eds. (1984)); Animal Cell Culture (R. I. Freshney, ed. 1986); and RNA Viruses: A Practical Approach, (Alan, J. Cann, Ed., Oxford University Press, 2000).

For purposes of the invention, "Nucleic acid", "nucleotide sequence" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Alternatively, this term may refer to a DNA that has been sufficiently separated from (e.g., substantially free of) other cellular components with which it would naturally be associated. "Isolated" is not meant to exclude artificial or synthetic mixtures with other compounds or materials, or the presence of impurities that do not interfere with the fundamental activity, and that may be present, for example, due to incomplete purification. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

According to the present invention, an isolated or biologically pure molecule or cell is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route. The term "promoter" or "promoter region" generally refers to the transcriptional regulatory regions of a gene. The "promoter region" may be found at the 5' or 3' side of the coding region, or within the coding region, or within introns. Typically, the "promoter region" is a nucleic acid sequence which is usually found upstream (5') to a coding sequence and which directs transcription of the nucleic acid sequence into mRNA. The "promoter region" typically provides a recognition site for RNA polymerase and the other factors necessary for proper initiation of transcription.

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., flower vs. root). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "vector" relates to a single or double stranded circular nucleic acid molecule that can be infected, transfected or transformed into cells and replicate independently or within the host cell genome. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. An "expression vector" is a specialized vector that contains a gene or nucleic acid sequence with the necessary regulatory regions needed for expression in a host cell.

DNA constructs or vectors of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., Embo J. 3:2717-2722 (1984). Electroporation techniques are described in Fromm et al., Proc. Natl. Acad. Sci. USA 82:5824 (1985). Ballistic transformation techniques are described in Klein et al., Nature 327:70-73 (1987).

*Agrobacterium tumefaciens*-mediated transformation techniques, including disarming and use of binary vectors, are well described in the scientific literature. See, for example, Horsch et al., Science 233:496-498 (1984), and Fraley et al., Proc. Natl. Acad. Sci. USA 80:4803 (1983).

Transformed plant cells that are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al., Ann. Rev. of Plant Phys. 38:467-486 (1987).

One of skill will recognize that after the expression cassette or vector is stably incorporated in transgenic plants and confirmed to be operable, it can be introduced into other plants by sexual crossing. Any of a number of standard breeding techniques can be used, depending upon the species to be crossed.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The terms "miRNA" and "microRNA" refer to about 10-35 nt, preferably about 15-30 nt, and more preferably about 19-26 nt, non-coding RNAs derived from endogenous genes encoded in the genomes of plants and animals. They are processed from longer hairpin-like precursors termed pre-miRNAs that are often hundreds of nucleotides in length. MicroRNAs assemble in complexes termed miRNPs and recognize their targets by antisense complementarity. These highly conserved, endogenously expressed RNAs are believed to regulate the expression of genes by binding to the 3'-untranslated regions (3'-UTR) of specific mRNAs as well as other regions on targeted mRNAs. Without being bound by theory, a possible mechanism of action assumes that if the microRNAs match 100% their target, i.e. the complementarity is complete, the target mRNA is cleaved, and the miRNA acts like a siRNA. However, if the match is incomplete, i.e. the complementarity is partial, then the translation of the target mRNA is blocked. The manner by which a miRNA base-pairs with its mRNA target correlates with its function: if the complementarity between a mRNA and its target is extensive, the RNA target is cleaved; if the complementarity is partial, the stability of the target mRNA in not affected but its translation is repressed.

The term "RNA interference" or "RNAi" refers generally to a process or system in which a RNA molecule changes the expression of a nucleic acid sequence with which RNA molecule shares substantial or total homology. The term "RNAi agent" refers to an RNA sequence that elicits RNAi.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting HCV may be between 15-35 nucleotides in length.

"Pri-miRNAs" are several hundred to thousands of base pairs in size. Pri-miRNA contains at least 1, and up to 6, nucleotide hairpin loop structures when transcribed from polycistronic units. They can be composed of multiple miRNAs, and in a particular arrangement of the invention five miRNAs are processed from one nucleic acid sequence. These sequences can also contain siRNA nucleic acids that repress gene transcription once processed in the RNAi system.

As used herein, "agricultural formulations" include formulations for use in the field. The phrase "agriculturally acceptable formulation" as used herein refers to a composition or formulation that allows for the effective distribution of the nucleic acid molecules of the instant invention in the physical location most suitable for their desired activity.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxiliary agent or vehicle with which an active agent of the present invention is administered. Agriculturally acceptable carriers can be sterile liquids, such as water and oils, including those of petroleum, animal, vegetable or synthetic origin. Water or aqueous saline solutions and aqueous dextrose and glycerol solutions are preferably employed as carriers.

With respect to single-stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (see Sambrook et al. (2001) *Molecular Cloning, A Laboratory Manual*, Cold Spring Harbor, N.Y.: Cold Spring Harbor Laboratory Press):

$$T_m=81.5° C.+16.6 \text{ Log } [Na+]+0.41(\% \text{ G+C})-0.63 (\% \text{ formamide})-600/\#bp \text{ in duplex}$$

As an illustration of the above formula, using [Na+]= [0.368] and 50% formamide, with GC content of 42% and an average probe size of 200 bases, the $T_m$ is 57° C. Depending upon the specific sequence involved, the $T_m$ of a DNA duplex decreases by 0.5-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high-stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1X SSC and 0.5% SDS at 65° C. for 15 minutes.

"Corresponding" means identical to or complementary to the designated sequence. The sequence may be generated in any manner, including chemical synthesis, DNA replication, reverse transcription or a combination thereof. Being "Complementary" means that a nucleic acid, such as DNA and RNA, encodes the only corresponding base pair that non-covalently connects sequences by two or three hydrogen bonds. There is only one complementary base for any of the bases found in DNA and in RNA, and skilled artisans can reconstruct a complementary strand for any single stranded nucleic acid.

The present invention also includes active portions, fragments, derivatives and functional or non-functional mimetics of the miRNAs of the invention. A "fragment" or "portion" of a sequence means a stretch of residues of at least about five to seven contiguous residues, often at least about seven to nine contiguous residues, typically at least about nine to fifteen contiguous residues and, most preferably, at least about fourteen or more contiguous residues.

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

A "derivative" of a polypeptide, polynucleotide or fragments thereof means a sequence modified by varying the sequence of the construct, e.g. by manipulation of the nucleic acid encoding the protein or by altering the protein itself. "Derivatives" of a gene or nucleotide sequence refers to any isolated nucleic acid molecule that contains significant sequence similarity to the gene or nucleotide sequence or a part thereof. In addition, "derivatives" include such isolated nucleic acids containing modified nucleotides or mimetics of naturally-occurring nucleotides.

The term "functional" as used herein implies that the nucleic or amino acid sequence is functional for the recited assay or purpose.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide can depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein. The term "gene" refers to a nucleic acid comprising an open reading frame encoding a polypeptide, including both exon and (optionally) intron sequences. The nucleic acid may also optionally include non coding sequences such as promoter or enhancer sequences. The term "intron" refers to a DNA sequence present in a given gene that is not translated into protein and is generally found between exons.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, depending on the complexity of the target sequence, the oligonucleotide probe typically contains about 10-50 or more nucleotides, more preferably, about 15-25 nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The terms "percent similarity", "percent identity" and "percent homology" when referring to a particular sequence are used as set forth in the University of Wisconsin GCG software program.

The term "delivery" as used herein refers to the introduction of foreign molecule (i.e., miRNA containing nanoparticle) into cells. The term "administration" as used herein means the introduction of a foreign molecule into a cell. The term is intended to be synonymous with the term "delivery".

The term "kit" refers to a combination of reagents and other materials.

II. Uses of miRNA Constructs

The present invention is based, at least in part, on the identification of new miRNAs in *sorghum*. The nucleic acids of the invention can be used to control gene expression in plants. In some embodiments, the expression cassettes encoding the miRNAs of the invention are prepared and introduced into plants. The encoded miRNAs then control expression of the endogenous target genes. Alternatively, one can modify the target gene so as to render it miRNA-resistant by modifying the sequence to decrease or inhibit pairing with the miRNA. The modifications will typically be selected such that the sequence of the encoded protein is not altered. The modified target gene can be incorporated into an expression cassette and introduced into a plant. Alternatively, an endogenous target gene can be modified using known techniques (e.g., homologous recombination).

Nucleic acid molecules encoding the miRNAs of the invention may be prepared by using recombinant DNA technology methods. The availability of nucleotide sequence information enables preparation of nucleic acid-based molecules of the invention by a variety of means. The RNAs may be used for a variety of purposes in accordance with the present invention. In a preferred embodiment of the invention, a nucleic acid delivery vehicle (i.e., an expression vector) for modulating target gene expression is provided wherein the expression vector comprises a nucleic acid sequence coding at least one miRNA, or a functional fragments thereof as described herein. Administration of miRNA or derivatives thereof encoding expression vectors to a plant results in the modulation of target gene expression, particularly genes involved in sugar metabolism and flowering.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of miRNA(s). For example, the miRNA constructs can be subcloned into a vector downstream of a tissue specific promoter/enhancer to target gene expression in a particular region of the plant (e.g., root, vs. leaves).

III. Agricultural Compositions

The expression vectors of the present invention may be incorporated into agricultural compositions that may be delivered to a plant. In a particular embodiment of the present invention, compositions comprising isolated nucleic acids which enable the recipient to produce biologically effective miRNAs that modulate target gene expression in the recipient plant are provided. Herein we describe a broad spectrum of the small RNA component of the *sorghum* transcriptome and provide new insights into how complex processes like carbohydrate metabolism and flowering time are regulated at the post-transcriptional level. Elucidation of this regulatory process provides an opportunity to improve biofuel production, for example, by increasing stem sugar rather than cellulose and increasing biomass because of delayed flowering (38). The compositions may be administered alone or in combination with at least one other agent, such as a stabilizing compound, which may be administered in any sterile, biocompatible carrier, including, but not limited to, saline, buffered saline, dextrose, and water. In preferred embodiments, the pharmaceutical compositions also contain a agriculturally acceptable excipient. Acceptable excipients include, but are not limited to, liquids such as water, saline, glycerol, sugars and ethanol.

After agricultural compositions have been prepared, they may be placed in an appropriate container or kit and labeled for use. For administration of miRNA-containing vectors, such labeling would include amount, frequency, and method of delivery.

IV. Kits and Articles of Manufacture

Any of the aforementioned compositions or methods can be incorporated into a kit which may contain at least one miRNA sequence or a polycistronic transcript of multiple miRNAs. If the agricultural composition in liquid form is under risk of being subjected to conditions which will compromise the stability of the miRNAs or vectors encoding the same, it may be preferred to produce the finished product containing the miRNAs in a solid form, e.g. as a freeze dried material, and store the product is such solid form. The product may then be reconstituted (e.g. dissolved or suspended) in a saline or in a buffered saline ready for use prior to administration.

Hence, the present invention provides a kit comprising (a) a first component containing miRNAs as defined hereinabove, optionally in solid form, and (b) a second component containing saline or a buffer solution (e.g. buffered saline) adapted for reconstitution (e.g. dissolution or suspension) or delivery of said miRNAs or a vector encoding the same. Preferably said saline or buffered saline has a pH in the range of 4.0-8.5, and a molarity of 20-2000 mM. In a preferred embodiment the saline or buffered saline has a pH of 6.0-8.0 and a molarity of 100-500 mM. In a most preferred embodiment the saline or buffered saline has a pH of 7.0-8.0 and a molarity of 120-250 mM.

VI. Agricultural Applications

As mentioned previously, a preferred embodiment of the invention comprises delivery of at least one vector encoding an miRNA or a polycistronic miRNA transcript to a plant to control flowering and/or sugar metabolism. Alternatively, inhibitors of the miRNAs which interfere with the functions of the miRNAs disclosed herein may be delivered to target plants of interest. Field trials can be designed to assess the safety, tolerability, pharmacokinetics, and pharmacodynamics of the miRNA constructs of the invention.

The following materials and methods are provided to facilitate practice of the present invention.

Plant Material

The grain (BTx623) and sweet (Rio) sorghum cultivars together with F2 plants derived from their cross were grown in the field of the Waksman Institute during the summer of 2008. The juice from three internodes of the main stem was harvested at the time of flowering and the Brix degree measured as previously described (M. Calviño, R. Bruggmann, J. Messing, Rice 1, 166 (2008).). The average Brix degree from three internodes per plant was used. Flowering time was measured as the number of leaves in the main stem at the time of anthesis.

In total, 15 plants for each parent and 553 F2 plants were scored for Brix degree and flowering time. The F2 plants selected for sequencing had either low Brix (Brix≤5)/early flowering (N0 leaves≤9) or high Brix (Brix≥13)/late flowering (N0 leaves≥14).

Construction of Small RNA Libraries

Total RNA from internode tissue was extracted at the time of flowering with the mirVana miRNA isolation kit (Ambion). RNA extraction was performed in 5 independent plants for each BTx623 and Rio, and 11 independent plants for each low Brix/early flowering and high Brix/late flowering F2 plants respectively. The total RNA (1 µg per sample) was pooled and then fractionated with the flashPage fractionator (Ambion) to isolate RNAs smaller that 40 nt in length. The isolated small RNAs were used to construct small RNA cDNA libraries with the SOLiD small RNA library construction kit (Ambion). The sequencing was carried out at the Waksman genomics laboratory. See the world wide web at solid.rutgers.edu.

Bioinformatic Analysis

We mapped the 25 nt long reads to the sorghum genome using the SHRiMP program (S. M. Rumble et al., PLoS Comput Biol 5, e1000386 (2009), with default parameter settings except the number of matches was limited to 10. SHRiMP allowed us to perform the alignment in SOLiD's colorspace. We used only alignments that matched perfectly to the genome starting from the first position in the read up to the sequencing primer. These reads were then clustered with Vmatch. See the world wide web at vmatch.de/to reduce the number of identical reads. We required 100% identity among the sequences of a cluster. We have further filtered the clustered reads against the repetitive elements of sorghum and used the remaining sequences for de novo prediction of miRNA.

Quantification of miRNA Expression

The TaqMan MicroRNA Assays (Applied Biosystems) was used to quantify the expression of miR172a, and the Custom TaqMan Small RNA Assays (Applied Biosystems) was used to quantify the expression of miR169d and miR395f respectively. The qRT-PCR reaction was done using the MyiQ Real-Time PCR Detection System (BIO-RAD Laboratories, Inc.). A relative quantification normalized against unit mass (10 ng total RNA) was performed as previously described (M. Calviño, R. Bruggmann, J. Messing, Rice 1, 166 (2008).

De novo Discovery of Sorghum miRNAs

For de novo prediction of potential miRNAs, we have used the miRDeep package (M. R. Friedländer et al., Nat Biotechnol 26, 407 (2008). As miRDeep does not take colorspace alignment as input, we had to reshap the output to miRDeep's blastparse format. Moreover, the SHRiMP alignment scores and the score used in the blastparse format of miRDeep had to be recalculated. We used the same formula and method as described by Goff et al. At this point, we also had to translate the color space two base encoding sequences into standard nucleotide base space sequences. As we considered only perfectly matching reads after the initial alignment to the genome, we could easily translate from color space to base space sequence. The subsequent de novo calling of miRNAs was carried out as described in Goff et al. (L. A. Goff et al., PLoS ONE 4, e7192 (2009).

Finally, the coordinates of de novo miRNAs predicted on the minus strand were corrected as miRDeep refers the coordinates to the 5' end of the minus strand. Though, conventionally the coordinates refer always to the 5' end of the plus strand.

Target Prediction and Validation

We have used the novel miRNAs for a target prediction. Firstly, we compared the sequences to the unspliced transcripts of sorghum (A. H. Paterson et al., Nature 457, 551 (2009).), with BLASTN using these parameters: −F F −W 7 −e 1 −q −2 −G−1. We scored each base of the alignment according to these criteria: match as 0; GU pairs as 0.5; gaps as 2; all other pairs were scored as 1. We doubled the score within the first 13 bases of the miRNA/alignment. We considered the gene as a potential target if the total score of the alignment was smaller than 7. In addition, we have classified the target according to the position of the hit within the unspliced transcript, i.e. 5'UTR, exon, intron and 3'UTR. Furthermore, the web resource known as MicroPC (W. Mhuantong, D. Wichadakul, BMC Genomics 10, 366 (2009), (See the world wide web at 3a.biotec.or.th/micropc) was used to identify the glycogenin gene as predicted target of miR169i* and PICKLE as predicted target of miR395f*, respectively.

The miRNA-mediated cleavage of mRNAs was performed through a modified procedure of the RLM-RACE protocol from Invitrogen. The sequence of the primers used in the modified RACE are provided below. The validation of predicted targets was performed in BTx623 or Rio cultivars only.

List of Primer Sequences Used in the Modified RLM-RACE Experiment

Gene ID Sequence of Reverse Primer

```
                                             (SEQ ID NO: 1)
   Sb01g049020  5'  TGCAGCCTTGTCTTTGTTTG  3'

(SEQ ID NO: 2)
   Sb01g033060  5'  CCTGGAACCTGTGGTGAAAT  3'

(SEQ ID NO: 3)
   Sb01g044240  5'  GCCCATATGGACGGAAGATA  3'
```

-continued

```
                                             (SEQ ID NO: 4)
   Sb02g007000  5'  CTGGTAGCCGGAGAACAACT  3'

(SEQ ID NO: 5)
   Sb03g042460  5'  TTGACAATGTCTGCCTGGTC  3'

(SEQ ID NO: 6)
   Sb03g041660  5'  CGCTGGTCAGCAATCTGATA  3'

(SEQ ID NO: 7)
   Sb04g003660  5'  GCACTCAAGTCCAGCACAAA  3'

(SEQ ID NO: 8)
   Sb06g030670  5'  TTTCATCAGTGCTTGCCAAT  3'

(SEQ ID NO: 9)
   Sb10g005630  5'  TGGCTGGATCTACCACTTCC  3'
```

Annotation of the miRNA gene targets into functional categories was based on the Phytozome database available on the world wide web at phytozome.net, the SALAD database on the web at salad.dna.affrc.go.jp/salad/en (7), the Kyoto Encyclopedia of Genes and Genomes (KEGG; also on the web at genome.jp/kegg) and the cell wall genomics database on the web at cellwall.genomics.purdue.edu.

The following examples illustrate certain embodiments of the invention. They are not intended to limit the scope of the invention in any way.

EXAMPLE I

Deep-sequencing of Small RNAs from Grain and Sweet *Sorghum* Stems

Figure 1B:
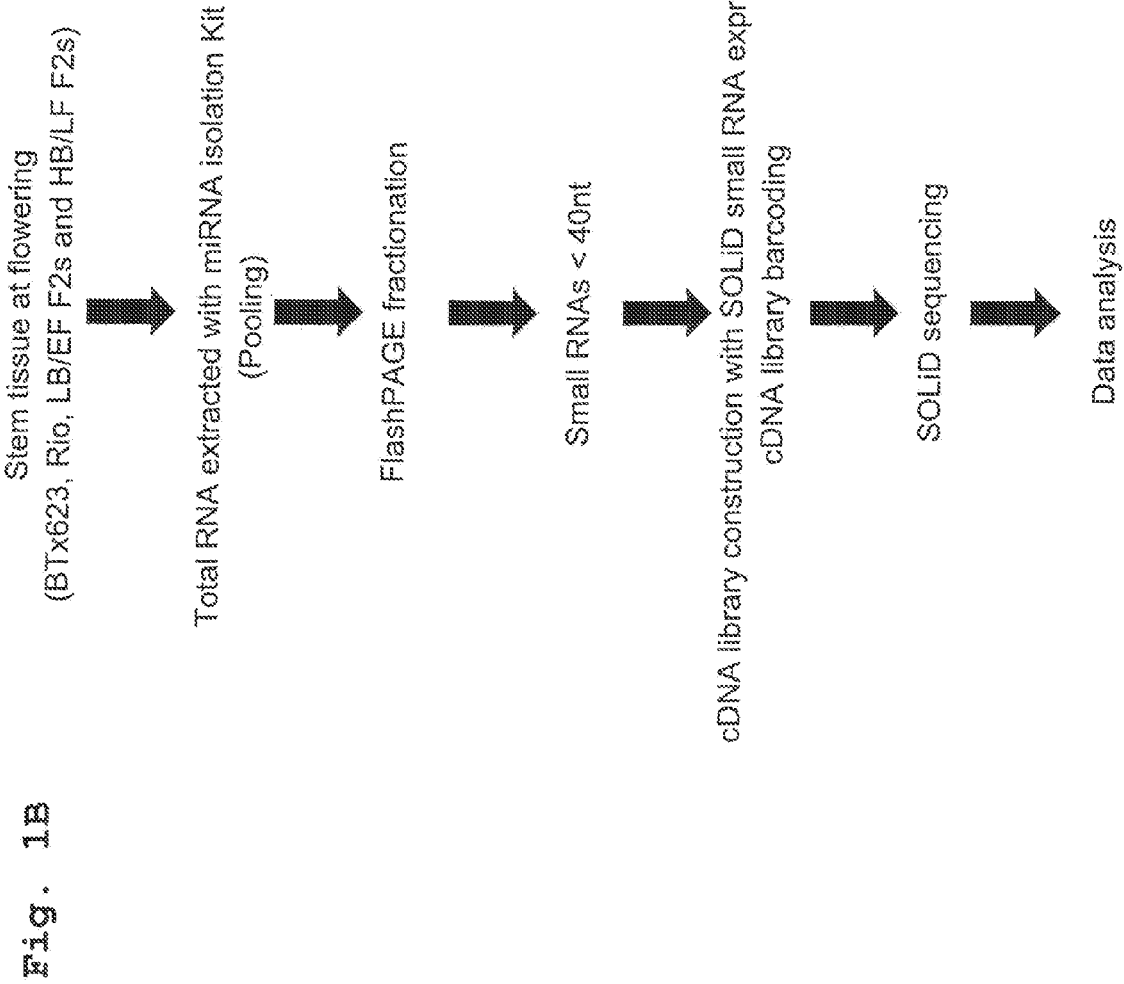

We constructed five small RNAs libraries from *sorghum* stem tissue at the time of flowering and sequenced them using the SOLiD platform (10). The libraries comprised samples from BTx623, Rio, low Brix and early flowering F2 plants (LB/EF F2s), high Brix and late flowering F2 plants (HB/LF F2s), and a "mixed library" (Mix), where small RNAs from the previous four libraries were mixed in equal proportions (FIGS. 1A, 1B and 1C).

We sequenced 38,336,769 reads in total, from which 23,008,945 reads (60%) matched perfectly to the BTx623 reference genome (Table 1). The reads with perfect matches that derived from repeats constituted 74 to 77% of the total reads depending on the library (FIG. 2A). The non-redundant set of sequences comprised 2,539,403 reads in total, and the reads that were sequenced only once (termed here "singlets") comprised 2,167,946 sequences, corresponding only to 9% of the perfect matches (Table 1), suggesting that our sequencing reached a high level of saturation. If we define a cluster as two or more reads with identical sequences, the number of clusters found ranged from 20,056 in the BTx623 library to 164,623 in the HB/LF F2s library (Table 1).

TABLE 1

| | Deep sequencing statistics of stem-derived small RNAs | | | | | | | | |
|---|---|---|---|---|---|---|---|---|---|
| Library | # raw sequences | # perfect matches | % | # singlets | % | # clusters | | Non-redundant set | % |
| Mix | 4,023,513 | 2,547,108 | 63 | 276,044 | 11 | 35,083 | | 311,127 | 8 |
| BTx623 | 2,115,266 | 1,348,361 | 64 | 169,063 | 12 | 20,056 | | 189,119 | 9 |
| Rio | 3,173,601 | 2,180,988 | 69 | 234,276 | 11 | 31,563 | | 265,839 | 8 |
| LB/EF F2s | 11,974,953 | 7,472,940 | 62 | 653,279 | 9 | 120,132 | | 773,411 | 6 |
| HB/LF F2s | 17,049,436 | 9,459,548 | 55 | 835,284 | 9 | 164,623 | | 999,907 | 6 |
| Total | 38,336,769 | 23,008,945 | 60 | 2,167,946 | 9 | 371,457 | | 2,539,403 | 8 |

Diversity in the Small RNA Content of *Sorghum* Stems

Figure 2B:
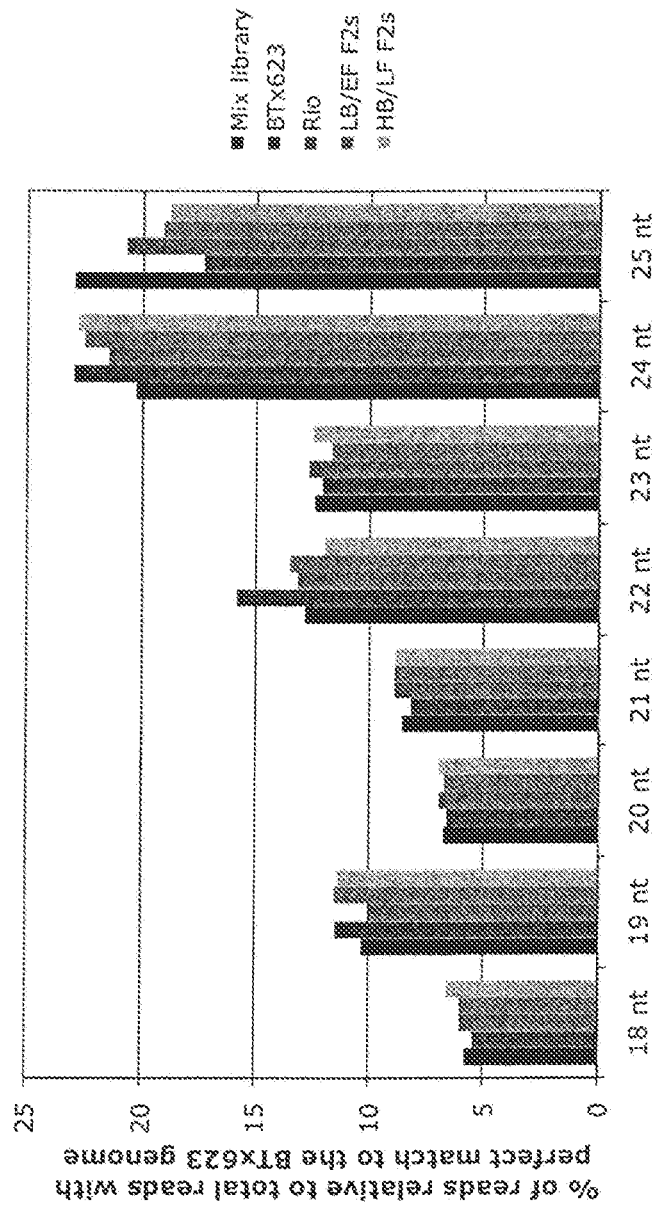
FIG. 2. Diversity in the small RNA content of *sorghum* stem. (A) Mapping of small RNAs (18-25 nt) with perfect match to different elements of the BTx623 reference genome with the term "other" representing intergenic regions. (B) Frequency and size distribution of small RNAs reads. (C) Size distribution of intron-associated small RNAs. (D) Size distribution of exon-associated small RNAs. (E) Promoter associated small RNAs (PASRs) in *sorghum*. The percentage of small RNA reads mapping to the promoter region relative to the total number of reads in each library is shown. (F and G) Graphs showing the frequency and distribution of 25 nt small RNAs (F), and the 18 nt small RNAs (G), along the promoter region. The region considered extends from 500 bp upstream from the beginning of the 5' UTR to 500 bp downstream of it. Each vertical line on the graph represents 100 bp interval. The abundance of the small RNA reads is shown on the y-axis.
Figure 2C:
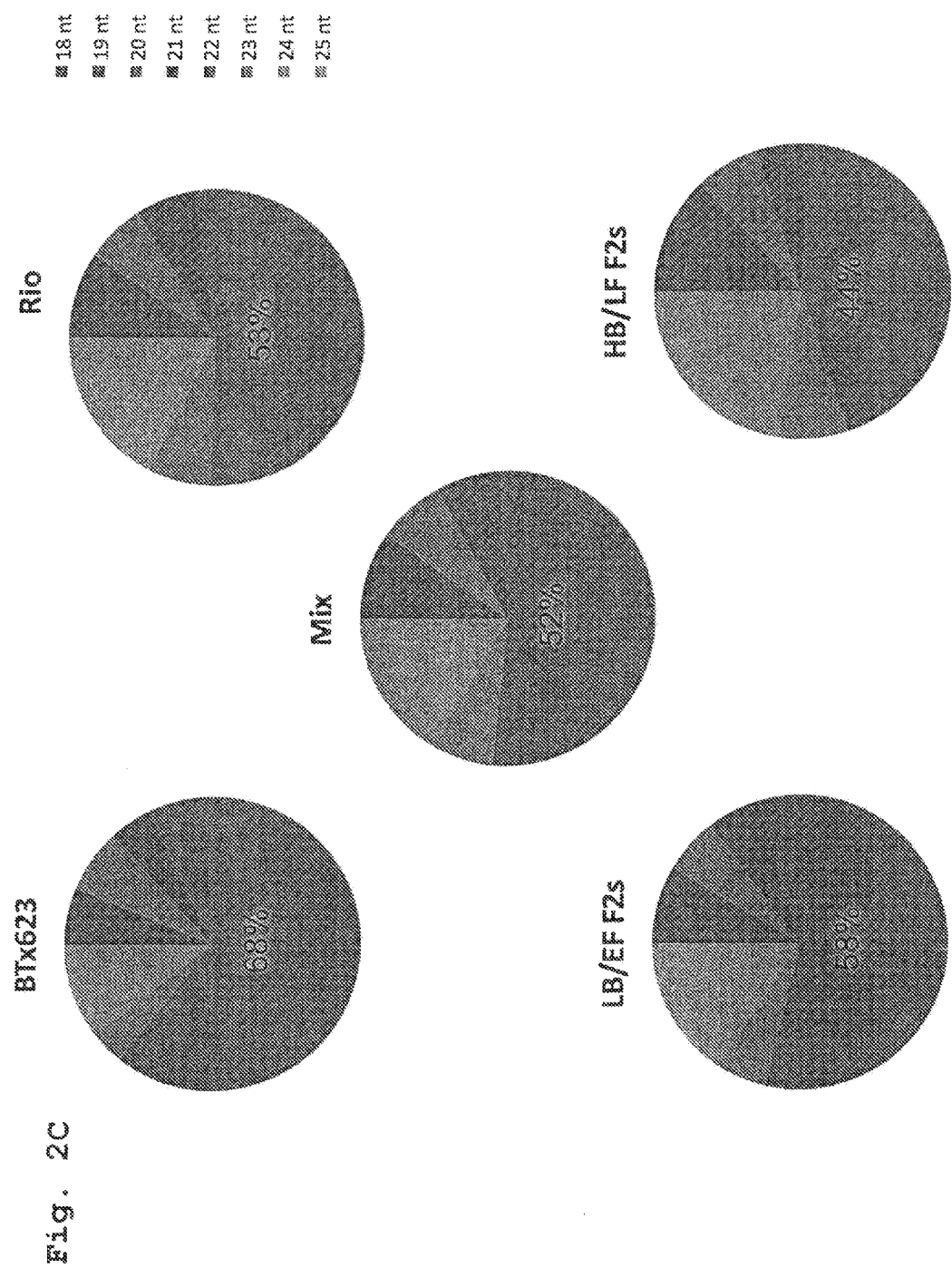
Figure 2D:
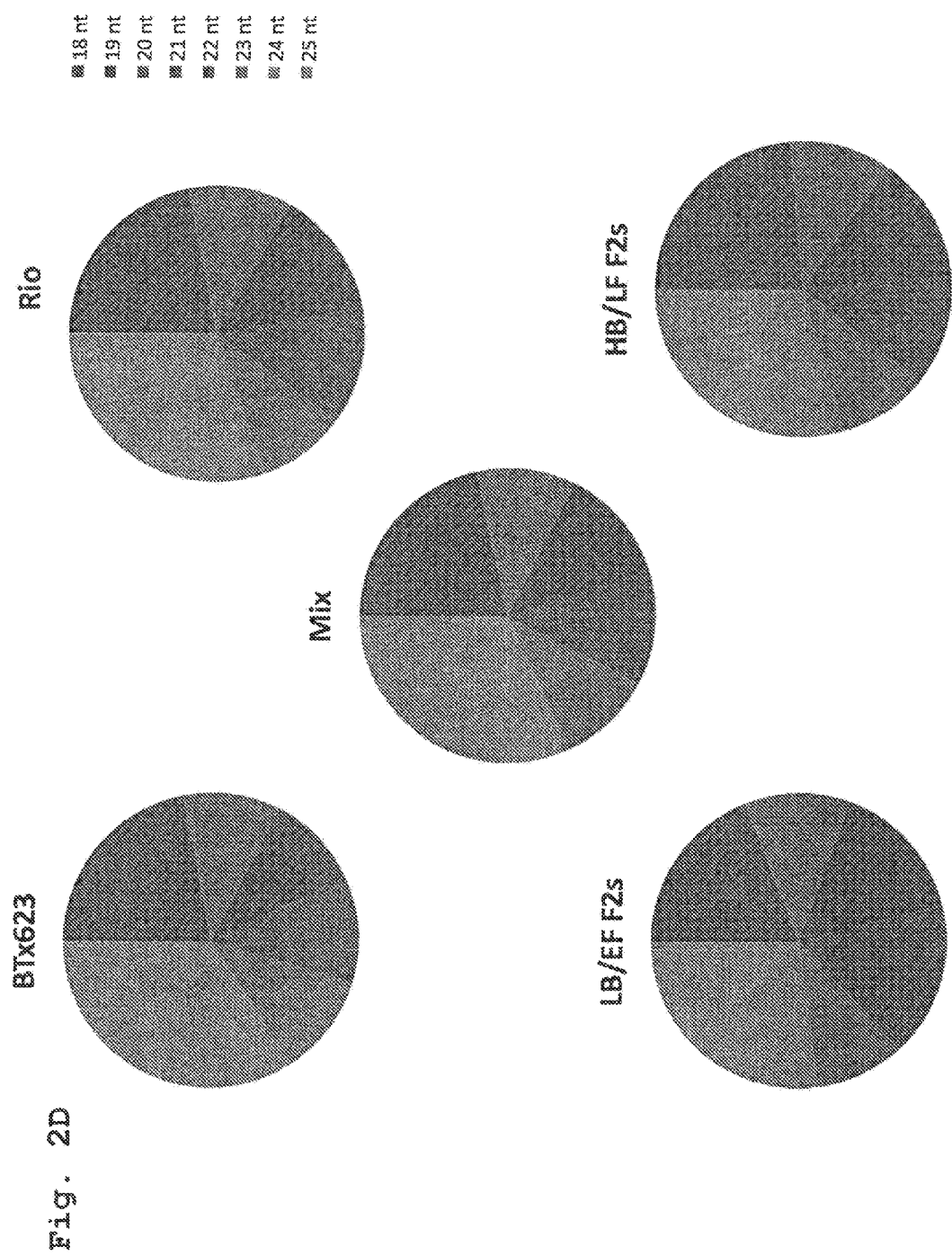

The frequency and size distribution of small RNAs from *sorghum* stems revealed two interesting aspects: a peak of 25 nt small RNAs with similar abundance as the 24 nt class, and a second peak of small RNAs with 22 nt that were more abundant than the 20 and 21 nt classes, respectively (FIG. 2B). This finding contrasted with the size distribution of small RNAs described for several monocot species (including small RNAs from *sorghum* inflorescence), in which the most abundant small RNAs were 21 and 24 nt in length, with maize being the exception, showing a larger 22 nt peak relative to the 21 nt peak (11). This led to the hypothesis that the 22 nt class of small RNAs are specific to maize (11). However, we have shown here that a 22 nt peak is also present in *sorghum* stem tissue. Furthermore, we found that the 22 nt small RNAs were highly enriched in intronic sequences relative to other small RNAs (FIG. 2C). This was most evident in the BTx623 library, where 68% of all reads that mapped to introns were 22 nt in length. This was in sharp contrast to the distribution of small RNAs that mapped to exons (FIG. 2D). A possible explanation for the origin of the intron-associated 22 nt small RNAs would be that they arise from transcription of intronic noncoding RNAs as has been described for animals (12-14).

Figure 2F:
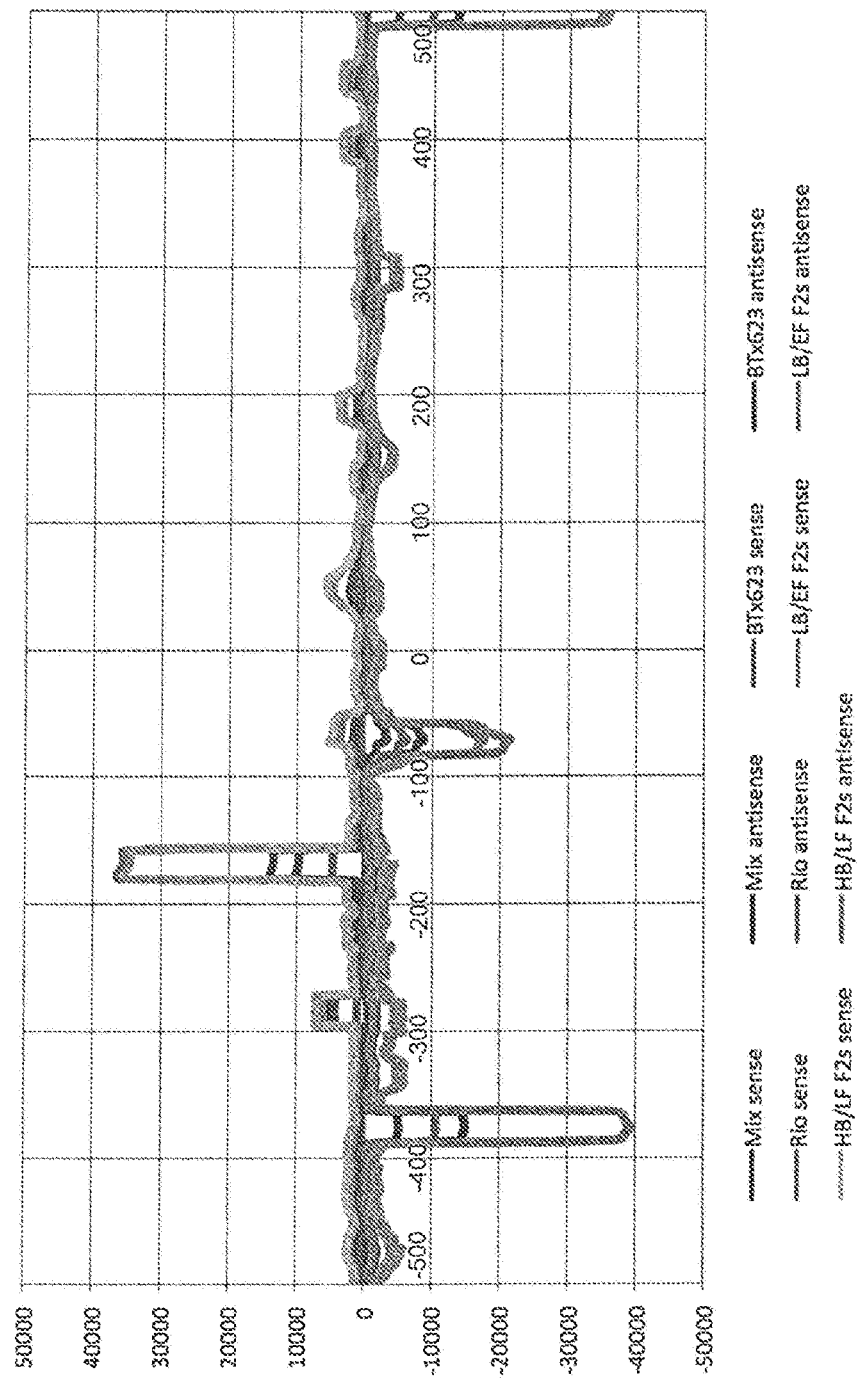
Figure 2G:
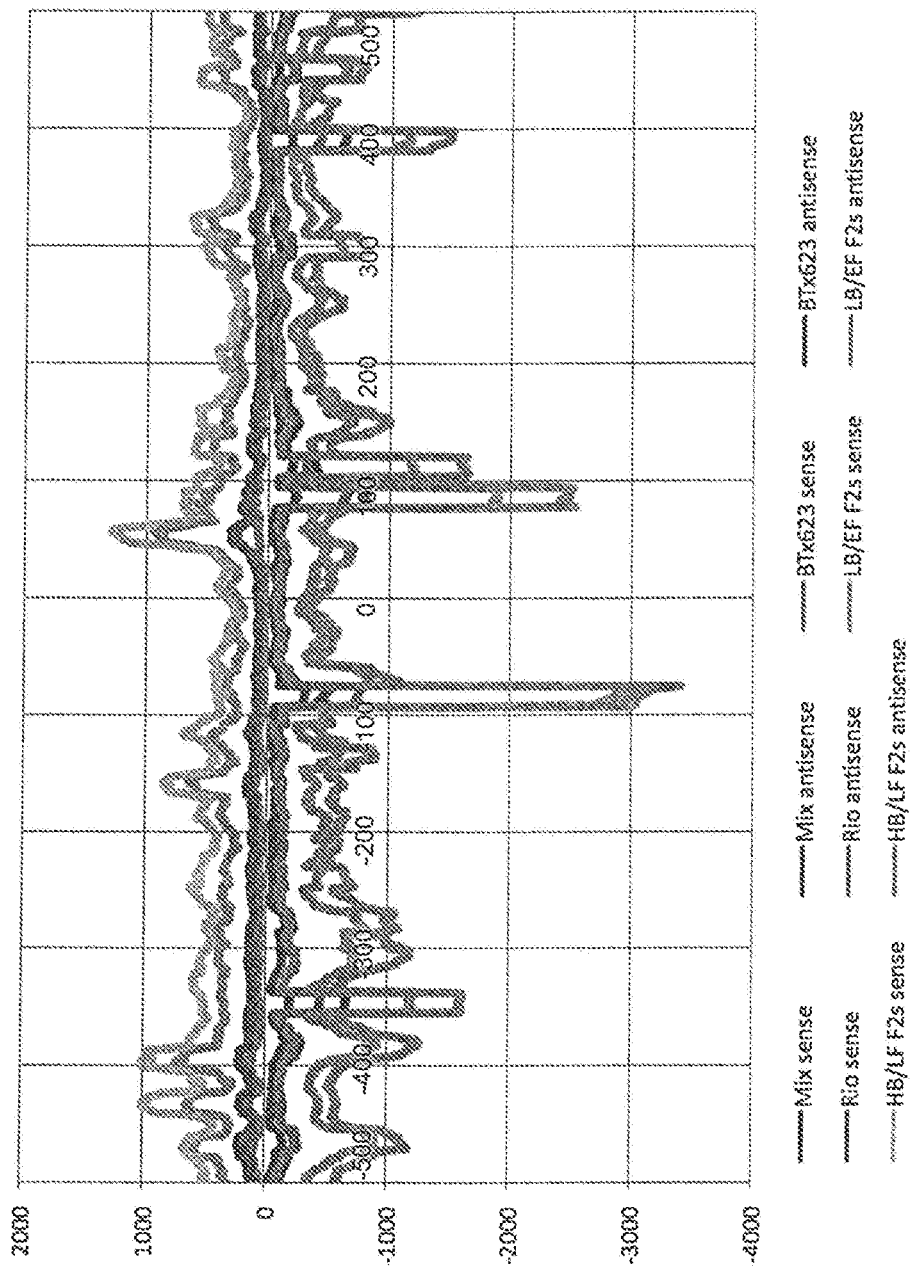

An interesting pattern was also observed for the 25 nt small RNA class, being preferentially enriched at the promoter regions of *sorghum* genes (FIG. 2E). We named these 25 nt small RNAs as "piccolo RNAs", to distinguish them from the previously described small RNAs in plants. The distribution of piccolo RNAs within the promoter region displayed very discrete peaks of high abundance in both sense and antisense strands (FIG. 2F). This distribution pattern contrasted greatly with the one displayed by the 18 nt class of small RNAs (FIG. 2G), recently shown to be the characteristic type of small RNAs associated with transcription start sites (TSS) in human, chicken and *Drosophila* (15, 16).

Interestingly, TSS-associated small RNAs were not found in *Arabidopsis*, and this led to the hypothesis that they probably do not exist in plants (16). To our knowledge, this is the first report describing the existence of promoter associated RNAs of 25 nt in length in plant species.

Because sequencing cycles were set to 25 nt at the time of our study, the size of piccolo RNAs could be longer.

In summary, we showed that the small RNA component from the stem transcriptome of *sorghum* is characterized by small RNAs of 22 nt in length that are associated with introns, and by a new class of small RNAs with at least 25 nt in length that are highly enriched in promoter regions. See Table A.

frequency of 10 reads or more for the sum of the five libraries. A list with the reads count for each known miRNA is provided in Table B.

Figure 3A:
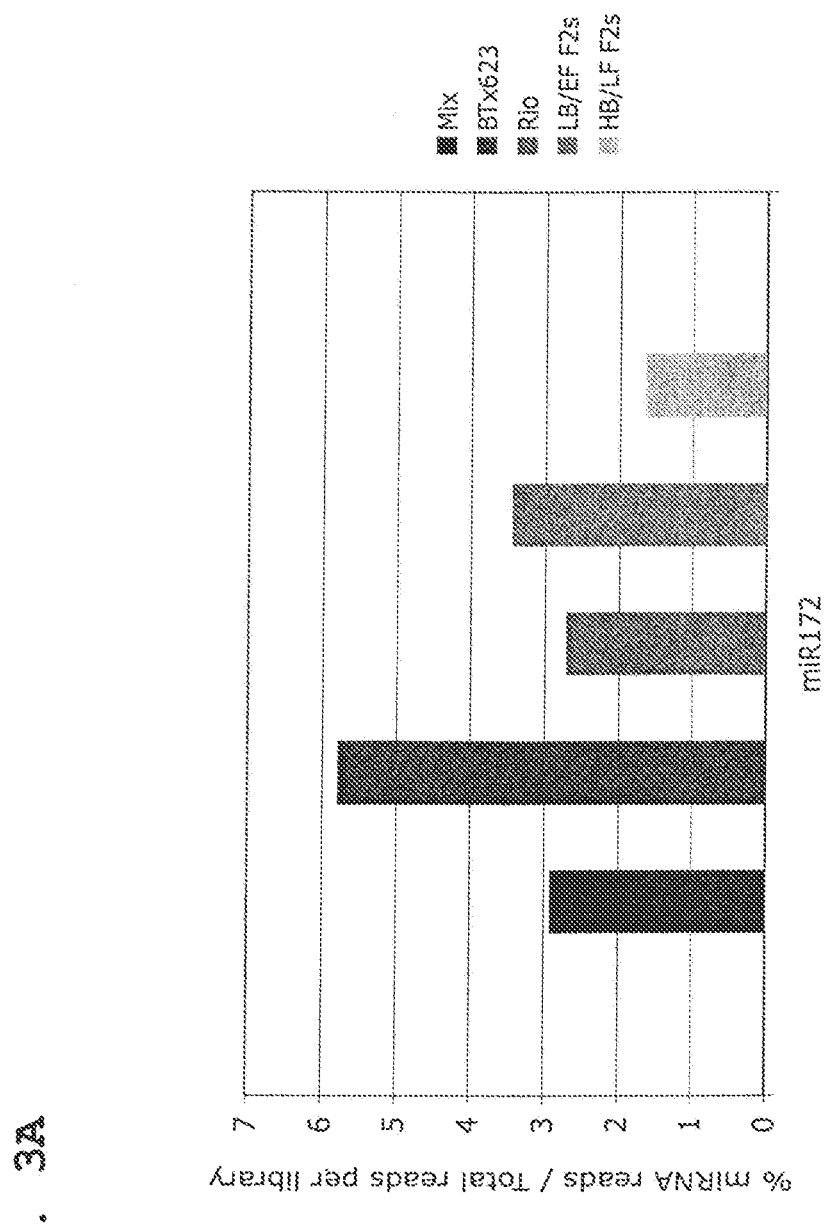
FIG. 3. The miR172 is the most abundantly expressed miRNA in *sorghum* stems. (A) The abundance of miR172 was the highest in the BTx623 library, comprising almost 6% of the total reads. (B) The rest of the known miRNAs were expressed at very low abundance (less that 0.5% of the total reads in the library) in stem tissue. (C) The abundance of 7 new predicted miRNAs are shown whose allelic variation in expression between BTx623 and Rio were inherited in the F2 progeny. Notice the very low abundance at which these miRNAs are expressed.
Figure 3B:
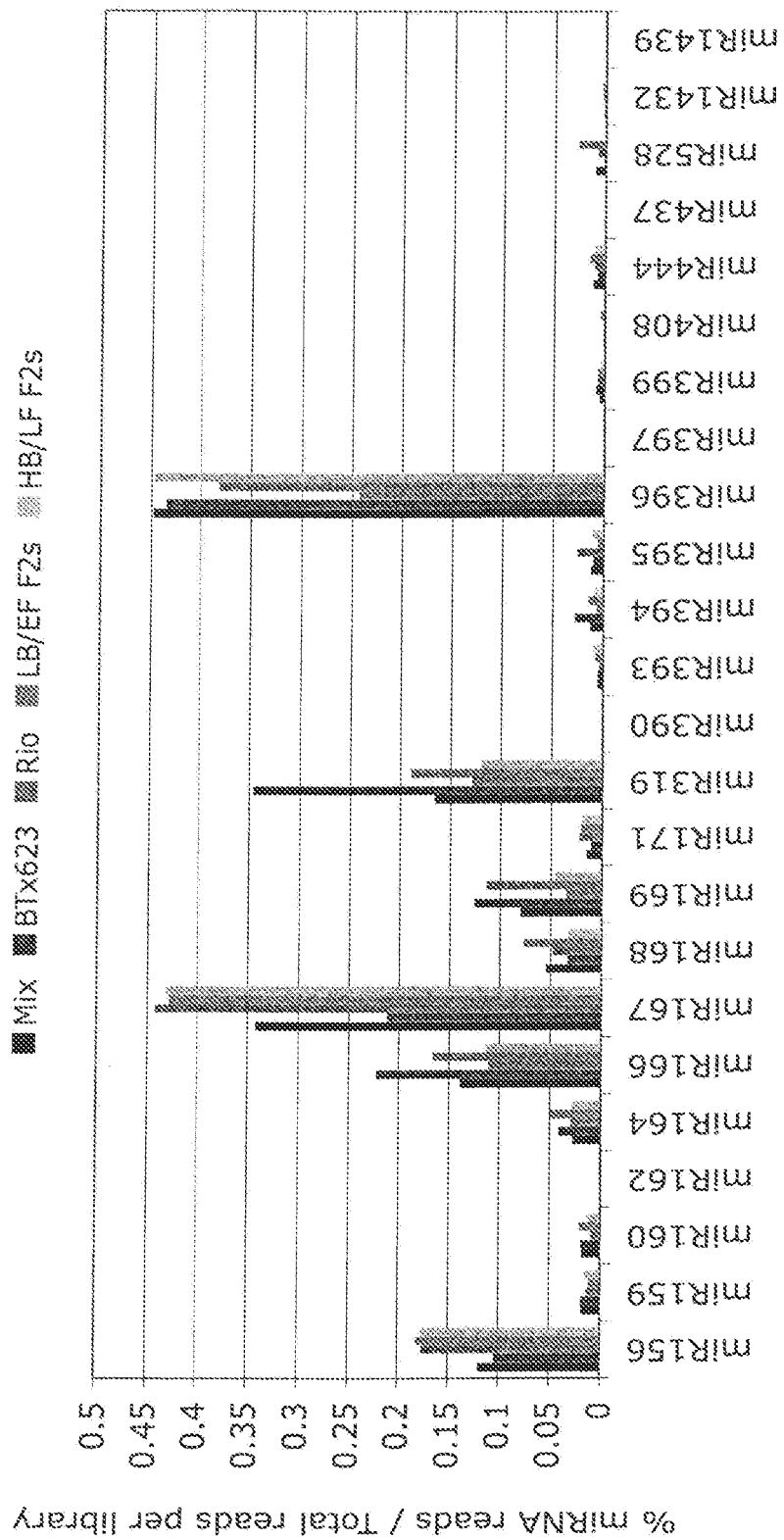

The most abundantly expressed miRNA family was miR172 (FIG. 3A), comprising almost 6% of the total reads with perfect match to the BTx623 genome. The rest of the known miRNAs had abundances below 0.5% (FIGS. 3B and

TABLE A 25 nt Hotspots in the *Sorghum* Genome

| Position | Length (bp) | N° of 25 nt reads | Annotation (Phytosome) | BLAST nucleotide collection (n/r n/t) hit | E-value | Identity |
|---|---|---|---|---|---|---|
| Library: Mix | | | | | | |
| Ch3: 72749847 ... 72749881 | 35 | 9381 | Intergenic | *Sorghum bicolor* strain b2 internal transcribed spacer 1 5.8S rRNA | 5E−10 | 100% |
| Ch1: 31857437 ... 31857496 | 60 | 5652 | Intergenic | *Sorghum bicolor* strain b2 internal transcribed spacer 1 5.8S rRNA | 2E−22 | 100% |
| Ch5: 36051996 ... 36052067 | 72 | 4689 | Intergenic | *Sorghum bicolor* strain b2 internal transcribed spacer 1 5.8S rRNA | 7E−29 | 100% |
| Ch10: 657846 ... 657883 | 38 | 3106 | Intergenic | *Arabidopsis thaliana* At5g59055 tRNA | 2E−09 | 97% |
| Ch5: 35985593 ... 35985714 | 122 | 2882 | Intergenic | *Sorghum bicolor* strain b2 internal transcribed spacer 1 5.8S rRNA | 4E−61 | 100% |
| Ch5: 35931714 ... 35931863 | 150 | 2369 | Intergenic | *Sorghum bicolor* strain b2 internal transcribed spacer 1 5.8S rRNA | 1E−77 | 100% |
| Ch3: 59743725 ... 59743785 | 61 | 1956 | Intergenic | *Arabidopsis thaliana* At5g40545 tRNA | 1E−15 | 93% |
| Ch5: 35976201 ... 35976253 | 53 | 1691 | Intergenic | *Setaria italica* genes for 25S rRNA, IGS and 17S rRNA | 5E−18 | 98% |
| Ch8: 47608635 ... 47608659 | 25 | 1352 | Intergenic | *Arabidopsis thaliana* At4g34975 tRNA | 2E−04 | 100% |
| Library: BTx623 | | | | | | |
| Ch3: 72749848 ... 72749881 | 34 | 3321 | Intergenic | *Sorghum bicolor* strain b2 internal transcribed spacer 1 5.8S rRNA | 2E−09 | 100% |
| Ch5: 36052031 ... 36052067 | 37 | 3111 | Intergenic | *Sorghum bicolor* strain b2 internal transcribed spacer 1 5.8S rRNA | 4E−11 | 100% |
| Ch5: 35931716 ... 35931758 | 43 | 2709 | Intergenic | *Sorghum bicolor* strain b2 internal transcribed spacer 1 5.8S rRNA | 1E−14 | 100% |
| Ch5: 35985655 ... 35985705 | 51 | 2287 | Intergenic | *Sorghum bicolor* strain b2 internal transcribed spacer 1 5.8S rRNA | 2E−17 | 100% |
| Ch1: 31853286 ... 31863315 | 30 | 1231 | Intergenic | *Oryza brachyantha* 26S-18S rRNA intergenic spacer | 3E−07 | 100% |
| Ch5: 35997943 ... 35997972 | 30 | 1227 | Intergenic | *Oryza brachyantha* 26S-18S rRNA intergenic spacer | 3E−07 | 100% |
| Ch5: 35976205 ... 35976252 | 48 | 1117 | Intergenic | *Avena sativa* rDNA spacer | 7E−07 | 100% |
| Library: Rio | | | | | | |
| Ch3: 72749847 ... 72749881 | 35 | 6727 | Intergenic | *Sorghum bicolor* strain b2 internal transcribed spacer 1 5.8S rRNA | 5E−10 | 100% |
| Ch5: 36052031 ... 36052067 | 37 | 5457 | Intergenic | *Sorghum bicolor* strain b2 internal transcribed spacer 1 5.8S rRNA | 4E−11 | 100% |
| Ch5: 35931716 ... 35931758 | 43 | 5622 | Intergenic | *Sorghum bicolor* strain b2 internal transcribed spacer 1 5.8S rRNA | 1E−14 | 100% |
| Ch5: 35985655 ... 35985713 | 59 | 4104 | Intergenic | *Sorghum bicolor* strain b2 internal transcribed spacer 1 5.8S rRNA | 8E−22 | 100% |
| Ch5: 35976203 ... 35976252 | 50 | 1583 | Intergenic | *Avena sativa* rDNA spacer | 7E−17 | 100% |
| Ch4: 50861835 ... 50861859 | 25 | 1362 | Intergenic | *Arabidopsis thaliana* At5g46595 tRNA | 2E−04 | 100% |
| Ch5: 35981272 ... 35981333 | 62 | 1282 | Intergenic | *Setaria italica* genes for 25S rRNA, IGS and 17S rRNA | 9E−22 | 98% |
| Library: LB/EF F2s | | | | | | |
| Ch3: 72749845 ... 72749881 | 37 | 23470 | Intergenic | *Sorghum bicolor* strain b2 internal transcribed spacer 1 5.8S rRNA | 4E−11 | 100% |
| Ch1: 31857435 ... 31857497 | 63 | 14104 | Intergenic | *Sorghum bicolor* strain b2 internal transcribed spacer 1 5.8S rRNA | 5E−24 | 100% |
| Ch5: 36051996 ... 36052068 | 73 | 12057 | Intergenic | *Sorghum bicolor* strain b2 internal transcribed spacer 1 5.8S rRNA | 2E−29 | 100% |
| Ch5: 35985593 ... 35985716 | 124 | 7413 | Intergenic | *Sorghum bicolor* strain b2 internal transcribed spacer 1 5.8S rRNA | 2E−57 | 100% |
| Ch4: 50861834 ... 50861859 | 26 | 6443 | Intergenic | *Arabidopsis thaliana* At5g46595 tRNA | 6E−05 | 100% |
| Ch5: 35931708 ... 35931865 | 158 | 5861 | Intergenic | *Sorghum bicolor* strain b2 internal transcribed spacer 1 5.8S rRNA | 4E−75 | 100% |
| Ch8: 47608634 ... 47608659 | 26 | 3034 | Intergenic | *Arabidopsis thaliana* At4g34975 tRNA | 6E−05 | 100% |
| Ch5: 35937803 ... 35937851 | 49 | 3007 | Intergenic | *Avena sativa* rDNA spacer | 4E−18 | 100% |
| Ch3: 59743724 ... 59743785 | 62 | 2116 | Intergenic | *Arabidopsis thaliana* At5g40545 tRNA | 3E−17 | 93% |
| Library: HB/LF F2s | | | | | | |
| Ch3: 72749845 ... 72749881 | 37 | 22694 | Intergenic | *Sorghum bicolor* strain b2 internal transcribed spacer 1 5.8S rRNA | 4E−11 | 100% |
| Ch1: 31857433 ... 31857497 | 65 | 13314 | Intergenic | *Sorghum bicolor* strain b2 internal transcribed spacer 1 5.8S rRNA | 4E−25 | 100% |
| Ch5: 36051996 ... 36052068 | 73 | 11712 | Intergenic | *Sorghum bicolor* strain b2 internal transcribed spacer 1 5.8S rRNA | 2E−29 | 100% |
| Ch4: 50861834 ... 50861859 | 26 | 8290 | Intergenic | *Arabidopsis thaliana* At5g46595 tRNA | 6E−05 | 100% |
| Ch5: 35985593 ... 35985718 | 126 | 7099 | Intergenic | *Sorghum bicolor* strain b2 internal transcribed spacer 1 5.8S rRNA | 1E−58 | 100% |
| Ch5: 35931708 ... 35931863 | 156 | 5796 | Intergenic | *Sorghum bicolor* strain b2 internal transcribed spacer 1 5.8S rRNA | 4E−75 | 100% |
| Ch8: 47608634 ... 47608659 | 26 | 3415 | Intergenic | *Arabidopsis thaliana* At4g34975 tRNA | 6E−05 | 100% |
| Ch5: 35976201 ... 35976260 | 60 | 2976 | Intergenic | *Setaria italica* genes for 25S rRNA, IGS and 17S rRNA | 5E−20 | 98% |
| Ch3: 59743724 ... 59743785 | 62 | 2372 | Intergenic | *Arabidopsis thaliana* At5g40545 tRNA | 3E−17 | 93% |

Figure 4A:
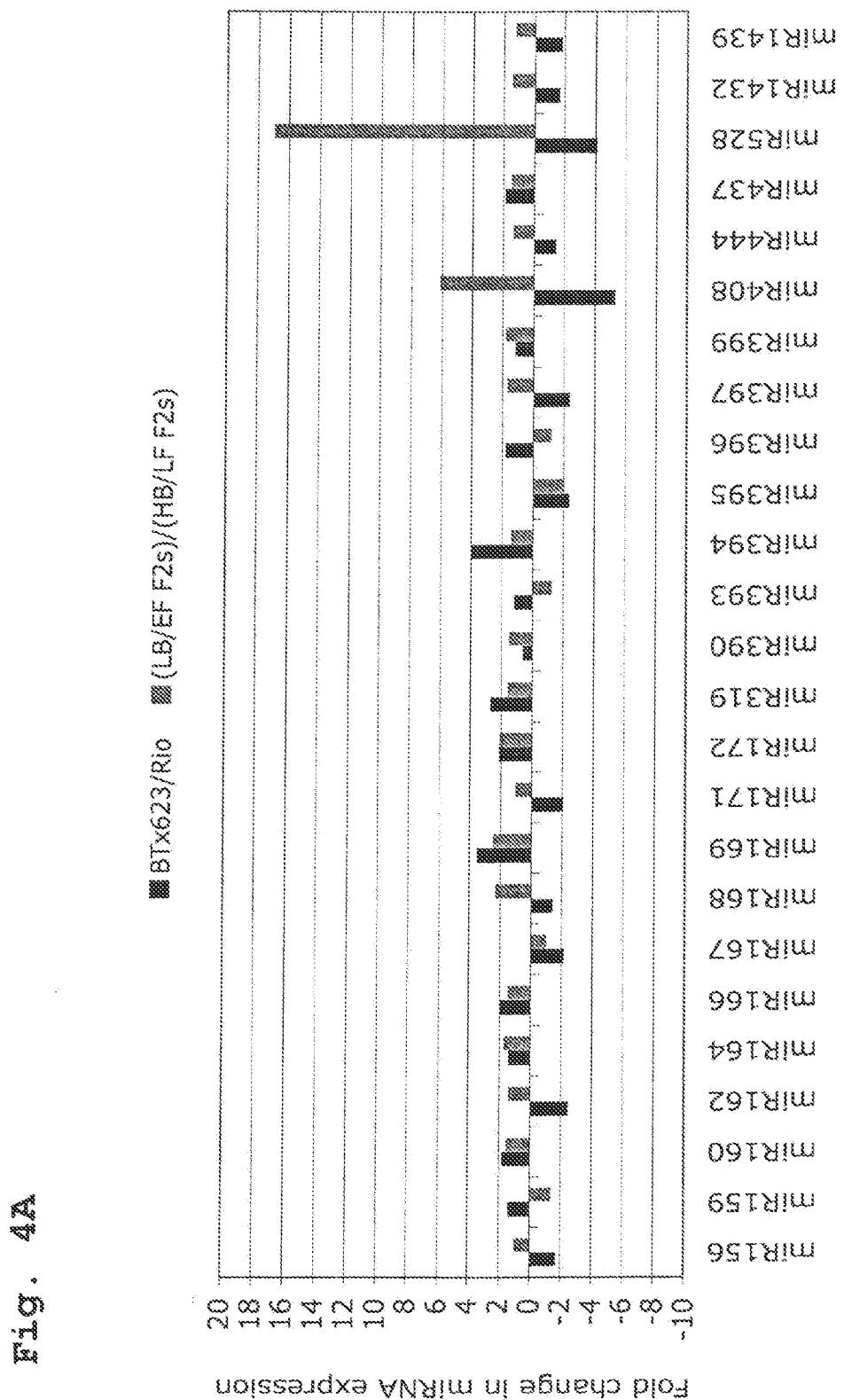
FIG. 4. Allelic variation in miRNA expression. The miRNA abundances were used to calculate their relative fold change in expression between BTx623 and Rio, and between the LB/EF F2s and HB/LF F2s libraries, respectively. Positive values in the y-axis of the graph denote fold changes in miRNA expression that are higher in BTx623 relative to Rio and higher in LB/EF F2s relative to HB/LF F2s libraries, respectively; the opposite is true for negative values. (A) The expression of miR169 and miR172 was at least twice as high in BTx623 relative to that in Rio and this difference was inherited in the F2. The opposite was true for miR395 expression. (B-D) Quantification of miRNA expression through Taqman Assay in pools of F2 plants with similar flowering time (10-11 leaves) but different sugar content (Brix 3-5 vs Brix 13-16). (B) High expression of miR169d in BTx623 relative to Rio correlates with low Brix in the F2 independently of flowering time. (C-D) F2 plants with similar flowering time display no differences in miR395f and miR172a expression regardless Brix degree. (E) The allelic variation in the expression of seven new miRNAs between BTx623 and Rio was inherited in the F2 plants selected. (F) The frequency count of small RNAs for each new miRNA was used to calculate its abundance. (G) The miRNA abundances were used to calculate their relative fold change in expression between BTx623 and Rio, and between the LB/EF F2s and HB/LF F2s libraries, respectively. Positive values in the y-axis of the graph denote fold changes in miRNA expression that are higher in BTx623 relative to Rio and higher in LB/EF F2s relative to HB/LF F2s libraries, respectively; the opposite is true for negative values. The miRNA "chromosome_4_684.BC_01" was not included in the graph because it was not detected in the Rio library.

Allelic Variation in the Expression of Known miRNAs Between Grain and Sweet *Sorghum* Correlated with Sugar Content and Flowering Time The sequencing consortium of the *sorghum* genome identified 149 predicted miRNAs (5), and we could detect the expression of 110 of them based on the following criteria: a miRNA was considered expressed only if its sequencing reads were detected in at least three libraries and with a 3C). When the ratio of miRNA abundances between the BTx623 and Rio libraries was compared to the ratio between the LB/EF F2s and HB/LF F2s libraries, we could identify miRNA families whose expression differences between the parents were inherited in the F2 plants (FIG. 4A). Considering a cutoff level of two-fold change in miRNA expression, we found that miR169 and miR172 were expressed higher in BTx623 relative to Rio, and higher in LB/EF F2s compared to HB/LF F2s. This means that high expression of these miR- NAs in BTx623 correlated with low Brix and early flowering in the F2 plants selected, and the opposite was true for miR395 (FIG. 4A).

Figure 4B:
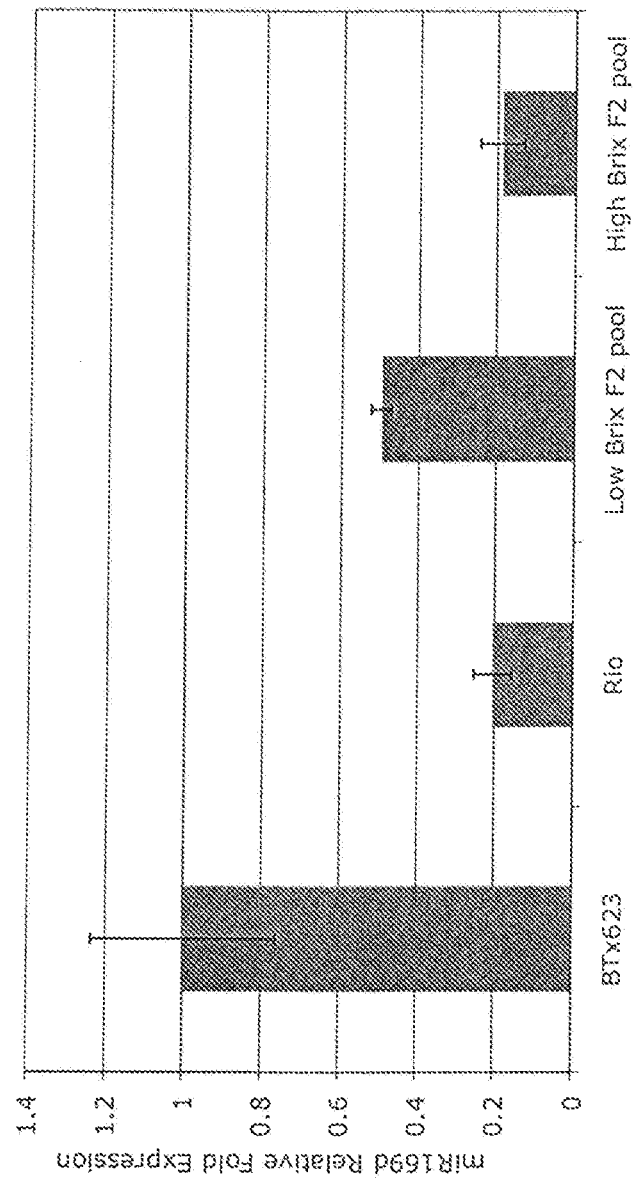
Figure 4C:
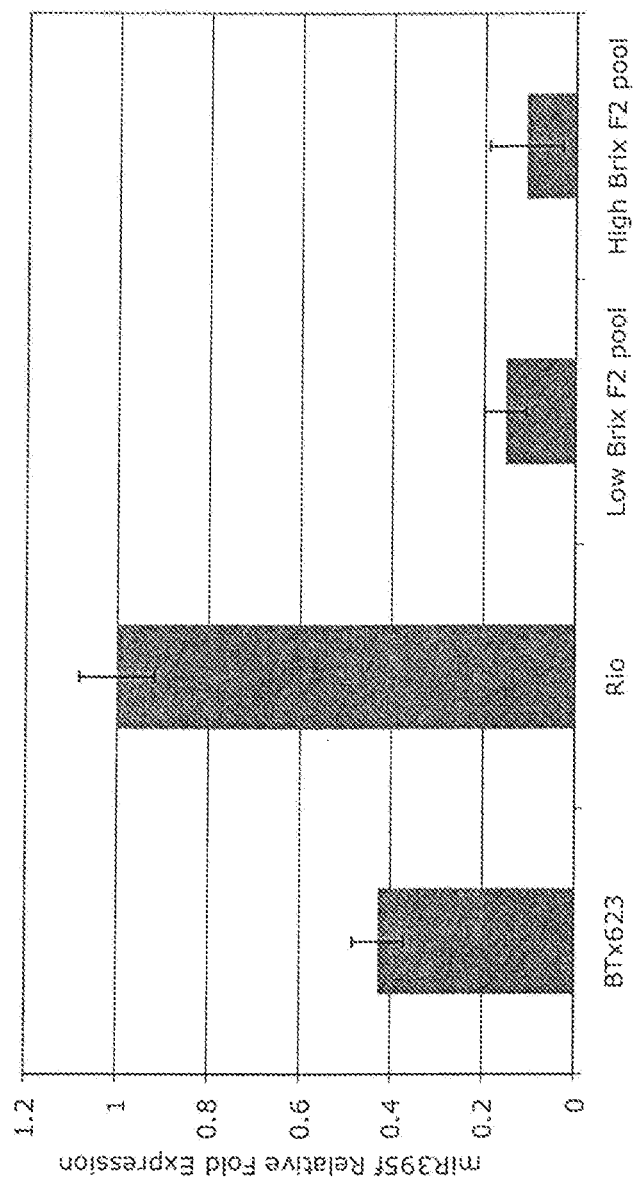
Figure 4D:
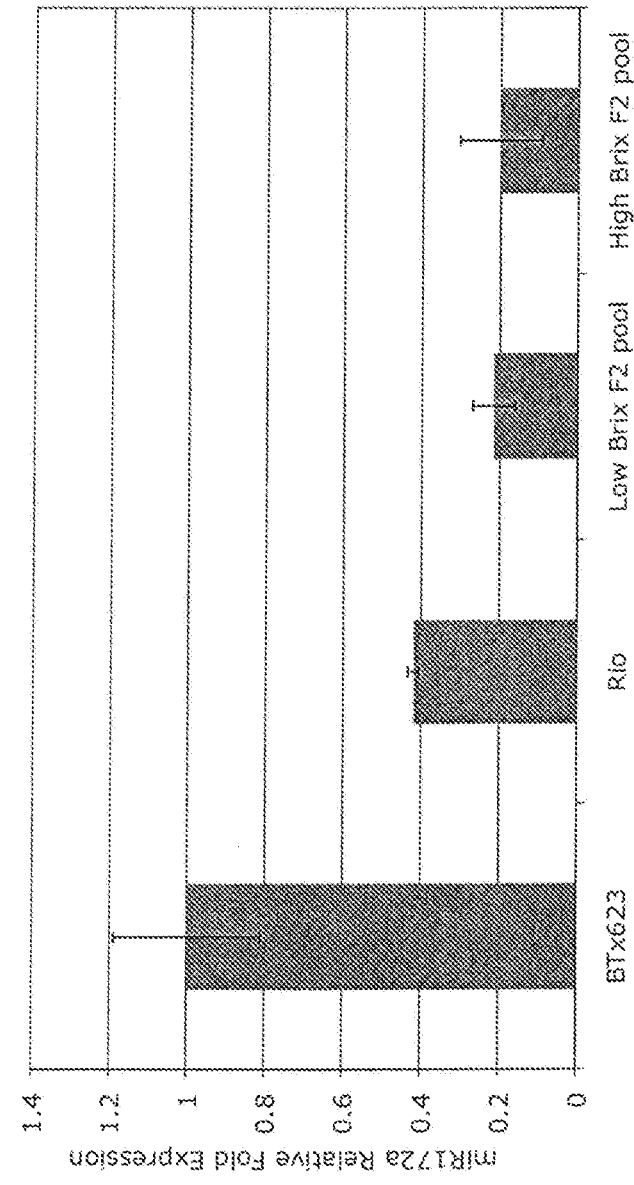
Figure 4F:
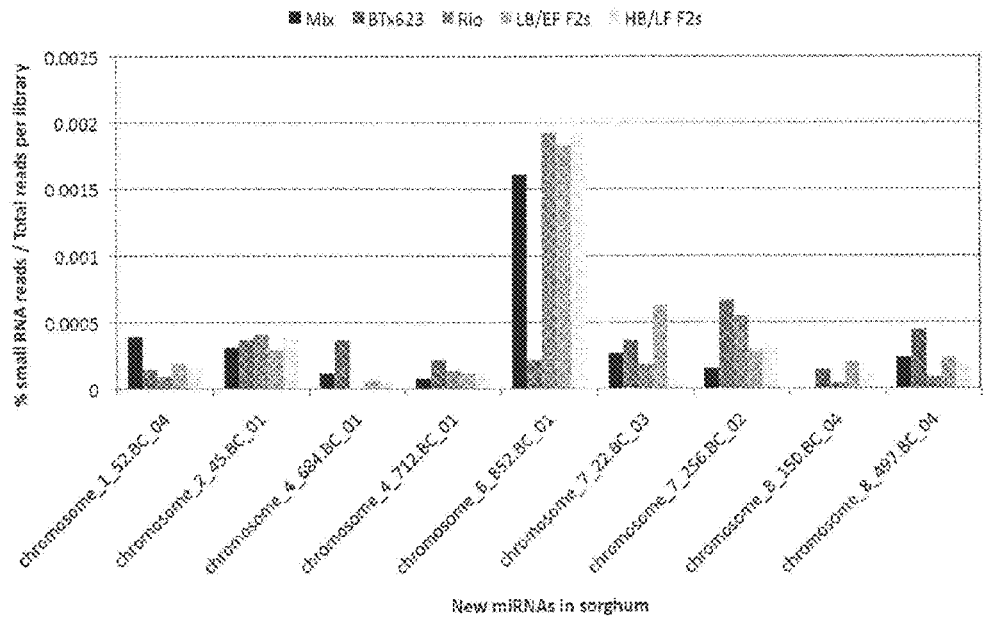
Figure 4G:
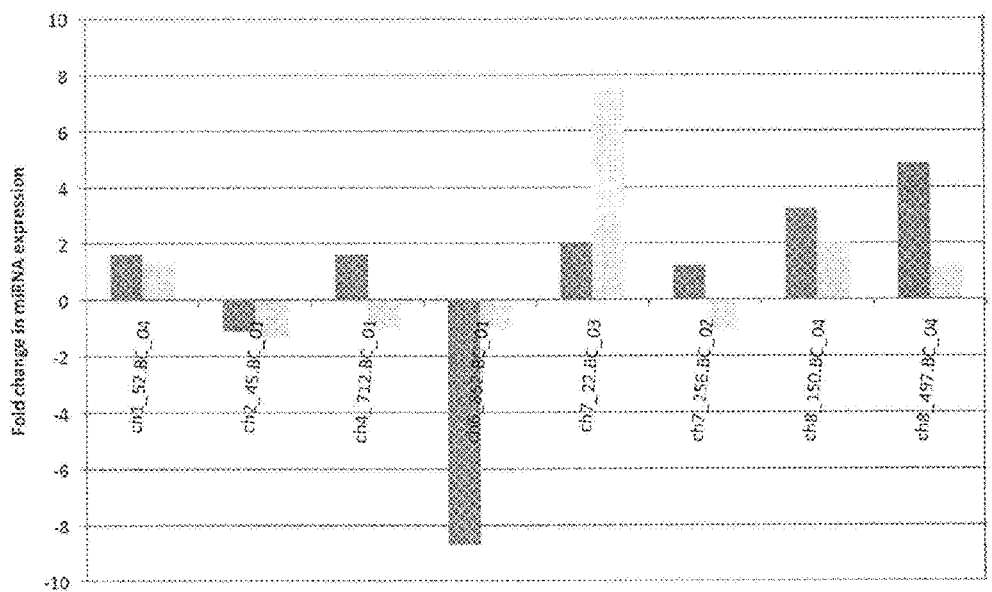

The observation that high expression of miR172 correlated with early flowering is consistent with the reported role of this miRNA in the promotion of flowering (17-21). Although miR169 and miR395 have known roles in drought stress and sulphur starvation, respectively (22, 23), our data suggested a novel function for these miRNAs in sugar accumulation and flowering time. Since the pool of F2 plants used for library construction were selected based on both phenotypes, it was not possible to assign the expression inheritance pattern of both miRNAs to either sugar accumulation or flowering time alone. For this reason, additional plants from the same F2 population differing in sugar content but with similar flowering time were selected and the expression of a representative member from each miRNA family, miR169d and miR395f respectively, was quantified using the TaqMan assay. We found that high expression of miR169d in BTx623 correlated with low Brix (FIG. 4B). This suggested that high expression levels of miR169 might lead to a reduction in stem sugar content regardless of flowering time. Surprisingly, high expression of miR395f in Rio relative to that in BTx623 did not correlate with sugar content in F2 plants (FIG. 4C). This indicates that high expression of miR395 would be required for flowering regardless of sugar content in the stem. Consistent with the role of miR172 in flowering, we did not observe any difference in the expression of miR172a in F2 plants with the same flowering time but different Brix (FIG. 4D).

Figure 5A:
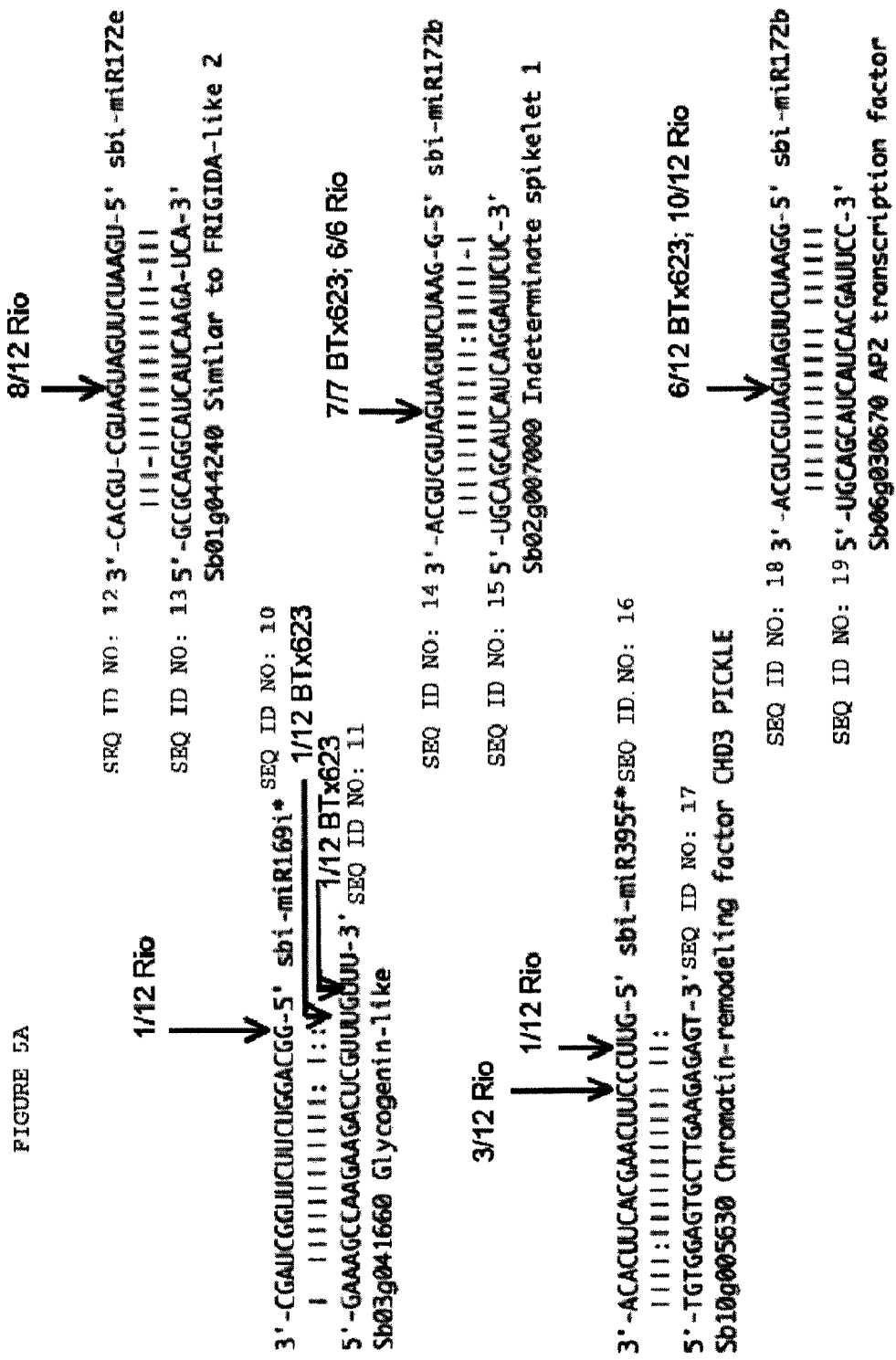
FIG. 5. Mapping of miRNA-guided cleavage sites in predicted target genes. The locations of the miRNA-cleavage sites are indicated with downward arrows and the frequency of the cleavages are indicated as the number of clones for each RACE product with respect to the total clones sequenced. (A) Validation of cleavage for target genes mediated by known miRNAs. (B) Validation of cleavage for target genes mediated by newly predicted miRNAs.

In summary, high expression of miR172 in BTx623 correlated with early flowering in the F2, whereas the opposite was true for miR395, high expression of this miRNA in Rio correlated with late flowering in the F2 plants selected. Regarding sugar content in the stem, high expression of miR169 in BTx623 correlated with low Brix in the F2 plants selected.
Genes Related to Sugar Metabolism and Flowering Time were Targets of miR169* and miR395*, Respectively The expression of miR169* was detected for all MIR169 gene copies except MIR169e and MIR169j (see our genome browser muesli.rutgers.edu/cgi-bin/gbrowse/sbicTest/. To our surprise, genes such as STARCH SYNTHASE isoform and GLYCOGENIN-like were identified as novel targets of miR169b* and miR169i* respectively (Table 2). In fact, the predicted miR169i*-mediated cleavage of the GLYCOGENIN-like mRNA was experimentally validated (FIG. 5). In animals, bacteria and yeast, carbon is stored as glycogen, and the priming molecules for glycogen biosynthesis are called glycogenins (24). Glycogen is the analogous form of starch in plants (25) but whether glycogenin-like proteins in plants are involved in starch biosynthesis is not clear (25). Our data provided the first evidence linking the MIR169 gene with carbohydrate metabolism.

We detected the expression of the miRNA* for all MIR395 gene copies. In addition, miR395* was expressed at higher levels relative to miR395. See our genome browser at muesli.rutgers.edu/cgi-bin/gbrowse/sbicTest/. Although miR395 has already a known role in sulfur starvation (23), the genes EMBRYONIC FLOWER 2 (EMF2), PICKLE (PKL) and CRYPTOCHROME 2 (CRY2) were identified as predicted targets of miR395f* and the cleavage product was confirmed for PKL (Table 2 and FIG. 5). All three genes have a role in the regulation of flowering time (26-31), but in addition EMF2 and PKL were also implicated in the repression of embryonic traits in *Arabidopsis* (26, 28, 30, 31). Thus, our data suggested for the first time a possible role of the MIR395 gene in the regulation of flowering time.

Figure 6:
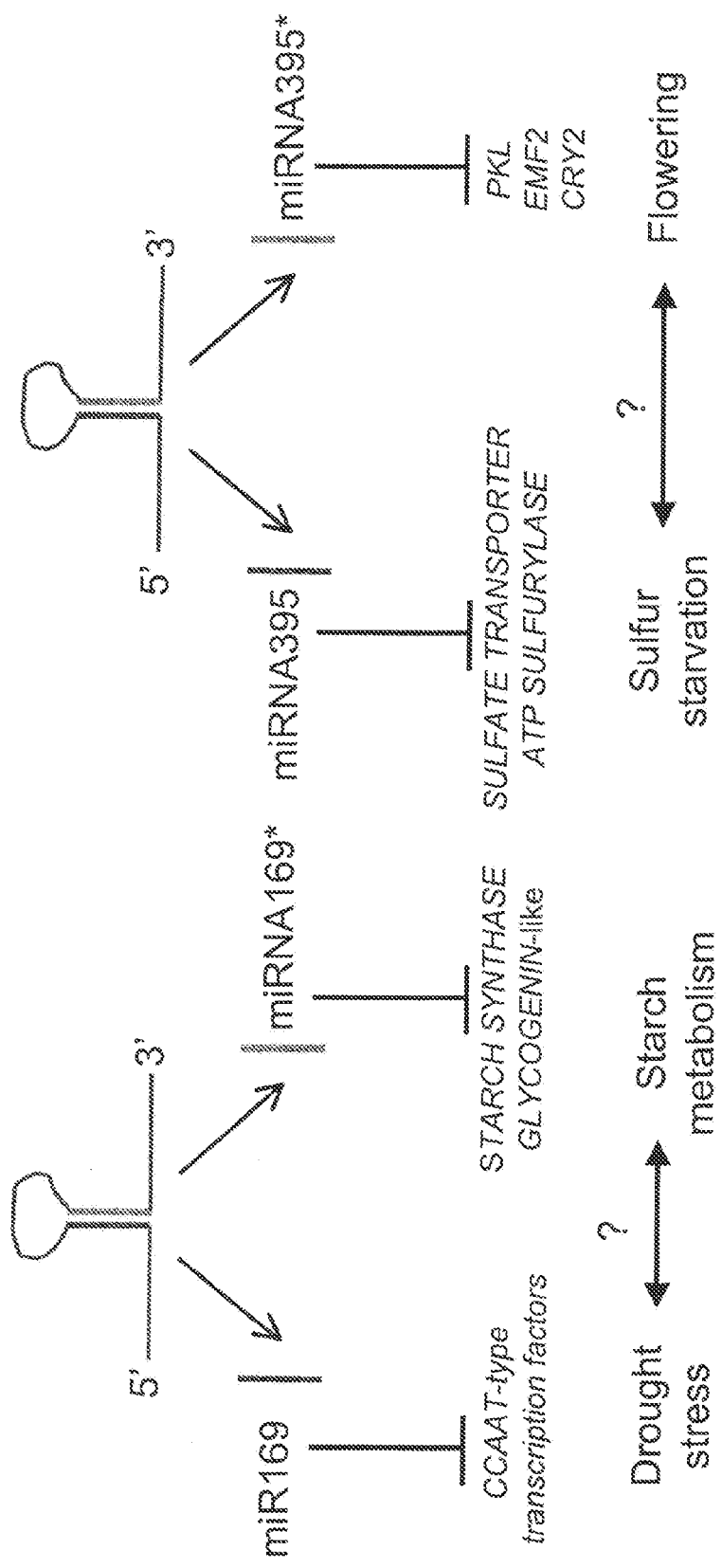
FIG. 6. Model describing the dual role of miR169 in drought stress and starch metabolism, and miR395 in sulfur starvation and flowering time. Through the selective production of miRNA/miRNA* species, a single miRNA could potentially regulate two different metabolic processes through the targeting of completely different classes of genes. The question marks symbolize the possibility of an interaction between drought and starch metabolism and sulfur and flowering respectively.

In summary, any given miRNA could potentially link two seemingly unrelated biological processes through the selective production of miRNA/miRNA* species (FIG. 6).

Figure 7:
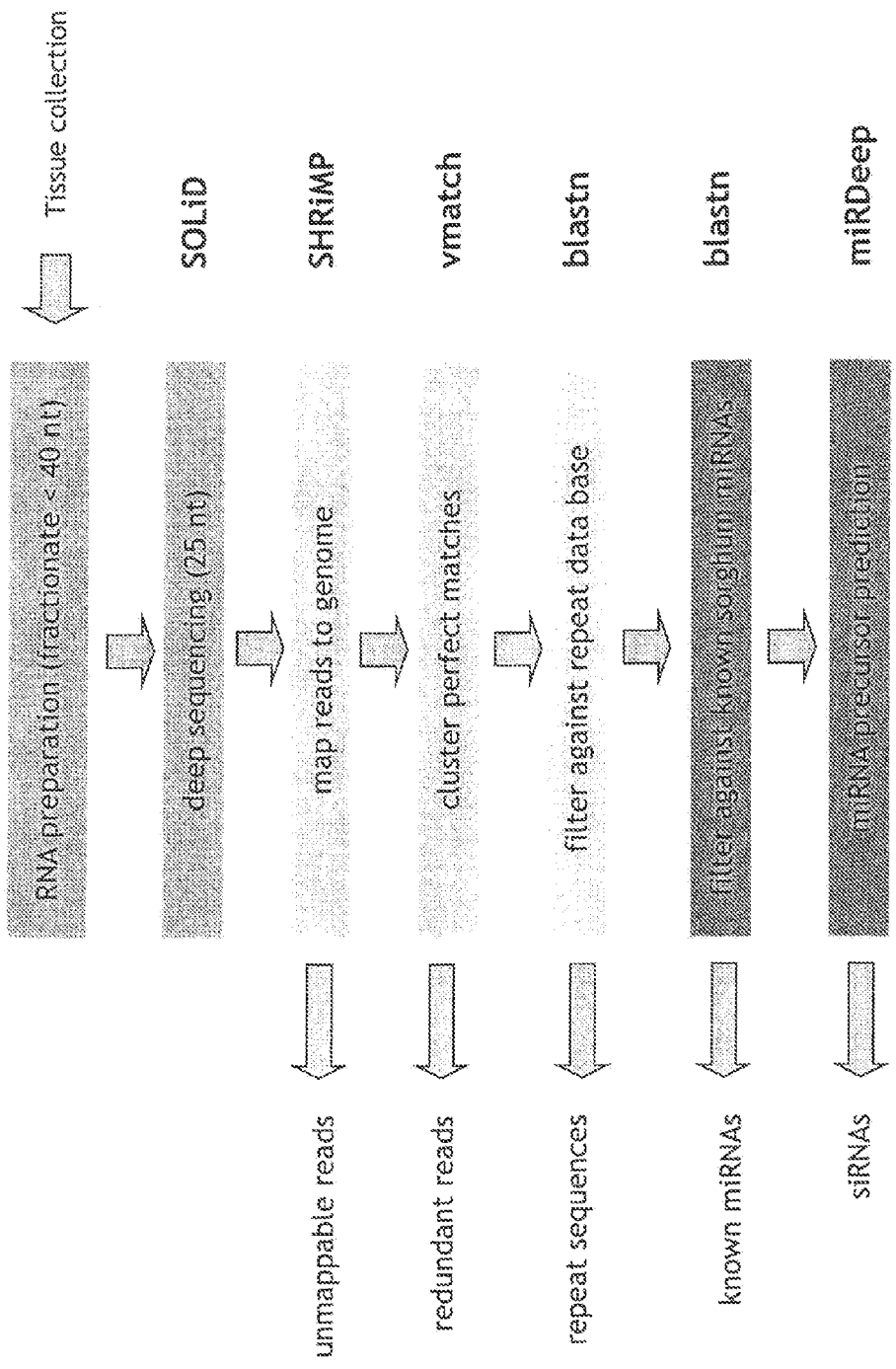
FIG. 7. Pipeline used for the de novo miRNA detection. All reads from SOLiD sequencing were mapped in colorspace to the *sorghum* genome using SHRiMP. Perfect matching reads were clustered with Vmatch then filtered against the *sorghum* repeat sequences and compared with known *sorghum* miRNAs to classify them. The remaining sequences were taken for de novo miRNA prediction using miRDeep.

In the case of miR172, we detected cleavage products for the genes INDETERMINATE SPIKELET 1 (IDS1) and an AP2 transcription factor (Table 2 and FIG. 5). In addition, a FRIGIDA-like 2 (FRL2) and a TYPE A RESPONSE REGULATOR 3 (RR3) were predicted as novel targets of miR172 (Table 2), being the cleavage product of FRL2 experimentally validated, too. The FRIGIDA-related genes are a major determinant of natural variation in the winter-annual habit between *Arabidopsis* accessions (32, 33), whereas the TYPE A RESPONSE REGULATOR 3 (ARR3) has a function in the circadian clock (34). Although *sorghum* is a crop from semi-arid regions (5), the miR172-mediated post-transcriptional regulation of FRL2 could have a role in the adaptation of *sorghum* to temperate climates. Consistent with this, a role of miR172 in the regulation of flowering time by ambient temperature in *Arabidopsis* has been recently described (35).
New miRNAs Targeting Flowering and Sugar Related Genes The miRDeep pipeline was adapted for de novo detection of miRNAs in *sorghum* (FIG. 7), and 223 new miRNA candidate genes were predicted (for a complete list of the new miRNAs refer to Tables C and G, and for their mature sequence and predicted gene targets refer to FIGS. 8-10). All predicted 223 miRNAs met the expression criteria used above for known miRNAs (Table D). Their expression abundance was very low, with the highest miRNA expression comprising only 0.08% of the BTx623 library. From all miRNAs that were expressed in *sorghum* stems, 19 of them were found to be within introns of protein coding genes (mirtrons), these included miR172c and miR437g, together with other 17 mirtrons from de novo predicted miRNAs (Table E).

Figure 3C:
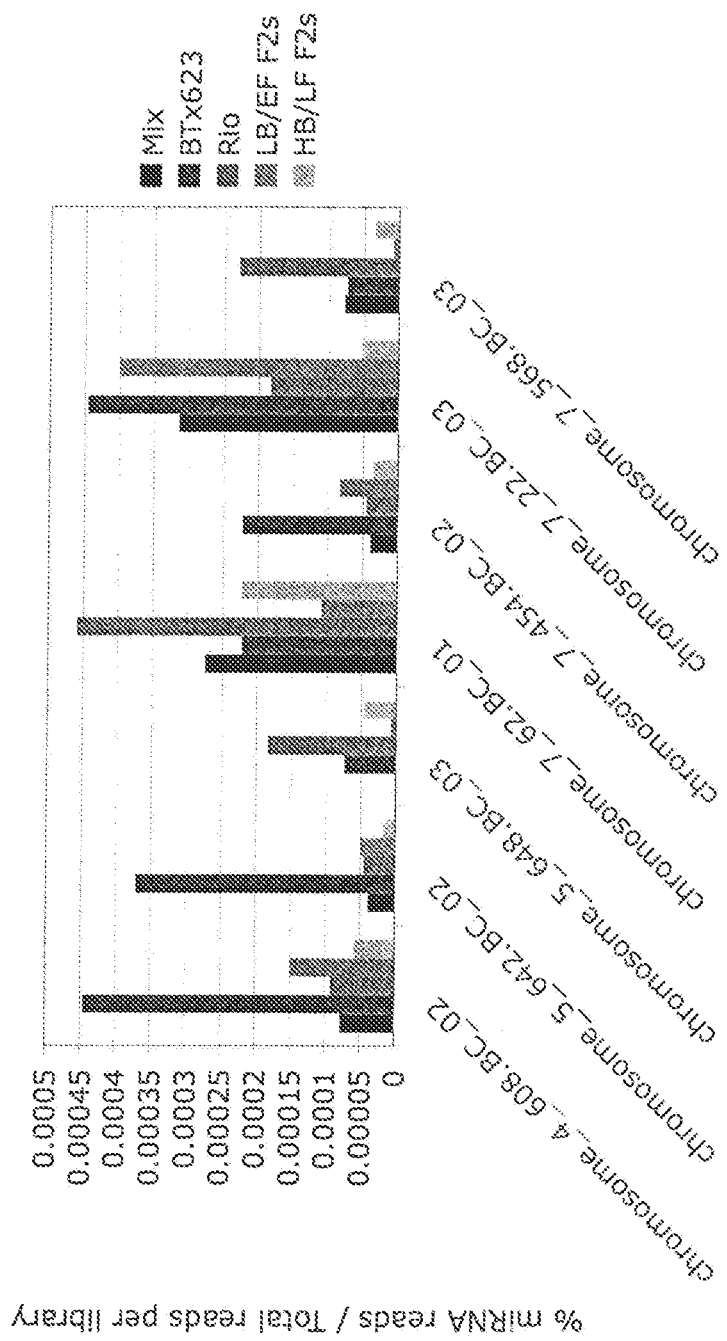

We were able to identify 7 miRNAs whose allelic variation in expression between BTx623 and Rio were inherited in the F2 offsprings (FIG. 4E and FIG. 3C). For three of them (chromosome_5_642.BC_02; chromosome_5_648.BC_03 and chromosome_7_568.BC_03), we could not find any putative target. For the remaining four miRNAs, their predicted target genes included an SNF2-type chromatin remodeling transcription factor (chromosome4_608.BC_02), an arbutin synthase glycosyltransferase and a cellulose synthase gene (chromosome_7_22.BC_03). Regarding miRNAs, whose expression levels did not differ between BTx623 and Rio or differed but the expression pattern was not inherited in the F2 generation, we identified 9 miRNAs whose predicted targets were involved in the regulation of flowering time and 14 miRNAs whose predicted targets were involved in carbohydrate metabolism (Table 3). We also identified new miRNAs having as predicted targets sugar transporters and cell wall-related genes (Table F).

Overall, we identified 223 putative miRNAs in total, from which 7 of them displayed allelic differences in expression that were inherited in F2 progeny. Additionally, several miRNAs had as predicted targets, genes involved in traits highly relevant for biofuel applications such as flowering time, carbohydrate and cell wall metabolism.
Several miRNAs and/or Their Targets Co-localized with Previously Reported QTLs for Brix and Flowering Time in *Sorghum*

Several regions in the *sorghum* genome have recently been identified as QTLs for Brix and flowering time (7, 8, 36). For example, a recombinant inbred line (RIL) population derived from BTx623 and Rio, the same lines as in this study, was used to detect QTLs for Brix on chromosomes 3, 6, and 7, respectively (7). The QTL on chromosome 3 had the greatest effect on Brix, explaining 25% of the trait variance, whereas the QTL on chromosome 7 contributed 14%, respectively (7). Interestingly, several miRNAs and/or their targets genes identified in this study, co-localized with the nearest simple sequence repeat (SSR) markers of published Brix QTLs (FIG. S8A). For example, several targets predicted for miR169abi* co-localized with the Brix QTL on chromosome 3 (FIG. 11), together with a FRUCTOKINASE 1 (FRK1) gene as predicted target of the miRNA chromosome4_712_mature.BC_01. Furthermore, the miRNA-mediated cleavage of FRK1 mRNA could also be experimentally demonstrated (FIG. 5B). In addition, the miR169 family members miR169cd and miR1691mn co-localized with the Brix QTLs on chromosomes 6, and 7, respectively.

Figure 11A:
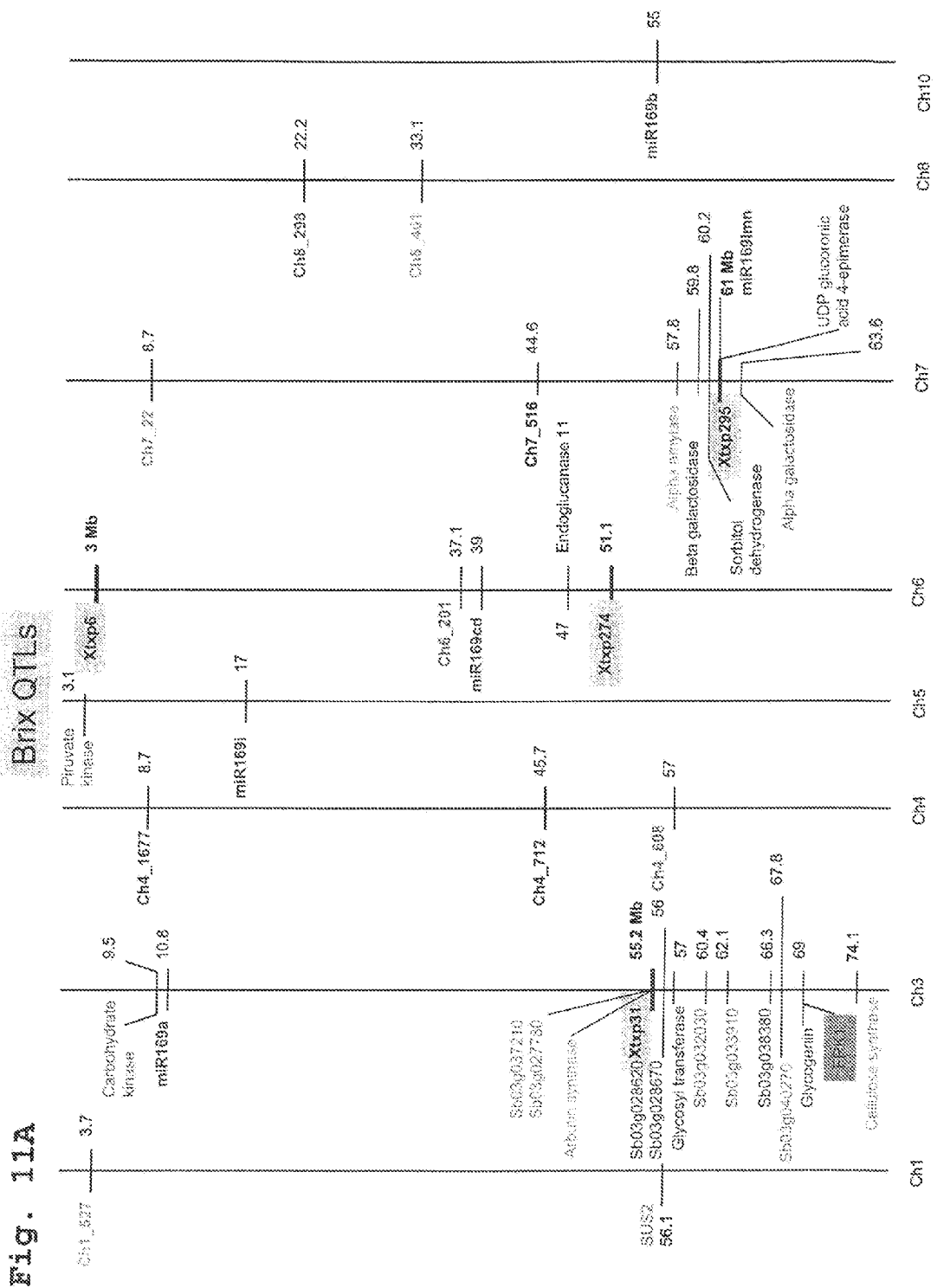
FIG. 11. The miRNAs and/or their targets co-localize with previously reported QTLs for sugar content and flowering time. The simple sequence repeats (SSRs) markers (named Xtxp) nearest to the previously reported flowering and Brix QTLs derived from a BTx623 x Rio RIL population (8), were placed in the BTx623 physical map and are shown in black and shaded yellow (Brix), and black and shaded orange (flowering), respectively. The markers Xtxp6 and Xtxp274 on chromosome 6 are flanking the QTL for Brix and flowering in the center. The miRNAs (in bold) and their target genes are shown in the same color. The genes targeted by two different miRNAs are shown in color font and shaded color. (A) Co-localization of miRNAs and their target genes with SSRs markers near Brix QTLs. (B) Co-localization of miRNAs and their targets genes with SSRs markers near flowering time QTLs.
Figure 11B:
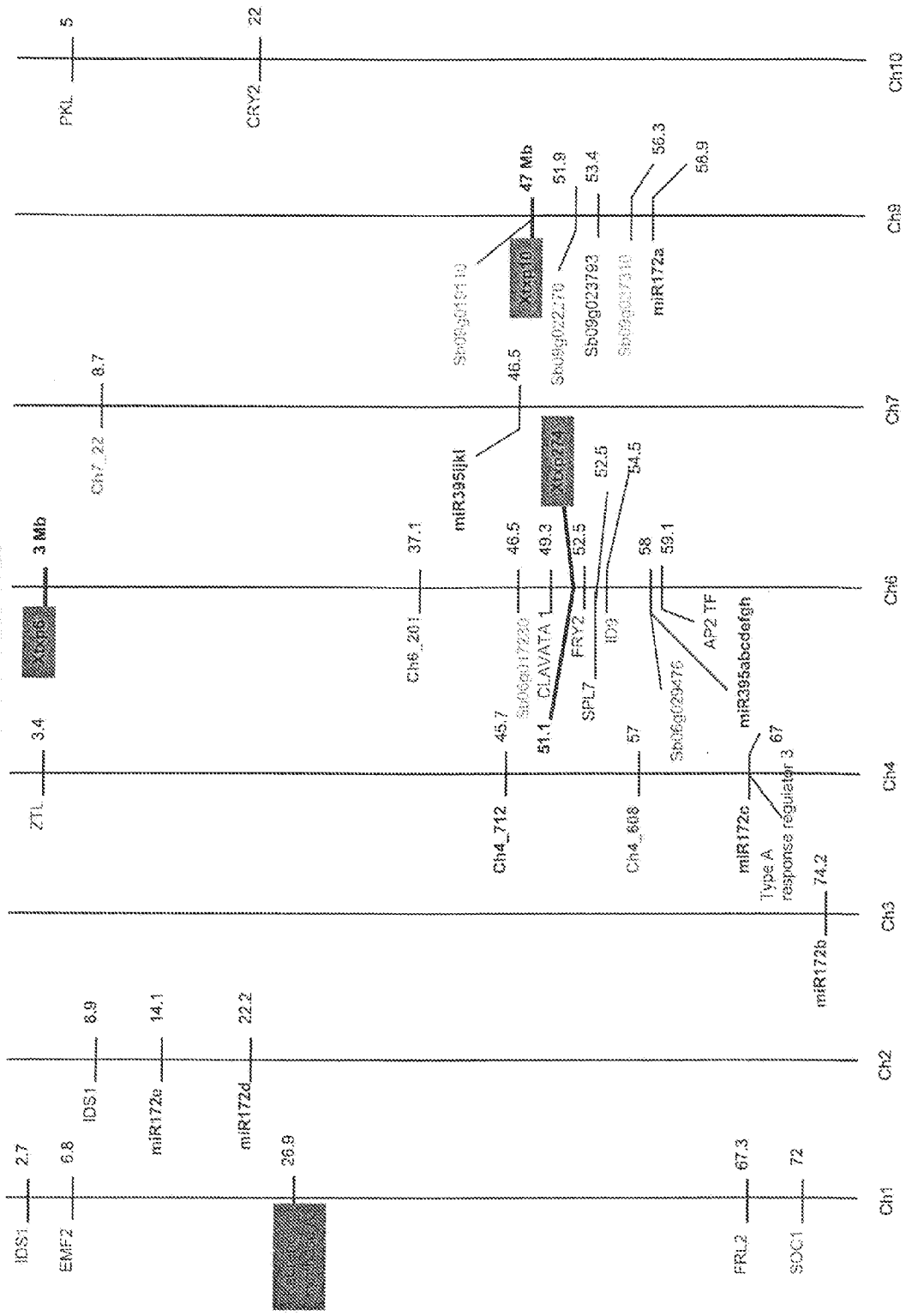

QTLs for flowering time in BTx623 and Rio, have been detected on chromosomes 6 and 9 (7). As with the Brix QTLs, several miRNAs and/or their predicted targets co-localized with SSR markers near these two QTLs (FIG. 11B). On chromosome 6, several miR172 targets as well as seven members of the MIR395 family including MIR395f are located near a QTL for flowering. In addition, MIR172a co-localized with the QTL for flowering on chromosome 9 (FIG. 11B).

Although a positive relationship between high sugar content and flowering time had been described in *sorghum* (8), the molecular mechanism remained unclear. In this work we could identify three miRNAs (ch4_712_mature.BC_01; ch6_201_mature.BC_02 and ch9_1189.mature.BC_09) that had predicted target genes involved in flowering and carbohydrate metabolism (Table 3). For example, ch6_201_mature.BC_02 had as predicted targets the clock gene ZEITLUPE (ZTL) and the flowering gene SUPPRESSOR OF CONSTANS 1 (SOC1), as well as the SUCROSE SYNTHASE 2 (SUS2) gene and we could experimentally validate their miRNA-mediated cleavage (FIG. S3B). Furthermore, this miRNA co-localized with a Brix and flowering QTL on chromosome 6 (FIGS. 11A and 11B).

In summary, the genomic location for several members of the MIR169, MIR172 and MIR395 gene families, and/or their predicted target genes co-localized with previously reported QTLs for Brix and flowering time, respectively. The same was true for many newly discovered miRNAs.

TABLE 2

Predicted targets of miR169, miR172 and miR395

| miRNA | Target gene | Gene function | Target site |
|---|---|---|---|
| sbi-miR169acdi | Sb08g021910 | CCAAT-binding transcription factor subunit B | 3' UTR |
| sbi-miR169cd | Sb05g026273 | GRAS family transcription factor | Exon |
| sbi-miR169bcdefgh | Sb01g045500 | CCAAT-binding transcription factor subunit B | 3' UTR |
| sbi-miR169efghi | Sb01g011220 | CCAAT-binding transcription factor subunit B | 3' UTR |
| sbi-miR169i | Sb02g003070 | TCP family transcription factor | 3' UTR |
| sbi-miR169a* | Sb03g038380 | Calcium/Calmodulin dependent protein kinase-related | Exon |
| sbi-miR169b* | Sb01g041700 | Glutamate decarboxylase | Exon |
|  | Sb10g008200 | Starch synthase isoform | Exon |
|  | Sb02g026670 | Calmodulin-like protein. Pfam EF-Hand domain | Exon |
|  | Sb03g028620 | Cytochrome P450 | Exon |
|  | Sb03g028670 | Cytochrome P450 | Exon |
|  | Sb04g003200 | Putative cycloartenol synthase | 3' UTR |
|  | Sb05g002790 | Microfibril-associated protein | Exon |
| sbi-miR169bfgh* | Sb01g036110 | Similar to Insulinase | Exon |
| sbi-miR169cd* | Sb05g024660 | BTB/POZ domain | Exon |
| sbi-miR169i* | Sb03g041660[1] | Similar Glycogenin-like protein | Exon✖ |
| sbi-miR172abcde | Sb01g003400 | Indeterminate spikelet 1 | Exon |
|  | Sb02g007000 | Indeterminate spikelet 1 | Exon✖ |
|  | Sb06g030670 | APETALA 2 transcription factor | Exon✖ |
|  | Sb09g002080 | APETALA 2 transcription factor | 3' UTR |
| sbi-miR172abcd | Sb10g025053 | Glossy 15 | Exon |
| sbi-miR172b | Sb06g023330 | Double-stranded RNA binding motif. Similar to AthFRY2/CPL1 | Exon |
|  | Sb06g019750 | Protein kinase similar to CLAVATA 1 | Exon |
| sbi-miR172e | Sb01g044240 | FRIGIDA-like protein 2 | Exon✖ |
|  | Sb04g038320 | Type A response regulator 3 | 3' UTR |
| sbi-miR395abcdef | Sb01g044100 | Sulfate transporter | 5' UTR |
|  | Sb01g008450 | ATP sulfurylase | Exon |
| sbi-miR395abcde* | Sb03g014780 | Chromating-remodeling complex ATPase chain | Exon |
|  | Sb03g026410 | ATP synthase beta subunit/transcription terminator factor rho-like | Exon |
| sbi-miR395f* | Sb01g007878 | Embryonic flower 2 | Exon |
|  | Sb10g005630[1] | Chromatin-remodeling factor CHD3 similar to PICKLE | Exon✖ |
|  | Sb10g013750 | Cryptochrome 2 | Exon |
|  | Sb09g023793 | Similar to NOT2/NOT3/NOT5 family protein | Exon |
|  | Sb10g012270 | Proton-dependent oligopeptide transport (POT) family protein | Exon |

[1]The target prediction was based on MicroPC web resource (Mhuantong and Wichadakul 2009)

✖miRNA-mediated cleavage of target genes was experimentally validated

TABLE 3

List of new miRNAs that target genes involved in flowering and the starch and sucrose pathways

| miRNA | Target gene | Gene function | Target site |
|---|---|---|---|
|  |  | Flowering |  |
| chromosome_1_970_mature.BC_03 | Sb03g035080 | Dof zinc finger similar to Ath CDF5 | Exon |
| chromosome_3_1462_mature.BC_04 | Sb04g024040 | F-box protein GID2 | Exon |
| chromosome_4_608_mature.BC_02 | Sb06g029476 | SWI/SNF helicase-like transcription factor | Exon |
| chromosome_4_712_mature.BC_01 | Sb01g021990 | Kaurene-synthase A | Exon |

TABLE 3-continued

List of new miRNAs that target genes involved in flowering and the starch and sucrose pathways

| miRNA | Target gene | Gene function | Target site |
|---|---|---|---|
| | Sb03g041900 | Gibberellin 20 oxidase 2 | Exon |
| | Sb03g043030 | Gibberellin response regulator like | Exon |
| | Sb03g047330 | Lux arrythmo | Exon |
| | Sb03g039060 | Similar to CONSTANS | 3' UTR |
| | Sb05g003660 | Similar Pseudo response regulator 9/5 | Exon |
| | Sb06g024630 | SBP7/SPL7 | Exon |
| chromosome_5_379_mature.BC_04 | Sb02g001110 | Casein kinase II subunit alpha | 5' UTR |
| chromosome_5_978_mature.BC_01 | Sb04g023680 | Cryptochrome 1a | 5' UTR |
| chromosome_6_201_mature.BC_02 | Sb01g021990 | Kaurene-synthase A | Exon |
| | Sb04g003660 | ZTL | Exon✘ |
| | Sb01g049020 | SOC1 | Exon✘ |
| | Sb06g025550 | Indeterminate 9 | 5' UTR |
| chromosome_8_618_mature.BC_05 | Sb07g024550 | Indeterminate 1 | Exon |
| chromosome_9_1189_mature.BC_05 | Sb07g024550 | Indeterminate 1 | Exon |
| | | Starch and sucrose | |
| chromosome_1_527_mature.BC_05 | Sb03g042460 | Fructokinase 1 | Exon |
| chromosome_1_1391_mature.BC_04 | Sb10g009270 | Endoglucanase 17 | Exon |
| chromosome_2_1061_mature.BC_05 | Sb01g035890 | Sucrose synthase 3 | Exon |
| chromosome_3_213_mature.BC_01 | Sb06g032760 | Endoglucanase 13 | Exon |
| chromosome_4_134_mature.BC_02 | Sb09g026080 | Hexokinase | 3' UTR |
| chromosome_4_557_mature.BC_02 | Sb10g006330 | Sucrose Synthase 1 | 5' UTR |
| chromosome_4_712_mature.BC_01 | Sb05g007310 | Sucrose phosphate synthase | Exon |
| | Sb06g031910 | Beta-fructofuranosidase | Exon |
| | Sb07g001140 | Beta-glucosidase | Exon |
| | Sb03g042460 | Fructokinase 1 | Exon✘ |
| | Sb03g010640 | Alpha glucosidase | Exon |
| | Sb09g019480 | Starch debranching enzyme | Exon |
| | Sb10g009270 | Endoglucanase 17 | Exon |
| | Sb10g030140 | Endoglucanase 18 | Exon |
| chromosome_4_1677_mature.BC_05 | Sb06g023760 | Beta-fructofuranosidase | Exon |
| | Sb06g031910 | Beta-fructofuranosidase | Exon |
| chromosome_6_201_mature.BC_02 | Sb01g033060 | Sucrose synthase 2 | Exon✘ |
| | Sb03g008810 | Ribokinase, PfkB carbohydrate kinase | Exon |
| | Sb05g002900 | Piruvate kinase | Exon |
| chromosome_7_516_mature.BC_03 | Sb06g017600 | Endoglucanase 11 | Exon |
| chromosome_7_1887_mature.BC_05 | Sb01g019850 | Beta amylase | Exon |
| chromosome_8_401_mature.BC_01 | Sb07g023020 | Alpha amylase isozyme | Exon |
| chromosome_9_1189_mature.BC_05 | Sb06g017600 | Endoglucanase 11 | Exon |
| chromosome_10_962_mature.BC_01 | Sb10g006330 | Sucrose Synthase 1 | Exon |

✘miRNA-mediated cleavage of target genes was experimentally validated

Conclusion

Here we have described the first characterization of the small RNA component of the transcriptome from *sorghum* stems. The choice of stems as plant material is interesting not only because it is the tissue were fermentable sugars do accumulate, but it is also the venue for the movement of small RNA duplexes (siRNAs and miRNAs) from source to sink tissues, as have been recently demonstrated. Thus, one could expect the small RNA component of the stem to be quite diverse or heterogeneous. Indeed, the unexpected finding of a high abundance peak of RNAs with 25 nt or more in length lead us to the finding of rRNA and tRNA genes that have not been annotated yet in the *sorghum* genome. We have also shown that the abundance of the 22 nt small RNAs in *sorghum* stem tissue was greater than the 20 and 21 nt small RNAs respectively. Our results contrast the recently proposed notion that the 22 nt peak of small RNAs is exclusive of maize. Furthermore, we found that up to 15% of all the 22 nt small RNAs in the BTx623 library were derived from miR172c, which has been previously predicted to have a length of 20 nt (Paterson et al. 2009). Recently, 22 nt miRNAs have been described to trigger siRNA biogenesis from target transcripts in *Arabidopsis*. Thus, it would be interesting to test if miR172c can also trigger siRNA biogenesis in *sorghum*.

As expected, the specific genetic material, tissue sample and developmental stage used in our study, allowed us to capture a broad spectrum of the small RNA component of the *sorghum* transcriptome. On the other hand, the specificity of the material permitted us to gain new insights into how complex traits like sugar accumulation and flowering time are regulated at the post-transcriptional level. Such regulation of gene expression provide an opportunity to manipulate biofuel traits, where stem sugar rather than cellulose and increased biomass because of delayed flowering could be enhanced. By taking a genetic approach in conjunction with deep-sequencing of stem-derived small RNAs, we were able to correlate allelic variation in miRNA expression between grain and sweet *sorghum*, with the sugar and flowering phenotypes of selected F2 plants derived from their cross. In the case of miR395, it is interesting to note that there was genotypic variation in the miR395/miR395* ratio, with the Rio genotype expressing both strands at equal proportions in contrast to a clear predominance of miR395 abundance over miR395* in BTx623. This is reminiscent of the recently proposed "arm switching" model of miRNA evolution described for nematodes species, in which the mature miRNA is produced from the 5' arm of the miRNA hairpin in a particular species but in a different nematode species the 5' arm of the same MIR gene gives rise to the miRNA* instead. Interestingly, it has been shown recently that miRNA* species have physiological relevance in *Drosophila*, since a significant number of them are well conserved, can be loaded into the RISC complex through their preferential association with ARGONAUTE2 (AGO2) rather that AGO1, and can also regulate the expression of target genes. Furthermore, the regulatory potential of miRNA* species in vertebrates has been recently demonstrated as well.

Finally, several of the miRNAs described in this study as well as their predicted target genes, co-localized with previously described Brix and flowering QTLs, providing a set of candidate genes as the first step to map-based cloning of the quantitative differences in phenotype between grain and sweet *sorghum* lines.

References for Example I

1. K. Glasziou, R. Gayler, *Bot Rev* 38, 471 (1972).
2. G. Hoffman-Thoma, K. Hinkel, P. Nicolay, J. Willenbrink, *Physiologia Plantarum* 97, 277 (1996).
3. J. Goldemberg, *Science* 315, 808 (2007).
4. L. Grivet, P. Arruda, *Curr Opin Plant Biol* 5, 122 (2002).
5. A. H. Paterson et al., *Nature* 457, 551 (2009).
6. K. B. Ritter, C. L. McIntyre, I. D. Godwin, D. R. Jordan, S. C. Chapman, *Euphytica* 157, 161 (2007).
7. S. Murray et al., *Crop Science* 48, 2165 (2008).
8. K. Ritter et al., *Molecular Breeding* 22, 367 (2008).
9. M. Calviño, R. Bruggmann, J. Messing, *Rice* 1, 166 (2008).
10. Materials and Methods
11. K. Nobuta et al., *Proc Natl Acad Sci USA* 105, 14958 (2008).
12. R. Louro, A. S. Smirnova, S. Verjovski-Almeida, *Genomics* 93, 291 (2009).
13. K. Okamura, J. W. Hagen, H. Duan, D. M. Tyler, E. C. Lai, *Cell* 130, 89 (2007).
14. J. G. Ruby, C. H. Jan, D. P. Bartel, *Nature* 448, 83 (2007).
15. R. J. Taft et al., *Nat Genet* 41, 572 (2009).
16. R. J. Taft, C. D. Kaplan, C. Simons, J. S. Mattick, *Cell Cycle* 8, 2332 (2009).
17. G. Chuck, R. Meeley, E. Irish, H. Sakai, S. Hake, *Nat Genet* 39, 1517 (2007).
18. N. Lauter, A. Kampani, S. Carlson, M. Goebel, S. P. Moose, *Proc Natl Acad Sci USA* 102, 9412 (2005).
19. J. Mathieu, L. J. Yant, F. Mürdter, F. Kütter, M. Schmid, *PLoS Biol* 7, e1000148 (2009).
20. G. Wu et al., *Cell* 138, 750 (2009).
21. Q. H. Zhu, N. M. Upadhyaya, F. Gubler, C. A. Helliwell, *BMC Plant Biol* 9, 149 (2009).
22. W. X. Li et al., *Plant Cell* 20, 2238 (2008).
23. C. G. Kawashima et al., *Plant J* 57, 313 (2009).
24. J. Lomako, W. M. Lomako, W. J. Whelan, *Biochim Biophys Acta* 1673, 45 (2004).
25. Y. Qi et al., *Planta* 221, 437 (2005).
26. J. Ogas, S. Kaufmann, J. Henderson, C. Somerville, *Proc Natl Acad Sci USA* 96, 13839 (1999).
27. S. El-Din El-Assal et al., *Plant Physiology* 133, 1504 (2003).
28. J. T. Henderson et al., *Plant Physiology* 134, 995 (2004).
29. M. Endo, N. Mochizuki, T. Suzuki, A. Nagatani, *Plant Cell* 19, 84 (2007).
30. D. Jiang, Y. Wang, Y. Wang, Y. He, *PLoS ONE* 3, e3404 (2008).
31. S. Y. Kim, T. Zhu, Z. R. Sung, *Plant Physiology* 152, 516 (2010).
32. S. D. Michaels, I. C. Bezerra, R. M. Amasino, *Proc Natl Acad Sci USA* 101, 3281 (2004).
33. M. R. Schläppi, *Plant Physiology* 142, 1728 (2006).
34. P. A. Salomé, J. P. To, J. J. Kieber, C. R. McClung, *Plant Cell* 18, 55 (2006).
35. H. Lee et al., *Nucleic Acids Res,* (2010).
36. S. C. Murray, W. L. Rooney, M. T. Hamblin, S. E. Mitchell, S. Kresovich, *The Plant Genome* 2, 48 (2009).
37. K. Swaminathan et al., *Genome Biol* 11, R12 (2010).
38. F. Torney, L. Moeller, A. Scarpa, K. Wang, *Current Opinion in Biotechnology* 18, 193 (2007).
39. M. Ghildiyal, J. Xu, H. Seitz, Z. Weng, P. D. Zamore, *RNA* 16, 43 (2010).

EXAMPLE II

Identification of miRNAs which influence flowering times, sugar metabolism, stress responses and sulfur storage provides the means to modulate these pathways via the introduction of nucleic molecules encoding or inhibiting the action of the same into recipient plants. Vectors useful for introducing heterologous nucleic acids into plants and methods of use of the same are known in the art. See for example, Segal et al., Genetics (2003) September;165(1):387-97. Also see U.S. Pat. No. 6,849,779.

In one approach, vectors comprising miR172 can be introduced into plants to increase expression thereof. As shown in Example I, alteration of miRNA172 levels in recipient plants should be effective to increase sugar content in stems thereby providing improved *sorghum* for the production of biofuels. Such plants also comprise an aspect of the invention.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

TABLE B

Frequency counts of small RNA reads for known miRNAs

| | | Count of mapped reads to miRNA genes for each library | | | | |
|---|---|---|---|---|---|---|
| Chromosome | miRNA | Mix | BTx623 | Rio | LB/EF F2s | HB/LF F2s |
| 4 | sbi-MIR156a | 336 | 136 | 464 | 1188 | 1830 |
| 3 | sbi-MIR156b | 655 | 416 | 867 | 3747 | 4123 |
| 3 | sbi-MIR156c | 635 | 321 | 796 | 3120 | 3617 |
| 2 | sbi-MIR156d | 3 | 1 | 2 | 12 | 10 |
| 10 | sbi-MIR156e | 26 | 26 | 21 | 151 | 101 |
| 2 | sbi-MIR156f | 345 | 82 | 349 | 857 | 1307 |
| 4 | sbi-MIR156g | 205 | 49 | 269 | 665 | 1050 |
| 6 | sbi-MIR156h | 218 | 49 | 276 | 704 | 1110 |
| 7 | sbi-MIR156i | 635 | 330 | 814 | 3213 | 3659 |
| 3 | sbi-MIR159 | 427 | 248 | 302 | 892 | 1496 |
| 3 | sbi-MIR159b | 55 | 19 | 4 | 24 | 48 |

TABLE B-continued

Frequency counts of small RNA reads for known miRNAs

Count of mapped reads to miRNA genes for each library

| Chromosome | miRNA | Mix | BTx623 | Rio | LB/EF F2s | HB/LF F2s |
|---|---|---|---|---|---|---|
| 4 | sbi-MIR160a | 90 | 45 | 45 | 296 | 249 |
| 10 | sbi-MIR160b | 106 | 88 | 58 | 331 | 272 |
| 7 | sbi-MIR160c | 92 | 45 | 43 | 312 | 253 |
| 1 | sbi-MIR160d | 90 | 45 | 44 | 312 | 253 |
| 2 | sbi-MIR160e | 90 | 45 | 44 | 312 | 255 |
| 4 | sbi-MIR162 | 2 | 1 | 4 | 11 | 10 |
| 9 | sbi-MIR164 | 222 | 141 | 231 | 1049 | 913 |
| 4 | sbi-MIR164b | 229 | 194 | 221 | 1224 | 817 |
| 1 | sbi-MIR164c | 1 | 1 | 0 | 7 | 2 |
| 2 | sbi-MIR164d | 137 | 91 | 111 | 617 | 506 |
| 9 | sbi-MIR164e | 125 | 134 | 93 | 790 | 482 |
| 1 | sbi-MIR166a | 703 | 615 | 492 | 2537 | 2076 |
| 1 | sbi-MIR166b | 254 | 142 | 135 | 762 | 881 |
| 1 | sbi-MIR166c | 245 | 177 | 161 | 764 | 705 |
| 4 | sbi-MIR166d | 289 | 279 | 239 | 1068 | 809 |
| 2 | sbi-MIR166e | 19 | 12 | 5 | 62 | 64 |
| 4 | sbi-MIR166f | 174 | 102 | 75 | 523 | 633 |
| 4 | sbi-MIR166g | 20 | 18 | 11 | 78 | 95 |
| 10 | sbi-MIR166h | 107 | 98 | 74 | 367 | 327 |
| 1 | sbi-MIR166i | 291 | 284 | 234 | 1072 | 804 |
| 1 | sbi-MIR166j | 702 | 612 | 492 | 2515 | 2059 |
| 8 | sbi-MIR166k | 755 | 655 | 511 | 2686 | 2328 |
| 1 | sbi-MIR167a | 120 | 39 | 102 | 359 | 551 |
| 1 | sbi-MIR167b | 524 | 232 | 463 | 1950 | 2688 |
| 10 | sbi-MIR167c | 1144 | 327 | 1098 | 5100 | 2828 |
| 2 | sbi-MIR167d | 979 | 255 | 1184 | 3363 | 4951 |
| 8 | sbi-MIR167e | 932 | 233 | 1130 | 3179 | 4714 |
| 1 | sbi-MIR167f | 1037 | 378 | 1222 | 3671 | 5144 |
| 3 | sbi-MIR167g | 941 | 237 | 1144 | 3248 | 4831 |
| 1 | sbi-MIR167h | 1403 | 557 | 1553 | 5094 | 7086 |
| 4 | sbi-MIR167.p2 | 1546 | 585 | 1672 | 5690 | 7524 |
| 8 | sbi-MIR167.p3 | 99 | 24 | 70 | 343 | 539 |
| 4 | sbi-MIR168 | 1397 | 459 | 1047 | 5736 | 3115 |
| 3 | sbi-MIR169a | 398 | 284 | 158 | 1551 | 1010 |
| 10 | sbi-MIR169b | 355 | 166 | 147 | 760 | 705 |
| 6 | sbi-MIR169c | 72 | 61 | 24 | 402 | 89 |
| 6 | sbi-MIR169d | 106 | 79 | 30 | 400 | 113 |
| 2 | sbi-MIR169f | 35 | 34 | 9 | 96 | 52 |
| 2 | sbi-MIR169g | 33 | 30 | 6 | 88 | 45 |
| 5 | sbi-MIR169i | 5 | 2 | 1 | 34 | 10 |
| 2 | sbi-MIR169e | 91 | 47 | 14 | 203 | 88 |
| 4 | sbi-MIR169h | 81 | 86 | 23 | 392 | 93 |
| 4 | sbi-MIR169j | 55 | 56 | 18 | 333 | 78 |
| 6 | sbi-MIR169k | 638 | 693 | 278 | 3319 | 1855 |
| 7 | sbi-MIR169l | 47 | 24 | 17 | 137 | 67 |
| 7 | sbi-MIR169m | 62 | 61 | 24 | 383 | 82 |
| 7 | sbi-MIR169n | 66 | 70 | 23 | 405 | 88 |
| 1 | sbi-MIR171a | 7 | 2 | 3 | 25 | 22 |
| 7 | sbi-MIR171b | 7 | 2 | 2 | 28 | 22 |
| 1 | sbi-MIR171d | 7 | 3 | 3 | 28 | 27 |
| 6 | sbi-MIR171e | 180 | 69 | 246 | 726 | 908 |
| 4 | sbi-MIR171f | 181 | 68 | 244 | 723 | 904 |
| 1 | sbi-MIR171h | 3 | 4 | 2 | 7 | 7 |
| 1 | sbi-MIR171i | 6 | 4 | 2 | 27 | 26 |
| 6 | sbi-MIR171k | 7 | 2 | 2 | 26 | 22 |
| 9 | sbi-MIR172a | 35138 | 37769 | 28459 | 124587 | 75185 |
| 3 | sbi-MIR172b | 647 | 503 | 96 | 978 | 515 |
| 4 | sbi-MIR172c | 34208 | 37173 | 28113 | 120975 | 72973 |
| 2 | sbi-MIR172e | 1167 | 567 | 555 | 4816 | 3725 |
| 2 | sbi-MIR172d | 3163 | 2178 | 2109 | 6411 | 4473 |
| 3 | sbi-MIR319 | 3935 | 4395 | 2673 | 13003 | 10606 |
| 3 | sbi-MIR319.p1 | 297 | 270 | 148 | 1164 | 735 |
| 1 | sbi-MIR390 | 3 | 1 | 0 | 6 | 5 |
| 6 | sbi-MIR393b | 151 | 73 | 104 | 610 | 949 |
| 3 | sbi-MIR393 | 3 | 7 | 2 | 12 | 13 |
| 2 | sbi-MIR394a | 171 | 191 | 74 | 569 | 489 |
| 4 | sbi-MIR394b | 175 | 198 | 82 | 579 | 519 |
| 6 | sbi-MIR395a | 7 | 8 | 14 | 23 | 39 |
| 6 | sbi-MIR395b | 10 | 24 | 26 | 50 | 76 |
| 6 | sbi-MIR395d | 20 | 13 | 21 | 26 | 56 |
| 6 | sbi-MIR395e | 21 | 26 | 33 | 46 | 82 |
| 6 | sbi-MIR395f | 40 | 17 | 74 | 52 | 144 |
| 6 | sbi-MIR395c | 21 | 14 | 20 | 31 | 75 |
| 6 | sbi-MIR395g | 19 | 14 | 30 | 31 | 70 |

TABLE B-continued

Frequency counts of small RNA reads for known miRNAs

Count of mapped reads to miRNA genes for each library

| Chromosome | miRNA | Mix | BTx623 | Rio | LB/EF F2s | HB/LF F2s |
|---|---|---|---|---|---|---|
| 6 | sbi-MIR395h | 83 | 21 | 151 | 87 | 263 |
| 7 | sbi-MIR395i | 8 | 2 | 12 | 12 | 33 |
| 7 | sbi-MIR395j | 21 | 3 | 34 | 26 | 78 |
| 7 | sbi-MIR395k | 18 | 1 | 28 | 12 | 51 |
| 7 | sbi-MIR395l | 65 | 10 | 140 | 69 | 214 |
| 4 | sbi-MIR396a | 193 | 38 | 102 | 473 | 572 |
| 10 | sbi-MIR396b | 191 | 38 | 97 | 472 | 575 |
| 4 | sbi-MIR396c | 705 | 621 | 337 | 2865 | 1988 |
| 4 | sbi-MIR396d | 5104 | 2553 | 2333 | 12123 | 19360 |
| 6 | sbi-MIR396e | 5222 | 2612 | 2428 | 12626 | 19719 |
| 4 | sbi-MIR397 | 1 | 0 | 2 | 8 | 6 |
| 3 | sbi-MIR399a | 5 | 3 | 9 | 32 | 24 |
| 4 | sbi-MIR399b | 5 | 12 | 7 | 58 | 24 |
| 9 | sbi-MIR399c | 6 | 3 | 10 | 33 | 23 |
| 10 | sbi-MIR399d | 86 | 76 | 94 | 308 | 233 |
| 10 | sbi-MIR399h | 6 | 4 | 12 | 40 | 30 |
| 6 | sbi-MIR399i | 15 | 10 | 12 | 46 | 29 |
| 4 | sbi-MIR399j | 6 | 4 | 12 | 40 | 30 |
| 3 | sbi-MIR408 | 41 | 5 | 43 | 364 | 75 |
| 4 | sbi-MIR444.p1 | 200 | 56 | 145 | 795 | 654 |
| 6 | sbi-MIR444.p3 | 113 | 49 | 93 | 359 | 408 |
| 1 | sbi-MIR437g | 1 | 1 | 0 | 6 | 5 |
| 1 | sbi-MIR528 | 259 | 26 | 171 | 2027 | 151 |
| 2 | sbi-MIR1432 | 48 | 26 | 68 | 280 | 243 |
| 9 | sbi-MIR1439.p1 | 2 | 0 | 3 | 12 | 12 |

TABLE C

List of new miRNAs in *sorghum*

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| Chromosome 1 | | | | | | | | | |
| chromosome_1_245.BC_01 | 7426502 | 7426720 | + | 21 | 7426572 | 7426701 | 21 | 7426523 | 7426652 |
| chromosome_1_827.BC_01 | 30266188 | 30266406 | + | 22 | 30266204 | 30266334 | 22 | 30266263 | 30266393 |
| chromosome_1_1396.BC_01 | 59548707 | 59548925 | + | 24 | 59548771 | 59548903 | 19 | 59548715 | 59548842 |
| chromosome_1_333.BC_01 | 10623817 | 10624035 | + | 25 | 10623839 | 10623972 | 25 | 10623878 | 10624011 |
| chromosome_1_686.BC_02 | 52670170 | 52670388 | + | 20 | 52670237 | 52670365 | 19 | 52670204 | 52670331 |
| chromosome_1_1088.BC_02 | 73137923 | 73138141 | + | 22 | 73137936 | 73138066 | 21 | 73138002 | 73138131 |
| chromosome_1_1016.BC_02 | 70200862 | 70201080 | + | 20 | 70200874 | 70201002 | 19 | 70200945 | 70201072 |
| chromosome_1_450.BC_02 | 26996128 | 26996346 | + | 20 | 26996202 | 26996330 | 20 | 26996131 | 26996259 |
| chromosome_1_862.BC_02 | 61161925 | 61162143 | + | 24 | 61161947 | 61162079 | 20 | 61161991 | 61162119 |
| chromosome_1_466.BC_02 | 28104732 | 28104950 | + | 19 | 28104783 | 28104910 | 18 | 28104746 | 28104872 |
| chromosome_1_398.BC_02 | 21449991 | 21450209 | + | 19 | 21450060 | 21450187 | 19 | 21450013 | 21450140 |
| chromosome_1_1560.BC_03 | 70027616 | 70027834 | + | 22 | 70027682 | 70027812 | 24 | 70027657 | 70027789 |
| chromosome_1_191.BC_03 | 7426502 | 7426726 | + | 23 | 7426531 | 7426665 | 21 | 7426564 | 7426696 |
| chromosome_1_40.BC_03 | 1791718 | 1791936 | + | 20 | 1791761 | 1791889 | 21 | 1791787 | 1791916 |
| chromosome_1_346.BC_03 | 12065225 | 12065443 | + | 23 | 12065266 | 12065397 | 24 | 12065297 | 12065429 |
| chromosome_1_1241.BC_03 | 58998763 | 58998981 | + | 21 | 58998783 | 58998912 | 18 | 58998820 | 58998946 |
| chromosome_1_350.BC_03 | 12127958 | 12128176 | + | 22 | 12128011 | 12128141 | 23 | 12127971 | 12128102 |
| chromosome_1_970.BC_03 | 49243733 | 49243951 | + | 19 | 49243796 | 49243923 | 19 | 49243822 | 49243949 |
| chromosome_1_375.BC_03 | 12875443 | 12875661 | + | 25 | 12875484 | 12875617 | 22 | 12875452 | 12875582 |
| chromosome_1_651.BC_03 | 22256944 | 22257162 | + | 24 | 22256993 | 22257125 | 23 | 22256953 | 22257084 |
| chromosome_1_345.BC_03 | 12065268 | 12065486 | + | 18 | 12065270 | 12065396 | 18 | 12065299 | 12065425 |
| chromosome_1_1337.BC_04 | 12088714 | 12088932 | + | 22 | 12088736 | 12088866 | 22 | 12088796 | 12088926 |
| chromosome_1_512.BC_04 | 5287266 | 5287484 | + | 23 | 5287350 | 5287481 | 23 | 5287287 | 5287418 |
| chromosome_1_882.BC_04 | 8457605 | 8457823 | + | 21 | 8457623 | 8457752 | 23 | 8457660 | 8457791 |
| chromosome_1_983.BC_04 | 9293698 | 9293916 | + | 18 | 9293757 | 9293883 | 18 | 9293730 | 9293856 |
| chromosome_1_754.BC_04 | 7395812 | 7396030 | + | 19 | 7395898 | 7396025 | 19 | 7395840 | 7395967 |
| chromosome_1_52.BC_04 | 574388 | 574606 | + | 19 | 574438 | 574565 | 19 | 574403 | 574530 |
| chromosome_1_1391.BC_04 | 12683183 | 12683401 | + | 18 | 12683211 | 12683337 | 18 | 12683248 | 12683374 |
| chromosome_1_2718.BC_05 | 17269612 | 17269830 | + | 23 | 17269667 | 17269798 | 21 | 17269645 | 17269774 |
| chromosome_1_527.BC_05 | 3707826 | 3708044 | + | 18 | 3707889 | 3708015 | 19 | 3707841 | 3707968 |
| chromosome_1_216.BC_05 | 1483152 | 1483370 | + | 19 | 1483216 | 1483343 | 22 | 1483191 | 1483321 |
| chromosome_1_595.BC_05 | 4260234 | 4260452 | + | 25 | 4260275 | 4260408 | 22 | 4260246 | 4260376 |
| Chromosome 2 | | | | | | | | | |
| chromosome_2_1473.BC_01 | 71061669 | 71061887 | + | 23 | 71061689 | 71061820 | 23 | 71061735 | 71061866 |
| chromosome_2_45.BC_01 | 1930828 | 1931046 | + | 18 | 1930837 | 1930963 | 18 | 1930911 | 1931037 |

TABLE C-continued

List of new miRNAs in *sorghum*

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| chromosome_2_902.BC_02 | 77661480 | 77661698 | + | 19 | 77661505 | 77661632 | 22 | 77661529 | 77661659 |
| chromosome_2_689.BC_03 | 48991679 | 48991897 | + | 21 | 48991714 | 48991843 | 22 | 48991741 | 48991871 |
| chromosome_2_3135.BC_04 | 54647513 | 54647731 | + | 20 | 54647548 | 54647676 | 23 | 54647577 | 54647708 |
| chromosome_2_790.BC_04 | 7717774 | 7717992 | + | 23 | 7717804 | 7717935 | 23 | 7717859 | 7717990 |
| chromosome_2_1490.BC_04 | 14065842 | 14066060 | + | 20 | 14065871 | 14065999 | 22 | 14065910 | 14066040 |
| chromosome_2_2159.BC_04 | 23325185 | 23325403 | + | 21 | 23325268 | 23325397 | 20 | 23325223 | 23325351 |
| chromosome_2_573.BC_04 | 5820867 | 5821085 | + | 25 | 5820949 | 5821082 | 25 | 5820884 | 5821017 |
| chromosome_2_721.BC_04 | 7147886 | 7148104 | + | 24 | 7147908 | 7148040 | 23 | 7147933 | 7148064 |
| chromosome_2_1464.BC_05 | 9193961 | 9194179 | + | 23 | 9194006 | 9194137 | 20 | 9194033 | 9194161 |
| chromosome_2_800.BC_05 | 4929446 | 4929664 | + | 23 | 4929468 | 4929599 | 23 | 4929523 | 4929654 |
| chromosome_2_3135.BC_05 | 26306294 | 26306512 | + | 21 | 26306334 | 26306463 | 21 | 26306311 | 26306440 |
| chromosome_2_1257.BC_05 | 7905274 | 7905492 | + | 21 | 7905330 | 7905459 | 23 | 7905296 | 7905427 |
| chromosome_2_2234.BC_05 | 14720976 | 14721194 | + | 24 | 14721021 | 14721153 | 24 | 14720996 | 14721128 |
| chromosome_2_1418.BC_05 | 8982285 | 8982503 | + | 24 | 8982308 | 8982440 | 22 | 8982343 | 8982473 |
| chromosome_2_1061.BC_05 | 6564443 | 6564661 | + | 18 | 6564508 | 6564634 | 18 | 6564477 | 6564603 |
| Chromosome 3 | | | | | | | | | |
| chromosome_3_1222.BC_01 | 64463912 | 64464130 | + | 21 | 64463932 | 64464061 | 21 | 64463980 | 64464109 |
| chromosome_3_397.BC_01 | 12450213 | 12450431 | + | 20 | 12450239 | 12450367 | 22 | 12450216 | 12450346 |
| chromosome_3_1128.BC_01 | 62015649 | 62015867 | + | 21 | 62015699 | 62015828 | 21 | 62015667 | 62015796 |
| chromosome_3_189.BC_01 | 6158157 | 6158375 | + | 23 | 6158179 | 6158310 | 23 | 6158225 | 6158356 |
| chromosome_3_1257.BC_01 | 65733952 | 65734170 | + | 18 | 65734042 | 65734168 | 18 | 65733982 | 65734108 |
| chromosome_3_1324.BC_01 | 68396564 | 68396782 | + | 24 | 68396622 | 68396754 | 24 | 68396595 | 68396727 |
| chromosome_3_1460.BC_01 | 74117994 | 74118212 | + | 18 | 74118001 | 74118127 | 18 | 74118043 | 74118169 |
| chromosome_3_47.BC_01 | 903355 | 903573 | + | 24 | 903407 | 903539 | 24 | 903366 | 903498 |
| chromosome_3_213.BC_01 | 7158612 | 7158830 | + | 19 | 7158680 | 7158807 | 20 | 7158646 | 7158774 |
| chromosome_3_39.BC_02 | 1528800 | 1529018 | + | 21 | 1528864 | 1528993 | 23 | 1528836 | 1528967 |
| chromosome_3_235.BC_02 | 11337364 | 11337582 | + | 20 | 11337451 | 11337579 | 20 | 11337430 | 11337558 |
| chromosome_3_562.BC_02 | 55328718 | 55328936 | + | 23 | 55328794 | 55328925 | 18 | 55328742 | 55328868 |
| chromosome_3_201.BC_02 | 9197165 | 9197383 | + | 21 | 9197218 | 9197347 | 25 | 9197176 | 9197309 |
| chromosome_3_514.BC_02 | 53307715 | 53307933 | + | 24 | 53307782 | 53307914 | 22 | 53307745 | 53307875 |
| chromosome_3_783.BC_02 | 67530313 | 67530531 | + | 25 | 67530345 | 67530478 | 23 | 67530374 | 67530505 |
| chromosome_3_107.BC_03 | 4540575 | 4540793 | + | 20 | 4540588 | 4540716 | 21 | 4540616 | 4540745 |
| chromosome_3_234.BC_03 | 9197788 | 9198006 | + | 23 | 9197844 | 9197975 | 21 | 9197875 | 9198004 |
| chromosome_3_1374.BC_04 | 12368774 | 12368992 | + | 20 | 12368802 | 12368930 | 20 | 12368837 | 12368965 |
| chromosome_3_954.BC_04 | 9321647 | 9321865 | + | 22 | 9321687 | 9321817 | 22 | 9321663 | 9321793 |
| chromosome_3_494.BC_04 | 5002679 | 5002897 | + | 22 | 5002717 | 5002847 | 19 | 5002749 | 5002876 |
| chromosome_3_215.BC_04 | 2081521 | 2081739 | + | 25 | 2081534 | 2081667 | 23 | 2081571 | 2081702 |
| chromosome_3_133.BC_04 | 1306612 | 1306830 | + | 19 | 1306634 | 1306761 | 21 | 1306678 | 1306807 |
| chromosome_3_1462.BC_04 | 13263113 | 13263331 | + | 18 | 13263122 | 13263248 | 18 | 13263154 | 13263280 |
| chromosome_3_1128.BC_04 | 10469325 | 10469543 | + | 24 | 10469392 | 10469524 | 24 | 10469359 | 10469491 |
| chromosome_3_821.BC_05 | 5098942 | 5099160 | + | 21 | 5098974 | 5099103 | 25 | 5098997 | 5099130 |
| chromosome_3_2132.BC_05 | 12834992 | 12835210 | + | 21 | 12835013 | 12835142 | 21 | 12835061 | 12835190 |
| chromosome_3_1435.BC_05 | 8752482 | 8752700 | + | 22 | 8752569 | 8752699 | 20 | 8752538 | 8752666 |
| chromosome_3_1223.BC_05 | 7696368 | 7696586 | + | 20 | 7696393 | 7696521 | 20 | 7696425 | 7696553 |
| chromosome_3_582.BC_05 | 3711612 | 3711830 | + | 24 | 3711637 | 3711769 | 23 | 3711665 | 3711796 |
| chromosome_3_851.BC_05 | 5462848 | 5463066 | + | 25 | 5462855 | 5462988 | 21 | 5462921 | 5463050 |
| chromosome_3_1127.BC_05 | 7158509 | 7158727 | + | 24 | 7158530 | 7158662 | 25 | 7158578 | 7158711 |
| chromosome_3_216.BC_05 | 1380827 | 1381045 | + | 19 | 1380849 | 1380976 | 20 | 1380880 | 1381008 |
| chromosome_3_468.BC_05 | 2844222 | 2844440 | + | 20 | 2844282 | 2844410 | 21 | 2844259 | 2844388 |
| Chromosome 4 | | | | | | | | | |
| chromosome_4_1028.BC_01 | 57083142 | 57083360 | + | 21 | 57083164 | 57083293 | 21 | 57083211 | 57083340 |
| chromosome_4_712.BC_01 | 45785396 | 45785614 | + | 18 | 45785462 | 45785588 | 19 | 45785428 | 45785555 |
| chromosome_4_684.BC_01 | 43242765 | 43242983 | + | 24 | 43242787 | 43242919 | 23 | 43242813 | 43242944 |
| chromosome_4_522.BC_01 | 18928653 | 18928871 | + | 24 | 18928734 | 18928866 | 24 | 18928661 | 18928793 |
| chromosome_4_83.BC_02 | 4139706 | 4139924 | + | 23 | 4139789 | 4139920 | 24 | 4139747 | 4139879 |
| chromosome_4_47.BC_02 | 2806728 | 2806956 | + | 23 | 2806731 | 2806867 | 22 | 2806818 | 2806953 |
| chromosome_4_608.BC_02 | 57049969 | 57050187 | + | 19 | 57049984 | 57050111 | 18 | 57050019 | 57050145 |
| chromosome_4_557.BC_02 | 54555310 | 54555528 | + | 19 | 54555314 | 54555441 | 23 | 54555345 | 54555476 |
| chromosome_4_134.BC_02 | 5979272 | 5979490 | + | 24 | 5979341 | 5979473 | 22 | 5979302 | 5979432 |
| chromosome_4_571.BC_03 | 41084010 | 41084228 | + | 20 | 41084063 | 41084191 | 23 | 41084031 | 41084162 |
| chromosome_4_2454.BC_04 | 41104168 | 41104386 | + | 22 | 41104251 | 41104381 | 22 | 41104224 | 41104354 |
| chromosome_4_1764.BC_04 | 13743465 | 13743683 | + | 23 | 13743538 | 13743669 | 24 | 13743467 | 13743599 |
| chromosome_4_831.BC_04 | 5805456 | 5805674 | + | 19 | 5805528 | 5805655 | 19 | 5805482 | 5805609 |
| chromosome_4_174.BC_05 | 1043442 | 1043660 | + | 23 | 1043464 | 1043595 | 24 | 1043512 | 1043644 |
| chromosome_4_785.BC_05 | 4139699 | 4139917 | + | 22 | 4139782 | 4139912 | 19 | 4139753 | 4139880 |
| chromosome_4_941.BC_05 | 4976389 | 4976607 | + | 24 | 4976455 | 4976587 | 20 | 4976407 | 4976535 |
| chromosome_4_626.BC_05 | 3152078 | 3152324 | + | 24 | 3152099 | 3152245 | 23 | 3152137 | 3152282 |
| chromosome_4_1911.BC_05 | 10424324 | 10424542 | + | 24 | 10424325 | 10424457 | 25 | 10424351 | 10424484 |
| chromosome_4_1912.BC_05 | 10424281 | 10424499 | + | 24 | 10424325 | 10424457 | 25 | 10424351 | 10424484 |
| chromosome_4_1677.BC_05 | 8737466 | 8737684 | + | 18 | 8737511 | 8737637 | 20 | 8737554 | 8737682 |

TABLE C-continued

List of new miRNAs in *sorghum*

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| Chromosome 5 | | | | | | | | | |
| chromosome_5_620.BC_01 | 35991780 | 35991998 | + | 23 | 35991798 | 35991929 | 20 | 35991832 | 35991960 |
| chromosome_5_1020.BC_01 | 57560746 | 57560964 | + | 22 | 57560813 | 57560943 | 22 | 57560770 | 57560900 |
| chromosome_5_70.BC_01 | 2390501 | 2390719 | + | 21 | 2390556 | 2390685 | 21 | 2390509 | 2390638 |
| chromosome_5_595.BC_01 | 35972458 | 35972676 | + | 24 | 35972500 | 35972632 | 24 | 35972527 | 35972659 |
| chromosome_5_737.BC_01 | 45964649 | 45964867 | + | 18 | 45964737 | 45964863 | 18 | 45964656 | 45964782 |
| chromosome_5_414.BC_01 | 14639628 | 14639846 | + | 24 | 14639697 | 14639829 | 24 | 14639660 | 14639792 |
| chromosome_5_978.BC_01 | 56200684 | 56200902 | + | 19 | 56200709 | 56200836 | 20 | 56200772 | 56200900 |
| chromosome_5_642.BC_02 | 56976805 | 56977023 | + | 22 | 56976823 | 56976953 | 22 | 56976865 | 56976995 |
| chromosome_5_468.BC_02 | 46744802 | 46745020 | + | 23 | 46744826 | 46744957 | 24 | 46744853 | 46744985 |
| chromosome_5_456.BC_02 | 46080609 | 46080827 | + | 22 | 46080635 | 46080765 | 22 | 46080675 | 46080805 |
| chromosome_5_455.BC_02 | 45878295 | 45878513 | + | 24 | 45878346 | 45878478 | 22 | 45878382 | 45878512 |
| chromosome_5_508.BC_02 | 49892025 | 49892243 | + | 24 | 49892035 | 49892167 | 24 | 49892073 | 49892205 |
| chromosome_5_612.BC_02 | 55180331 | 55180549 | + | 23 | 55180376 | 55180507 | 22 | 55180346 | 55180476 |
| chromosome_5_657.BC_02 | 58061752 | 58061970 | + | 25 | 58061830 | 58061963 | 22 | 58061807 | 58061937 |
| chromosome_5_509.BC_03 | 35939610 | 35939828 | + | 24 | 35939663 | 35939795 | 25 | 35939630 | 35939763 |
| chromosome_5_468.BC_03 | 30952732 | 30952950 | + | 23 | 30952756 | 30952887 | 24 | 30952813 | 30952945 |
| chromosome_5_148.BC_03 | 5711015 | 5711233 | + | 19 | 5711092 | 5711219 | 19 | 5711059 | 5711186 |
| chromosome_5_574.BC_03 | 36068848 | 36069066 | + | 24 | 36068869 | 36069001 | 21 | 36068896 | 36069025 |
| chromosome_5_737.BC_03 | 52069704 | 52069922 | + | 18 | 52069792 | 52069918 | 18 | 52069744 | 52069870 |
| chromosome_5_648.BC_03 | 47253576 | 47253794 | + | 25 | 47253637 | 47253770 | 21 | 47253664 | 47253793 |
| chromosome_5_609.BC_03 | 43098003 | 43098221 | + | 25 | 43098042 | 43098175 | 23 | 43098005 | 43098136 |
| chromosome_5_456.BC_04 | 3769844 | 3770062 | + | 22 | 3769870 | 3770000 | 23 | 3769908 | 3770039 |
| chromosome_5_74.BC_04 | 852222 | 852440 | + | 23 | 852291 | 852422 | 22 | 852266 | 852396 |
| chromosome_5_646.BC_04 | 5397961 | 5398179 | + | 23 | 5398016 | 5398147 | 22 | 5397977 | 5398107 |
| chromosome_5_631.BC_04 | 5062982 | 5063200 | + | 24 | 5063051 | 5063183 | 23 | 5063025 | 5063156 |
| chromosome_5_1387.BC_04 | 12954340 | 12954558 | + | 25 | 12954359 | 12954492 | 25 | 12954395 | 12954528 |
| chromosome_5_379.BC_04 | 3047742 | 3047960 | + | 18 | 3047758 | 3047884 | 19 | 3047819 | 3047946 |
| chromosome_5_661.BC_04 | 5454601 | 5454819 | + | 24 | 5454667 | 5454799 | 23 | 5454635 | 5454766 |
| chromosome_5_181.BC_05 | 1482116 | 1482334 | + | 18 | 1482198 | 1482324 | 18 | 1482138 | 1482264 |
| chromosome_5_1255.BC_05 | 8374317 | 8374535 | + | 25 | 8374380 | 8374513 | 20 | 8374338 | 8374466 |
| chromosome_5_139.BC_05 | 1149586 | 1149804 | + | 20 | 1149603 | 1149731 | 24 | 1149632 | 1149764 |
| Chromosome 6 | | | | | | | | | |
| chromosome_6_657.BC_01 | 49334150 | 49334368 | + | 20 | 49334212 | 49334340 | 19 | 49334162 | 49334289 |
| chromosome_6_146.BC_01 | 8616424 | 8616642 | + | 22 | 8616491 | 8616621 | 24 | 8616465 | 8616597 |
| chromosome_6_145.BC_01 | 8616466 | 8616684 | + | 22 | 8616491 | 8616621 | 22 | 8616548 | 8616678 |
| chromosome_6_166.BC_01 | 10062440 | 10062658 | + | 21 | 10062461 | 10062590 | 23 | 10062502 | 10062633 |
| chromosome_6_801.BC_01 | 54609029 | 54609247 | + | 23 | 54609115 | 54609246 | 24 | 54609049 | 54609181 |
| chromosome_6_852.BC_01 | 56307517 | 56307735 | + | 22 | 56307542 | 56307672 | 22 | 56307579 | 56307709 |
| chromosome_6_323.BC_01 | 36252403 | 36252621 | + | 24 | 36252456 | 36252588 | 24 | 36252415 | 36252547 |
| chromosome_6_235.BC_02 | 42197879 | 42198097 | + | 22 | 42197957 | 42198087 | 22 | 42197931 | 42198061 |
| chromosome_6_657.BC_02 | 62142098 | 62142316 | + | 21 | 62142146 | 62142275 | 18 | 62142168 | 62142294 |
| chromosome_6_555.BC_02 | 58149231 | 58149449 | + | 20 | 58149297 | 58149425 | 18 | 58149274 | 58149400 |
| chromosome_6_166.BC_02 | 31431683 | 31431901 | + | 21 | 31431704 | 31431833 | 25 | 31431736 | 31431869 |
| chromosome_6_357.BC_02 | 48274451 | 48274669 | + | 25 | 48274473 | 48274606 | 25 | 48274534 | 48274667 |
| chromosome_6_201.BC_02 | 37144624 | 37144842 | + | 18 | 37144642 | 37144768 | 18 | 37144670 | 37144795 |
| chromosome_6_313.BC_03 | 32230496 | 32230714 | + | 22 | 32230506 | 32230636 | 24 | 32230533 | 32230665 |
| chromosome_6_336.BC_03 | 35870213 | 35870431 | + | 22 | 35870254 | 35870384 | 21 | 35870288 | 35870417 |
| chromosome_6_337.BC_03 | 35870171 | 35870389 | + | 23 | 35870204 | 35870335 | 22 | 35870229 | 35870359 |
| chromosome_6_805.BC_03 | 56307471 | 56307689 | + | 21 | 56307473 | 56307602 | 21 | 56307528 | 56307657 |
| chromosome_6_632.BC_03 | 49334146 | 49334364 | + | 23 | 49334170 | 49334301 | 22 | 49334201 | 49334331 |
| chromosome_6_159.BC_03 | 8684276 | 8684494 | + | 24 | 8684340 | 8684472 | 20 | 8684318 | 8684446 |
| chromosome_6_888.BC_04 | 15123597 | 15123815 | + | 23 | 15123603 | 15123734 | 21 | 15123670 | 15123799 |
| chromosome_6_67.BC_04 | 554774 | 554992 | + | 22 | 554826 | 554956 | 24 | 554783 | 554915 |
| chromosome_6_889.BC_04 | 15123555 | 15123773 | + | 23 | 15123602 | 15123733 | 20 | 15123561 | 15123689 |
| chromosome_6_1475.BC_04 | 39647152 | 39647370 | + | 25 | 39647159 | 39647292 | 21 | 39647187 | 39647316 |
| chromosome_6_351.BC_05 | 2421512 | 2421730 | + | 22 | 2421574 | 2421704 | 22 | 2421551 | 2421681 |
| chromosome_6_200.BC_05 | 1379126 | 1379344 | + | 20 | 1379144 | 1379272 | 20 | 1379201 | 1379329 |
| chromosome_6_201.BC_05 | 1397640 | 1397858 | + | 20 | 1397702 | 1397830 | 20 | 1397675 | 1397803 |
| chromosome_6_202.BC_05 | 1397599 | 1397817 | + | 20 | 1397623 | 1397751 | 20 | 1397677 | 1397805 |
| chromosome_6_972.BC_05 | 9717365 | 9717583 | + | 25 | 9717405 | 9717538 | 25 | 9717442 | 9717575 |
| chromosome_6_1147.BC_05 | 15089799 | 15090017 | + | 24 | 15089804 | 15089936 | 23 | 15089834 | 15089965 |
| chromosome_6_180.BC_05 | 1207524 | 1207742 | + | 24 | 1207531 | 1207663 | 20 | 1207612 | 1207740 |
| Chromosome 7 | | | | | | | | | |
| chromosome_7_287.BC_01 | 8606527 | 8606745 | + | 22 | 8606565 | 8606695 | 24 | 8606606 | 8606738 |
| chromosome_7_243.BC_01 | 7722615 | 7722833 | + | 22 | 7722699 | 7722829 | 22 | 7722662 | 7722792 |
| chromosome_7_49.BC_01 | 1304239 | 1304457 | + | 24 | 1304246 | 1304378 | 24 | 1304277 | 1304409 |
| chromosome_7_294.BC_01 | 8897278 | 8897496 | + | 24 | 8897337 | 8897469 | 25 | 8897310 | 8897443 |
| chromosome_7_62.BC_01 | 1863068 | 1863286 | + | 25 | 1863146 | 1863279 | 25 | 1863074 | 1863207 |
| chromosome_7_395.BC_02 | 52628062 | 52628280 | + | 22 | 52628127 | 52628257 | 22 | 52628086 | 52628216 |
| chromosome_7_256.BC_02 | 15969322 | 15969540 | + | 25 | 15969325 | 15969458 | 25 | 15969389 | 15969522 |
| chromosome_7_454.BC_02 | 55721818 | 55722036 | + | 25 | 55721902 | 55722035 | 22 | 55721857 | 55721987 |

TABLE C-continued

List of new miRNAs in *sorghum*

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| chromosome_7_366.BC_03 | 14773724 | 14773942 | + | 18 | 14773807 | 14773933 | 18 | 14773766 | 14773892 |
| chromosome_7_516.BC_03 | 44603435 | 44603653 | + | 18 | 44603469 | 44603595 | 22 | 44603446 | 44603576 |
| chromosome_7_568.BC_03 | 51831832 | 51832050 | + | 24 | 51831842 | 51831974 | 25 | 51831913 | 51832046 |
| chromosome_7_454.BC_03 | 30877273 | 30877491 | + | 24 | 30877306 | 30877438 | 24 | 30877277 | 30877409 |
| chromosome_7_22.BC_03 | 877244 | 877462 | + | 20 | 877269 | 877397 | 23 | 877292 | 877423 |
| chromosome_7_287.BC_03 | 8855212 | 8855430 | + | 22 | 8855250 | 8855380 | 21 | 8855280 | 8855409 |
| chromosome_7_483.BC_04 | 4175091 | 4175309 | + | 19 | 4175144 | 4175271 | 18 | 4175106 | 4175232 |
| chromosome_7_1053.BC_04 | 9092869 | 9093087 | + | 24 | 9092924 | 9093056 | 22 | 9092894 | 9093024 |
| chromosome_7_627.BC_05 | 4071783 | 4072001 | + | 21 | 4071785 | 4071914 | 23 | 4071856 | 4071987 |
| chromosome_7_159.BC_05 | 901857 | 902075 | + | 22 | 901929 | 902059 | 22 | 901863 | 901993 |
| chromosome_7_1887.BC_05 | 16365788 | 16366006 | + | 18 | 16365830 | 16365956 | 20 | 16365857 | 16365985 |
| chromosome_7_628.BC_05 | 4071740 | 4071958 | + | 24 | 4071788 | 4071920 | 20 | 4071820 | 4071948 |
| Chromosome 8 | | | | | | | | | |
| chromosome_8_401.BC_01 | 33145817 | 33146035 | + | 18 | 33145867 | 33145993 | 18 | 33145846 | 33145972 |
| chromosome_8_751.BC_01 | 53091509 | 53091727 | + | 18 | 53091531 | 53091657 | 18 | 53091588 | 53091714 |
| chromosome_8_208.BC_01 | 8468733 | 8468951 | + | 25 | 8468787 | 8468920 | 25 | 8468760 | 8468893 |
| chromosome_8_765.BC_01 | 53381583 | 53381801 | + | 19 | 53381628 | 53381755 | 19 | 53381654 | 53381781 |
| chromosome_8_533.BC_03 | 49871187 | 49871405 | + | 20 | 49871233 | 49871361 | 19 | 49871195 | 49871322 |
| chromosome_8_216.BC_03 | 11557635 | 11557853 | + | 19 | 11557647 | 11557774 | 19 | 11557668 | 11557795 |
| chromosome_8_497.BC_04 | 4848342 | 4848560 | + | 21 | 4848383 | 4848512 | 20 | 4848428 | 4848556 |
| chromosome_8_150.BC_04 | 1629110 | 1629328 | + | 22 | 1629180 | 1629310 | 23 | 1629138 | 1629269 |
| chromosome_8_216.BC_04 | 2247491 | 2247709 | + | 19 | 2247503 | 2247630 | 19 | 2247572 | 2247699 |
| chromosome_8_681.BC_04 | 7206216 | 7206434 | + | 24 | 7206280 | 7206412 | 23 | 7206254 | 7206385 |
| chromosome_8_190.BC_05 | 1557321 | 1557539 | + | 22 | 1557402 | 1557532 | 20 | 1557344 | 1557472 |
| chromosome_8_468.BC_05 | 3155112 | 3155330 | + | 20 | 3155180 | 3155308 | 22 | 3155139 | 3155269 |
| chromosome_8_618.BC_05 | 4378988 | 4379206 | + | 19 | 4379030 | 4379157 | 20 | 4379054 | 4379182 |
| chromosome_8_297.BC_05 | 2224286 | 2224504 | + | 19 | 2224291 | 2224418 | 19 | 2224336 | 2224463 |
| chromosome_8_298.BC_05 | 2224244 | 2224462 | + | 19 | 2224330 | 2224457 | 19 | 2224297 | 2224424 |
| Chromosome 9 | | | | | | | | | |
| chromosome_9_506.BC_01 | 44748115 | 44748333 | + | 24 | 44748177 | 44748309 | 21 | 44748137 | 44748266 |
| chromosome_9_544.BC_02 | 55105109 | 55105327 | + | 21 | 55105131 | 55105260 | 23 | 55105177 | 55105308 |
| chromosome_9_554.BC_02 | 55441635 | 55441853 | + | 20 | 55441708 | 55441836 | 20 | 55441661 | 55441789 |
| chromosome_9_19.BC_02 | 1285782 | 1286000 | + | 25 | 1285836 | 1285969 | 22 | 1285869 | 1285999 |
| chromosome_9_1410.BC_05 | 9601262 | 9601480 | + | 22 | 9601324 | 9601454 | 24 | 9601290 | 9601422 |
| chromosome_9_721.BC_05 | 4452093 | 4452311 | + | 24 | 4452115 | 4452247 | 19 | 4452160 | 4452287 |
| chromosome_9_1189.BC_05 | 7590118 | 7590336 | + | 21 | 7590169 | 7590298 | 21 | 7590119 | 7590248 |
| chromosome_9_1132.BC_05 | 7187470 | 7187688 | + | 22 | 7187471 | 7187601 | 22 | 7187556 | 7187686 |
| Chromosome 10 | | | | | | | | | |
| chromosome_10_93.BC_01 | 3709798 | 3710016 | + | 22 | 3709870 | 3710000 | 20 | 3709829 | 3709957 |
| chromosome_10_293.BC_01 | 9715817 | 9716035 | + | 25 | 9715901 | 9716034 | 25 | 9715823 | 9715956 |
| chromosome_10_962.BC_01 | 57054835 | 57055053 | + | 18 | 57054922 | 57055048 | 18 | 57054859 | 57054985 |
| chromosome_10_593.BC_02 | 58928507 | 58928725 | + | 22 | 58928587 | 58928717 | 22 | 58928554 | 58928684 |
| chromosome_10_295.BC_02 | 18366558 | 18366776 | + | 21 | 18366608 | 18366737 | 22 | 18366581 | 18366711 |
| chromosome_10_73.BC_03 | 2727316 | 2727534 | + | 24 | 2727382 | 2727514 | 25 | 2727343 | 2727476 |
| chromosome_10_792.BC_03 | 56170687 | 56170905 | + | 18 | 56170748 | 56170874 | 18 | 56170688 | 56170814 |
| chromosome_10_77.BC_03 | 2869845 | 2870063 | + | 20 | 2869846 | 2869974 | 20 | 2869877 | 2870005 |
| chromosome_10_1038.BC_04 | 8933922 | 8934140 | + | 18 | 8933981 | 8934107 | 22 | 8933926 | 8934056 |
| chromosome_10_766.BC_04 | 6613106 | 6613324 | + | 23 | 6613171 | 6613302 | 24 | 6613141 | 6613273 |
| chromosome_10_1088.BC_04 | 9544939 | 9545157 | + | 22 | 9544975 | 9545105 | 18 | 9545003 | 9545129 |
| chromosome_10_1564.BC_05 | 10350410 | 10350628 | + | 23 | 10350441 | 10350572 | 21 | 10350498 | 10350627 |
| chromosome_10_1885.BC_05 | 13819559 | 13819777 | + | 21 | 13819633 | 13819762 | 22 | 13819567 | 13819697 |
| chromosome_10_880.BC_05 | 5730338 | 5730556 | + | 22 | 5730360 | 5730490 | 19 | 5730404 | 5730531 |
| chromosome_10_216.BC_05 | 1572675 | 1572893 | + | 23 | 1572755 | 1572886 | 21 | 1572683 | 1572812 |
| chromosome_10_283.BC_05 | 2016636 | 2016854 | + | 21 | 2016699 | 2016828 | 25 | 2016657 | 2016790 |
| chromosome_10_73.BC_05 | 522969 | 523187 | + | 24 | 523035 | 523167 | 24 | 522996 | 523128 |

TABLE D

Frequency counts of small RNA reads for new miRNAs

| | Count of mapped reads to miRNA genes for each library | | | | |
|---|---|---|---|---|---|
| miRNA | Mix | BTx623 | Rio | LB/EF F2s | HB/LF F2s |
| chromosome_1_1396.BC_01 | 24 | 9 | 16 | 91 | 108 |
| chromosome_1_245.BC_01 | 254 | 142 | 135 | 762 | 882 |
| chromosome_1_333.BC_01 | 13 | 0 | 4 | 24 | 18 |
| chromosome_1_827.BC_01 | 5 | 5 | 8 | 10 | 14 |
| chromosome_1_1016.BC_02 | 4 | 7 | 3 | 12 | 19 |

TABLE D-continued

Frequency counts of small RNA reads for new miRNAs

Count of mapped reads to miRNA genes for each library

| miRNA | Mix | BTx623 | Rio | LB/EF F2s | HB/LF F2s |
|---|---|---|---|---|---|
| chromosome_1_1088.BC_02 | 8 | 12 | 2 | 12 | 21 |
| chromosome_1_398.BC_02 | 2 | 7 | 1 | 8 | 10 |
| chromosome_1_450.BC_02 | 2 | 3 | 5 | 11 | 15 |
| chromosome_1_466.BC_02 | 11 | 12 | 14 | 30 | 34 |
| chromosome_1_862.BC_02 | 26 | 15 | 16 | 63 | 96 |
| chromosome_1_686.BC_02 | 0 | 2 | 0 | 6 | 5 |
| chromosome_1_1241.BC_03 | 12 | 3 | 11 | 19 | 34 |
| chromosome_1_191.BC_03 | 254 | 142 | 135 | 762 | 882 |
| chromosome_1_345.BC_03 | 3 | 2 | 3 | 6 | 15 |
| chromosome_1_346.BC_03 | 3 | 2 | 3 | 7 | 14 |
| chromosome_1_350.BC_03 | 5 | 7 | 13 | 47 | 42 |
| chromosome_1_651.BC_03 | 5 | 4 | 4 | 17 | 21 |
| chromosome_1_40.BC_03 | 9 | 2 | 4 | 19 | 20 |
| chromosome_1_970.BC_03 | 5 | 5 | 4 | 14 | 23 |
| chromosome_1_1560.BC_03 | 1 | 0 | 3 | 4 | 6 |
| chromosome_1_375.BC_03 | 1 | 1 | 2 | 7 | 5 |
| chromosome_1_1337.BC_04 | 4 | 1 | 5 | 5 | 10 |
| chromosome_1_1391.BC_04 | 28 | 14 | 30 | 95 | 136 |
| chromosome_1_52.BC_04 | 4 | 4 | 4 | 20 | 24 |
| chromosome_1_754.BC_04 | 14 | 7 | 6 | 49 | 53 |
| chromosome_1_882.BC_04 | 4 | 1 | 3 | 13 | 11 |
| chromosome_1_983.BC_04 | 0 | 2 | 4 | 16 | 29 |
| chromosome_1_512.BC_04 | 2 | 1 | 0 | 9 | 5 |
| chromosome_1_2718.BC_05 | 7 | 12 | 2 | 16 | 18 |
| chromosome_1_527.BC_05 | 64 | 34 | 52 | 217 | 282 |
| chromosome_1_216.BC_05 | 3 | 3 | 3 | 2 | 15 |
| chromosome_1_595.BC_05 | 11 | 2 | 2 | 7 | 37 |
| chromosome_2_1473.BC_01 | 35 | 6 | 27 | 70 | 120 |
| chromosome_2_45.BC_01 | 6 | 5 | 6 | 9 | 25 |
| chromosome_2_902.BC_02 | 15 | 13 | 22 | 53 | 67 |
| chromosome_2_689.BC_03 | 2 | 0 | 5 | 4 | 9 |
| chromosome_2_1490.BC_04 | 7 | 4 | 4 | 32 | 32 |
| chromosome_2_2159.BC_04 | 3 | 2 | 1 | 10 | 8 |
| chromosome_2_573.BC_04 | 21 | 10 | 15 | 80 | 123 |
| chromosome_2_3135.BC_04 | 5 | 1 | 3 | 4 | 5 |
| chromosome_2_721.BC_04 | 3 | 1 | 2 | 10 | 3 |
| chromosome_2_790.BC_04 | 7 | 1 | 2 | 4 | 6 |
| chromosome_2_1257.BC_05 | 1 | 1 | 2 | 5 | 18 |
| chromosome_2_1418.BC_05 | 0 | 0 | 2 | 5 | 15 |
| chromosome_2_2234.BC_05 | 0 | 0 | 4 | 4 | 10 |
| chromosome_2_3135.BC_05 | 7 | 4 | 10 | 13 | 29 |
| chromosome_2_800.BC_05 | 17 | 5 | 18 | 29 | 48 |
| chromosome_2_1061.BC_05 | 4 | 1 | 0 | 5 | 8 |
| chromosome_2_1464.BC_05 | 1 | 0 | 4 | 1 | 5 |
| chromosome_3_1128.BC_01 | 10 | 3 | 12 | 14 | 34 |
| chromosome_3_1222.BC_01 | 22 | 4 | 28 | 67 | 78 |
| chromosome_3_1257.BC_01 | 28 | 6 | 35 | 45 | 127 |
| chromosome_3_1324.BC_01 | 12 | 7 | 14 | 44 | 51 |
| chromosome_3_189.BC_01 | 13 | 3 | 9 | 37 | 56 |
| chromosome_3_213.BC_01 | 22 | 2 | 27 | 62 | 84 |
| chromosome_3_397.BC_01 | 9 | 3 | 11 | 18 | 27 |
| chromosome_3_47.BC_01 | 13 | 13 | 16 | 51 | 79 |
| chromosome_3_1460.BC_01 | 6 | 2 | 2 | 6 | 7 |
| chromosome_3_235.BC_02 | 7 | 9 | 2 | 13 | 17 |
| chromosome_3_562.BC_02 | 4 | 5 | 4 | 10 | 9 |
| chromosome_3_201.BC_02 | 4 | 2 | 1 | 7 | 8 |
| chromosome_3_39.BC_02 | 6 | 9 | 0 | 5 | 6 |
| chromosome_3_514.BC_02 | 0 | 4 | 1 | 5 | 4 |
| chromosome_3_783.BC_02 | 0 | 2 | 1 | 2 | 8 |
| chromosome_3_234.BC_03 | 6 | 1 | 6 | 16 | 22 |
| chromosome_3_107.BC_03 | 0 | 1 | 4 | 6 | 7 |
| chromosome_3_1128.BC_04 | 7 | 5 | 3 | 13 | 27 |
| chromosome_3_133.BC_04 | 2 | 4 | 0 | 4 | 11 |
| chromosome_3_1374.BC_04 | 21 | 6 | 23 | 72 | 70 |
| chromosome_3_1462.BC_04 | 2 | 5 | 4 | 12 | 11 |
| chromosome_3_215.BC_04 | 1 | 4 | 11 | 17 | 17 |
| chromosome_3_494.BC_04 | 6 | 2 | 0 | 15 | 15 |
| chromosome_3_954.BC_04 | 9 | 3 | 1 | 17 | 15 |
| chromosome_3_1127.BC_05 | 3 | 1 | 7 | 16 | 28 |
| chromosome_3_1223.BC_05 | 14 | 3 | 22 | 47 | 54 |
| chromosome_3_2132.BC_05 | 27 | 22 | 39 | 95 | 128 |
| chromosome_3_216.BC_05 | 1 | 2 | 3 | 6 | 11 |
| chromosome_3_468.BC_05 | 5 | 2 | 3 | 14 | 16 |
| chromosome_3_582.BC_05 | 7 | 2 | 6 | 14 | 27 |

TABLE D-continued

Frequency counts of small RNA reads for new miRNAs

Count of mapped reads to miRNA genes for each library

| miRNA | Mix | BTx623 | Rio | LB/EF F2s | HB/LF F2s |
|---|---|---|---|---|---|
| chromosome_3_851.BC_05 | 6 | 0 | 16 | 26 | 26 |
| chromosome_3_1435.BC_05 | 0 | 0 | 1 | 9 | 8 |
| chromosome_3_821.BC_05 | 1 | 1 | 1 | 0 | 8 |
| chromosome_4_684.BC_01 | 3 | 5 | 0 | 4 | 7 |
| chromosome_4_712.BC_01 | 2 | 2 | 1 | 3 | 8 |
| chromosome_4_1028.BC_01 | 9 | 0 | 2 | 24 | 28 |
| chromosome_4_522.BC_01 | 3 | 3 | 1 | 6 | 28 |
| chromosome_4_134.BC_02 | 4 | 5 | 6 | 3 | 12 |
| chromosome_4_83.BC_02 | 17 | 8 | 12 | 37 | 72 |
| chromosome_4_47.BC_02 | 10 | 6 | 6 | 26 | 46 |
| chromosome_4_557.BC_02 | 8 | 11 | 11 | 33 | 50 |
| chromosome_4_608.BC_02 | 2 | 6 | 2 | 18 | 10 |
| chromosome_4_571.BC_03 | 7 | 1 | 7 | 27 | 30 |
| chromosome_4_831.BC_04 | 3 | 1 | 8 | 16 | 28 |
| chromosome_4_1764.BC_04 | 2 | 1 | 4 | 7 | 8 |
| chromosome_4_2454.BC_04 | 2 | 0 | 0 | 4 | 4 |
| chromosome_4_626.BC_05 | 7 | 10 | 4 | 35 | 33 |
| chromosome_4_785.BC_05 | 21 | 9 | 16 | 51 | 101 |
| chromosome_4_941.BC_05 | 9 | 2 | 2 | 9 | 16 |
| chromosome_4_1677.BC_05 | 0 | 1 | 2 | 3 | 9 |
| chromosome_4_174.BC_05 | 2 | 0 | 2 | 1 | 6 |
| chromosome_4_1911.BC_05 | 2 | 2 | 3 | 15 | 16 |
| chromosome_4_1912.BC_05 | 3 | 1 | 4 | 14 | 17 |
| chromosome_5_1020.BC_01 | 16 | 6 | 7 | 31 | 24 |
| chromosome_5_414.BC_01 | 6 | 14 | 8 | 34 | 40 |
| chromosome_5_595.BC_01 | 1806 | 1137 | 1293 | 5188 | 5759 |
| chromosome_5_620.BC_01 | 82 | 30 | 56 | 269 | 236 |
| chromosome_5_737.BC_01 | 2 | 0 | 0 | 4 | 8 |
| chromosome_5_978.BC_01 | 14 | 10 | 5 | 23 | 28 |
| chromosome_5_70.BC_01 | 16 | 10 | 5 | 28 | 50 |
| chromosome_5_456.BC_02 | 2 | 3 | 3 | 9 | 17 |
| chromosome_5_468.BC_02 | 567 | 272 | 483 | 1915 | 2410 |
| chromosome_5_508.BC_02 | 4 | 6 | 0 | 14 | 8 |
| chromosome_5_657.BC_02 | 14 | 7 | 9 | 35 | 35 |
| chromosome_5_455.BC_02 | 1 | 3 | 1 | 3 | 4 |
| chromosome_5_612.BC_02 | 0 | 4 | 1 | 4 | 6 |
| chromosome_5_642.BC_02 | 1 | 5 | 1 | 6 | 3 |
| chromosome_5_148.BC_03 | 9 | 3 | 10 | 21 | 42 |
| chromosome_5_468.BC_03 | 10 | 0 | 15 | 24 | 12 |
| chromosome_5_509.BC_03 | 187 | 80 | 165 | 508 | 621 |
| chromosome_5_574.BC_03 | 28 | 11 | 33 | 119 | 113 |
| chromosome_5_609.BC_03 | 0 | 0 | 3 | 4 | 3 |
| chromosome_5_648.BC_03 | 0 | 1 | 4 | 1 | 8 |
| chromosome_5_737.BC_03 | 0 | 1 | 3 | 2 | 6 |
| chromosome_5_631.BC_04 | 2 | 0 | 4 | 5 | 16 |
| chromosome_5_646.BC_04 | 6 | 6 | 0 | 17 | 12 |
| chromosome_5_661.BC_04 | 2 | 0 | 2 | 13 | 12 |
| chromosome_5_74.BC_04 | 3 | 2 | 6 | 7 | 15 |
| chromosome_5_1387.BC_04 | 1 | 0 | 0 | 3 | 6 |
| chromosome_5_379.BC_04 | 0 | 2 | 0 | 4 | 7 |
| chromosome_5_456.BC_04 | 0 | 0 | 2 | 7 | 7 |
| chromosome_5_181.BC_05 | 1 | 1 | 1 | 5 | 10 |
| chromosome_5_1255.BC_05 | 4 | 2 | 3 | 9 | 16 |
| chromosome_5_139.BC_05 | 2 | 2 | 1 | 18 | 13 |
| chromosome_6_145.BC_01 | 2 | 2 | 0 | 4 | 14 |
| chromosome_6_146.BC_01 | 2 | 2 | 1 | 4 | 15 |
| chromosome_6_166.BC_01 | 12 | 0 | 10 | 15 | 28 |
| chromosome_6_323.BC_01 | 8 | 8 | 12 | 32 | 51 |
| chromosome_6_657.BC_01 | 14 | 6 | 11 | 11 | 22 |
| chromosome_6_801.BC_01 | 180 | 69 | 246 | 726 | 908 |
| chromosome_6_852.BC_01 | 43 | 3 | 51 | 105 | 154 |
| chromosome_6_201.BC_02 | 3 | 4 | 1 | 2 | 0 |
| chromosome_6_235.BC_02 | 4 | 8 | 0 | 9 | 7 |
| chromosome_6_657.BC_02 | 1 | 3 | 2 | 4 | 0 |
| chromosome_6_166.BC_02 | 3 | 2 | 0 | 3 | 5 |
| chromosome_6_357.BC_02 | 5 | 2 | 3 | 13 | 14 |
| chromosome_6_555.BC_02 | 4 | 9 | 0 | 12 | 5 |
| chromosome_6_159.BC_03 | 1 | 2 | 3 | 5 | 11 |
| chromosome_6_313.BC_03 | 1 | 1 | 2 | 5 | 11 |
| chromosome_6_336.BC_03 | 2 | 5 | 3 | 16 | 16 |
| chromosome_6_337.BC_03 | 2 | 5 | 3 | 16 | 16 |
| chromosome_6_805.BC_03 | 43 | 3 | 51 | 105 | 154 |
| chromosome_6_632.BC_03 | 14 | 6 | 11 | 11 | 22 |
| chromosome_6_67.BC_04 | 3 | 2 | 3 | 7 | 11 |

TABLE D-continued

Frequency counts of small RNA reads for new miRNAs

Count of mapped reads to miRNA genes for each library

| miRNA | Mix | BTx623 | Rio | LB/EF F2s | HB/LF F2s |
|---|---|---|---|---|---|
| chromosome_6_888.BC_04 | 3 | 4 | 7 | 14 | 15 |
| chromosome_6_889.BC_04 | 2 | 4 | 5 | 13 | 13 |
| chromosome_6_1475.BC_04 | 5 | 5 | 1 | 7 | 9 |
| chromosome_6_351.BC_05 | 2 | 3 | 0 | 15 | 8 |
| chromosome_6_972.BC_05 | 5 | 1 | 4 | 16 | 21 |
| chromosome_6_200.BC_05 | 11 | 4 | 9 | 41 | 54 |
| chromosome_6_201.BC_05 | 4 | 1 | 3 | 9 | 14 |
| chromosome_6_202.BC_05 | 3 | 0 | 3 | 9 | 11 |
| chromosome_6_1147.BC_05 | 3 | 2 | 0 | 4 | 17 |
| chromosome_6_180.BC_05 | 4 | 1 | 3 | 5 | 5 |
| chromosome_7_243.BC_01 | 12 | 2 | 6 | 18 | 37 |
| chromosome_7_294.BC_01 | 18 | 3 | 22 | 48 | 65 |
| chromosome_7_49.BC_01 | 2 | 8 | 3 | 26 | 23 |
| chromosome_7_62.BC_01 | 7 | 3 | 10 | 13 | 38 |
| chromosome_7_287.BC_01 | 3 | 4 | 0 | 4 | 5 |
| chromosome_7_256.BC_02 | 0 | 3 | 4 | 5 | 6 |
| chromosome_7_395.BC_02 | 5 | 6 | 1 | 18 | 14 |
| chromosome_7_454.BC_02 | 1 | 3 | 1 | 10 | 6 |
| chromosome_7_22.BC_03 | 8 | 6 | 4 | 48 | 9 |
| chromosome_7_366.BC_03 | 12 | 3 | 8 | 28 | 17 |
| chromosome_7_454.BC_033 | 3 | 1 | 3 | 10 | 9 |
| chromosome_7_516.BC_03 | 3 | 2 | 4 | 3 | 9 |
| chromosome_7_568.BC_03 | 2 | 1 | 5 | 1 | 6 |
| chromosome_7_287.BC_03 | 2 | 0 | 4 | 9 | 9 |
| chromosome_7_1053.BC_04 | 2 | 3 | 5 | 12 | 17 |
| chromosome_7_483.BC_04 | 3 | 5 | 1 | 9 | 7 |
| chromosome_7_1887.BC_05 | 13 | 7 | 9 | 24 | 39 |
| chromosome_7_159.BC_05 | 0 | 0 | 2 | 5 | 8 |
| chromosome_7_627.BC_05 | 0 | 0 | 2 | 2 | 7 |
| chromosome_7_628.BC_05 | 0 | 0 | 2 | 1 | 7 |
| chromosome_8_765.BC_01 | 5 | 1 | 6 | 26 | 40 |
| chromosome_8_208.BC_01 | 3 | 2 | 0 | 4 | 4 |
| chromosome_8_401.BC_01 | 2 | 0 | 0 | 4 | 5 |
| chromosome_8_751.BC_01 | 5 | 2 | 2 | 5 | 4 |
| chromosome_8_533.BC_03 | 4 | 3 | 6 | 11 | 22 |
| chromosome_8_216.BC_03 | 3 | 7 | 2 | 9 | 8 |
| chromosome_8_150.BC_04 | 5 | 3 | 1 | 15 | 15 |
| chromosome_8_216.BC_04 | 11 | 3 | 9 | 23 | 24 |
| chromosome_8_681.BC_04 | 2 | 2 | 1 | 9 | 18 |
| chromosome_8_497.BC_04 | 2 | 4 | 3 | 7 | 6 |
| chromosome_8_190.BC_05 | 2 | 6 | 2 | 8 | 16 |
| chromosome_8_297.BC_05 | 13 | 8 | 14 | 51 | 67 |
| chromosome_8_298.BC_05 | 17 | 10 | 17 | 62 | 80 |
| chromosome_8_618.BC_05 | 2 | 3 | 1 | 3 | 10 |
| chromosome_8_468.BC_05 | 1 | 1 | 2 | 4 | 6 |
| chromosome_9_506.BC_01 | 5 | 0 | 1 | 7 | 4 |
| chromosome_9_19.BC_02 | 4 | 10 | 1 | 10 | 9 |
| chromosome_9_554.BC_02 | 4 | 10 | 3 | 22 | 20 |
| chromosome_9_544.BC_02 | 1 | 4 | 1 | 1 | 6 |
| chromosome_9_1189.BC_05 | 1 | 2 | 3 | 18 | 22 |
| chromosome_9_721.BC_05 | 6 | 3 | 4 | 7 | 19 |
| chromosome_9_1132.BC_05 | 6 | 1 | 2 | 5 | 6 |
| chromosome_9_1410.BC_05 | 2 | 2 | 2 | 4 | 5 |
| chromosome_10_293.BC_01 | 26 | 21 | 38 | 85 | 107 |
| chromosome_10_93.BC_01 | 34 | 17 | 23 | 109 | 99 |
| chromosome_10_962.BC_01 | 15 | 2 | 10 | 21 | 36 |
| chromosome_10_593.BC_02 | 8 | 7 | 6 | 25 | 35 |
| chromosome_10_295.BC_02 | 4 | 4 | 1 | 3 | 9 |
| chromosome_10_73.BC_03 | 6 | 3 | 9 | 6 | 24 |
| chromosome_10_77.BC_03 | 3 | 4 | 4 | 3 | 10 |
| chromosome_10_792.BC_03 | 574 | 103 | 594 | 3344 | 470 |
| chromosome_10_1088.BC_04 | 6 | 4 | 7 | 20 | 22 |
| chromosome_10_766.BC_04 | 1 | 2 | 4 | 8 | 11 |
| chromosome_10_1038.BC_04 | 0 | 1 | 0 | 4 | 5 |
| chromosome_10_1564.BC_05 | 1 | 1 | 1 | 11 | 6 |
| chromosome_10_1885.BC_05 | 4 | 3 | 10 | 28 | 32 |
| chromosome_10_73.BC_05 | 3 | 3 | 1 | 3 | 11 |
| chromosome_10_880.BC_05 | 11 | 1 | 13 | 16 | 36 |
| chromosome_10_216.BC_05 | 2 | 1 | 1 | 1 | 6 |
| chromosome_10_283.BC_05 | 0 | 1 | 2 | 2 | 8 |

TABLE E

List of new miRNAs that are within introns of protein coding genes

| miRNA ID | start | stop | strand |
|---|---|---|---|
| chromosome_1_333.BC_01 | 10623817 | 10624035 | + |
| chromosome_1_1241.BC_03 | 58998763 | 58998981 | + |
| chromosome_2_1490.BC_04 | 14065842 | 14066060 | + |
| chromosome_2_689.BC_03 | 48991679 | 48991897 | + |
| chromosome_2_3135.BC_05 | 26306294 | 26306512 | + |
| chromosome_2_3135.BC_04 | 54647513 | 54647731 | + |
| chromosome_3_1462.BC_04 | 13263113 | 13263331 | + |
| chromosome_4_2454.BC_04 | 41104168 | 41104386 | + |
| chromosome_4_571.BC_03 | 41084010 | 41084228 | + |
| chromosome_5_737.BC_03 | 52069704 | 52069922 | + |
| chromosome_5_1020.BC_01 | 57560746 | 57560964 | + |
| chromosome_6_337.BC_03 | 35870171 | 35870389 | + |
| chromosome_6_1147.BC_05 | 15089799 | 15090017 | + |
| chromosome_6_336.BC_03 | 35870213 | 35870431 | + |
| chromosome_7_454.BC_02 | 55721818 | 55722036 | + |
| chromosome_8_468.BC_05 | 3155112 | 3155330 | + |
| chromosome_9_721.BC_05 | 4452093 | 4452311 | + |

TABLE F

List of new miRNAs that target genes encoding sugar transporters and cell wall related proteins

| miRNA | Target gene | Gene function | Target site |
|---|---|---|---|
| | | Sugar transport | |
| chromosome_4_712_mature.BC_01 | Sb04g036140 | Monosaccharide transporter 6 | Exon |
| chromosome_4_1677_mature.BC_05 | Sb01g016730 | Monosaccharide transporter 2 | Exon |
| | Sb08g016530 | Sugar transporter | Exon |
| chromosome_7_516_mature.BC_03 | Sb10g031000 | Hexose transporter | Exon |
| | | Cell wall metabolism | |
| chromosome_1_882_mature.BC_04 | Sb10g003090 | Pectate lyase homolog | Exon |
| chromosome_1_970_mature.BC_03 | Sb09g020980 | Class III peroxidase 124 precursor | Exon |
| | Sb09g021000 | Class III peroxidase 124 precursor | Exon |
| | Sb03g035080 | Cinnamoyl CoA reductase | Exon |
| chromosome_1_983_mature.BC_04 | Sb04g037050 | Alcohol dehydrogenase class-3 (EC 1.1.1.1) | Exon |
| chromosome_2_45_mature.BC_01 | Sb01g027960 | Xyloglucan endotransglucosylase/hydrolase protein 28 precursor | 3' UTR |
| chromosome_2_1061_mature.BC_05 | Sb01g048630 | Callose synthase 1 catalytic subunit | Exon |
| chromosome_2_1490_mature.BC_04 | Sb05g019040 | O-methyltransferase ZRP4 | Exon |
| chromosome_3_133_mature.BC_04 | Sb09g000430 | Polygalacturonase inhibiting protein 2 precursor | Exon |
| chromosome_3_216_mature.BC_05 | Sb06g000490 | Class III peroxidase 52 precursor | Exon |
| chromosome_4_712_mature.BC_01 | Sb07g024870 | Beta-galactosidase 11 precursor | Exon |
| | Sb10g022620 | Beta-galactosidase 9 precursor | Exon |
| | Sb10g024490 | Cinnamoyl CoA reductase | Exon |
| | Sb10g024500 | Cinnamoyl CoA reductase | Exon |
| | Sb04g010000 | Expansin-A24 precursor | Exon |
| | Sb04g010160 | Expansin-A23 precursor | Exon |
| | Sb04g010170 | Expansin-A23 precursor | Exon |
| | Sb04g028090 | Expansin-A5 precursor | Exon |
| | Sb04g032830 | Expansin-B11 precursor | Exon |
| | Sb06g023380 | Expansin-B17 precursor | Exon |
| | Sb02g041050 | Esterase | Exon |
| | Sb03g001870 | Esterase | Exon |
| | Sb02g037310 | Fasciclin-like arabinogalactan-protein | Exon |
| | Sb05g026710 | O-methyltransferase | Exon |
| | Sb05g026730 | O-methyltransferase | Exon |
| | Sb03g013070 | Pectinacetylesterase | Exon |
| | Sb02g001130 | Peroxidase | Exon |
| | Sb10g010040 | Peroxidase 49 | Exon |
| | Sb10g005820 | Glutathione peroxidase | Exon |
| | Sb01g028610 | Class III peroxidase 120 precursor | Exon |
| | Sb02g029340 | Class III peroxidase 123 precursor | Exon |
| | Sb04g026510 | Phenylalanine ammonia-lyase | Exon |
| | Sb02g022220 | Polygalacturonase isoenzyme 1 beta subunit-like | Exon |
| | Sb03g013310 | Polygalacturonase PG2 | Exon |
| | Sb07g025220 | Sorbitol dehydrogenase | Exon |
| chromosome_4_1677_mature.BC_05 | Sb02g039600 | Alcohol dehydrogenase | Exon |
| | Sb03g029770 | Glycosyl transferase family 1 protein-like | Exon |
| | Sb02g001045 | 4-coumarate--CoA ligase 1 | Exon |
| | Sb02g001050 | 4-coumarate--CoA ligase 1 | Exon |
| | Sb07g007810 | 4-coumarate--CoA ligase 1 | Exon |
| | Sb01g037900 | Pectinesterase family protein | Exon |
| | Sb02g042780 | Pectinesterase | Exon |
| | Sb03g016510 | Peroxidase family protein | Exon |
| | Sb07g026520 | UDP-glucuronic acid 4-epimerase isoform 3 | Exon |
| | Sb01g020070 | Xyloglucan galactosyltransferase KATAMARI 1 | Exon |
| chromosome_5_181_mature.BC_05 | Sb06g033440 | Glutathione peroxidase-like protein GPX15Hv | Exon |
| | Sb08g000990 | Class III peroxidase 135 precursor | 3' UTR |
| chromosome_5_379_mature.BC_04 | Sb07g021680 | Cinnamoyl CoA reductase | Exon |
| | Sb02g010110 | Cellulose synthase-7 | Exon |
| | Sb03g004320 | Cellulose synthase-1 | Exon |

TABLE F-continued

List of new miRNAs that target genes encoding sugar transporters and cell wall related proteins

| miRNA | Target gene | Gene function | Target site |
|---|---|---|---|
| | Sb04g008640 | Cationic peroxidase 1 precursor | Exon |
| | Sb01g049890 | LysM domain containing protein | Exon |
| chromosome_5_737_mature.BC_03 | Sb06g026010 | Xyloglucan galactosyltransferase | Exon |
| chromosome_7_22_mature.BC_03 | Sb03g028190 | Arbutin synthase-like | Exon |
| | Sb03g047220 | Cellulose synthase | Exon |
| | Sb09g018400 | Esterase | Exon |
| | Sb09g018440 | Esterase | Exon |
| chromosome_7_366_mature.BC_03 | Sb06g024650 | Expansin-B15 precursor | Exon |
| | Sb10g028460 | Class III peroxidase 93 precursor | Exon |
| chromosome_7_627_mature.BC_05 | Sb03g013170 | S-adenosylmethionine synthetase 1 | Exon |
| chromosome_7_1887_mature.BC_05 | Sb02g033070 | Expansin-like A3 precursor | Exon |
| | Sb02g035070 | Brittle stalk-2-like protein 5 | Exon |
| chromosome_8_297_mature.BC_05 | Sb03g011930 | S-adenosylmethionine synthetase 1 | Exon |
| chromosome_8_298_mature.BC_05 | Sb07g028620 | Alkaline alpha galactosidase 3 | Exon |
| chromosome_8_618_mature.BC_05 | Sb09g025540 | O-methyltransferase ZRP4 | Exon |
| | Sb09g025560 | O-methyltransferase ZRP4 | Exon |
| | Sb05g025950 | Extensin-like protein precursor | Exon |
| chromosome_8_751_mature.BC_01 | Sb01g016630 | 4-coumarate--CoA ligase 1 | Exon |
| chromosome_9_1189_mature.BC_05 | Sb01g045200 | Glycosyl transferase, group 1 family protein | 5' UTR |
| | Sb10g008060 | Glycosyl transferase protein A-like | Exon |
| | Sb10g006230 | Pectin methylesterase | Exon |
| | Sb10g028480 | Peroxidase ATP8a | Exon |
| chromosome_10_792_mature.BC_03 | Sb02g000470 | Class III peroxidase 97 precursor | Exon |
| chromosome_10_962_mature.BC_01 | Sb03g047440 | Pectinacetylesterase | Exon |

TABLE G

List of new predicted MIR genes in sorghum

| MIR gene ID | Position | Strand | miRNA size | miRNA sequence 5'-3' | miRNA* sequence 5'-3' | miRNA* size |
|---|---|---|---|---|---|---|
| chromosome_1_52.BC_04 | Ch1: 574386 . . . 574497 | + | 19 | AAGATCTGTGGC GCCGAGC | TCGGCGCTAAGA TCTCTGG | 19 |
| chromosome_2_45.BC_01 | Ch2: 1930828 . . .1930937 | + | 18 | CCAATCTAAACA GGCCCT | GACCTGTTTAGA TTGGGA | 18 |
| chromosome_4_684.BC_01 | Ch4: 43242765 . . . 43242874 | + | 24 | ATGACAGAGCTC CGGCAGAGATAT | TTCTCCGCCGAG CTTATCTGTGG | 23 |
| chromosome_4_712.BC_01 | Ch4: 45785396 . . . 45785505 | + | 18 | CGCGCCGCCGTC CAGCGG | CTTGGCCGGTGC ACGCGTC | 19 |
| chromosome_6_852.BC_01 | Ch6: 56307517 . . . 56307626 | + | 22 | ACCACCAACCCC ACCGCTTCTC | GAAGCGGTGGTG TTGGTGGTGA | 22 |
| chromosome_7_22.BC_03* | Ch7: 877244 . . . 877353 | + | 20 | CGTCGCTGTCGC GCGCGCTG | GGTCAGGGCAGA GCACGCA | 19 |
| chromosome_7_256.BC_02 | Ch7: 15969322 . . . 15969431 | + | 25 | TAACACGAACCG GTGCATAAAGGA TC | CCCTTTAGCACC GGTTCGTGTTACA | 25 |
| chromosome_8_150.BC_04 | Ch8: 1629110 . . . 1629219 | + | 22 | ATCTTTGCCGGG TGTCTCTGAC | CAGCAAACATTC GGCAAAGAAAA | 23 |
| chromosome_8_497.BC_04 | Ch8: 4848342 . . . 4848451 | + | 21 | GCTTGAGTTTAT CAGCCGAGT | ATGGCTTATCAG CCAAGTGA | 20 |

*All the small RNA reads mapped to "chromosome_7_22.BC_03" were derived from the predicted miRNA* strand
miRNA sequences from top to bottom are SEQ ID NOs: 28-36 and miRNA* sequences from top to bottom are SEQ ID NOs: 37-45

---

What is claimed is:

1. A composition comprising at least one miRNA selected from [the group consisting of] sbi-miR395abcdef, sbi-miR395abcde*, and sbi-miR395f*, in a biologically compatible carrier, for modulating expression of a plant target gene, said target gene encoding a protein which regulates flowering in sorghum and said miRNA optionally comprising a detectable label.

2. The composition of claim 1, wherein said at least one miRNA is cloned into an expression vector.

3. The composition of claim 1, wherein said miRNA is a piccolo RNA associated with a promoter and comprises at least 25 nucleotides.

4. The composition of claim 1, wherein said miRNA is miR395 which hybridizes to a gene target selected from the group consisting of Sb01g044100, Sb01g008450, Sb03g014780, Sb03g026410, Sb01g007878, Sb10g005630, Sb10g013750, Sb09g023793, Sb10g012270 and said biological parameter is flowering.

5. A method for modulating flowering in a plant or plant cell comprising contacting said plant or plant cell with [an effective amount of] the composition as claimed in claim 1 or claim 2.

6. The composition of claim 1, wherein said miRNA is sbi-miR395f* and said target gene is at least one of embryonic flower 2 (EMF2), PICKLE (PKL) and CRYPTOCHROME 2 (CRY2).

* * * * *

SEQUENCE LISTING

<160> NUMBER OF SEQ ID NOS: 793

<210> SEQ ID NO 1
<211> LENGTH: 20

-continued

```
<212> TYPE: DNA
<213> ORGANISM: Artificial Sequence
<220> FEATURE:
<223> OTHER INFORMATION: Primer

<400> SEQUENCE: 1
tgcagccttg tctttgtttg                                          20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cctggaacct gtggtgaaat                                          20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gcccatatgg acggaagata                                          20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctggtagccg gagaacaact                                          20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ttgacaatgt ctgcctggtc                                          20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cgctggtcag caatctgata                                          20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
```

```
gcactcaagt ccagcacaaa                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tttcatcagt gcttgccaat                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tggctggatc taccacttcc                                              20

<210> SEQ ID NO 10
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 10
ggcaggucuu cuuggcuagc                                              20

<210> SEQ ID NO 11
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 11
gaaagccaag aagacucguu uguuu                                        25

<210> SEQ ID NO 12
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 12
ugaaucuuga ugaugcugca c                                            21

<210> SEQ ID NO 13
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 13
gcgcaggcau caucaagauc a                                            21

<210> SEQ ID NO 14
<211> LENGTH: 19
<212> TYPE: RNA
<213> ORGANISM: Artificial Sequence
```

```
<220> FEATURE:
<223> OTHER INFORMATION: Synthetic Sequence

<400> SEQUENCE: 14
ggaucuugau gaugcugca                                                    19

<210> SEQ ID NO 15
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 15
ugcagcauca ucaggauucu c                                                 21

<210> SEQ ID NO 16
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 16
guucccuuca agcacuucac a                                                 21

<210> SEQ ID NO 17
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 17
tgtggagtgc ttgaagagag t                                                 21

<210> SEQ ID NO 18
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 18
ggaaucuuga ugaugcugca                                                   20

<210> SEQ ID NO 19
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 19
ugcagcauca ucacgauucc                                                   20

<210> SEQ ID NO 20
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 20
ucaucuccuu gucaugca                                                     18
```

<210> SEQ ID NO 21
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 21
ugaaggagaa ggagaugaat ctgcgcaaga gcaa                              34

<210> SEQ ID NO 22
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 22
ucaucuccuu gucaugca                                                18

<210> SEQ ID NO 23
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 23
ucacaugaca aggaaugaag acctttggag g                                 31

<210> SEQ ID NO 24
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 24
ucaucuccuu gucaugca                                                18

<210> SEQ ID NO 25
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 25
uccaugacaa ggagagca                                                18

<210> SEQ ID NO 26
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 26
cgcgccgccg uccagcgg                                                18

<210> SEQ ID NO 27
<211> LENGTH: 34
<212> TYPE: DNA
<213> ORGANISM: Artificial Sequence
<220> FEATURE:
<223> OTHER INFORMATION: Synthetic Sequence

```
<400> SEQUENCE: 27
cctccgcgcg acggcgagc gcgagttcat gttc                          34

<210> SEQ ID NO 28
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 28
aagatctgtg gcgccgagc                                          19

<210> SEQ ID NO 29
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 29
ccaatctaaa caggccct                                           18

<210> SEQ ID NO 30
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 30
atgacagagc tccggcagag atat                                    24

<210> SEQ ID NO 31
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 31
cgcgccgccg tccagcgg                                           18

<210> SEQ ID NO 32
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 32
accaccaacc ccaccgcttc tc                                      22

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 33
cgtcgctgtc gcgcgcgctg                                         20

<210> SEQ ID NO 34
```

```
<210> SEQ ID NO 34
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 34
taacacgaac cggtgctaaa ggatc                                              25

<210> SEQ ID NO 35
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 35
atctttgccg ggtgtctctg ac                                                 22

<210> SEQ ID NO 36
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 36
gcttgagttt atcagccgag t                                                  21

<210> SEQ ID NO 37
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 37
tcggcgctaa gatctctgg                                                     19

<210> SEQ ID NO 38
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 38
gacctgttta gattggga                                                      18

<210> SEQ ID NO 39
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 39
ttctccgccg agcttatctg tgg                                                23

<210> SEQ ID NO 40
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 40
```

-continued cttggccggt gcacgcgtc                                              19

<210> SEQ ID NO 41
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 41
gaagcggtgg tgttggtggt ga                                          22

<210> SEQ ID NO 42
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 42
ggtcagggca gagcacgca                                              19

<210> SEQ ID NO 43
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 43
ccctttagca ccggttcgtg ttaca                                       25

<210> SEQ ID NO 44
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 44
cagcaaacat tcggcaaaga aaa                                         23

<210> SEQ ID NO 45
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 45
atggcttatc agccaagtga                                             20

<210> SEQ ID NO 46
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 46
uagccaagga ugacuugccu a                                           21

<210> SEQ ID NO 47
<211> LENGTH: 21
<212> TYPE: RNA

<213> ORGANISM: Artificial Sequence
<220> FEATURE:
<223> OTHER INFORMATION: Synthetic Sequence

<400> SEQUENCE: 47
uaggcaaggc cuacuuggcu a            21

<210> SEQ ID NO 48
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 48
uagccaagaa ugacuugccu a            21

<210> SEQ ID NO 49
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 49
uaggcaaggc cuacuuggcu a            21

<210> SEQ ID NO 50
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 50
gugaaguguu uggggaacu c            21

<210> SEQ ID NO 51
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 51
gaguuucccc aaacacuuca u            21

<210> SEQ ID NO 52
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 52
augaaguguu uggggaacu c            21

<210> SEQ ID NO 53
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 53
gaguuucccc aaacacuuca u            21

```
<210> SEQ ID NO 54
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 54
gggaagaggu gcgaggau                                              18

<210> SEQ ID NO 55
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 55
auccucgcac gcucccuccc                                            20

<210> SEQ ID NO 56
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 56
uucuuugccg agagccugc                                             19

<210> SEQ ID NO 57
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 57
gcagucucuc ggaagagaa                                             19

<210> SEQ ID NO 58
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 58
uucuuugccg agagccugc                                             19

<210> SEQ ID NO 59
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 59
gcagucucuc ggaagagaa                                             19

<210> SEQ ID NO 60
<211> LENGTH: 18
<212> TYPE: RNA
<213> ORGANISM: Artificial Sequence
<220> FEATURE:
```

```
<223> OTHER INFORMATION: Synthetic Sequence

<400> SEQUENCE: 60
ucaucuccuu gucaugca                                                    18

<210> SEQ ID NO 61
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 61
aguaugacaa ggaaauga                                                    18

<210> SEQ ID NO 62
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 62
ugcauuguga gugcccuua                                                   19

<210> SEQ ID NO 63
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 63
uaagggcacu cacaauaca                                                   19

<210> SEQ ID NO 64
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 64
cgcacggcgg cggcgcgacg g                                                21

<210> SEQ ID NO 65
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 65
ccgucgccgc cgccgccgcc g                                                21

<210> SEQ ID NO 66
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 66
cgcacggcgg cggcgcgacg g                                                21
```

```
<210> SEQ ID NO 67
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 67
ccgccgccgc cgccgcccug cg                                               22

<210> SEQ ID NO 68
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 68
caauccacau gcguuggggu gg                                               22

<210> SEQ ID NO 69
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 69
ccaccucaac acaugcggau ug                                               22

<210> SEQ ID NO 70
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 70
caauccacau gcguuggggu gg                                               22

<210> SEQ ID NO 71
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 71
ccacaccaac acauguggau ug                                               22

<210> SEQ ID NO 72
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 72
caauccacau gcguuggggu gg                                               22

<210> SEQ ID NO 73
<211> LENGTH: 22
<212> TYPE: RNA
<213> ORGANISM: Artificial Sequence
<220> FEATURE:
<223> OTHER INFORMATION: Synthetic Sequence
```

```
<400> SEQUENCE: 73
ccacuucaac acauguggau ug                                    22

<210> SEQ ID NO 74
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 74
caauccacau gcguuggggu gg                                    22

<210> SEQ ID NO 75
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 75
ccacuccaac acauguggau ug                                    22

<210> SEQ ID NO 76
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 76
acauguguug gaguggauug ggg                                   23

<210> SEQ ID NO 77
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 77
cuccaaucca caccaacaca ugu                                   23

<210> SEQ ID NO 78
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 78
acauguguug gaguggauug ggg                                   23

<210> SEQ ID NO 79
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 79
ccccaaucca cuucaacaca ugu                                   23

<210> SEQ ID NO 80
<211> LENGTH: 23
```

```
<212> TYPE: RNA
<213> ORGANISM: Artificial Sequence
<220> FEATURE:
<223> OTHER INFORMATION: Synthetic Sequence

<400> SEQUENCE: 80
acauguguug gaguggauug ggg                                             23

<210> SEQ ID NO 81
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 81
ccccaaucca cuccaacaca ugu                                             23

<210> SEQ ID NO 82
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 82
acauguguug agguggauug ggg                                             23

<210> SEQ ID NO 83
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 83
ccccaaucca cuccaacaca ugu                                             23

<210> SEQ ID NO 84
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 84
acauguguug agguggauug ggg                                             23

<210> SEQ ID NO 85
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 85
cuccaaucua ccucaacacg ugu                                             23

<210> SEQ ID NO 86
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 86
```

```
aaauuccacc cuaauccacu ccaa                                          24

<210> SEQ ID NO 87
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 87
uuggaguaga uuggggugga auuu                                          24

<210> SEQ ID NO 88
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 88
aaauuccacc cuaauccacu ccaa                                          24

<210> SEQ ID NO 89
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 89
uuggagugga uuggggugga auuu                                          24

<210> SEQ ID NO 90
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 90
aucccaaucc acaccaacac acau                                          24

<210> SEQ ID NO 91
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 91 auguguuug gugugguug gagu                                            24

<210> SEQ ID NO 92
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 92
uagccaagga ugacuugccu a                                             21

<210> SEQ ID NO 93
<211> LENGTH: 22
<212> TYPE: RNA
<213> ORGANISM: Artificial Sequence
```

```
<220> FEATURE:
<223> OTHER INFORMATION: Synthetic Sequence

<400> SEQUENCE: 93
uagagcaagu cguccuugga ua                                        22

<210> SEQ ID NO 94
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 94
cagccaagga ugacuugccg g                                         21

<210> SEQ ID NO 95
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 95
ccggcaacuc aucaguggcu g                                         21

<210> SEQ ID NO 96
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 96
cagccaagga ugacuugccg a                                         21

<210> SEQ ID NO 97
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 97
uccggcaaau cauccuuggc g                                         21

<210> SEQ ID NO 98
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 98
cagccaagga ugacuugccg g                                         21

<210> SEQ ID NO 99
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 99
uccggcaaau cauccuuggc g                                         21
```

```
<210> SEQ ID NO 100
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 100
uaggcaaguc auccuuggcu a                                              21

<210> SEQ ID NO 101
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 101
uagccaagga ugcagccua                                                 19

<210> SEQ ID NO 102
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 102
ucggcaaguc auccuuggcu g                                              21

<210> SEQ ID NO 103
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 103
cugccggagg augacuugcc ga                                             22

<210> SEQ ID NO 104
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 104
ccggcaaguc auccuuggcu g                                              21

<210> SEQ ID NO 105
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 105
cuaguccaag gaugacuuac cgg                                            23

<210> SEQ ID NO 106
<211> LENGTH: 21
<212> TYPE: RNA
<213> ORGANISM: Artificial Sequence
<220> FEATURE:
<223> OTHER INFORMATION: Synthetic Sequence
```

```
<400> SEQUENCE: 106
caggcaaguc auccuuggcu a                                              21

<210> SEQ ID NO 107
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 107
uaguccaagg augacuuacc gg                                             22

<210> SEQ ID NO 108
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 108
ccggcaaguc auccuuggcu g                                              21

<210> SEQ ID NO 109
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 109
cagcaaggag gaccugccgg                                                20

<210> SEQ ID NO 110
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 110
uaggcaaguc auucuuggcu a                                              21

<210> SEQ ID NO 111
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 111
uaaccaagaa ugaguugccu c                                              21

<210> SEQ ID NO 112
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 112
ccggcaaguc auccuuggcu g                                              21

<210> SEQ ID NO 113
```

-continued

```
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 113
cagccuggau gacugccgg                                                    19

<210> SEQ ID NO 114
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 114
ucggcaaguc auccuuggcu g                                                 21

<210> SEQ ID NO 115
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 115
cagccaggau aguugccga                                                    19

<210> SEQ ID NO 116
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 116
ccggcaaguc auccuuggcu g                                                 21

<210> SEQ ID NO 117
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 117
cgccaaagau gacuugcugg                                                   20

<210> SEQ ID NO 118
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 118
ccggcaaguc auccuuggcu g                                                 21

<210> SEQ ID NO 119
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 119
```

```
caccaaagau gacuugcugg                                              20

<210> SEQ ID NO 120
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 120
uaggcaaguc auccuuggcu a                                            21

<210> SEQ ID NO 121
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 121
uagccaagga ugcagccua                                               19

<210> SEQ ID NO 122
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 122
ucggcaaguc auccuuggcu g                                            21

<210> SEQ ID NO 123
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 123
cagccacagg augaguugcg a                                            21

<210> SEQ ID NO 124
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 124
ucggcaaguc auccuuggcu g                                            21

<210> SEQ ID NO 125
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 125
cgccaaggag cuugccga                                                18

<210> SEQ ID NO 126
<211> LENGTH: 21
<212> TYPE: RNA
```

```
<213> ORGANISM: Artificial Sequence
<220> FEATURE:
<223> OTHER INFORMATION: Synthetic Sequence

<400> SEQUENCE: 126
ccggcaaguc auccuuggcu g                                              21

<210> SEQ ID NO 127
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 127
ccgccaagga ugaccgccgg                                                20

<210> SEQ ID NO 128
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 128
ccggcaaguc auccuuggcu g                                              21

<210> SEQ ID NO 129
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 129
ccgccaagga ugaccgccgg                                                20

<210> SEQ ID NO 130
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 130
uaggcaaguc auccuuggcu a                                              21

<210> SEQ ID NO 131
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 131
uagccaagga ugcugcua                                                  18

<210> SEQ ID NO 132
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 132
ccggcaaguc auccuuggcu g                                              21
```

<210> SEQ ID NO 133
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 133
aagccaagga ugauuccgg                                          19

<210> SEQ ID NO 134
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 134
agaaucuuga ugaugcugca                                         20

<210> SEQ ID NO 135
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 135
ugcagcauca ucaggauucu                                         20

<210> SEQ ID NO 136
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 136
ggaaucuuga ugaugcugca                                         20

<210> SEQ ID NO 137
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 137
ugcagcauca ucaggauucu c                                       21

<210> SEQ ID NO 138
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 138
ggaaucuuga ugaugcugca                                         20

<210> SEQ ID NO 139
<211> LENGTH: 20
<212> TYPE: RNA
<213> ORGANISM: Artificial Sequence
<220> FEATURE:

```
<223> OTHER INFORMATION: Synthetic Sequence

<400> SEQUENCE: 139
uggagcacca ucaagauucu                                              20

<210> SEQ ID NO 140
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 140
agaaucuuga ugaugcugca                                              20

<210> SEQ ID NO 141
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 141
uggagcacca ucaagauucu                                              20

<210> SEQ ID NO 142
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 142
agaaucuuga ugaugcugca                                              20

<210> SEQ ID NO 143
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 143
ucagcaugau caagcauucu                                              20

<210> SEQ ID NO 144
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 144
ggaaucuuga ugaugcugca                                              20

<210> SEQ ID NO 145
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 145
uugcugcauc auaagauucc                                              20
```

```
<210> SEQ ID NO 146
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 146
ggaaucuuga ugaugcugca                                               20

<210> SEQ ID NO 147
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 147
cgcagcauca ucaggauucc                                               20

<210> SEQ ID NO 148
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 148
agaaucuuga ugaugcugca                                               20

<210> SEQ ID NO 149
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 149
cgcagcauca ucaggauucc                                               20

<210> SEQ ID NO 150
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 150
agaaucuuga ugaugcugca                                               20

<210> SEQ ID NO 151
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 151
ugcaagcauc aucaaggcuc u                                             21

<210> SEQ ID NO 152
<211> LENGTH: 20
<212> TYPE: RNA
<213> ORGANISM: Artificial Sequence
<220> FEATURE:
<223> OTHER INFORMATION: Synthetic Sequence
```

```
<400> SEQUENCE: 152
agaaucuuga ugaugcugca                                              20

<210> SEQ ID NO 153
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 153
ugagcaucau caaaauucau                                              20

<210> SEQ ID NO 154
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 154
ugaaucuuga ugaugcugca c                                            21

<210> SEQ ID NO 155
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 155
gcgcaggcau caucaagauc a                                            21

<210> SEQ ID NO 156
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 156
ugaaucuuga ugaugcugca c                                            21

<210> SEQ ID NO 157
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 157
cugcagcauc aucaggauuc u                                            21

<210> SEQ ID NO 158
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 158
ugaaucuuga ugaugcugca c                                            21

<210> SEQ ID NO 159
<211> LENGTH: 21
```

```
<212> TYPE: RNA
<213> ORGANISM: Artificial Sequence
<220> FEATURE:
<223> OTHER INFORMATION: Synthetic Sequence

<400> SEQUENCE: 159
gugacagcau aucaacauuc a                                              21

<210> SEQ ID NO 160
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 160
ugaaucuuga ugaugcugca c                                              21

<210> SEQ ID NO 161
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 161
guacagcaca cucaagauuc a                                              21

<210> SEQ ID NO 162
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 162
ugaaucuuga ugaugcugca c                                              21

<210> SEQ ID NO 163
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 163
gcugcagauc augaagauuc a                                              21

<210> SEQ ID NO 164
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 164
ugaaucuuga ugaugcugca c                                              21

<210> SEQ ID NO 165
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 165
```

```
gcugcagcau caucacgauu cc                                              22

<210> SEQ ID NO 166
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 166
agaaucuuga ugaugcugca                                                 20

<210> SEQ ID NO 167
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 167
ugcagcauca ucacgauucc                                                 20

<210> SEQ ID NO 168
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 168
ggaaucuuga ugaugcugca                                                 20

<210> SEQ ID NO 169
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 169
ugcagcauca ucacgauucc                                                 20

<210> SEQ ID NO 170
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 170
gugaaguguu uggggggaacu c                                              21

<210> SEQ ID NO 171
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 171
gaguuccucc aagcacuuca u                                               21

<210> SEQ ID NO 172
<211> LENGTH: 21
<212> TYPE: RNA
<213> ORGANISM: Artificial Sequence
```

```
<220> FEATURE:
<223> OTHER INFORMATION: Synthetic Sequence

<400> SEQUENCE: 172
augaaguguu uggggggaacu c                                          21

<210> SEQ ID NO 173
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 173
gaguuccucc aagcacuuca u                                           21

<210> SEQ ID NO 174
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 174
gaguuccccc aaacacuuca c                                           21

<210> SEQ ID NO 175
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 175
gugaaguuuu uggggaauc                                              19

<210> SEQ ID NO 176
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 176
gaguuccccc aaacacuuca c                                           21

<210> SEQ ID NO 177
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 177
gugauguguu uggggaauc                                              19

<210> SEQ ID NO 178
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 178
gaguuccccc aaacacuuca u                                           21
```

```
<210> SEQ ID NO 179
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 179
augaauguug ggggaaauc                                                  19

<210> SEQ ID NO 180
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 180
gaguuccccc aaacacuuca u                                               21

<210> SEQ ID NO 181
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 181
augaaguguu uugggagcuc                                                 20

<210> SEQ ID NO 182
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 182
gaguuccccc aaacacuuca u                                               21

<210> SEQ ID NO 183
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 183
augaagguug ggggaacuac                                                 20

<210> SEQ ID NO 184
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 184
uuaaugugaa uccaauga                                                   18

<210> SEQ ID NO 185
<211> LENGTH: 18
<212> TYPE: RNA
<213> ORGANISM: Artificial Sequence
<220> FEATURE:
<223> OTHER INFORMATION: Synthetic Sequence
```

<400> SEQUENCE: 185
ucauuggaug cacaguag					18

<210> SEQ ID NO 186
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 186
uuaaugugaa uccaauga					18

<210> SEQ ID NO 187
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 187
ucauuggcau ugacauuga					19

<210> SEQ ID NO 188
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 188
agaucugugg ugccgagcu					19

<210> SEQ ID NO 189
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 189
cugcucggca ccaagaucu					19

<210> SEQ ID NO 190
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 190
cgugccugau agugccgug					19

<210> SEQ ID NO 191
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 191
cucggcacca gcaggcacg					19

<210> SEQ ID NO 192

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 192
cugagggugc aaguggga                                                   18

<210> SEQ ID NO 193
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 193
cucccacugc accuucag                                                   18

<210> SEQ ID NO 194
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 194
guccgcgaca accacgaag                                                  19

<210> SEQ ID NO 195
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 195
cuucguggau guucgcgac                                                  19

<210> SEQ ID NO 196
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 196
guccgcgaca accacgaag                                                  19

<210> SEQ ID NO 197
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 197
cuucgagguu gucgaugac                                                  19

<210> SEQ ID NO 198
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 198
```
guccgcgaca accacgaag                                           19

<210> SEQ ID NO 199
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 199
cuucgagguu gucgaugac                                           19

<210> SEQ ID NO 200
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 200
guccgcgaca accacgaag                                           19

<210> SEQ ID NO 201
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 201
cuucgucguc gucgcggac                                           19

<210> SEQ ID NO 202
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 202
acaaagcuca acuucacu                                            18

<210> SEQ ID NO 203
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 203
agugaaguug cuauuugu                                            18

<210> SEQ ID NO 204
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 204
acaaagcuca acuucacu                                            18

<210> SEQ ID NO 205
<211> LENGTH: 19
<212> TYPE: RNA

```
<213> ORGANISM: Artificial Sequence
<220> FEATURE:
<223> OTHER INFORMATION: Synthetic Sequence

<400> SEQUENCE: 205
agugaagucg agcuugagu                                                    19

<210> SEQ ID NO 206
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 206
aagaucugug gcgccgagc                                                    19

<210> SEQ ID NO 207
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 207
gcucguucgc caagaucuu                                                    19

<210> SEQ ID NO 208
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 208
cuucccaugg uucgacggg                                                    19

<210> SEQ ID NO 209
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 209
cccgacgaaa caugggacag                                                   20

<210> SEQ ID NO 210
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 210
agccgcccuu acugugagca                                                   20

<210> SEQ ID NO 211
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 211
ugaucacagu caagggcgcc u                                                 21
```

<210> SEQ ID NO 212
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 212
ccucaacaca uguggauug                                                        19

<210> SEQ ID NO 213
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 213
aaauccaaau cuguugagg                                                        19

<210> SEQ ID NO 214
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 214
guuggagaaa cugcaauagg uu                                                    22

<210> SEQ ID NO 215
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 215
aaccuauugc ugauucaucc aac                                                   23

<210> SEQ ID NO 216
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 216
ucggaccagg cuucauuccc c                                                     21

<210> SEQ ID NO 217
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 217
ugggaaugaa gccucguccg c                                                     21

<210> SEQ ID NO 218
<211> LENGTH: 18
<212> TYPE: RNA
<213> ORGANISM: Artificial Sequence
<220> FEATURE:

<223> OTHER INFORMATION: Synthetic Sequence

<400> SEQUENCE: 218
uugagguaga uuggagug                                                          18

<210> SEQ ID NO 219
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 219
cgcuccaacu cuaccuuaa                                                         19

<210> SEQ ID NO 220
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 220
uugagguaga uuggagug                                                          18

<210> SEQ ID NO 221
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 221
cuacuccaac uaccucag                                                          18

<210> SEQ ID NO 222
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 222
ccucgacucc gcgugcgcau c                                                      21

<210> SEQ ID NO 223
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 223
gaugcgcacg cggagcgacg g                                                      21

<210> SEQ ID NO 224
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 224
ugcaaucgga ccgguaaaaa                                                        20

<210> SEQ ID NO 225
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 225
uuuauaccac uccgauugca                                              20

<210> SEQ ID NO 226
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 226
gcgggagcuc cuccuuagcc uggu                                         24

<210> SEQ ID NO 227
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 227
accaggcuaa ggaggaacuc ccgg                                         24

<210> SEQ ID NO 228
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 228
acgccugagg gugcaagugg gag                                          23

<210> SEQ ID NO 229
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 229 gucccuugc acccucaggc cgu                                           23

<210> SEQ ID NO 230
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 230
ggugggccgg ucauggcggg g                                            21

<210> SEQ ID NO 231
<211> LENGTH: 23
<212> TYPE: RNA
<213> ORGANISM: Artificial Sequence
<220> FEATURE:
<223> OTHER INFORMATION: Synthetic Sequence

```
<400> SEQUENCE: 231
ccccguccau gacccggccc ucc                                              23

<210> SEQ ID NO 232
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 232
ugaagucgcc cgccauggcc gcga                                             24

<210> SEQ ID NO 233
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 233
ucgcggucau ggcgggcggc uuca                                             24

<210> SEQ ID NO 234
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 234
uggcgacggc ggucucggcc guac                                             24

<210> SEQ ID NO 235
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 235
guacggccga gaccgccgca gccg                                             24

<210> SEQ ID NO 236
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 236
acgaagggcg ugagugcggg g                                                21

<210> SEQ ID NO 237
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 237
ccccgacauc acgcgcuucg u                                                21

<210> SEQ ID NO 238
<211> LENGTH: 19
```

```
<212> TYPE: RNA
<213> ORGANISM: Artificial Sequence
<220> FEATURE:
<223> OTHER INFORMATION: Synthetic Sequence

<400> SEQUENCE: 238
uugcucuuag aaguugugc                                                19

<210> SEQ ID NO 239
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 239
gcacagcaac uaagagcaa                                                19

<210> SEQ ID NO 240
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 240
cgucguggug ggggacgugg                                               20

<210> SEQ ID NO 241
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 241
ccagucccac cacuacgacg                                               20

<210> SEQ ID NO 242
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 242
cgucguggug ggggacgugg                                               20

<210> SEQ ID NO 243
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 243
caacgucucc cuccacgacg                                               20

<210> SEQ ID NO 244
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 244
```
ccagauccca ccagcgggcg u                                               21

<210> SEQ ID NO 245
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 245
acgccugcug gugggaccug g                                               21

<210> SEQ ID NO 246
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 246
ccaaucuaaa caggcccu                                                   18

<210> SEQ ID NO 247
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 247
agggccuguu uccaaugg                                                   18

<210> SEQ ID NO 248
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 248
ccguacaagc uguagcuagg                                                 20

<210> SEQ ID NO 249
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 249
ccuagccaga gcuguccgg                                                  20

<210> SEQ ID NO 250
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 250
uggccuuugu cgugugug                                                   18

<210> SEQ ID NO 251
<211> LENGTH: 18
<212> TYPE: RNA
<213> ORGANISM: Artificial Sequence

```
<220> FEATURE:
<223> OTHER INFORMATION: Synthetic Sequence

<400> SEQUENCE: 251
gcaccacggc aaaggcca                                                 18

<210> SEQ ID NO 252
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 252
uggccuuugu cgugugug                                                 18

<210> SEQ ID NO 253
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 253
cacauaccga aaaggcca                                                 18

<210> SEQ ID NO 254
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 254
uggccuuugu cgugugug                                                 18

<210> SEQ ID NO 255
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 255
ucacacacga caaaagca                                                 18

<210> SEQ ID NO 256
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 256
cacacuucuc aaugcgaa                                                 18

<210> SEQ ID NO 257
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 257
uuuacauuga gcagugug                                                 18
```

```
<210> SEQ ID NO 258
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 258
caaguuccac ucuaauccac                                              20

<210> SEQ ID NO 259
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 259
guggauucag aauggaauug                                              20

<210> SEQ ID NO 260
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 260
cucaccuuca guucggauug ua                                           22

<210> SEQ ID NO 261
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 261
uacaauccca acuggaggug ac                                           22

<210> SEQ ID NO 262
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 262
ccucgggaug ccccuggcgg c                                            21

<210> SEQ ID NO 263
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 263
cgccgccggg gcagcccgag g                                            21

<210> SEQ ID NO 264
<211> LENGTH: 20
<212> TYPE: RNA
<213> ORGANISM: Artificial Sequence
<220> FEATURE:
<223> OTHER INFORMATION: Synthetic Sequence
```

```
<400> SEQUENCE: 264
aguucgagcc ggagguggcg                                               20

<210> SEQ ID NO 265
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 265
cuccaccucc ggcuccaacc                                               20

<210> SEQ ID NO 266
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 266
guguuggagu ggauuggg                                                 18

<210> SEQ ID NO 267
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 267
cccaucacac ugcaacac                                                 18

<210> SEQ ID NO 268
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 268
uugaggugga uuggagugga                                               20

<210> SEQ ID NO 269
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 269 uccauccaa uccaacacaa                                                20

<210> SEQ ID NO 270
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 270
auuugccccg ccaagcaugg                                               20

<210> SEQ ID NO 271
```

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 271
ccgaugcuug gggggcaauu                                               20

<210> SEQ ID NO 272
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 272
gaagucggag ccguuucgg                                                19

<210> SEQ ID NO 273
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 273
ccgaaccgga cuccgacucc                                               20

<210> SEQ ID NO 274
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 274
gaagucggag ccguuucgg                                                19

<210> SEQ ID NO 275
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 275
ccgcaacggc uucgccuuc                                                19

<210> SEQ ID NO 276
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 276
gcucggacgg gccagugu                                                 18

<210> SEQ ID NO 277
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 277
```

```
accucuggcc cgucgagc                                                18

<210> SEQ ID NO 278
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 278
gcucggacgg gccagugu                                                18

<210> SEQ ID NO 279
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 279 acacugguc cuccgagc                                                 18

<210> SEQ ID NO 280
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 280
aacuccagca gagcccua                                                19

<210> SEQ ID NO 281
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 281 uggggcugc ugcugcaguu                                               20

<210> SEQ ID NO 282
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 282
aacuccagca gagcccua                                                19

<210> SEQ ID NO 283
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 283
aaggggucuc cgcuggaguu                                              20

<210> SEQ ID NO 284
<211> LENGTH: 21
<212> TYPE: RNA
```

```
<213> ORGANISM: Artificial Sequence
<220> FEATURE:
<223> OTHER INFORMATION: Synthetic Sequence

<400> SEQUENCE: 284
gcugagcugc uagcuuccau a                                              21

<210> SEQ ID NO 285
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 285
uaugggaagu aggagcucag c                                              21

<210> SEQ ID NO 286
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 286
ccagcggcuc cuucacccac accg                                           24

<210> SEQ ID NO 287
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 287
cggugugggu gaaggagcug cugg                                           24

<210> SEQ ID NO 288
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 288
uggagcaccc gucagcggcc cu                                             22

<210> SEQ ID NO 289
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 289
agguccgcga cggcgugcuc ca                                             22

<210> SEQ ID NO 290
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 290
uccacuccaa uccacuccaa c                                              21
```

```
<210> SEQ ID NO 291
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 291
gguggagugg auuguacugg a                                              21

<210> SEQ ID NO 292
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 292
gaacaacggc cgggacguc                                                 19

<210> SEQ ID NO 293
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 293
gacguccggc cgguguuc                                                  19

<210> SEQ ID NO 294
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 294
gaacaacggc cgggacguc                                                 19

<210> SEQ ID NO 295
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 295
gaccgacccg gccguguuc                                                 19

<210> SEQ ID NO 296
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 296
cgcggccaga gcagcggcgg cgcu                                           24

<210> SEQ ID NO 297
<211> LENGTH: 26
<212> TYPE: RNA
<213> ORGANISM: Artificial Sequence
<220> FEATURE:
```

```
<223> OTHER INFORMATION: Synthetic Sequence

<400> SEQUENCE: 297
agcucacgcc gcugcaucug gccgcg                                        26

<210> SEQ ID NO 298
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 298
ugcauuguga gugcccuua                                                19

<210> SEQ ID NO 299
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 299
uaagggcaau cacaaggaa                                                19

<210> SEQ ID NO 300
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 300
gaggcgcugc uguccuccac ac                                            22

<210> SEQ ID NO 301
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 301
ggugcaggac agcagccgcc uc                                            22

<210> SEQ ID NO 302
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 302
aaucaauuuc aacacaugu                                                19

<210> SEQ ID NO 303
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 303
acauuugaug aaauugaug                                                19
```

```
<210> SEQ ID NO 304
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 304
cgcgccgccg uccagcgg                                                 18

<210> SEQ ID NO 305
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 305
ccguggaggg cggcgucg                                                 18

<210> SEQ ID NO 306
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 306
cgcgccgccg uccagcgg                                                 18

<210> SEQ ID NO 307
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 307
aagcuggacg gcggcggg                                                 18

<210> SEQ ID NO 308
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 308
cgcgccgccg uccagcgg                                                 18

<210> SEQ ID NO 309
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 309
cgcgcuggac ggcgccagcg                                               20

<210> SEQ ID NO 310
<211> LENGTH: 18
<212> TYPE: RNA
<213> ORGANISM: Artificial Sequence
<220> FEATURE:
<223> OTHER INFORMATION: Synthetic Sequence
```

```
<400> SEQUENCE: 310
cgcgccgccg uccagcgg                                              18

<210> SEQ ID NO 311
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 311
ccgcuggcgg uggcgccg                                              18

<210> SEQ ID NO 312
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 312
cgcgccgccg uccagcgg                                              18

<210> SEQ ID NO 313
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 313
cgcgcuggac gcggcgcu                                              18

<210> SEQ ID NO 314
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 314
cgcgccgccg uccagcgg                                              18

<210> SEQ ID NO 315
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 315
ccgcaggcgg cggcggcg                                              18

<210> SEQ ID NO 316
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 316
cgcgccgccg uccagcgg                                              18

<210> SEQ ID NO 317
<211> LENGTH: 19
```

```
<212> TYPE: RNA
<213> ORGANISM: Artificial Sequence
<220> FEATURE:
<223> OTHER INFORMATION: Synthetic Sequence

<400> SEQUENCE: 317
ccgcguggcg gcggucgcg                                              19

<210> SEQ ID NO 318
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 318
cgcgccgccg uccagcgg                                               18

<210> SEQ ID NO 319
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 319
gcgcuggcgg cggcagcg                                               18

<210> SEQ ID NO 320
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 320
cgcgccgccg uccagcgg                                               18

<210> SEQ ID NO 321
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 321
ccgccgacgg cggcggcg                                               18

<210> SEQ ID NO 322
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 322
cgcgccgccg uccagcgg                                               18

<210> SEQ ID NO 323
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 323
```

-continued uggcuggacg gcggcggg					18

<210> SEQ ID NO 324
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 324
cgcgccgccg uccagcgg					18

<210> SEQ ID NO 325
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 325
gcgcuggagg cggcggcg					18

<210> SEQ ID NO 326
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 326
cgcgccgccg uccagcgg					18

<210> SEQ ID NO 327
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 327
ccgcgcggac ggcgagcgcg					20

<210> SEQ ID NO 328
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 328
cgcgccgccg uccagcgg					18

<210> SEQ ID NO 329
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 329
ccgcggagac ggcggcgg					18

<210> SEQ ID NO 330
<211> LENGTH: 18
<212> TYPE: RNA
<213> ORGANISM: Artificial Sequence

```
<220> FEATURE:
<223> OTHER INFORMATION: Synthetic Sequence

<400> SEQUENCE: 330
cgcgccgccg uccagcgg                                                 18

<210> SEQ ID NO 331
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 331
cccauggacg gcggagcg                                                 18

<210> SEQ ID NO 332
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 332
cgcgccgccg uccagcgg                                                 18

<210> SEQ ID NO 333
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 333
ccgccgagac ggcggcggcg                                               20

<210> SEQ ID NO 334
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 334
cgcgccgccg uccagcgg                                                 18

<210> SEQ ID NO 335
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 335
ccgcggagac ggcggcgg                                                 18

<210> SEQ ID NO 336
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 336
cgcgccgccg uccagcgg                                                 18
```

<210> SEQ ID NO 337
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 337
ccgcuggagg ugcggccg                                                   18

<210> SEQ ID NO 338
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 338
cgcgccgccg uccagcgg                                                   18

<210> SEQ ID NO 339
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 339
cgcgcuggcg gcggcgcu                                                   18

<210> SEQ ID NO 340
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 340
cgcgccgccg uccagcgg                                                   18

<210> SEQ ID NO 341
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 341
ccugcuggcg gcggcggcg                                                  19

<210> SEQ ID NO 342
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 342
cgcgccgccg uccagcgg                                                   18

<210> SEQ ID NO 343
<211> LENGTH: 18
<212> TYPE: RNA
<213> ORGANISM: Artificial Sequence
<220> FEATURE:
<223> OTHER INFORMATION: Synthetic Sequence

```
<400> SEQUENCE: 343
gcgauggacg gcgccgcg                                                 18

<210> SEQ ID NO 344
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 344
cgcgccgccg uccagcgg                                                 18

<210> SEQ ID NO 345
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 345
gcgcuggacg gcgccgcg                                                 18

<210> SEQ ID NO 346
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 346
cgcgccgccg uccagcgg                                                 18

<210> SEQ ID NO 347
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 347
cacgcggacg gcggcgcug                                                19

<210> SEQ ID NO 348
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 348
cgcgccgccg uccagcgg                                                 18

<210> SEQ ID NO 349
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 349
acgcggacgg cggcgcug                                                 18

<210> SEQ ID NO 350
```

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 350
cgcgccgccg uccagcgg                                                18

<210> SEQ ID NO 351
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 351
cacgcggacg gcggcgcug                                               19

<210> SEQ ID NO 352
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 352
cgcgccgccg uccagcgg                                                18

<210> SEQ ID NO 353
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 353
ccgcucggag guggcgcg                                                18

<210> SEQ ID NO 354
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 354
cgcgccgccg uccagcgg                                                18

<210> SEQ ID NO 355
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 355
cggcagugac ggcggcgcg                                               19

<210> SEQ ID NO 356
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 356
```
cgcgccgccg uccagcgg                                                         18

<210> SEQ ID NO 357
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 357
cggcagcgac ggcggcgcg                                                        19

<210> SEQ ID NO 358
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 358
cgcgccgccg uccagcgg                                                         18

<210> SEQ ID NO 359
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 359
gcgcuggagg gcgucgcg                                                         18

<210> SEQ ID NO 360
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 360
cgcgccgccg uccagcgg                                                         18

<210> SEQ ID NO 361
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 361
ccgcgggcgg cggcggcg                                                         18

<210> SEQ ID NO 362
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 362
cgcgccgccg uccagcgg                                                         18

<210> SEQ ID NO 363
<211> LENGTH: 18
<212> TYPE: RNA

```
<213> ORGANISM: Artificial Sequence
<220> FEATURE:
<223> OTHER INFORMATION: Synthetic Sequence

<400> SEQUENCE: 363
ccgcaggcgg cggcgucg                                                       18

<210> SEQ ID NO 364
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 364
cgcgccgccg uccagcgg                                                       18

<210> SEQ ID NO 365
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 365
gccgcggacg gcggcgag                                                       18

<210> SEQ ID NO 366
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 366
cgcgccgccg uccagcgg                                                       18

<210> SEQ ID NO 367
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 367
gccgcggacg gcggcgag                                                       18

<210> SEQ ID NO 368
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 368
cgcgccgccg uccagcgg                                                       18

<210> SEQ ID NO 369
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 369
ccgcugccac ggcggccg                                                       18
```

<210> SEQ ID NO 370
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 370
cgcgccgccg uccagcgg                                                 18

<210> SEQ ID NO 371
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 371
cgcgcuggcc ggcggcccg                                                19

<210> SEQ ID NO 372
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 372
cgcgccgccg uccagcgg                                                 18

<210> SEQ ID NO 373
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 373
ccgcgggacg acggcgacg                                                19

<210> SEQ ID NO 374
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 374
cgcgccgccg uccagcgg                                                 18

<210> SEQ ID NO 375
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 375
ccgcguacgg cggcggcg                                                 18

<210> SEQ ID NO 376
<211> LENGTH: 18
<212> TYPE: RNA
<213> ORGANISM: Artificial Sequence
<220> FEATURE:

<223> OTHER INFORMATION: Synthetic Sequence

<400> SEQUENCE: 376
cgcgccgccg uccagcgg                                                          18

<210> SEQ ID NO 377
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 377
cgcgcuggcc ggcggggcg                                                         19

<210> SEQ ID NO 378
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 378
cgcgccgccg uccagcgg                                                          18

<210> SEQ ID NO 379
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 379
ccgccggacg ucggcgcg                                                          18

<210> SEQ ID NO 380
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 380
cgcgccgccg uccagcgg                                                          18

<210> SEQ ID NO 381
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 381
ccgcugaacu ggggcgcg                                                          18

<210> SEQ ID NO 382
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 382
cgcgccgccg uccagcgg                                                          18

```
<210> SEQ ID NO 383
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 383
uccguggacg guggcgcg                                                 18

<210> SEQ ID NO 384
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 384
cgcgccgccg uccagcgg                                                 18

<210> SEQ ID NO 385
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 385
ccgcaggccg ccggcgcg                                                 18

<210> SEQ ID NO 386
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 386
cgcgccgccg uccagcgg                                                 18

<210> SEQ ID NO 387
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 387
ccugcuggcg gcgcgcgcg                                                19

<210> SEQ ID NO 388
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 388
cgcggccaga gcagcggcgg cgcu                                          24

<210> SEQ ID NO 389
<211> LENGTH: 26
<212> TYPE: RNA
<213> ORGANISM: Artificial Sequence
<220> FEATURE:
<223> OTHER INFORMATION: Synthetic Sequence
```

```
<400> SEQUENCE: 389
agcucacgcc gcugcaucug gccgcg                                    26

<210> SEQ ID NO 390
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 390
gcggcccggg cgcagggcga ggu                                       23

<210> SEQ ID NO 391
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 391
accucgcccu gcgcccgcgc cgc                                       23

<210> SEQ ID NO 392
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 392
ccgccuccac ggccaaugc                                            19

<210> SEQ ID NO 393
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 393
gcacuggccg cggcggcgg                                            19

<210> SEQ ID NO 394
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 394
ccgccuccac ggccaaugc                                            19

<210> SEQ ID NO 395
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 395
gcacugccca uggaggcgg                                            19

<210> SEQ ID NO 396
<211> LENGTH: 19
```

```
<212> TYPE: RNA
<213> ORGANISM: Artificial Sequence
<220> FEATURE:
<223> OTHER INFORMATION: Synthetic Sequence

<400> SEQUENCE: 396
ccgccuccac ggccaaugc                                                    19

<210> SEQ ID NO 397
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 397
gcaguggccu uggaggagg                                                    19

<210> SEQ ID NO 398
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 398
ccgccuccac ggccaaugc                                                    19

<210> SEQ ID NO 399
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 399
gcauuggccu uggcggcgug                                                   20

<210> SEQ ID NO 400
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 400
uccauccacg gcggccgc                                                     18

<210> SEQ ID NO 401
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 401
gcagccggcg uggcugga                                                     18

<210> SEQ ID NO 402
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 402
```
uccauccacg gcggccgc                                              18

<210> SEQ ID NO 403
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 403
gcggcggccg uggagggc                                              18

<210> SEQ ID NO 404
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 404
uccauccacg gcggccgc                                              18

<210> SEQ ID NO 405
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 405
gcgggcgcug uggcugga                                              18

<210> SEQ ID NO 406
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 406
uccauccacg gcggccgc                                              18

<210> SEQ ID NO 407
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 407
gcgcccgccg ugggugga                                              18

<210> SEQ ID NO 408
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 408
uccauccacg gcggccgc                                              18

<210> SEQ ID NO 409
<211> LENGTH: 19
<212> TYPE: RNA
<213> ORGANISM: Artificial Sequence

```
<220> FEATURE:
<223> OTHER INFORMATION: Synthetic Sequence

<400> SEQUENCE: 409
gcggcggcgc guggaagga                                                    19

<210> SEQ ID NO 410
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 410
uccauccacg gcggccgc                                                     18

<210> SEQ ID NO 411
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 411
gcggccgcug gagaugga                                                     18

<210> SEQ ID NO 412
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 412
uccauccacg gcggccgc                                                     18

<210> SEQ ID NO 413
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 413
gcggccgcag gggcugga                                                     18

<210> SEQ ID NO 414
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 414
uccauccacg gcggccgc                                                     18

<210> SEQ ID NO 415
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 415
gcgggccgcc gaggagga                                                     18
```

```
<210> SEQ ID NO 416
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 416
uccauccacg gcggccgc                                                 18

<210> SEQ ID NO 417
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 417
gcgcgccgcc gaggagga                                                 18

<210> SEQ ID NO 418
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 418
uccauccacg gcggccgc                                                 18

<210> SEQ ID NO 419
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 419
ggcugccgcc guggagga                                                 18

<210> SEQ ID NO 420
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 420
uccauccacg gcggccgc                                                 18

<210> SEQ ID NO 421
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 421
ggggcggccg uggaagga                                                 18

<210> SEQ ID NO 422
<211> LENGTH: 18
<212> TYPE: RNA
<213> ORGANISM: Artificial Sequence
<220> FEATURE:
<223> OTHER INFORMATION: Synthetic Sequence
```

```
<400> SEQUENCE: 422
uccauccacg gcggccgc                                                 18

<210> SEQ ID NO 423
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 423
gcggccgccg uggagcggca                                               20

<210> SEQ ID NO 424
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 424
uccauccacg gcggccgc                                                 18

<210> SEQ ID NO 425
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 425
gcaggccggc uggaugga                                                 18

<210> SEQ ID NO 426
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 426
uccauccacg gcggccgc                                                 18

<210> SEQ ID NO 427
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 427
gccggccggc gugugga                                                  18

<210> SEQ ID NO 428
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 428
uccauccacg gcggccgc                                                 18

<210> SEQ ID NO 429
```

-continued

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 429
gcugucgccg uggacgga                                                 18

<210> SEQ ID NO 430
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 430
acccgggcuu cggcguugcc                                               20

<210> SEQ ID NO 431
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 431
ggcaacgccg aagcccgggc u                                             21

<210> SEQ ID NO 432
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 432
ccuuugucga gugcccgc                                                 18

<210> SEQ ID NO 433
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 433
gcgcgcaucg acaacagg                                                 18

<210> SEQ ID NO 434
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 434
ccuuugucga gugcccgc                                                 18

<210> SEQ ID NO 435
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 435
```
gcggugcacc gacaacgg                                                      18

<210> SEQ ID NO 436
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 436
ggacucgguc gcucgagggu ag                                                 22

<210> SEQ ID NO 437
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 437
cuacgccucg gcgaccgagu uc                                                 22

<210> SEQ ID NO 438
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 438
gagaugugug uuuacacac                                                     19

<210> SEQ ID NO 439
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 439
gggugaaaca ccacaucuc                                                     19

<210> SEQ ID NO 440
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 440
cacgugucag ccacgucagc a                                                  21

<210> SEQ ID NO 441
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 441
ugcugacguu ggcuggacac gg                                                 22

<210> SEQ ID NO 442
<211> LENGTH: 24
<212> TYPE: RNA

```
<213> ORGANISM: Artificial Sequence
<220> FEATURE:
<223> OTHER INFORMATION: Synthetic Sequence

<400> SEQUENCE: 442
ucggcuuacc cauguucaag ugcc                                        24

<210> SEQ ID NO 443
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 443
ggcacuugca cauggguaag ccga                                        24

<210> SEQ ID NO 444
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 444
uucuuugccg agagccugc                                              19

<210> SEQ ID NO 445
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 445
gaagccucuc uggcaaagaa                                             20

<210> SEQ ID NO 446
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 446
cccaacacau auagauug                                               18

<210> SEQ ID NO 447
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 447
caagcuauau gcuguuggc                                              19

<210> SEQ ID NO 448
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 448
cccaacacau auagauug                                               18
```

```
<210> SEQ ID NO 449
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 449
caacuauacu gaguuggg                                                   18

<210> SEQ ID NO 450
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 450 gagguccca ccugcaugcg                                                  20

<210> SEQ ID NO 451
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 451
cgcagcagga ggaggaccuc                                                 20

<210> SEQ ID NO 452
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 452
uugcuugaga uaugauggag ccg                                             23

<210> SEQ ID NO 453
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 453
uggcuccauc auaucuacaa caa                                             23

<210> SEQ ID NO 454
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 454
gggaagaggu gcgaggau                                                   18

<210> SEQ ID NO 455
<211> LENGTH: 18
<212> TYPE: RNA
<213> ORGANISM: Artificial Sequence
<220> FEATURE:
```

<223> OTHER INFORMATION: Synthetic Sequence

<400> SEQUENCE: 455
cucgucgccc cucuuccc                                                    18

<210> SEQ ID NO 456
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 456
gggaagaggu gcgaggau                                                    18

<210> SEQ ID NO 457
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 457
auccucgcca agcucuuccc                                                  20

<210> SEQ ID NO 458
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 458
gggaagaggu gcgaggau                                                    18

<210> SEQ ID NO 459
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 459
guccucgcac cucuuugc                                                    18

<210> SEQ ID NO 460
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 460
gggaagaggu gcgaggau                                                    18

<210> SEQ ID NO 461
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 461
gauccuccac cucuaccc                                                    18

```
<210> SEQ ID NO 462
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 462
gggaagaggu gcgaggau                                                 18

<210> SEQ ID NO 463
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 463
auccucgccc ucguuacc                                                 18

<210> SEQ ID NO 464
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 464
gggaagaggu gcgaggau                                                 18

<210> SEQ ID NO 465
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 465
cuccucccuc cucuuccc                                                 18

<210> SEQ ID NO 466
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 466
auccacaugu guuaaggugg                                               20

<210> SEQ ID NO 467
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 467
ucaccuugac agauguggau                                               20

<210> SEQ ID NO 468
<211> LENGTH: 23
<212> TYPE: RNA
<213> ORGANISM: Artificial Sequence
<220> FEATURE:
<223> OTHER INFORMATION: Synthetic Sequence
```

```
<400> SEQUENCE: 468 uggggagcc ggcggcgcuc cug                                              23

<210> SEQ ID NO 469
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 469
cagcagcgcc gccggcccag cca                                             23

<210> SEQ ID NO 470
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 470
agcugggacu ugggccgugc                                                 20

<210> SEQ ID NO 471
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 471
gcgacggucc aaguaccagc u                                               21

<210> SEQ ID NO 472
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 472
agaggccagu gccggucuug aaggu                                           25

<210> SEQ ID NO 473
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 473
accuucaaga ccggcaccgg ccugu                                           25

<210> SEQ ID NO 474
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 474
ugagccgaac caauaucacu cau                                             23

<210> SEQ ID NO 475
<211> LENGTH: 23
```

```
<212> TYPE: RNA
<213> ORGANISM: Artificial Sequence
<220> FEATURE:
<223> OTHER INFORMATION: Synthetic Sequence

<400> SEQUENCE: 475
ccgggugaua uugguucggc uca                                             23

<210> SEQ ID NO 476
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 476
aggccaagga agaggagauu cg                                              22

<210> SEQ ID NO 477
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 477
cgcaucuccu ccuccucggc cu                                              22

<210> SEQ ID NO 478
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 478
gcuggcuccu cuggccaccc ag                                              22

<210> SEQ ID NO 479
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 479
cucgauggcc agaggagcga gc                                              22

<210> SEQ ID NO 480
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 480
gcgaaucuaa uggaugggag                                                 20

<210> SEQ ID NO 481
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 481
```
cuccaaucuc auuggauucg c         21

<210> SEQ ID NO 482
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 482
ucaucuccuu gucaugca         18

<210> SEQ ID NO 483
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 483
agcauuacaa gagagauga         19

<210> SEQ ID NO 484
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 484
ucaucuccuu gucaugca         18

<210> SEQ ID NO 485
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 485
ugcauugaca aggaaaucga         20

<210> SEQ ID NO 486
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 486
ucaucuccuu gucaugca         18

<210> SEQ ID NO 487
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 487
ucacaugaca aggaauga         18

<210> SEQ ID NO 488
<211> LENGTH: 18
<212> TYPE: RNA
<213> ORGANISM: Artificial Sequence

```
<220> FEATURE:
<223> OTHER INFORMATION: Synthetic Sequence

<400> SEQUENCE: 488
ucaucuccuu gucaugca                                                    18

<210> SEQ ID NO 489
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 489
ugaaggagaa ggagauga                                                    18

<210> SEQ ID NO 490
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 490
ucaucuccuu gucaugca                                                    18

<210> SEQ ID NO 491
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 491
uccaugacaa ggagagca                                                    18

<210> SEQ ID NO 492
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 492
ucaucuccuu gucaugca                                                    18

<210> SEQ ID NO 493
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 493
uggauguaca agcagauga                                                   19

<210> SEQ ID NO 494
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 494
ucaucuccuu gucaugca                                                    18
```

```
<210> SEQ ID NO 495
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 495
ugaagugaaa ggagauga                                                       18

<210> SEQ ID NO 496
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 496
ccgggccaaa uugccgugcu                                                     20

<210> SEQ ID NO 497
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 497
agcacgagca auuuggccag c                                                   21

<210> SEQ ID NO 498
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 498
ucccgguguc caaccacugc u                                                   21

<210> SEQ ID NO 499
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 499
agcauguggu uggacagggg ga                                                  22

<210> SEQ ID NO 500
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 500
gaucaguuga agaugacgga g                                                   21

<210> SEQ ID NO 501
<211> LENGTH: 21
<212> TYPE: RNA
<213> ORGANISM: Artificial Sequence
<220> FEATURE:
<223> OTHER INFORMATION: Synthetic Sequence
```

```
<400> SEQUENCE: 501
cucgucaucu ucaaccgcau c                                              21

<210> SEQ ID NO 502
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 502
ggcaaagcau ccggcacucg gc                                             22

<210> SEQ ID NO 503
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 503
gccggagugc cgaugcuuug cu                                             22

<210> SEQ ID NO 504
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 504
gacgggucga gggagagcac gg                                             22

<210> SEQ ID NO 505
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 505
ccgugcuuuc ccucgacacc gac                                            23

<210> SEQ ID NO 506
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 506
ggcccucccc gaccggug                                                  18

<210> SEQ ID NO 507
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 507
cagccggccg aggagggcc                                                 19

<210> SEQ ID NO 508
```

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 508
ggcccucccc gaccggug                                                 18

<210> SEQ ID NO 509
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 509
caccggugcu gggagcggcc                                               20

<210> SEQ ID NO 510
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 510
ggcccucccc gaccggug                                                 18

<210> SEQ ID NO 511
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 511
cagccggccg uggagggcc                                                19

<210> SEQ ID NO 512
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 512
ggggaagcgc gaccgccgug g                                             21

<210> SEQ ID NO 513
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 513
ccucggcggu ggcgccuccc c                                             21

<210> SEQ ID NO 514
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 514
```

```
ggggaagcgc gaccgccgug g                                              21

<210> SEQ ID NO 515
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 515
ccacggcggu ggcgccuucu cc                                             22

<210> SEQ ID NO 516
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 516 gagguccega ugcggacg                                                  18

<210> SEQ ID NO 517
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 517
cgccagcacc gggaccuc                                                  18

<210> SEQ ID NO 518
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 518 gagguccega ugcggacg                                                  18

<210> SEQ ID NO 519
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 519
cgccccaucg cggaccuc                                                  18

<210> SEQ ID NO 520
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 520 gagguccega ugcggacg                                                  18

<210> SEQ ID NO 521
<211> LENGTH: 19
<212> TYPE: RNA
```

```
<213> ORGANISM: Artificial Sequence
<220> FEATURE:
<223> OTHER INFORMATION: Synthetic Sequence

<400> SEQUENCE: 521
cguccgcauc gccgacguc                                                  19

<210> SEQ ID NO 522
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 522 gagguccega ugcggacg                                                   18

<210> SEQ ID NO 523
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 523
cgucccguca ucguggaccu c                                               21

<210> SEQ ID NO 524
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 524
ggcacacggu auaccugg                                                   18

<210> SEQ ID NO 525
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 525
ccagggauuc cguguucc                                                   18

<210> SEQ ID NO 526
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 526
ggcacacggu auaccugg                                                   18

<210> SEQ ID NO 527
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 527
ccaguacacc cgugugcc                                                   18
```

```
<210> SEQ ID NO 528
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 528
gcgcgcagcc gcucgcgauu cgcc                                         24

<210> SEQ ID NO 529
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 529
ggagaacccc gagcggcugc gcgc                                         24

<210> SEQ ID NO 530
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 530
gcguuucuuu gccgggacc                                               19

<210> SEQ ID NO 531
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 531
ugcccggcaa agaacacgc                                               19

<210> SEQ ID NO 532
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 532
gcugggugca caacggcggc ggcg                                         24

<210> SEQ ID NO 533
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 533
gcgccgccgc cgcuggcacc cagc                                         24

<210> SEQ ID NO 534
<211> LENGTH: 22
<212> TYPE: RNA
<213> ORGANISM: Artificial Sequence
<220> FEATURE:
```

```
<223> OTHER INFORMATION: Synthetic Sequence

<400> SEQUENCE: 534
caggaggcug gcuggcgcgc uc                                              22

<210> SEQ ID NO 535
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 535
gaagggcgcc ugccagccuc cug                                             23

<210> SEQ ID NO 536
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 536
aagggcagca ccggcucggg aa                                              22

<210> SEQ ID NO 537
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 537
uucccgcgcc ggugcugccg cgu                                             23

<210> SEQ ID NO 538
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 538
gcgcgcgcug caggccaugu                                                 20

<210> SEQ ID NO 539
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 539
acauggccuc cggcgcgccc                                                 20

<210> SEQ ID NO 540
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 540
gcgcgcgcug caggccaugu                                                 20
```

```
<210> SEQ ID NO 541
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 541
accuggcgcu gcagugcgcg c                                              21

<210> SEQ ID NO 542
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 542
gcgcgcgcug caggccaugu                                                20

<210> SEQ ID NO 543
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 543
acauggucgu gcagcgcgcc                                                20

<210> SEQ ID NO 544
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 544
gcgcgcgcug caggccaugu                                                20

<210> SEQ ID NO 545
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 545
acaaggacug cagcgcgagc                                                20

<210> SEQ ID NO 546
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 546
gcgcgcgcug caggccaugu                                                20

<210> SEQ ID NO 547
<211> LENGTH: 22
<212> TYPE: RNA
<213> ORGANISM: Artificial Sequence
<220> FEATURE:
<223> OTHER INFORMATION: Synthetic Sequence
```

```
<400> SEQUENCE: 547
acauggccug caacagccgc gc                                              22

<210> SEQ ID NO 548
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 548
gcgcgcgcug caggccaugu                                                 20

<210> SEQ ID NO 549
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 549
acauggccgg cugcggcgcg c                                               21

<210> SEQ ID NO 550
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 550
gcgcgcgcug caggccaugu                                                 20

<210> SEQ ID NO 551
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 551
acauggccgg cugcggcgcg c                                               21

<210> SEQ ID NO 552
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 552
cacuccaauc caccccaaca ca                                              22

<210> SEQ ID NO 553
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 553
ugugcugugg guggauagga gug                                             23

<210> SEQ ID NO 554
<211> LENGTH: 19
```

<212> TYPE: RNA
<213> ORGANISM: Artificial Sequence
<220> FEATURE:
<223> OTHER INFORMATION: Synthetic Sequence

<400> SEQUENCE: 554
uggaagucca ccaaugaca                                                    19

<210> SEQ ID NO 555
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 555
uguccauggu ggacuucaa                                                    19

<210> SEQ ID NO 556
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 556
uggaagucca ccaaugaca                                                    19

<210> SEQ ID NO 557
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 557
uugucauugg uggaccuca                                                    19

<210> SEQ ID NO 558
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 558
gcuugaguuu aucagccgag u                                                 21

<210> SEQ ID NO 559
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 559
aguaggcuga caaacucaag c                                                 21

<210> SEQ ID NO 560
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 560
cggcgcagag aagcgagugu                                              20

<210> SEQ ID NO 561
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 561
acagcucggu uccugcgccg                                              20

<210> SEQ ID NO 562
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 562
gccucuuggu aguagucg                                                18

<210> SEQ ID NO 563
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 563
cgacgacuac gaggaggc                                                18

<210> SEQ ID NO 564
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 564
gccucuuggu aguagucg                                                18

<210> SEQ ID NO 565
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 565
cgacuucacu accaagggc                                               19

<210> SEQ ID NO 566
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 566
ccgaccaugg uggugguqq                                               19

<210> SEQ ID NO 567
<211> LENGTH: 19
<212> TYPE: RNA
<213> ORGANISM: Artificial Sequence

```
<220> FEATURE:
<223> OTHER INFORMATION: Synthetic Sequence

<400> SEQUENCE: 567
ccaccacgac cacguucgg                                                        19

<210> SEQ ID NO 568
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 568
ccgaccaugg ugguggugg                                                        19

<210> SEQ ID NO 569
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 569
ccaccaccac caucggcag                                                        19

<210> SEQ ID NO 570
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 570
ccgaccaugg ugguggugg                                                        19

<210> SEQ ID NO 571
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 571
ccauccacca gcauggcgg                                                        19

<210> SEQ ID NO 572
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 572
ccgaccaugg uggugguqg                                                        19

<210> SEQ ID NO 573
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 573
ccauccacca gcauggcgg                                                        19
```

```
<210> SEQ ID NO 574
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 574
ccgaccaugg uggguggugg                                                   19

<210> SEQ ID NO 575
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 575
ccaccaccac cagcuccgg                                                    19

<210> SEQ ID NO 576
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 576
gucgacucga agcuggugua                                                   20

<210> SEQ ID NO 577
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 577
uucgccagcu ucgagacgac                                                   20

<210> SEQ ID NO 578
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 578
guggauugga guggaacuu                                                    19

<210> SEQ ID NO 579
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 579 aaguccacu ccuuccauc                                                     19

<210> SEQ ID NO 580
<211> LENGTH: 18
<212> TYPE: RNA
<213> ORGANISM: Artificial Sequence
<220> FEATURE:
<223> OTHER INFORMATION: Synthetic Sequence
```

-continued

```
<400> SEQUENCE: 580
aaccgguguu aaaggguc                                                 18

<210> SEQ ID NO 581
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 581
gacccuuuug caccaguu                                                 18

<210> SEQ ID NO 582
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 582
aaccgguguu aaaggguc                                                 18

<210> SEQ ID NO 583
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 583
gacgcuuaac agccgguu                                                 18

<210> SEQ ID NO 584
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 584
aaguugucau uggugggcu                                                19

<210> SEQ ID NO 585
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 585
agccacaaca cugacaacuu                                               20

<210> SEQ ID NO 586
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 586
gcaucaaucc acaaguguu                                                19

<210> SEQ ID NO 587
```

```
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 587
agcacuugug cauucaugc                                                    19

<210> SEQ ID NO 588
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 588
uauuugccga gcgcuauuu                                                    19

<210> SEQ ID NO 589
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 589
aagauaucga ucggcaaaua                                                   20

<210> SEQ ID NO 590
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 590
gccugcuccc uugggucgug c                                                 21

<210> SEQ ID NO 591
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 591
gcucgacgca agggugcagg c                                                 21

<210> SEQ ID NO 592
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 592
cgcacggcgg cggcgcgacg g                                                 21

<210> SEQ ID NO 593
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 593
```
ccgcucgcgc cgccgccgcg gg 22

<210> SEQ ID NO 594
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 594
cgcacggcgg cggcgcgacg g 21

<210> SEQ ID NO 595
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 595
ccgucgcgcc gccgcagaug ucg 23

<210> SEQ ID NO 596
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 596
cgcacggcgg cggcgcgacg g 21

<210> SEQ ID NO 597
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 597
cacgacgcgc gcgccgccgu gcg 23

<210> SEQ ID NO 598
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 598
cgcacggcgg cggcgcgacg g 21

<210> SEQ ID NO 599
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 599
ccguccgcgc cgcgccgcgc g 21

<210> SEQ ID NO 600
<211> LENGTH: 21
<212> TYPE: RNA

<213> ORGANISM: Artificial Sequence
<220> FEATURE:
<223> OTHER INFORMATION: Synthetic Sequence

<400> SEQUENCE: 600
cgcacggcgg cggcgcgacg g               21

<210> SEQ ID NO 601
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 601
ccgucgucuc cgccgccggc g               21

<210> SEQ ID NO 602
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 602
cgcacggcgg cggcgcgacg g               21

<210> SEQ ID NO 603
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 603
ccgccgcccg ccgccgucgc g               21

<210> SEQ ID NO 604
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 604
gggcuuugua gucaggucac               20

<210> SEQ ID NO 605
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 605
gugccugagu acaaagcucc               20

<210> SEQ ID NO 606
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 606
cccaauccac accaacacac au              22

-continued

```
<210> SEQ ID NO 607
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 607
aagugugcug guguggauuc gg                                                  22

<210> SEQ ID NO 608
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 608
cucgggaaag cuuucuccga                                                     20

<210> SEQ ID NO 609
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 609
ugggagaaag uuuucccuga g                                                   21

<210> SEQ ID NO 610
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 610
caacacaugu ggauugag                                                       18

<210> SEQ ID NO 611
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 611
cucaagccua cuguguug                                                       18

<210> SEQ ID NO 612
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 612
caacacaugu ggauugag                                                       18

<210> SEQ ID NO 613
<211> LENGTH: 18
<212> TYPE: RNA
<213> ORGANISM: Artificial Sequence
<220> FEATURE:
```

<223> OTHER INFORMATION: Synthetic Sequence

<400> SEQUENCE: 613
cccaauccaa ugugcuug                                                18

<210> SEQ ID NO 614
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 614
caacacaugu ggauugag                                                18

<210> SEQ ID NO 615
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 615
cucaauccag cauaugaug                                               19

<210> SEQ ID NO 616
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 616
ucgccagauc auguugca                                                18

<210> SEQ ID NO 617
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 617
ugcaccauga ucucgguga                                               19

<210> SEQ ID NO 618
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 618
ucgccagauc auguugca                                                18

<210> SEQ ID NO 619
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 619
ugcaccauga ucauggcga                                               19

```
<210> SEQ ID NO 620
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 620
cguucgcugg ggaugacgac g                                              21

<210> SEQ ID NO 621
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 621
cgucgucauc cccggcggcc g                                              21

<210> SEQ ID NO 622
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 622
ugcucggacg acaugcagag accu                                           24

<210> SEQ ID NO 623
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 623
aggugcucug caugucgguc cagca                                          25

<210> SEQ ID NO 624
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 624
cagccaagga ugacuugccg a                                              21

<210> SEQ ID NO 625
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 625
uaggcaaauc auucuuggcu g                                              21

<210> SEQ ID NO 626
<211> LENGTH: 21
<212> TYPE: RNA
<213> ORGANISM: Artificial Sequence
<220> FEATURE:
<223> OTHER INFORMATION: Synthetic Sequence
```

```
<400> SEQUENCE: 626
cagccaagga ugacuugccg g                                              21

<210> SEQ ID NO 627
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 627
cuggcaacuc auccuuggcu u                                              21

<210> SEQ ID NO 628
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 628
uagccaagga ugacuugccu g                                              21

<210> SEQ ID NO 629
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 629
caggcaauuc auucuuggcu u                                              21

<210> SEQ ID NO 630
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 630
uagccaagga ugacuugccu g                                              21

<210> SEQ ID NO 631
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 631
cuggcaacuc auccuuggcu ua                                             22

<210> SEQ ID NO 632
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 632
uagccaagga ugacuugccu a                                              21

<210> SEQ ID NO 633
<211> LENGTH: 21
```

```
<212> TYPE: RNA
<213> ORGANISM: Artificial Sequence
<220> FEATURE:
<223> OTHER INFORMATION: Synthetic Sequence

<400> SEQUENCE: 633
uggcaacuca uccuuggcuu a                                             21

<210> SEQ ID NO 634
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 634
uagccaagga ugacuugccu a                                             21

<210> SEQ ID NO 635
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 635
uaggcaaauc auucuuggcu ga                                            22

<210> SEQ ID NO 636
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 636
uagccaagaa ugacuugccu a                                             21

<210> SEQ ID NO 637
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 637
ucaggcaauu cauucuuggc uu                                            22

<210> SEQ ID NO 638
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 638
uagccaagaa ugacuugccu a                                             21

<210> SEQ ID NO 639
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 639
```
gagucaaguc acucuuggcu a                          21

<210> SEQ ID NO 640
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 640
ugaaucuuga ugaugcugca c                          21

<210> SEQ ID NO 641
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 641
gcugcagcau caucaggauu cu                         22

<210> SEQ ID NO 642
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 642
ugaaucuuga ugaugcugca c                          21

<210> SEQ ID NO 643
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 643
gaugcagauc aucaggauuc a                          21

<210> SEQ ID NO 644
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 644
ggaaucuuga ugaugcugca                            20

<210> SEQ ID NO 645
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 645
ugcaacauaa ucaagacuuc c                          21

<210> SEQ ID NO 646
<211> LENGTH: 20
<212> TYPE: RNA
<213> ORGANISM: Artificial Sequence

```
<220> FEATURE:
<223> OTHER INFORMATION: Synthetic Sequence

<400> SEQUENCE: 646
ggaaucuuga ugaugcugca                                            20

<210> SEQ ID NO 647
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 647
ugcagcauca ucaggauucu c                                          21

<210> SEQ ID NO 648
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 648
agaaucuuga ugaugcugca                                            20

<210> SEQ ID NO 649
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 649
ugcagcauca ucaggauucu                                            20

<210> SEQ ID NO 650
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 650
uuaaugugaa uccaauga                                              18

<210> SEQ ID NO 651
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 651
ucauugaauu cgcauuag                                              18

<210> SEQ ID NO 652
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 652
agaucugugg ugccgagcu                                             19
```

```
<210> SEQ ID NO 653
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 653
agcccggcac cacagauuu                                              19

<210> SEQ ID NO 654
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 654
guccgcgaca accacgaag                                              19

<210> SEQ ID NO 655
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 655
cuucuuguug ucgcuggac                                              19

<210> SEQ ID NO 656
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 656
cgugccugau agugccgug                                              19

<210> SEQ ID NO 657
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 657
cacggcacca ugcacgcacg                                             20

<210> SEQ ID NO 658
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 658
caauccacau gcguuggggu gg                                          22

<210> SEQ ID NO 659
<211> LENGTH: 22
<212> TYPE: RNA
<213> ORGANISM: Artificial Sequence
<220> FEATURE:
<223> OTHER INFORMATION: Synthetic Sequence
```

```
<400> SEQUENCE: 659
ccacccaaca cauguggaug ug                                           22

<210> SEQ ID NO 660
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 660
cuucccaugg uucgacggg                                               19

<210> SEQ ID NO 661
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 661
ccuguucaac caugggaag                                               19

<210> SEQ ID NO 662
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 662
ccucaacaca uguggauug                                               19

<210> SEQ ID NO 663
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 663
caauucacau guguggggg                                               19

<210> SEQ ID NO 664
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 664
uugagguaga uuggagug                                                18

<210> SEQ ID NO 665
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 665
cuacuccaau ccaccucaa                                               19

<210> SEQ ID NO 666
```

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 666
acaaagcuca acuucacu                                                       18

<210> SEQ ID NO 667
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 667
auugaaggug agcauuugu                                                      19

<210> SEQ ID NO 668
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 668
uugcucuuag aaguugugc                                                      19

<210> SEQ ID NO 669
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 669
gcacaacuua uaagacaua                                                      19

<210> SEQ ID NO 670
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 670 acauguuug gaguggauug ggg                                                  23

<210> SEQ ID NO 671
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 671
cacccuaauc cacccaacac augu                                                24

<210> SEQ ID NO 672
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 672
```
gcacacuucu caaagcaaau ucaau    25

<210> SEQ ID NO 673
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 673
auuguauucg cuuugagaag ugugc    25

<210> SEQ ID NO 674
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 674
ccaaucuaaa caggcccu    18

<210> SEQ ID NO 675
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 675
aaggccuguu uggauugu    18

<210> SEQ ID NO 676
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 676
ccaaucuaaa caggcccu    18

<210> SEQ ID NO 677
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 677
agggccuguu uggaucgu    18

<210> SEQ ID NO 678
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 678
uggccuuugu cgugugug    18

<210> SEQ ID NO 679
<211> LENGTH: 18
<212> TYPE: RNA

```
<213> ORGANISM: Artificial Sequence
<220> FEATURE:
<223> OTHER INFORMATION: Synthetic Sequence

<400> SEQUENCE: 679
caccacacga aauggcca                                                 18

<210> SEQ ID NO 680
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 680
caaguuccac ucuaauccac                                               20

<210> SEQ ID NO 681
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 681
guggauugaa guggaacuug                                               20

<210> SEQ ID NO 682
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 682
acauguguug ggguagauug g                                             21

<210> SEQ ID NO 683
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 683
ccuaauccac ccaacacaug u                                             21

<210> SEQ ID NO 684
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 684
cacacuucuc aaugcgaa                                                 18

<210> SEQ ID NO 685
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 685
uucgauugag gaauugug                                                 18
```

```
<210> SEQ ID NO 686
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 686
guguuggagu ggauuggg                                                        18

<210> SEQ ID NO 687
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 687
cccuaaucca cccaacac                                                        18

<210> SEQ ID NO 688
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 688
uugaggugga uuggagugga                                                      20

<210> SEQ ID NO 689
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 689
ucuacuccaa uccaccucaa                                                      20

<210> SEQ ID NO 690
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 690
aaauuccacc cuaauccacu ccaa                                                 24

<210> SEQ ID NO 691
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 691 uuggaggugga uuaagguaga aauu                                                24

<210> SEQ ID NO 692
<211> LENGTH: 24
<212> TYPE: RNA
<213> ORGANISM: Artificial Sequence
<220> FEATURE:
```

<223> OTHER INFORMATION: Synthetic Sequence

<400> SEQUENCE: 692
aucccaaucc acaccaacac acau                                              24

<210> SEQ ID NO 693
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 693
auauguguug gaguggauug gggu                                              24

<210> SEQ ID NO 694
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 694
aacuccagca gagccccua                                                    19

<210> SEQ ID NO 695
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 695
uagaggcacu gcuggagcu                                                    19

<210> SEQ ID NO 696
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 696
uuaggaugcc cgccucgguu                                                   20

<210> SEQ ID NO 697
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 697
aaccguggcg ggcauuguaa                                                   20

<210> SEQ ID NO 698
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 698
uccacuccaa uccacuccaa c                                                 21

```
<210> SEQ ID NO 699
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 699
auuggugugg guuggagugg a                                             21

<210> SEQ ID NO 700
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 700
ugcauuguga gugcccuua                                                19

<210> SEQ ID NO 701
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 701
uuagggcacu cacaaugca                                                19

<210> SEQ ID NO 702
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 702
gaggcgcugc uguccuccac ac                                            22

<210> SEQ ID NO 703
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 703
gugcggaggg cagcagcgcc ac                                            22

<210> SEQ ID NO 704
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 704
aaucaauuuc aacacaugu                                                19

<210> SEQ ID NO 705
<211> LENGTH: 19
<212> TYPE: RNA
<213> ORGANISM: Artificial Sequence
<220> FEATURE:
<223> OTHER INFORMATION: Synthetic Sequence
```

```
<400> SEQUENCE: 705
acauguguug gaguggauu                                                  19

<210> SEQ ID NO 706
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 706
cgcgccgccg uccagcgg                                                   18

<210> SEQ ID NO 707
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 707
ccgcugcaag gccggcgcg                                                  19

<210> SEQ ID NO 708
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 708
cgcgccgccg uccagcgg                                                   18

<210> SEQ ID NO 709
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 709
ccgcucgauc ggggcgcg                                                   18

<210> SEQ ID NO 710
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 710
acaauguuga auagcuagca gauu                                            24

<210> SEQ ID NO 711
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 711
aaucugcuag ccauuuaaca gugu                                            24

<210> SEQ ID NO 712
<211> LENGTH: 24
```

```
<212> TYPE: RNA
<213> ORGANISM: Artificial Sequence
<220> FEATURE:
<223> OTHER INFORMATION: Synthetic Sequence

<400> SEQUENCE: 712
acacaugugg auugagguga aucc                                          24

<210> SEQ ID NO 713
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 713
ggauucacau caaucuacau augu                                          24

<210> SEQ ID NO 714
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 714
ccgccuccac ggccaaugc                                                19

<210> SEQ ID NO 715
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 715
gcauaggccg uguaggcag                                                19

<210> SEQ ID NO 716
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 716
acauguauug gaguggauug g                                             21

<210> SEQ ID NO 717
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 717
ccuaauccac ccaacacaug u                                             21

<210> SEQ ID NO 718
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 718
```

```
uccauccacg gcggccgc                                                18

<210> SEQ ID NO 719
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 719
gcggcgaucg uggaugga                                                18

<210> SEQ ID NO 720
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 720
uccauccacg gcggccgc                                                18

<210> SEQ ID NO 721
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 721
gcggccgcgc gugguggu                                                18

<210> SEQ ID NO 722
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 722
ccaaccggug uuaaaggg                                                18

<210> SEQ ID NO 723
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 723
ccauuuaaca gcguuugg                                                18

<210> SEQ ID NO 724
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 724
ccuuugucga gugcccgc                                                18

<210> SEQ ID NO 725
<211> LENGTH: 19
<212> TYPE: RNA
<213> ORGANISM: Artificial Sequence
```

```
<220> FEATURE:
<223> OTHER INFORMATION: Synthetic Sequence

<400> SEQUENCE: 725
ucgggcacuc ggcaaagag                                                  19

<210> SEQ ID NO 726
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 726
gagaugugug uuuacacac                                                  19

<210> SEQ ID NO 727
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 727
gugugcaaac acacaucuc                                                  19

<210> SEQ ID NO 728
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 728
ucggcuuacc cauguucaag ugcc                                            24

<210> SEQ ID NO 729
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 729
ggcacuugca cauggguaag ccga                                            24

<210> SEQ ID NO 730
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 730
cccaacacau auagauug                                                   18

<210> SEQ ID NO 731
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 731
caaucuacau auguuggg                                                   18
```

```
<210> SEQ ID NO 732
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 732
cccaacacau auagauug                                                 18

<210> SEQ ID NO 733
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 733
cuaucuauau cuguugagg                                                19

<210> SEQ ID NO 734
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 734
cccaauccac aacaacacac au                                            22

<210> SEQ ID NO 735
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 735
auauguguug gaguggauug gg                                            22

<210> SEQ ID NO 736
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 736
gggaagaggu gcgaggau                                                 18

<210> SEQ ID NO 737
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 737
agccugcauc cucuuccc                                                 18

<210> SEQ ID NO 738
<211> LENGTH: 20
<212> TYPE: RNA
<213> ORGANISM: Artificial Sequence
<220> FEATURE:
<223> OTHER INFORMATION: Synthetic Sequence
```

```
<400> SEQUENCE: 738
auccacaugu guuaaggugg                                                   20

<210> SEQ ID NO 739
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 739
uccacccaac acauguggau                                                   20

<210> SEQ ID NO 740
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 740
gcgaaucuaa uggaugggag                                                   20

<210> SEQ ID NO 741
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 741
cugcccaucc aacagauucg c                                                 21

<210> SEQ ID NO 742
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 742
ucaucuccuu gucaugca                                                     18

<210> SEQ ID NO 743
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 743
ugcugacaag gaagagga                                                     18

<210> SEQ ID NO 744
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 744
aucccaaucc acaccaacac acau                                              24

<210> SEQ ID NO 745
```

```
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 745
auauguguug gaguggauug gggu                                              24

<210> SEQ ID NO 746
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 746
ggcaaagcau ccggcacucg gc                                                22

<210> SEQ ID NO 747
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 747
gccgaguguc auaugcuuug cc                                                22

<210> SEQ ID NO 748
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 748
ggcccucccc gaccggug                                                     18

<210> SEQ ID NO 749
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 749
cgcucggauc ggggagggcc                                                   20

<210> SEQ ID NO 750
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 750 gagguccccga ugcggacg                                                    18

<210> SEQ ID NO 751
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 751
```

```
cuucagcauc cggaccuc                                                    18

<210> SEQ ID NO 752
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 752
ggcacacggu auaccugg                                                    18

<210> SEQ ID NO 753
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 753
acagguauac cggugugac                                                   19

<210> SEQ ID NO 754
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 754
aacacacaug gauugaagug aauac                                            25

<210> SEQ ID NO 755
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 755
agauucacuu caauccaugu guauu                                            25

<210> SEQ ID NO 756
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 756
caggaggcug gcuggcgcgc uc                                               22

<210> SEQ ID NO 757
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 757
cacgcgccag ccagccugcc ug                                               22

<210> SEQ ID NO 758
<211> LENGTH: 24
<212> TYPE: RNA
```

```
<213> ORGANISM: Artificial Sequence
<220> FEATURE:
<223> OTHER INFORMATION: Synthetic Sequence

<400> SEQUENCE: 758
uuggggugga uuggagugga acuu                                          24

<210> SEQ ID NO 759
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 759
aaguucuacu ccaauccacc ucaa                                          24

<210> SEQ ID NO 760
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 760
aaauuccacc ccaauccacu ccaa                                          24

<210> SEQ ID NO 761
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 761
uugguguggg uuggagugga auuu                                          24

<210> SEQ ID NO 762
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 762
cacuccaauc caccccaaca ca                                            22

<210> SEQ ID NO 763
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 763
uguauuggug ugguuggag ug                                             22

<210> SEQ ID NO 764
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 764
uggaagucca ccaaugaca                                                19
```

<210> SEQ ID NO 765
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 765
ugucauuugu gguguucca                                                    19

<210> SEQ ID NO 766
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 766
gcuugaguuu aucagccgag u                                                 21

<210> SEQ ID NO 767
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 767
auucgccuga uaagcucaag c                                                 21

<210> SEQ ID NO 768
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 768
gccucuuggu aguagucg                                                     18

<210> SEQ ID NO 769
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 769
cuacuacuac caaggaagc                                                    19

<210> SEQ ID NO 770
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 770
ccgaccaugg ugguggugg                                                    19

<210> SEQ ID NO 771
<211> LENGTH: 19
<212> TYPE: RNA
<213> ORGANISM: Artificial Sequence
<220> FEATURE:

<223> OTHER INFORMATION: Synthetic Sequence

<400> SEQUENCE: 771
ccaccacuac cuggucugg                                                    19

<210> SEQ ID NO 772
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 772
guggauugga guggaacuu                                                    19

<210> SEQ ID NO 773
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 773
aaguucuacu ccaauccac                                                    19

<210> SEQ ID NO 774
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 774
aaguugucau uggugggcu                                                    19

<210> SEQ ID NO 775
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 775
agcccaccac ugacuacuu                                                    19

<210> SEQ ID NO 776
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 776
gcaucaaucc acaaguguu                                                    19

<210> SEQ ID NO 777
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 777
aacauaugug gauugaugu                                                    19

```
<210> SEQ ID NO 778
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 778
uauuugccga gcgcuauuu                                                    19

<210> SEQ ID NO 779
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 779
aaauagcugc uagcaaaua                                                    19

<210> SEQ ID NO 780
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 780
cgcacggcgg cggcgcgacg g                                                 21

<210> SEQ ID NO 781
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 781
ccgccgccgc cgccgcccgu gcg                                               23

<210> SEQ ID NO 782
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 782
cccgguuggu gagaccaacc gg                                                22

<210> SEQ ID NO 783
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 783
ccgguugguc ucaugaaccg gg                                                22

<210> SEQ ID NO 784
<211> LENGTH: 22
<212> TYPE: RNA
<213> ORGANISM: Artificial Sequence
<220> FEATURE:
<223> OTHER INFORMATION: Synthetic Sequence
```

```
<400> SEQUENCE: 784
acugcucagc gucucacggc ac                                           22

<210> SEQ ID NO 785
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 785
gugcugugag aggcugaaca gu                                           22

<210> SEQ ID NO 786
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 786
cccaauccac accaacacac au                                           22

<210> SEQ ID NO 787
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 787
auguguauug guguggguug gag                                          23

<210> SEQ ID NO 788
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 788
acauguggau ugaugcgaau ccgac                                        25

<210> SEQ ID NO 789
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 789
gucggauuca caucaaucua cauau                                        25

<210> SEQ ID NO 790
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 790
caacacaugu ggauugag                                                18

<210> SEQ ID NO 791
<211> LENGTH: 19
```

```
<212> TYPE: RNA
<213> ORGANISM: Artificial Sequence
<220> FEATURE:
<223> OTHER INFORMATION: Synthetic Sequence

<400> SEQUENCE: 791
caucaaucua cauauguug                                                    19

<210> SEQ ID NO 792
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 792
ucgccagauc auguugca                                                     18

<210> SEQ ID NO 793
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 793
uggcaacaug augcuggcaa                                                   20
```